(12) United States Patent
Chang et al.

(10) Patent No.: US 9,682,143 B2
(45) Date of Patent: *Jun. 20, 2017

(54) COMBINATION THERAPY FOR INDUCING IMMUNE RESPONSE TO DISEASE

(71) Applicant: IBC Pharmaceuticals, Inc., Morris Plains, NJ (US)

(72) Inventors: Chien-Hsing Chang, Downingtown, PA (US); David M. Goldenberg, Mendham, NJ (US); Edmund A. Rossi, Woodland Park, NJ (US); Diane Rossi, Woodland Park, NJ (US)

(73) Assignee: IBC Pharmaceuticals, Inc., Morris Plains, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/106,737

(22) Filed: Dec. 14, 2013

(65) Prior Publication Data

US 2014/0099254 A1    Apr. 10, 2014

Related U.S. Application Data

(63) Continuation-in-part of application No. 13/966,450, filed on Aug. 14, 2013, now Pat. No. 9,315,567.

(60) Provisional application No. 61/807,998, filed on Apr. 3, 2013, provisional application No. 61/733,268, filed on Dec. 4, 2012, provisional application No. 61/682,965, filed on Aug. 14, 2012.

(51) Int. Cl.
| *A61K 47/48* | (2006.01) |
| *C07K 16/28* | (2006.01) |
| *C07K 16/30* | (2006.01) |
| *A61K 38/21* | (2006.01) |
| *A61K 45/06* | (2006.01) |
| *A61K 39/395* | (2006.01) |
| *C07K 16/44* | (2006.01) |
| *A61K 9/00* | (2006.01) |
| *A61K 39/00* | (2006.01) |

(52) U.S. Cl.
CPC ........ *A61K 39/3955* (2013.01); *A61K 9/0019* (2013.01); *A61K 38/21* (2013.01); *A61K 38/212* (2013.01); *A61K 39/39558* (2013.01); *A61K 45/06* (2013.01); *A61K 47/4853* (2013.01); *A61K 47/48384* (2013.01); *A61K 47/48569* (2013.01); *C07K 16/2803* (2013.01); *C07K 16/2809* (2013.01); *C07K 16/2833* (2013.01); *C07K 16/2863* (2013.01); *C07K 16/2887* (2013.01); *C07K 16/30* (2013.01); *C07K 16/3007* (2013.01); *C07K 16/44* (2013.01); *A61K 2039/505* (2013.01); *A61K 2039/507* (2013.01); *A61K 2039/54* (2013.01); *C07K 2317/31* (2013.01); *C07K 2317/54* (2013.01); *C07K 2317/55* (2013.01); *C07K 2317/622* (2013.01); *C07K 2317/73* (2013.01)

(58) Field of Classification Search
CPC .......... A61K 39/39558; A61K 2300/00; A61K 38/21; A61K 38/212; A61K 38/215; A61K 38/195; A61K 47/48384; A61K 45/06; A61K 39/3955; C07K 16/2803; C07K 16/2845; C07K 16/2809; C07K 16/30; C07K 16/3007; C07K 2317/55; C07K 2039/507; C07K 2039/505; C07K 2317/31; C07K 2317/54; C07K 2039/54; C07K 2317/73; C07K 2317/622
See application file for complete search history.

(56) References Cited

U.S. PATENT DOCUMENTS

| 4,046,722 A | 9/1977 | Rowland |
| 4,699,784 A | 10/1987 | Shih et al. |
| 4,868,109 A | 9/1989 | Lansdorp et al. |
| 5,770,198 A | 6/1998 | Coller et al. |

(Continued)

FOREIGN PATENT DOCUMENTS

| WO | 99/54440 | 10/1999 |
| WO | 00/68248 | 11/2000 |

(Continued)

OTHER PUBLICATIONS

Yu et al., Investigative Ophthalmology & Visual Science 49(2): 522-527, Feb. 2008.*

(Continued)

*Primary Examiner* — Phuong Huynh
(74) *Attorney, Agent, or Firm* — Richard A. Nakashima

(57) ABSTRACT

The present invention concerns combinations of two or more agents for inducing an immune response to cancer or infectious disease. Agents may include leukocyte redirecting complexes, antibody-drug conjugates, interferons (preferably interferon-α), and/or checkpoint inhibitor antibodies. The leukocyte redirecting complexes have at least one binding site for a leukocyte antigen and at least one binding site for an antigen on a diseased cell or pathogen. Preferably, the complex is a DNL™ complex. More preferably, the complex comprises a bispecific antibody (bsAb). Most preferably, the bsAb is an anti-CD3×anti-CD19 bispecific antibody, although antibodies against other leukocyte antigens and/or disease-associated antigens may be used. The complex is capable of targeting effector T cells, NK cells, monocytes or neutrophils to induce leukocyte-mediated cytotoxicity of cells associated with cancer or infectious disease. The cytotoxic immune response is enhanced by co-administration of interferon, checkpoint inhibitor antibody and/or ADC.

13 Claims, 24 Drawing Sheets

(56) References Cited

U.S. PATENT DOCUMENTS

| | | | |
|---|---|---|---|
| 5,871,945 A | 2/1999 | Lockerbie et al. | |
| 6,261,537 B1 | 7/2001 | Klaveness et al. | |
| 6,306,393 B1 | 10/2001 | Goldenberg et al. | |
| 6,524,854 B1 | 2/2003 | Monia et al. | |
| 7,060,506 B2 | 6/2006 | Craig | |
| 7,238,785 B2* | 7/2007 | Govindan | A61K 51/1045 424/133.1 |
| 7,312,318 B2* | 12/2007 | Hansen et al. | 530/387.3 |
| 7,521,056 B2 | 4/2009 | Chang et al. | |
| 7,527,787 B2 | 5/2009 | Chang et al. | |
| 7,534,866 B2 | 5/2009 | Chang et al. | |
| 7,550,143 B2 | 6/2009 | Chang et al. | |
| 7,666,400 B2 | 2/2010 | Chang et al. | |
| 7,858,070 B2 | 12/2010 | Chang et al. | |
| 7,871,622 B2 | 1/2011 | Chang et al. | |
| 7,901,680 B2 | 3/2011 | Chang et al. | |
| 7,906,121 B2 | 3/2011 | Chang et al. | |
| 7,981,398 B2 | 7/2011 | Chang et al. | |
| 8,003,111 B2 | 8/2011 | Chang et al. | |
| 8,034,352 B2 | 10/2011 | Chang et al. | |
| 8,158,129 B2 | 4/2012 | Chang et al. | |
| 8,163,291 B2 | 4/2012 | Chang et al. | |
| 8,211,440 B2 | 7/2012 | Chang et al. | |
| 8,246,960 B2 | 8/2012 | Chang et al. | |
| 8,277,817 B2 | 10/2012 | Chang et al. | |
| 8,282,934 B2 | 10/2012 | Chang et al. | |
| 8,349,332 B2 | 1/2013 | Chang et al. | |
| 8,394,926 B2* | 3/2013 | Lutterbuse | A61K 45/06 424/135.1 |
| 8,435,540 B2 | 5/2013 | Chang et al. | |
| 8,475,794 B2 | 7/2013 | Chang et al. | |
| 8,481,041 B2 | 7/2013 | Chang et al. | |
| 8,491,914 B2 | 7/2013 | Chang et al. | |
| 8,551,480 B2 | 10/2013 | Chang et al. | |
| 8,562,988 B2 | 10/2013 | Chang et al. | |
| 8,597,659 B2 | 12/2013 | Chang et al. | |
| 2002/0103345 A1* | 8/2002 | Zhu | 530/388.15 |
| 2003/0198956 A1 | 10/2003 | Makowski et al. | |
| 2003/0232420 A1 | 12/2003 | Braun et al. | |
| 2004/0018587 A1 | 1/2004 | Makowski et al. | |
| 2004/0126361 A1 | 7/2004 | Saifer et al. | |
| 2005/0003403 A1 | 1/2005 | Rossi et al. | |
| 2005/0136050 A1* | 6/2005 | Kufer | C07K 16/2809 424/133.1 |
| 2005/0153923 A1* | 7/2005 | Kinch | 514/44 |
| 2006/0210475 A1 | 9/2006 | Goldenberg et al. | |
| 2007/0264265 A1 | 11/2007 | Goldenberg et al. | |
| 2007/0274998 A1 | 11/2007 | Utku | |
| 2009/0111143 A1 | 4/2009 | Goldenberg et al. | |
| 2010/0303827 A1 | 12/2010 | Sharma et al. | |
| 2011/0020273 A1 | 1/2011 | Chang et al. | |
| 2011/0064754 A1 | 3/2011 | Taylor et al. | |
| 2011/0143417 A1 | 6/2011 | Chang et al. | |
| 2011/0158905 A1 | 6/2011 | Goldenberg et al. | |
| 2011/0189083 A1 | 8/2011 | Chang et al. | |
| 2012/0093769 A1 | 4/2012 | Chang et al. | |
| 2012/0196346 A1 | 8/2012 | Chang et al. | |
| 2012/0276100 A1 | 11/2012 | Chang et al. | |
| 2012/0276608 A1 | 11/2012 | Chang et al. | |
| 2013/0078183 A1 | 3/2013 | Chang et al. | |
| 2013/0109073 A1 | 5/2013 | Chang et al. | |
| 2013/0164816 A1 | 6/2013 | Chang et al. | |
| 2013/0177532 A1 | 7/2013 | Chang et al. | |
| 2013/0217091 A1 | 8/2013 | Chang et al. | |
| 2013/0295005 A1 | 11/2013 | Chang et al. | |
| 2014/0242079 A1 | 8/2014 | Bacac et al. | |
| 2014/0242080 A1 | 8/2014 | Jaeger et al. | |
| 2014/0242081 A1 | 8/2014 | Hammond et al. | |
| 2016/0145354 A1 | 5/2016 | Bacac et al. | |

FOREIGN PATENT DOCUMENTS

| | | |
|---|---|---|
| WO | WO2005040220 * | 5/2005 |
| WO | 2006/107617 | 10/2006 |
| WO | 2006/107786 | 10/2006 |
| WO | 2007/046893 | 4/2007 |
| WO | 2007/075270 | 7/2007 |
| WO | 2011/025904 | 3/2011 |

OTHER PUBLICATIONS

Jubala et al., Vet Pathol 42: 468-476, 2005.*
Stein et al., Cancer Res 50:1330-1336, 1990.*
Hay et al., Nature Biotechnology 32(1): 40-51, Jan. 2014.*
Kumar et al., Expert Opinion Drug discov. 7(11): 1093-1106, 2012.*
Schoonjans et al., J Immunology 165: 7050-7057, 2000.*
Singh et al., Nature Biotechnology 30(7): 648-657, Jul. 2012.*
Wong et al., The Oncologist 17:346-358, 2012.*
Tol et al., N Engl J Med. 5;360(6):563-72, Feb. 2009.*
Wolf et al., Reviews Drug Discovery today 10(18): 1237-1244, Sep. 2005.*
Stancovski et al., PNAS 88: 8691-8695, 1991.*
Golay et al., Archives of Biochemistry and Biophysics 526: 146-153, 2012.*
Abbas et al., Cellular and Molecular Immunology, W.B. Saunders Comp. 1991, p. 43.
Alto et al., "Bioinformatic design of A-kinase anchoring protein-in silico: a potent and selective peptide antagonist of type II protein kinase A anchoring" Proc. Natl. Acad. Sci USA Apr. 15, 2003; 100(8):4445-50.
Backer et al., "Self-Assembled "Dock and Lock" System for Linking Payloads to Targeting Proteins" Bioconjugate Chem., 2006, 17(4):912-919.
Baillie et al., "Compartmentalisation of phospodiesterases and protein kinase A: opposites attract" FEBS Letters 2005; 579:3264-3270.
Banky et al., "Dimerization/Docking Domain of the Type Iα Regulatory Subunit of cAMP-dependent Protein Kinase" J. Biol. Chem. 273:35048-55, 1998.
Basu et al., "Structure-Function Engineering of Interferon-β-1b for Improving Stability, Solubility, Potency, Immunogenicity, and Pharmacokinetic Properties by Site-Selective Mono-PEGylation" Bioconjugate Chem. 2006; 17:618-630.
Belardelli et al., "Interferon-alpha in tumor immunity and immunotherapy" Cytokine Growth Factor Rev. 13(2):119-134 (2002).
Belardelli et al., "International Meeting on Cancer Vaccines: How Can We Enhance Efficacy of Therapeutic Vaccines?" Cancer Res. 64:6827-6830 (2004).
Belardelli et al., "The neglected role of type I interferon in the T-cell response: implications for its clinical use" Immunol. Today 17(8):369-72 (1996).
Biron et al., "Natural killer cells in antiviral defense: function and regulation by innate cytokines" Annu. Rev. Immunol. 17:189-220 (1999).
Brunda et al., "Modulation of Murine Natural Killer Cell Activity in Vitro and in Vivo by Recombinant Human Interferons" Cancer Res. 44:597-601 (1984).
Burns-Hamuro et al., "Distinct interaction modes of an AKAP bound to two regulatory subunit isoforms of protein kinase A revealed by amide hydrogen/deuterium exchange" Protein Science (2005), 14:2982-2992.
Carr et al., "Interaction of the Regulatory Subunit (RII) of cAMP-dependent Protein Kinase with RII-anchoring Proteins Occurs through an Amphipathic Helix Binding Motif" J. Biol. Chem. 266:14188-92 (1991).
Carr et al., "Identification of Sperm-specific Proteins That Interact with A-kinase Anchoring Proteins in a Manner Similar to the Type II Regulatory Subunit of PKA" J. Biol. Chem. 276(20):17332-17338 (2001).
Carrero et al., "Lymphocytes are detrimental during the early innate immune response against Listeria monocytogenes" J. Exp. Med. 203(4):933-940 (2006).
Chang et al., "The Dock and Lock Method: A Novel Platform Technology for Building Multivalent, Multifunctional Structures of

(56) References Cited

OTHER PUBLICATIONS

Defined Composition with Retained Bioactivity" Clin. Cancer Res. Sep. 15, 2007;13(18 Suppl), pp. 5586-5591.
Chmura et al., "Antibodies with infinite affinity" Proc. Natl. Acad. Sci. USA 98(15):8480-8484 (2001).
Colledge et al., "AKAPs: from structure to function" Trends Cell Biol. 6:216-21 (1999).
Corbin et al., "Regulation of Adenosine 3',5'-Monophosphate-dependent Protein Kinase" J. Biol. Chem. 248:1813-21 (1973).
Dhalluin et al., "Structural and Biophysical Characterization of the 40 kDa PEG-Interferon-α2a and Its Individual Positional Isomers" Bioconjugate Chem. 2005;16:504-517.
Dodart et al., "Immunotherapy for Alzheimer's Disease: will vaccination work?" Trends Mol. Med. 9(3):85-87 (2003).
Doherty et al., "Site-Specific PEGylation of Engineered Cysteine Analogues of Recombinant Human Granulocyte-Macrophage Colony-Stimulating Factor" Bioconjugate Chem. 2005;16:1291-1298.
Ferrantini et al., "IFN-α1 Gene Expression into a Metastatic Murine Adenocarcinoma (TS/A) Results in CD8+ T Cell-Mediated Tumor Rejection and Development of Antitumor Immunity" J. Immunol. 153:4604-15 (1994).
Ferrantini et al., "Interferon-α and cancer: Mechanisms of action and new perspectives of clinical use" Biochimie 89: 884-893 (2007).
Foser et al., "Improved biological and transcriptional activity of monopegylated interferon-α-2a isomers." The Pharmacogenomics J 3:312-319 (2003).
Gillies et al., "High-level expression of chimeric antibodies using adapted cDNA variable region cassettes" J. Immunol. Methods 125 (1989) 191-202.
Glennie et al., "Mechanisms of killing by anti-CD20 monoclonal antibodies" Mol. Immunol. 44:3823-3837 (2007).
Gold et al., "A Novel Bispecific, Trivalent Antibody Construct for Targeting Pancreatic Carcinoma", Cancer Res. 68:4819-26, 2008.
Gold et al., "Molecular Basis of AKAP Specificity for PKA Regulatory Subunits" Mol. Cell Nov. 3, 2006;24(3):383-95.
Goldenberg et al., "Multifunctional Antibodies by the Dock-and-Lock Method for Improved Cancer Imaging and Therapy by Pretargeting" J. Nucl. Med. 49:158-63, 2008.
Goldenberg et al., "Properties and structure-function relationships of veltuzumab (hA20), a humanized anti-CD20 monoclonal antibody" Blood 113:1062-70 (2009).
Goodson et al., "Site-Directed PEGylation of Recombinant Interleukin-2 at its Glycosylation Site" Nat. Biotechnology Apr. 1990;8(4):343-6.
Grace et al., "Site of Pegylation and Polyethylene Glycol Molecule Size Attenuate Interferon-α Antiviral and Antiproliferative Activities through the JAK/STAT Signaling Pathway" J. Biol. Chem. 2005;280(8):6327-6336.
Grimley et al., "Prolonged STAT1 Activation Related to the Growth Arrest of Malignant Lymphoma Cells by Interferon-α" Blood 91(8):3017-27 (1998).
Gutterman et al., "Leukocyte Interferon-Induced Tumor Regression in Human Metastatic Breast Cancer, Multiple Myeloma, and Malignant Lymphoma" Ann. Intern. Med. 93(3):399-406 (1980).
Gutterman et al., "Cytokine therapeutics: Lessons from interferon α" Proc. Natl. Acad. Sci. USA 91:1198-205 (1994).
Harris et al., "Effect of pegylation on pharmaceuticals" Nat. Rev. Drug. Discov. 2:214-221 (2003).
Hausken et al. "Mutational Analysis of the A-Kinase Anchoring Protein (AKAP)-binding Site on RII" J. Biol. Chem. 271:29016-22 (1996).
Hodneland et al., Selective immobilization of proteins to self-assembled monolayers presenting active site-directed capture ligands, Proc. Natl. Acad. Sci. USA 2002; 99:5048-5052.
Huang et al., "Targeting IFN-α to B Cell Lymphoma by a Tumor-Specific Antibody Elicits Potent Antitumor Activities" J. Immunol. 179:6881-88 (2007).
Hundsrucker et al., "High-affinity AKAP7σ-protein kinase A interaction yields novel protein kinase A-anchoring disruptor peptides" Biochem. J. (2006) 396, 297-306.
Kimby et al., "Long-term molecular remissions in patients with indolent lymphoma treated with rituximab as a single agent or in combination with interferon alpha-2a: A randomized phase II study from the Nordic Lymphoma Group" Leuk. Lymphoma 49(1):102-112 (2008).
Kinderman et al., "A Dynamic Mechanism for AKAP Binding to RII Isoforms of cAMP-Dependent Protein Kinase" Mol. Cell 24(3):397-408 (2006).
Kinstler et al., "Characterization and Stability of N-terminally PEGylated rhG-CSF" Pharm. Res. 1996;13(7):996-1002.
Kramer et al., "Cell and virus sensitivity studies with recombinant human alpha interferons" J. Interferon. Res. 3 (4):425-35 (1983).
Le Bon et al., "Type I Interferons Potently Enhance Humoral Immunity and Can Promote Isotype Switching by Stimulating Dendritic Cells In Vivo" Immunity 14:461-470 (2001).
Lee et al., "Solid-Phase PEGylation of Recombinant Interferon α-2a for Site-Specific Modification: Process Performance, Characterization, and in Vitro Bioactivity" Bioconjugate Chem. 2007; 18:1728-34.
Lohmann et al., "High-affinity binding of the regulatory subunit (RII) of cAMP-dependent protein kinase to microtubule-associated and other cellular proteins" Proc. Natl. Acad. Sci. USA 81:6723-27 (1984).
Luft et al., "Type I IFNs Enhance the Terminal Differentiation of Dendritic Cells" J. Immunol. 161:1947-1953 (1998).
Mason, Anthony J., "Functional Analysis of the Cysteine Residues of Activin A" Mol. Endocrinol. 8:325-32 (1994).
Amann et al., "Antitumor activity of an EpCAM/CD3-bispecific BiTE antibody during long-term treatment of mice in the absence of T-cell anergy and sustained cytokine release", J Immunother. Jun. 2009;32(5):452-64.
Baeuerle et al., "Bispecific T-cell engaging antibodies for cancer therapy", Cancer Res. Jun. 15, 2009;69(12):4941-4.
Bargou et al., "Tumor regression in cancer patients by very low doses of a T cell-engaging antibody", Science. Aug. 15, 2008;321(5891):974-7.
Bassan et al., "Toward victory in adult ALL: blinatumomab joins in", Blood. Dec. 20, 2012;120(26):5094-5.
Moore et al., "Application of dual affinity retargeting molecules to achieve optimal redirected T-cell killing of B-cell lymphoma", Blood. Apr. 28, 2011;117(17):4542-51.
Nitta et al., Preliminary trial of specific targeting therapy against malignant glioma, Lancet. Feb. 17, 1990;335 (8686):368-71.
Nagorsen et al., Immunotherapy of lymphoma and leukemia with T-cell engaging BiTE antibody blinatumomab, Leuk Lymphoma. Jun. 2009;50(6):886-91.
Portell et al., "Clinical and pharmacologic aspects of blinatumomab in the treatment of B-cell acute lymphoblastic leukemia", Clin Pharmacol. Apr. 12, 2013;5(Suppl 1):5-11.
Portner et al., "T and NK cells of B cell NHL patients exert cytotoxicity against lymphoma cells following binding of bispecific tetravalent antibody CD19 × CD3 or CD19 × CD16", Cancer Immunol Immunother. Oct. 2012;61(10):1869-75.
Topp et al., "Long-term follow-up of hematologic relapse-free survival in a phase 2 study of blinatumomab in patients with MRD in B-lineage ALL", Blood. Dec. 20, 2012;120(26):5185-7.
Traunecker et al., "Bispecific single chain molecules (Janusins) target cytotoxic lymphocytes on HIV infected cells", EMBO J. Dec. 1991;10(12):3655-9.
Veri et al., "Therapeutic control of B cell activation via recruitment of Fcgamma receptor IIb (CD32B) inhibitory function with a novel bispecific antibody scaffold", Arthritis Rheum. Jul. 2010;62(7):1933-43.
Wei et al., "Disulfide-stabilized diabody antiCD19/antiCD3 exceeds its parental antibody in tumor-targeting activity", Cell Oncol (Dordr). Dec. 2012;35(6):423-34.
Zhou et al., "A fully human CD19/CD3 bi-specific antibody triggers potent and specific cytotoxicity by unstimulated T lymphocytes against non-Hodgkin's lymphoma", Biotechnol Lett. Jul. 2012;34(7):1183-91.

(56) References Cited

OTHER PUBLICATIONS

Matarrese et al., "Type I Interferon Gene Transfer Sensitizes Melanoma Cells to Apoptosis via a Target Activity on Mitochondrial Function" Am. J. Pathol. 2002, 160(4):1507-1520.
Mecchia et al., "Type I consensus interferon (CIFN) gene transfer into human melanoma cells up-regulates p53 and enhances cisplatin-induced apoptosis: implications for new therapeutic strategies with IFN-alpha" Gene Ther. (2000) 7, 167-179.
Newlon et al., "A Novel Mechanism of PKA Anchoring Revealed by Solution Structures of Anchoring Complexes" EMBO J. 2001; 20:1651-1662.
Newlon et al., "The molecular basis for protein kinase A anchoring revealed by solution NMR" Nature Struct Biol. 1999; 3:222-227.
Ngo et al., "Computational Complexity, Protein Structure Prediction, and the Levinthal Paradox", The Protein Folding Problem and Tertiary Structure Prediction, Ch. 14, pp. 492-495, (Mertz & Le Grand, Eds.), Birkhauser Boston, 1994.
Osborn et al., "Pharmacokinetic and Pharmacodynamic Studies of a Human Serum Albumin-Interferon-α Fusion Protein in Cynomolgus Monkeys" J. Pharmacol. Exp. Ther. 303(2):540-548 (2002).
Oyen et al., "Human testis cDNA for the regulatory subunit RIIα of cAMP-dependent protein kinase encodes an alternate amino-terminal region" FEBS Letters 246:57-64, 1989.
Ozzello et al., "Conjugation of interferon alpha to a humanized monoclonal antibody (HuBrE-3v1) enhances the selective localization and antitumor effects of interferon in breast cancer xenografts" Breast Cancer Res. Treat. 48: 135-147 (1998).
Paquette et al., "Interferon-α and granulocyte-macrophage colony-stimulating factor differentiate peripheral blood monocytes into potent antigen-presenting cells" J. Leukoc. Biol. 64:358-367; 1998.
Pelham et al., "Interferon-α conjugation to human osteogenic sarcoma monoclonal antibody 791T/36" Cancer Immunol. Immuother 1983;15(3):210-216.
Pepinsky et al., "Improved Pharmacokinetic Properties of a Polyethylene Glycol-Modified Form of Interferon-β-1a with Preserved in Vitro Bioactivity" Pharmacol. Exp. Ther. 2001; 297(3):1059-1066.
Pilling et al., "Interferon-β mediates stromal cell rescue of T cells from apoptosis" Eur. J. Immunol. 29:1041-1050 (1999).
Rabjohn et al., "Molecular Cloning and Epitope Analysis of the Peanut Allergen Ara h 3" J. Clinical Investigation 103 (4):535-542 (1999).
Raefsky et al., "Studies of Interferon as a regulator of hematopoietic cells proliferation" J. Immunol. 135 (4):2507-2512 (1985).
Rose et al., "Structural basis of dimerization, coactivator recognition and MODY3 mutations in HNF-1α" Nature Struct. Biol. 2000; 7:744-748.
Rosendahl et al., "A Long-Acting, Highly Potent Interferon α-2 Conjugate Created Using Site-Specific PEGylation" Bioconjugate Chem. 2005;16:200-207.
Rossi et al., "Novel Designs of Multivalent Anti-CD20 Humanized Antibodies as Improved Lymphoma Therapeutics" Cancer Res. 68:8384-92 (2008).
Rossi et al., "Stably tethered multifunctional structures of defined composition made by the dock and lock method for use in cancer targeting" Proc. Natl. Acad. Sci. Epub Apr. 24, 2006, vol. 103, No. 18, pp. 6841-6846.
Rossi et al., "Optimization of Multivalent Bispecific Antibodies and Immunocytokines with Improved in Vivo Properties", Bioconjug Chem. Jan. 16, 2013;24(1):63-71.
Rustandi et al., "The Ca2+-Dependent Interaction of S100B(ββ) with a Peptide Derived from p53", Biochemistry 1998; 37: 1951-1960.
Sabaawy et al., "Enhancement of 5-fluorouracil cytotoxicity on human colon cancer cells by retrovirus-mediated interferon-α gene transfer" Int. J. Oncol. Jun. 1999; 14(6):1143-51.
Salles et al., "Rituximab combined with chemotherapy and interferon in follicular lymphoma patients: results of the GELA-GOELAMS FL2000 study" Blood 2008; 112:4824-4831.

Santini et al., "Type I Interferon as a Powerful Adjuvant for Monocyte-derived Dendritic Cell Development and Activity In Vivo and in Hu-PBL-SCID Mice" J. Exp. Med. 191(10):1777-1788 (2000).
Scott et al., "Type II Regulatory Subunit Dimerization Determines the Subcellular Localization of the cAMP-dependent Protein Kinase" J. Biol. Chem. 265:21561-66 (1990).
Scott et al., "Cyclic nucleotide-dependent protein kinases" Pharmacol. Ther. 1991;50(1):123-45.
Seffernick et al., "Melamine Deaminase and Atrazine Chlorohydrolase: 98 Percent Identical but Functionally Different" J. Bacteriol. 183(8):2405-2410 (2001).
Sharkey et al., "Improved Therapeutic Results by Pretargeted Radioimmunotherapy of Non-Hodgkin's Lymphoma with a New Recombinant, Trivalent, Anti-CD20, Bispecific Antibody" Cancer Res. 68:5282-90 (2008).
Sharkey et al., "Metastatic Human Colonic Carcinoma: Molecular Imaging with Pretargeted SPECT and PET in a Mouse Model" Radiology 246:497-507 (2008).
Sidky et al., "Inhibition of Angiogenesis by Interferons: Effects on Tumor- and Lymphocyte-induced Vascular Responses" Cancer Res. 47:5155-5161, Oct. 1, 1987.
Stein et al., "Characterization of a New Humanized Anti-CD20 Monoclonal Antibody, IMMU-106, and Its Use in Combination with the Humanized Anti-CD22 Antibody, Epratuzumab, for the Therapy of Non-Hodgkin's Lymphoma" Clin. Cancer Res. vol. 10, 2868-2878, Apr. 15, 2004.
Stein et al., "Characterization of a humanized IgG4 anti-HLA-DR monoclonal antibody that lacks effector cell functions but retains direct antilymphoma activity and increases the potency of rituximab" Blood 2006;108:2736-2744.
Stokka et al., "Characterization of A-kinase-anchoring disruption using a solution-based assay" Biochem. J. (2006) 400, 493-499.
Stryer et al., "Levels of Structure in Protein Architecture", Biochemistry, 3rd Ed., pp. 31-33, W.H. Freeman & Co., New York, 1988.
Takaoka et al., "Integration of interferon-α/β signalling to p53 responses in tumour suppression and antiviral defence" Nature Jul. 31, 2003;424(6948):516-23.
Taylor, S., "cAMP-dependent Protein Kinase" J. Biol. Chem. 1989;264(15):8443-8446.
Walsh et al., "An Adenosine 3', 5'-Monophosphate-dependant Protein Kinase from Rabbit Skeletal Muscle" J. Biol. Chem. 243(13):3763-3774 (1968).
Weck et al., "Comparison of the Antiviral Activities of Various Cloned Human Interferon-α Subtypes in Mammalian Cell Cultures" J. Gen. Virol. (1981), 57, 233-237.
Winkler et al., "Changing the Antigen Binding Specificity by Single Point Mutations of an Anti-p24 (HIV-1) Antibody" J. Immunol. 165:4505-14 (2000).
Witkowski et al., "Conversion of a β-Ketoacyl Synthase to a Malonyl Decarboxylase by Replacement of the Active-Site Cysteine with Glutamine" Biochemistry 38(36):11643-50 (1999).
Wong et al., "AKAP Signalling Complexes: Focal Points in Space and Time" Nat. Rev. Mol. Cell Biol. 12:959-70 (2004).
Zhu et al., "Inhibition of tumor growth and metastasis by targeting tumor-associated angiogenesis with antagonists to the receptors of vascular endothelial growth factor" Invest. New Drugs 17:195-212, 1999.
Cardillo et al., "Targeting both IGF-1R and mTOR synergistically inhibits growth of renal cell carcinoma in vitro", BMC Cancer. Apr. 1, 2013;13:170.
Chang et al., "A new method to produce monoPEGylated dimeric cytokines shown with human interferon-α2b", Bioconjug Chem. Oct. 21, 2009;20(10):1899-907.
Chang et al., "A novel class of anti-HIV agents with multiple copies of enfuvirtide enhances inhibition of viral replication and cellular transmission in vitro", PLoS One. 2012;7(7):e41235.
Chang et al., "Evaluation of a novel hexavalent humanized anti-IGF-1R antibody and its bivalent parental IgG in diverse cancer cell lines", PLoS One. 2012;7(8):e44235.
Goldenberg et al., "Cancer Imaging and Therapy with Bispecific Antibody Pretargeting", Update Cancer Ther. Mar. 2007;2(1):19-31.

(56) References Cited

OTHER PUBLICATIONS

Govindan et al., "Designing immunoconjugates for cancer therapy", Expert Opin Biol Ther. Jul. 2012;12(7):873-90.
Liu et al., "Trop-2-targeting tetrakis-ranpirnase has potent antitumor activity against triple-negative breast cancer", Mol Cancer. Mar. 10, 2014;13:53.
Rossi et al., "Hexavalent bispecific antibodies represent a new class of anticancer therapeutics: 1. Properties of anti-CD20/CD22 antibodies in lymphoma", Blood. Jun. 11, 2009;113(24):6161-71.
Rossi et al., "CD20-targeted tetrameric interferon-alpha, a novel and potent immunocytokine for the therapy of B-cell lymphomas", Blood. Oct. 29, 2009;114(18):3864-71.
Rossi et al., "The dock-and-lock method combines recombinant engineering with site-specific covalent conjugation to generate multifunctional structures", Bioconjug Chem. Mar. 21, 2012;23(3):309-23.
Rossi et al., "Complex and defined biostructures with the dock-and-lock method", Trends Pharmacol Sci. Sep. 2012;33(9):474-81.
Rossi et al., "A new class of bispecific antibodies to redirect T cells for cancer immunotherapy", MAbs. Mar.-Apr. 2014;6(2):381-91.
Sharkey et al., "Improved cancer therapy and molecular imaging with multivalent, multispecific antibodies", Cancer Biother Radiopharm. Feb. 2010;25(1):1-12.
Allard et al., "Targeting CD73 enhances the antitumor activity of anti-PD-1 and anti-CTLA-4 mAbs", Clin Cancer Res. Oct. 15, 2013;19(20):5626-35.
Callahan et al., "At the bedside: CTLA-4- and PD-1-blocking antibodies in cancer immunotherapy", J Leukoc Biol. Jul. 2013;94(1):41-53.
Flieger et al., "A bispecific single-chain antibody directed against EpCAM/CD3 in combination with the cytokines interferon alpha and interleukin-2 efficiently retargets T and CD3+CD56+ natural-killer-like T lymphocytes to EpCAM-expressing tumor cells", Cancer Immunol Immunother. Oct. 2000;49(8):441-8.
Gleason et al., "Bispecific and trispecific killer cell engagers directly activate human NK cells through CD16 signaling and induce cytotoxicity and cytokine production", Mol Cancer Ther. Dec. 2012;11(12):2674-84.
Intlekofer et al., "At the bench: preclinical rationale for CTLA-4 and PD-1 blockade as cancer immunotherapy", J Leukoc Biol. Jul. 2013;94(1):25-39.
Kipriyanov et al., "Synergistic antitumor effect of bispecific CD19 × CD3 and CD19 × CD16 diabodies in a preclinical model of non-Hodgkin's lymphoma", J Immunol. Jul. 1, 2002;169(1):137-44.
Kyi et al., "Checkpoint blocking antibodies in cancer immunotherapy", FEBS Lett. Jan. 21, 2014;588(2):368-76.
Lum et al., "Targeted T-cell Therapy in Stage IV Breast Cancer: A Phase I Clinical Trial", Clin Cancer Res. May 15, 2015;21(10):2305-14.
Morales-Kastresana et al., "Combined immunostimulatory monoclonal antibodies extend survival in an aggressive transgenic hepatocellular carcinoma mouse model", Clin Cancer Res. Nov. 15, 2013;19(22):6151-62.
Oberst et al., "CEA/CD3 bispecific antibody MEDI-565/AMG 211 activation of T cells and subsequent killing of human tumors is independent of mutations commonly found in colorectal adenocarcinomas", MAbs. 2014;6(6):1571-84.
Peng et al., "The CEA/CD3-bispecific antibody MEDI-565 (MT111) binds a nonlinear epitope in the full-length but not a short splice variant of CEA", PLoS One 2012;7(5):e36412.
Podojil et al., "Targeting the B7 family of co-stimulatory molecules: successes and challenges", BioDrugs. Feb. 2013;27(1):1-13.
Rossi et al., "A New Platform for Trivalent Bispecific Antibodies Used for T-Cell Redirected Killing of B-Cell Malignancies", Nov. 15, 2013; Blood: 122 (21).
Rossi et al., "A novel Trop-2/CD3 trivalent bispecific antibody effectively redirects T cells to kill target human pancreatic and gastric cancer cells", Proceedings of the 105th Annual Meeting of the American Association for Cancer Research; Apr. 5-9, 2014; San Diego, CA; Cancer Res 2014;74(19 Suppl):Abstract # 2655.
Rossi et al., Novel T-cell redirecting trivalent bispecific antibodies, Proceedings of the 104th Annual Meeting of the American Association for Cancer Research; Apr. 6-10, 2013; Washington, DC; Cancer Res 2013;73(8 Suppl):Abstract # 4747.
Rossi et al., "Redirected T-cell killing of solid cancers targeted with an anti-CD3/Trop-2-bispecific antibody is enhanced in combination with interferon-α", Mol Cancer Ther. Oct. 2014;13(10):2341-51.
Shubert et al., "A recombinant triplebody with specificity for CD19 and HLA-DR mediates preferential binding to antigen double-positive cells by dual-targeting", MAbs. Jan.-Feb. 2012;4(1):45-56.
Topalian et al., "Targeting the PD-1/B7-H1(PD-L1) pathway to activate anti-tumor immunity", Curr Opin Immunol. Apr. 2012;24(2):207-12.
Vallera et al., "A bispecific recombinant immunotoxin, DT2219, targeting human CD19 and CD22 receptors in a mouse xenograft model of B-cell leukemia/lymphoma", Clin Cancer Res. May 15, 2005;11(10):3879-88.
Bacac et al., "A Novel Carcinoembryonic Antigen T-Cell Bispecific Antibody (CEA TCB) for the Treatment of Solid Tumors", Clin Cancer Res. Jul. 1, 2016;22(13):3286-97.
Goldenberg et al., "Effect of interferon-α on redirected T-cell killing of pancreatic and gastric cancers", 2014 ASCO Annual Meeting, Abstr 3056.
Lehmann et al., "In vivo imaging of the activity of CEA TCB, a novel T-cell bispecific antibody, reveals specific tumor targeting and fast induction of T-cell mediated tumor killing", Clin Cancer Res. Apr. 26, 2016, [Epub ahead of print].
Motzer et al., "Phase II trial of branched peginterferon-alpha 2a (40 kDa) for patients with advanced renal cell carcinoma", Ann Oncol. Nov. 2002;13(11):1799-805.
Sharkey et al., "A new Tri-Fab bispecific antibody for pretargeting Trop-2-expressing epithelial cancers", J Nucl Med. Oct. 2012;53(10):1625-32.
Final Rejection, dated Feb. 3, 2016, and Abandonment Notice, dated Aug. 29, 2016, issued in U.S. Appl. No. 14/233,406, filed May 12, 2014.

* cited by examiner (19)-3s-mediated cell-to-cell association of Daudi and Jurkat Comparison of DART and BITE cell-cell association vs. (19)-3s cell-cell association using Daudi B lymphocytes and Jurkat T cells

*Figure from Moore et al. Blood 2011. 117:4542-4551.

| | | | Expression* | IC50 (pM) | Max lysis (%) |
|---|---|---|---|---|---|
| (20)-3s | CD20 | Daudi | 1 | <0.3 | ~90 |
| (19)-3s | CD19 | Daudi | 1 | 1 | ~60 |
| (22)-3s | CD22 | Daudi | 1 | ~5 | ~60 |
| | | | | | |
| (20)-3s | CD20 | Nalmawa | 0.11 | 30 | 53 |
| (19)-3s | CD19 | Namalwa | 1.67 | 63 | 60 |
| (22)-3s | CD22 | Namalwa | 0.06 | ND | 42 |
| | | | | | |
| (20)-3s | CD20 | Jeko-1 | 1.02 | 1 | 90 |
| (19)-3s | CD19 | Jeko-1 | 1.93 | 3000 | 50 |
| | | | | | |
| (20)-3s | CD20 | Ramos | TBD | TBD | TBD |
| (19)-3s | CD19 | Ramos | 0.84 | 0.17 | 79 |
| | | | | | |
| (20)-3s | CD20 | Nalm6 | TBD | TBD | TBD |
| (19)-3s | CD19 | Nalm6 | 0.75 | 6 | ~93 |
| | | | | | |
| (20)-3s | CD20 | Raji | TBD | TBD | TBD |
| (19)-3s | CD19 | Raji | 2.55 | >3000 | 41 |
| | | | | | |
| (C2)-3s | | Daudi | | | |
| | | Jeko-1 | | 20 | 88 |

(A) Therapeutic Efficacy of (E1)-3s *plus* E1*-2b
T-Cell Retargeting in Capan-1 Tumor-Bearing Mice (B) Therapeutic Efficacy of (E1)-3s *plus* PEGASYS
T-Cell Retargeting in Capan-1 Tumor-Bearing Mice

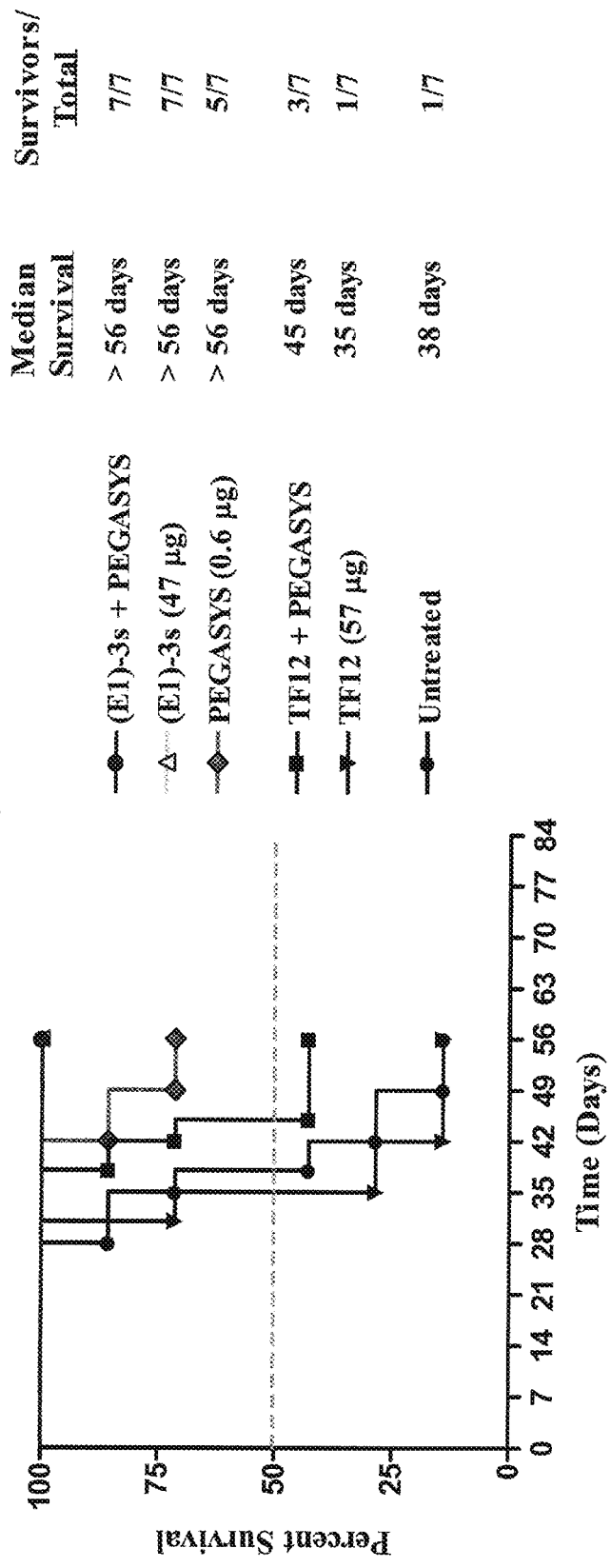

SEQUENCE LISTING

```
<160> NUMBER OF SEQ ID NOS: 105

<210> SEQ ID NO 1
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Ser His Ile Gln Ile Pro Pro Gly Leu Thr Glu Leu Leu Gln Gly Tyr
1               5                  10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 2
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Cys Gly His Ile Gln Ile Pro Pro Gly Leu Thr Glu Leu Leu Gln Gly
1               5                  10                  15

Tyr Thr Val Glu Val Leu Arg Gln Gln Pro Pro Asp Leu Val Glu Phe
            20                  25                  30

Ala Val Glu Tyr Phe Thr Arg Leu Arg Glu Ala Arg Ala
        35                  40                  45
```

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln Ile Glu Tyr Leu Ala Lys Gln Ile Val Asp Asn Ala Ile Gln Gln
1               5                   10                  15

Ala

<210> SEQ ID NO 4
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Cys Gly Gln Ile Glu Tyr Leu Ala Lys Gln Ile Val Asp Asn Ala Ile
1               5                   10                  15

Gln Gln Ala Gly Cys
            20

<210> SEQ ID NO 5
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Ser Leu Arg Glu Cys Glu Leu Tyr Val Gln Lys His Asn Ile Gln Ala
1               5                   10                  15

Leu Leu Lys Asp Ser Ile Val Gln Leu Cys Thr Ala Arg Pro Glu Arg
            20                  25                  30

Pro Met Ala Phe Leu Arg Glu Tyr Phe Glu Arg Leu Glu Lys Glu Glu
        35                  40                  45

Ala Lys
    50

<210> SEQ ID NO 6
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Ser Cys Gly Gly Ser Leu Arg Glu Cys Glu Leu Tyr Val Gln Lys
1               5                   10                  15

His Asn Ile Gln Ala Leu Leu Lys Asp Ser Ile Val Gln Leu Cys Thr
            20                  25                  30

Ala Arg Pro Glu Arg Pro Met Ala Phe Leu Arg Glu Tyr Phe Glu Arg
        35                  40                  45

Leu Glu Lys Glu Glu Ala Lys
    50                  55

```
<210> SEQ ID NO 7
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Cys Gly Phe Glu Glu Leu Ala Trp Lys Ile Ala Lys Met Ile Trp Ser
1               5                   10                  15

Asp Val Phe Gln Gln Gly Cys
            20

<210> SEQ ID NO 8
<211> LENGTH: 51
<212> TYPE: PRT
<213> ORGANISM: Homo sapiens

<400> SEQUENCE: 8

Ser Leu Arg Glu Cys Glu Leu Tyr Val Gln Lys His Asn Ile Gln Ala
1               5                   10                  15

Leu Leu Lys Asp Val Ser Ile Val Gln Leu Cys Thr Ala Arg Pro Glu
            20                  25                  30

Arg Pro Met Ala Phe Leu Arg Glu Tyr Phe Glu Lys Leu Glu Lys Glu
        35                  40                  45

Glu Ala Lys
    50

<210> SEQ ID NO 9
<211> LENGTH: 54
<212> TYPE: PRT
<213> ORGANISM: Homo sapiens

<400> SEQUENCE: 9

Ser Leu Lys Gly Cys Glu Leu Tyr Val Gln Leu His Gly Ile Gln Gln
1               5                   10                  15

Val Leu Lys Asp Cys Ile Val His Leu Cys Ile Ser Lys Pro Glu Arg
            20                  25                  30

Pro Met Lys Phe Leu Arg Glu His Phe Glu Lys Leu Glu Lys Glu Glu
        35                  40                  45

Asn Arg Gln Ile Leu Ala
    50

<210> SEQ ID NO 10
<211> LENGTH: 44
<212> TYPE: PRT
<213> ORGANISM: Homo sapiens

<400> SEQUENCE: 10

Ser His Ile Gln Ile Pro Pro Gly Leu Thr Glu Leu Leu Gln Gly Tyr
1               5                   10                  15

Thr Val Glu Val Gly Gln Gln Pro Pro Asp Leu Val Asp Phe Ala Val
            20                  25                  30

Glu Tyr Phe Thr Arg Leu Arg Glu Ala Arg Arg Gln
        35                  40

<210> SEQ ID NO 11
<211> LENGTH: 44
<212> TYPE: PRT
```

<213> ORGANISM: Homo sapiens

<400> SEQUENCE: 11

Ser Ile Glu Ile Pro Ala Gly Leu Thr Glu Leu Leu Gln Gly Phe Thr
1               5                   10                  15

Val Glu Val Leu Arg His Gln Pro Ala Asp Leu Leu Glu Phe Ala Leu
            20                  25                  30

Gln His Phe Thr Arg Leu Gln Gln Glu Asn Glu Arg
        35                  40

<210> SEQ ID NO 12
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Thr His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 13
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Ser Lys Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 14
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Ser Arg Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 15
<211> LENGTH: 44
<212> TYPE: PRT
<213> ORGANISM: Artificial Sequence
<220> FEATURE:

<223> OTHER INFORMATION: Description of Artificial Sequence: Synthetic
    polypeptide

<400> SEQUENCE: 15

Ser His Ile Asn Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 16
<211> LENGTH: 44
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 16

Ser His Ile Gln Ile Pro Pro Ala Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 17
<211> LENGTH: 44
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 17

Ser His Ile Gln Ile Pro Pro Gly Leu Ser Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 18
<211> LENGTH: 44
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 18

Ser His Ile Gln Ile Pro Pro Gly Leu Thr Asp Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 19
<211> LENGTH: 44
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 19

Ser His Ile Gln Ile Pro Pro Gly Leu Thr Glu Leu Leu Asn Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 20
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Ser His Ile Gln Ile Pro Pro Gly Leu Thr Glu Leu Leu Gln Ala Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 21
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Ser His Ile Gln Ile Pro Pro Gly Leu Thr Glu Leu Leu Gln Gly Tyr
1               5                   10                  15

Ser Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 22
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Ser His Ile Gln Ile Pro Pro Gly Leu Thr Glu Leu Leu Gln Gly Tyr
1               5                   10                  15

Thr Val Asp Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 23
<211> LENGTH: 44
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 23

Ser His Ile Gln Ile Pro Pro Gly Leu Thr Glu Leu Leu Gln Gly Tyr
1               5                   10                  15

Thr Val Glu Val Leu Lys Gln Gln Pro Pro Asp Leu Val Glu Phe Ala
            20                  25                  30

Val Glu Tyr Phe Thr Arg Leu Arg Glu Ala Arg Ala
            35                  40

<210> SEQ ID NO 24
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Ser His Ile Gln Ile Pro Pro Gly Leu Thr Glu Leu Leu Gln Gly Tyr
1               5                   10                  15

Thr Val Glu Val Leu Arg Asn Gln Pro Pro Asp Leu Val Glu Phe Ala
            20                  25                  30

Val Glu Tyr Phe Thr Arg Leu Arg Glu Ala Arg Ala
            35                  40

<210> SEQ ID NO 25
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Ser His Ile Gln Ile Pro Pro Gly Leu Thr Glu Leu Leu Gln Gly Tyr
1               5                   10                  15

Thr Val Glu Val Leu Arg Gln Asn Pro Pro Asp Leu Val Glu Phe Ala
            20                  25                  30

Val Glu Tyr Phe Thr Arg Leu Arg Glu Ala Arg Ala
            35                  40

<210> SEQ ID NO 26
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Ser His Ile Gln Ile Pro Pro Gly Leu Thr Glu Leu Leu Gln Gly Tyr
1               5                   10                  15

Thr Val Glu Val Leu Arg Gln Gln Pro Pro Glu Leu Val Glu Phe Ala
            20                  25                  30

Val Glu Tyr Phe Thr Arg Leu Arg Glu Ala Arg Ala
            35                  40

<210> SEQ ID NO 27
<211> LENGTH: 44
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Asp Phe Ala
            20                  25                  30

Val Glu Tyr Phe Thr Arg Leu Arg Glu Ala Arg Ala
        35                  40

<210> SEQ ID NO 28
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Leu
            20                  25                  30

Val Glu Tyr Phe Thr Arg Leu Arg Glu Ala Arg Ala
        35                  40

<210> SEQ ID NO 29
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ile
            20                  25                  30

Val Glu Tyr Phe Thr Arg Leu Arg Glu Ala Arg Ala
        35                  40

<210> SEQ ID NO 30
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Val
            20                  25                  30

Val Glu Tyr Phe Thr Arg Leu Arg Glu Ala Arg Ala
        35                  40

<210> SEQ ID NO 31
```

-continued

```
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Asp Tyr Phe Thr Arg Leu Arg Glu Ala Arg Ala
        35                  40

<210> SEQ ID NO 32
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Asn Ile Glu Tyr Leu Ala Lys Gln Ile Val Asp Asn Ala Ile Gln Gln
1               5                   10                  15

Ala

<210> SEQ ID NO 33
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gln Leu Glu Tyr Leu Ala Lys Gln Ile Val Asp Asn Ala Ile Gln Gln
1               5                   10                  15

Ala

<210> SEQ ID NO 34
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gln Val Glu Tyr Leu Ala Lys Gln Ile Val Asp Asn Ala Ile Gln Gln
1               5                   10                  15

Ala

<210> SEQ ID NO 35
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gln Ile Asp Tyr Leu Ala Lys Gln Ile Val Asp Asn Ala Ile Gln Gln
1               5                   10                  15
```

```
<210> SEQ ID NO 36
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gln Ile Glu Phe Leu Ala Lys Gln Ile Val Asp Asn Ala Ile Gln Gln
1               5                   10                  15

Ala

<210> SEQ ID NO 37
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gln Ile Glu Thr Leu Ala Lys Gln Ile Val Asp Asn Ala Ile Gln Gln
1               5                   10                  15

Ala

<210> SEQ ID NO 38
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gln Ile Glu Ser Leu Ala Lys Gln Ile Val Asp Asn Ala Ile Gln Gln
1               5                   10                  15

Ala

<210> SEQ ID NO 39
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gln Ile Glu Tyr Ile Ala Lys Gln Ile Val Asp Asn Ala Ile Gln Gln
1               5                   10                  15

Ala

<210> SEQ ID NO 40
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gln Ile Glu Tyr Val Ala Lys Gln Ile Val Asp Asn Ala Ile Gln Gln
```

```
                   1               5                  10                  15
Ala

<210> SEQ ID NO 41
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gln Ile Glu Tyr Leu Ala Arg Gln Ile Val Asp Asn Ala Ile Gln Gln
  1               5                  10                  15

Ala

<210> SEQ ID NO 42
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gln Ile Glu Tyr Leu Ala Lys Asn Ile Val Asp Asn Ala Ile Gln Gln
  1               5                  10                  15

Ala

<210> SEQ ID NO 43
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gln Ile Glu Tyr Leu Ala Lys Gln Ile Val Glu Asn Ala Ile Gln Gln
  1               5                  10                  15

Ala

<210> SEQ ID NO 44
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gln Ile Glu Tyr Leu Ala Lys Gln Ile Val Asp Gln Ala Ile Gln Gln
  1               5                  10                  15

Ala

<210> SEQ ID NO 45
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45
```

Gln Ile Glu Tyr Leu Ala Lys Gln Ile Val Asp Asn Ala Ile Asn Gln
1               5                   10                  15

Ala

<210> SEQ ID NO 46
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gln Ile Glu Tyr Leu Ala Lys Gln Ile Val Asp Asn Ala Ile Gln Asn
1               5                   10                  15

Ala

<210> SEQ ID NO 47
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gln Ile Glu Tyr Leu Ala Lys Gln Ile Val Asp Asn Ala Ile Gln Gln
1               5                   10                  15

Leu

<210> SEQ ID NO 48
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gln Ile Glu Tyr Leu Ala Lys Gln Ile Val Asp Asn Ala Ile Gln Gln
1               5                   10                  15

Ile

<210> SEQ ID NO 49
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gln Ile Glu Tyr Leu Ala Lys Gln Ile Val Asp Asn Ala Ile Gln Gln
1               5                   10                  15

Val

<210> SEQ ID NO 50
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

```
Gln Ile Glu Tyr Val Ala Lys Gln Ile Val Asp Tyr Ala Ile His Gln
1               5                   10                  15

Ala

<210> SEQ ID NO 51
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gln Ile Glu Tyr Lys Ala Lys Gln Ile Val Asp His Ala Ile His Gln
1               5                   10                  15

Ala

<210> SEQ ID NO 52
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gln Ile Glu Tyr His Ala Lys Gln Ile Val Asp His Ala Ile His Gln
1               5                   10                  15

Ala

<210> SEQ ID NO 53
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gln Ile Glu Tyr Val Ala Lys Gln Ile Val Asp His Ala Ile His Gln
1               5                   10                  15

Ala

<210> SEQ ID NO 54
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Pro Leu Glu Tyr Gln Ala Gly Leu Leu Val Gln Asn Ala Ile Gln Gln
1               5                   10                  15

Ala Ile

<210> SEQ ID NO 55
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
```

-continued

<400> SEQUENCE: 55

Leu Leu Ile Glu Thr Ala Ser Ser Leu Val Lys Asn Ala Ile Gln Leu
1               5                   10                  15

Ser Ile

<210> SEQ ID NO 56
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Leu Ile Glu Glu Ala Ala Ser Arg Ile Val Asp Ala Val Ile Glu Gln
1               5                   10                  15

Val Lys

<210> SEQ ID NO 57
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Ala Leu Tyr Gln Phe Ala Asp Arg Phe Ser Glu Leu Val Ile Ser Glu
1               5                   10                  15

Ala Leu

<210> SEQ ID NO 58
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Leu Glu Gln Val Ala Asn Gln Leu Ala Asp Gln Ile Ile Lys Glu Ala
1               5                   10                  15

Thr

<210> SEQ ID NO 59
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Phe Glu Glu Leu Ala Trp Lys Ile Ala Lys Met Ile Trp Ser Asp Val
1               5                   10                  15

Phe

<210> SEQ ID NO 60
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Glu Leu Val Arg Leu Ser Lys Arg Leu Val Glu Asn Ala Val Leu Lys
1               5                   10                  15

Ala Val

<210> SEQ ID NO 61
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Thr Ala Glu Glu Val Ser Ala Arg Ile Val Gln Val Val Thr Ala Glu
1               5                   10                  15

Ala Val

<210> SEQ ID NO 62
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gln Ile Lys Gln Ala Ala Phe Gln Leu Ile Ser Gln Val Ile Leu Glu
1               5                   10                  15

Ala Thr

<210> SEQ ID NO 63
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Leu Ala Trp Lys Ile Ala Lys Met Ile Val Ser Asp Val Met Gln Gln
1               5                   10                  15

<210> SEQ ID NO 64
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Asp Leu Ile Glu Glu Ala Ala Ser Arg Ile Val Asp Ala Val Ile Glu
1               5                   10                  15

Gln Val Lys Ala Ala Gly Ala Tyr
            20

<210> SEQ ID NO 65
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 65

Leu Glu Gln Tyr Ala Asn Gln Leu Ala Asp Gln Ile Ile Lys Glu Ala
1               5                   10                  15

Thr Glu

<210> SEQ ID NO 66
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Phe Glu Glu Leu Ala Trp Lys Ile Ala Lys Met Ile Trp Ser Asp Val
1               5                   10                  15

Phe Gln Gln Cys
            20

<210> SEQ ID NO 67
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gln Ile Glu Tyr Leu Ala Lys Gln Ile Pro Asp Asn Ala Ile Gln Gln
1               5                   10                  15

Ala

<210> SEQ ID NO 68
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Lys Gly Ala Asp Leu Ile Glu Glu Ala Ala Ser Arg Ile Val Asp Ala
1               5                   10                  15

Val Ile Glu Gln Val Lys Ala Ala Gly
            20                  25

<210> SEQ ID NO 69
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Lys Gly Ala Asp Leu Ile Glu Glu Ala Ala Ser Arg Ile Pro Asp Ala
1               5                   10                  15

Pro Ile Glu Gln Val Lys Ala Ala Gly
            20                  25

<210> SEQ ID NO 70
<211> LENGTH: 25
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 70

Pro Glu Asp Ala Glu Leu Val Arg Leu Ser Lys Arg Leu Val Glu Asn
1               5                   10                  15

Ala Val Leu Lys Ala Val Gln Gln Tyr
            20                  25

<210> SEQ ID NO 71
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Pro Glu Asp Ala Glu Leu Val Arg Thr Ser Lys Arg Leu Val Glu Asn
1               5                   10                  15

Ala Val Leu Lys Ala Val Gln Gln Tyr
            20                  25

<210> SEQ ID NO 72
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Pro Glu Asp Ala Glu Leu Val Arg Leu Ser Lys Arg Asp Val Glu Asn
1               5                   10                  15

Ala Val Leu Lys Ala Val Gln Gln Tyr
            20                  25

<210> SEQ ID NO 73
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Pro Glu Asp Ala Glu Leu Val Arg Leu Ser Lys Arg Leu Pro Glu Asn
1               5                   10                  15

Ala Val Leu Lys Ala Val Gln Gln Tyr
            20                  25

<210> SEQ ID NO 74
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Pro Glu Asp Ala Glu Leu Val Arg Leu Ser Lys Arg Leu Pro Glu Asn
1               5                   10                  15

Ala Pro Leu Lys Ala Val Gln Gln Tyr
```

```
              20                  25

<210> SEQ ID NO 75
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Pro Glu Asp Ala Glu Leu Val Arg Leu Ser Lys Arg Leu Val Glu Asn
1               5                   10                  15

Ala Val Glu Lys Ala Val Gln Gln Tyr
              20                  25

<210> SEQ ID NO 76
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Glu Glu Gly Leu Asp Arg Asn Glu Glu Ile Lys Arg Ala Ala Phe Gln
1               5                   10                  15

Ile Ile Ser Gln Val Ile Ser Glu Ala
              20                  25

<210> SEQ ID NO 77
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Leu Val Asp Asp Pro Leu Glu Tyr Gln Ala Gly Leu Leu Val Gln Asn
1               5                   10                  15

Ala Ile Gln Gln Ala Ile Ala Glu Gln
              20                  25

<210> SEQ ID NO 78
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gln Tyr Glu Thr Leu Leu Ile Glu Thr Ala Ser Ser Leu Val Lys Asn
1               5                   10                  15

Ala Ile Gln Leu Ser Ile Glu Gln Leu
              20                  25

<210> SEQ ID NO 79
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 79

Leu Glu Lys Gln Tyr Gln Glu Gln Leu Glu Glu Val Ala Lys Val
1               5                   10                  15

Ile Val Ser Met Ser Ile Ala Phe Ala
            20                  25

<210> SEQ ID NO 80
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Asn Thr Asp Glu Ala Gln Glu Glu Leu Ala Trp Lys Ile Ala Lys Met
1               5                   10                  15

Ile Val Ser Asp Ile Met Gln Gln Ala
            20                  25

<210> SEQ ID NO 81
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Val Asn Leu Asp Lys Lys Ala Val Leu Ala Glu Lys Ile Val Ala Glu
1               5                   10                  15

Ala Ile Glu Lys Ala Glu Arg Glu Leu
            20                  25

<210> SEQ ID NO 82
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Asn Gly Ile Leu Glu Leu Glu Thr Lys Ser Ser Lys Leu Val Gln Asn
1               5                   10                  15

Ile Ile Gln Thr Ala Val Asp Gln Phe
            20                  25

<210> SEQ ID NO 83
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Thr Gln Asp Lys Asn Tyr Glu Asp Glu Leu Thr Gln Val Ala Leu Ala
1               5                   10                  15

Leu Val Glu Asp Val Ile Asn Tyr Ala
            20                  25

<210> SEQ ID NO 84
<211> LENGTH: 25
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Glu Thr Ser Ala Lys Asp Asn Ile Asn Ile Glu Glu Ala Ala Arg Phe
1               5                   10                  15

Leu Val Glu Lys Ile Leu Val Asn His
            20                  25

<210> SEQ ID NO 85
<211> LENGTH: 330
<212> TYPE: PRT
<213> ORGANISM: Homo sapiens

<400> SEQUENCE: 85

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Ala Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300
```

```
Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 86
<211> LENGTH: 330
<212> TYPE: PRT
<213> ORGANISM: Homo sapiens

<400> SEQUENCE: 86

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 87
```

```
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Ser or Thr
<220> FEATURE:
<221> NAME/KEY: MOD_RES
<222> LOCATION: (2)..(2)
<223> OTHER INFORMATION: His, Lys or Arg
<220> FEATURE:
<221> NAME/KEY: MOD_RES
<222> LOCATION: (4)..(4)
<223> OTHER INFORMATION: Gln or Asn
<220> FEATURE:
<221> NAME/KEY: MOD_RES
<222> LOCATION: (8)..(8)
<223> OTHER INFORMATION: Gly or Ala
<220> FEATURE:
<221> NAME/KEY: MOD_RES
<222> LOCATION: (10)..(10)
<223> OTHER INFORMATION: Thr or Ser
<220> FEATURE:
<221> NAME/KEY: MOD_RES
<222> LOCATION: (11)..(11)
<223> OTHER INFORMATION: Glu or Asp
<220> FEATURE:
<221> NAME/KEY: MOD_RES
<222> LOCATION: (14)..(14)
<223> OTHER INFORMATION: Gln or Asn
<220> FEATURE:
<221> NAME/KEY: MOD_RES
<222> LOCATION: (15)..(15)
<223> OTHER INFORMATION: Gly or Ala
<220> FEATURE:
<221> NAME/KEY: MOD_RES
<222> LOCATION: (17)..(17)
<223> OTHER INFORMATION: Thr or Ser
<220> FEATURE:
<221> NAME/KEY: MOD_RES
<222> LOCATION: (19)..(19)
<223> OTHER INFORMATION: Glu or Asp
<220> FEATURE:
<221> NAME/KEY: MOD_RES
<222> LOCATION: (22)..(22)
<223> OTHER INFORMATION: Arg or Lys
<220> FEATURE:
<221> NAME/KEY: MOD_RES
<222> LOCATION: (23)..(24)
<223> OTHER INFORMATION: Gln or Asn
<220> FEATURE:
<221> NAME/KEY: MOD_RES
<222> LOCATION: (27)..(27)
<223> OTHER INFORMATION: Asp or Glu
<220> FEATURE:
<221> NAME/KEY: MOD_RES
<222> LOCATION: (30)..(30)
<223> OTHER INFORMATION: Glu or Asp
<220> FEATURE:
<221> NAME/KEY: MOD_RES
<222> LOCATION: (32)..(32)
<223> OTHER INFORMATION: Ala, Leu, Ile or Val
<220> FEATURE:
<221> NAME/KEY: MOD_RES
<222> LOCATION: (34)..(34)
<223> OTHER INFORMATION: Glu or Asp
<220> FEATURE:
<221> NAME/KEY: MOD_RES
<222> LOCATION: (37)..(37)
<223> OTHER INFORMATION: Thr or Ser
<220> FEATURE:
<221> NAME/KEY: MOD_RES
<222> LOCATION: (38)..(38)
<223> OTHER INFORMATION: Arg or Lys
<220> FEATURE:
```

<220> FEATURE:
<221> NAME/KEY: MOD_RES
<222> LOCATION: (40)..(40)
<223> OTHER INFORMATION: Arg or Lys
<220> FEATURE:
<221> NAME/KEY: MOD_RES
<222> LOCATION: (41)..(41)
<223> OTHER INFORMATION: Glu or Asp
<220> FEATURE:
<221> NAME/KEY: MOD_RES
<222> LOCATION: (42)..(42)
<223> OTHER INFORMATION: Ala, Leu, Ile or Val
<220> FEATURE:
<221> NAME/KEY: MOD_RES
<222> LOCATION: (43)..(43)
<223> OTHER INFORMATION: Arg or Lys
<220> FEATURE:
<221> NAME/KEY: MOD_RES
<222> LOCATION: (44)..(44)
<223> OTHER INFORMATION: Ala, Leu, Ile or Val

<400> SEQUENCE: 87

Xaa Xaa Ile Xaa Ile Pro Pro Xaa Leu Xaa Xaa Leu Leu Xaa Xaa Tyr
1               5                   10                  15

Xaa Val Xaa Val Leu Xaa Xaa Xaa Pro Pro Xaa Leu Val Xaa Phe Xaa
            20                  25                  30

Val Xaa Tyr Phe Xaa Xaa Leu Xaa Xaa Xaa Xaa Xaa
        35                  40

<210> SEQ ID NO 88
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gln or Asn
<220> FEATURE:
<221> NAME/KEY: MOD_RES
<222> LOCATION: (2)..(2)
<223> OTHER INFORMATION: Ile, Leu or Val
<220> FEATURE:
<221> NAME/KEY: MOD_RES
<222> LOCATION: (3)..(3)
<223> OTHER INFORMATION: Glu or Asp
<220> FEATURE:
<221> NAME/KEY: MOD_RES
<222> LOCATION: (4)..(4)
<223> OTHER INFORMATION: Tyr, Phe, Thr or Ser
<220> FEATURE:
<221> NAME/KEY: MOD_RES
<222> LOCATION: (5)..(5)
<223> OTHER INFORMATION: Leu, Ile or Val
<220> FEATURE:
<221> NAME/KEY: MOD_RES
<222> LOCATION: (7)..(7)
<223> OTHER INFORMATION: Lys or Arg
<220> FEATURE:
<221> NAME/KEY: MOD_RES
<222> LOCATION: (8)..(8)
<223> OTHER INFORMATION: Gln or Asn
<220> FEATURE:
<221> NAME/KEY: MOD_RES
<222> LOCATION: (11)..(11)
<223> OTHER INFORMATION: Asp or Glu
<220> FEATURE:
<221> NAME/KEY: MOD_RES
<222> LOCATION: (12)..(12)
<223> OTHER INFORMATION: Asn or Gln
<220> FEATURE:
<221> NAME/KEY: MOD_RES
<222> LOCATION: (15)..(16)
<223> OTHER INFORMATION: Gln or Asn

```
<220> FEATURE:
<221> NAME/KEY: MOD_RES
<222> LOCATION: (17)..(17)
<223> OTHER INFORMATION: Ala, Leu, Ile or Val

<400> SEQUENCE: 88

Xaa Xaa Xaa Xaa Xaa Ala Xaa Xaa Ile Val Xaa Xaa Ala Ile Xaa Xaa
1               5                   10                  15

Xaa

<210> SEQ ID NO 89
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Ser or Thr
<220> FEATURE:
<221> NAME/KEY: MOD_RES
<222> LOCATION: (4)..(4)
<223> OTHER INFORMATION: Gln or Asn
<220> FEATURE:
<221> NAME/KEY: MOD_RES
<222> LOCATION: (10)..(10)
<223> OTHER INFORMATION: Thr or Ser
<220> FEATURE:
<221> NAME/KEY: MOD_RES
<222> LOCATION: (18)..(18)
<223> OTHER INFORMATION: Val, Ile, Leu or Ala
<220> FEATURE:
<221> NAME/KEY: MOD_RES
<222> LOCATION: (23)..(23)
<223> OTHER INFORMATION: Gln or Asn
<220> FEATURE:
<221> NAME/KEY: MOD_RES
<222> LOCATION: (33)..(33)
<223> OTHER INFORMATION: Val, Ile, Leu or Ala
<220> FEATURE:
<221> NAME/KEY: MOD_RES
<222> LOCATION: (34)..(34)
<223> OTHER INFORMATION: Glu or Asp
<220> FEATURE:
<221> NAME/KEY: MOD_RES
<222> LOCATION: (37)..(37)
<223> OTHER INFORMATION: Thr or Ser
<220> FEATURE:
<221> NAME/KEY: MOD_RES
<222> LOCATION: (38)..(38)
<223> OTHER INFORMATION: Arg or Lys
<220> FEATURE:
<221> NAME/KEY: MOD_RES
<222> LOCATION: (40)..(40)
<223> OTHER INFORMATION: Arg or Lys
<220> FEATURE:
<221> NAME/KEY: MOD_RES
<222> LOCATION: (42)..(42)
<223> OTHER INFORMATION: Ala, Leu, Ile or Val
<220> FEATURE:
<221> NAME/KEY: MOD_RES
<222> LOCATION: (44)..(44)
<223> OTHER INFORMATION: Ala, Leu, Ile or Val

<400> SEQUENCE: 89

Xaa His Ile Xaa Ile Pro Pro Gly Leu Xaa Glu Leu Leu Gln Gly Tyr
1               5                   10                  15

Thr Xaa Glu Val Leu Arg Xaa Gln Pro Pro Asp Leu Val Glu Phe Ala
            20                  25                  30

Xaa Xaa Tyr Phe Xaa Xaa Leu Xaa Glu Xaa Arg Xaa
            35                  40
```

```
<210> SEQ ID NO 90
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Lys Ala Ser Gln Ser Val Asp Tyr Asp Gly Asp Ser Tyr Leu Asn
1               5                   10                  15

<210> SEQ ID NO 91
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Asp Ala Ser Asn Leu Val Ser
1               5

<210> SEQ ID NO 92
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gln Gln Ser Thr Glu Asp Pro Trp Thr
1               5

<210> SEQ ID NO 93
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Ser Tyr Trp Met Asn
1               5

<210> SEQ ID NO 94
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Gln Ile Trp Pro Gly Asp Gly Asp Thr Asn Tyr Asn Gly Lys Phe Lys
1               5                   10                  15

Gly

<210> SEQ ID NO 95
<211> LENGTH: 15
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 95

Arg Glu Thr Thr Thr Val Gly Arg Tyr Tyr Tyr Ala Met Asp Tyr
1               5                   10                  15

<210> SEQ ID NO 96
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
                20                  25                  30

Thr Met His Trp Val Lys Gln Arg Pro Gly Gln Gly Leu Glu Trp Ile
            35                  40                  45

Gly Tyr Ile Asn Pro Ser Arg Gly Tyr Thr Asn Tyr Asn Gln Lys Phe
        50                  55                  60

Lys Asp Lys Ala Thr Leu Thr Thr Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Thr Leu Thr Val Ser Ser
        115

<210> SEQ ID NO 97
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Gly Gly Gly Gly Ser Gly Gly Gly Ser Gly Gly Gly Gly Ser
1               5                   10                  15

<210> SEQ ID NO 98
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Asp Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
                20                  25                  30

Asn Trp Tyr Gln Gln Lys Ser Gly Thr Ser Pro Lys Arg Trp Ile Tyr
            35                  40                  45

Asp Thr Ser Lys Leu Ala Ser Gly Val Pro Ala His Phe Arg Gly Ser
        50                  55                  60

```
Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Lys Arg
            100                 105

<210> SEQ ID NO 99
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Gly Gly Gly Gly Ser
1               5

<210> SEQ ID NO 100
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

His His His His His His Gly Gly Gly Ser Gly
1               5                   10

<210> SEQ ID NO 101
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Cys Gly Gln Ile Glu Tyr Leu Ala Lys Gln Ile Val Asp Asn Ala Ile
1               5                   10                  15

Gln Gln Ala Gly Cys
            20

<210> SEQ ID NO 102
<211> LENGTH: 4
<212> TYPE: PRT
<213> ORGANISM: Homo sapiens

<400> SEQUENCE: 102

Pro Lys Ser Cys
1

<210> SEQ ID NO 103
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Gly Ser Gly Gly Gly Gly Ser Gly Gly Gly Ser His Ile Gln Ile
1               5                   10                  15
```

```
Pro Pro Gly Leu Thr Glu Leu Leu Gln Gly Tyr Thr Val Glu Val Leu
            20                  25                  30

Arg Gln Gln Pro Pro Asp Leu Val Glu Phe Ala Val Glu Tyr Phe Thr
        35                  40                  45

Arg Leu Arg Glu Ala Arg Ala
    50                  55

<210> SEQ ID NO 104
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Gly Ser Gly Gly Gly Gly Ser Gly Gly Gly Gly Ser Gln Ile Glu Tyr
1               5                   10                  15

Leu Ala Lys Gln Ile Val Asp Asn Ala Ile Gln Gln Ala
            20                  25

<210> SEQ ID NO 105
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 105

His His His His His His
1               5
```

COMBINATION THERAPY FOR INDUCING IMMUNE RESPONSE TO DISEASE

CROSS REFERENCE TO RELATED APPLICATIONS

This application is a continuation-in-part of U.S. patent application Ser. No. 13/966,450, filed Aug. 14, 2013, which claimed the benefit under 35 U.S.C. 119(e) of provisional U.S. Patent Applications 61/807,998, filed Apr. 3, 2013; 61/733,268, filed Dec. 4, 2012, and 61/682,965, filed Aug. 14, 2012, each priority application incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Dec. 10, 2013, is named IBC138US2 SL.txt and is 49,230 bytes in size.

FIELD

The present invention concerns combinations of two or more agents for inducing an immune response to diseases, such as cancer or infectious disease. Exemplary agents may include: (i) leukocyte redirecting bispecific antibodies, (ii) antibody-drug conjugates, (iii) interferons such as such as interferon-$\alpha$, interferon-$\beta$ or interferon-$\lambda$ (most preferably interferon-$\alpha$), and/or (iv) checkpoint inhibitor antibodies. Any combination of two or more such agents may be utilized in the subject methods and compositions. The combinations may be administered simultaneously or sequentially. Such combinations may comprise any two agents, any three agents, or all four types of agents.

In certain embodiments, the present invention concerns compositions and methods of use of leukocyte redirecting complexes. Leukocytes of use may include T cells, NK cells, monocytes, and neutrophils. Preferably, the complexes comprise bispecific antibodies with one binding site for an antigen expressed on a T cell, NK cell, monocyte, or neutrophil and another binding site for an antigen expressed on a diseased cell or pathogen. In more preferred embodiments, the complexes are made as DOCK-AND-LOCK™ complexes, in which the components are attached together using the binding interaction between dimerization and docking domain (DDD) moieties from human protein kinase A (PKA) regulatory subunits and anchor domain (AD) moieties from AKAPs (A-kinase anchor proteins). However, other methods of making bispecific antibody complexes are known and may be used. The subject complexes may comprise one or more antibodies or antigen-binding antibody fragments that bind to an antigen expressed on T cells, such as CD2, CD3, CD4, CD5, CD6, CD8, CD25, CD28, CD30, CD40, CD40L, CD44, CD45, CD69 or CD90 (most preferably CD3), and one or more antibodies or antibody fragments that bind to an antigen on a target cell, such as CD19, CD20, CD22, CD33, CD66e (CEACAM5), CEACAM6, EpCAM, HER2/neu, EGF receptor, Trop-2, MUC5ac, or another tumor-associated antigen (TAA), or an antigen expressed on a different diseased cell or pathogenic micro-organism. Specific target antigens of use are discussed in more detail below. The bispecific antibody redirects effector T cells, monocytes, NK cells or neutrophils to target diseased cells, tissues or pathogens and induces an immune response against the target.

Other embodiments concern use of interferons, such as interferon-$\alpha$, interferon-$\beta$ or interferon-$\lambda$ (most preferably interferon-$\alpha$). Interferons are cytokine type immunomodulators that can enhance immune system function by activating NK cells and macrophages. Interferons can also have direct effects as antipathogenic agents and act in part by inducing expression of target antigens or other effector proteins.

Checkpoint inhibitor antibodies have been used primarily in cancer therapy. Immune checkpoints refer to inhibitory pathways in the immune system that are responsible for maintaining self-tolerance and modulating the degree of immune system response to minimize peripheral tissue damage. However, tumor cells can also activate immune system checkpoints to decrease the effectiveness of immune response against tumor tissues. Exemplary checkpoint inhibitor antibodies against cytotoxic T-lymphocyte antigen 4 (CTLA4, also known as CD152), programmed cell death protein 1 (PD1, also known as CD279) and programmed cell death 1 ligand 1 (PD-L1, also known as CD274), are described below and may be used in combination with one or more other agents to enhance the effectiveness of immune response against disease cells, tissues or pathogens.

The efficacy of immune system induction for disease therapy may be enhanced by combination with other agents that, for example, reduce tumor burden prior to administration of immunomodulators or that release immunogenic antigens from killed tumor cells. Antibody-drug conjugates (ADCs) can effectively reduce tumor burden in many types of cancers. Numerous exemplary ADCs are known in the art, such as IMMU-130 (labetuzumab-SN-38), IMMU-132 (hRS7-SN-38) and milatuzumab-doxorubicin or antibody conjugates of pro-2-pyrrolinodoxorubicin (Pro2PDox), as discussed below. Any such known ADC may be used in combination with one, two or three immunomodulating agents as described herein.

Different combinations of use may include a leukocyte redirecting bispecific antibody (bsAb) plus an interferon (e.g., interferon-$\alpha$); a leukocyte redirecting bsAb plus a checkpoint inhibitor antibody; a leukocyte redirecting bsAb plus IFN plus a checkpoint inhibitor antibody; an ADC plus a checkpoint inhibitor antibody; an ADC plus IFN plus a checkpoint inhibitor antibody; an ADC plus a leukocyte redirecting bsAb plus a checkpoint inhibitor antibody; or an ADC plus a leukocyte redirecting bsAb plus IFN plus a checkpoint inhibitor antibody. As discussed above, any combination of the different types of agents disclosed herein may be used for disease treatment.

BACKGROUND

Use of bispecific antibodies (bsAbs) to redirect effector T cells for the targeted killing of tumor cells has shown considerable promise both pre-clinically and clinically (see, e.g., Topp et al., 2012, Blood 120:5185-87; Bargou et al., 2008, Science 321:974-77). The bispecific antibodies developed to date contain a first binding site specific to CD3 for T-cell recruitment and activation and a second binding site for a targeted disease-associated antigen, such as CD19 (Bassan, 2012, Blood 120:5094-95). The bispecific antibody brings CD3$^+$ T cells into direct contact with targeted disease cells and induces cell-mediated cytotoxicity (Bassan, 2012). Anti-CD3 X anti-CD19 bispecific antibodies have been reported to produce a complete and durable molecular remission at very low concentrations in approximately 70% of adult patients with MRD$^+$ ALL (Topp et al., 2012, Blood 120:5185-87). Bispecific antibodies recognizing gliomas and the CD3 epitope on T cells have been successfully used in treating brain tumors in human patients (Nitta, et al. *Lancet* 1990; 355:368-371).

Leukocyte redirecting bsAbs are not limited to T cells. The bispecific killer engagers (BiKEs) comprising scFvs against the NK cell antigen CD16 and a tumorassociated antigen (e.g., CD19, CD22, CD33) have also shown potent anti-cancer activity (e.g., Miller, Hematology Soc Hematol Educ Pogram 2013:247-53). Other alternatives include trispecific killer engagers (TriKEs), such as anti-CD16×anti-CD19×anti-CD22 (Miller, 2013; Gleason et al., 2012, Mol Cancer Ther 11:2674-84). An anti-CD16×anti-CD33 BiKE was used to treat AML and myelodysplastic syndrome (Miller, 2013; Wiernik et al., 2013, Clin Cancer Res 19:3844-55). In refractory AML, a CD16×CD33 BiKE led to potent tumor cell killing and cytokine production by NK cells. Inhibition of ADAM17 enhanced the CD16×CD33 BiKE response (Miller, 2013). Other trispecific, trivalent constructs, for example against CD16/CD19/HLA-DR, have been reported (Schubert et al., 2012, mAbs 4:45-56).

Numerous methods to produce bispecific antibodies are known (see, e.g. U.S. Pat. No. 7,405,320). Bispecific antibodies can be produced by the quadroma method, which involves the fusion of two different hybridomas, each producing a monoclonal antibody recognizing a different antigenic site (Milstein and Cuello, *Nature* 1983; 305:537-540). The fused hybridomas are capable of synthesizing two different heavy chains and two different light chains, which can associate randomly to give a heterogeneous population of 10 different antibody structures of which only one of them, amounting to ⅛ of the total antibody molecules, will be bispecific, and therefore must be further purified from the other forms. Fused hybridomas are often less stable cytogenetically than the parent hybridomas, making the generation of a production cell line more problematic.

Another method for producing bispecific antibodies uses heterobifunctional cross-linkers to chemically tether two different monoclonal antibodies, so that the resulting hybrid conjugate will bind to two different targets (Staerz, et al. *Nature* 1985; 314:628-631; Perez, et al. *Nature* 1985; 316: 354-356). Bispecific antibodies generated by this approach are essentially heteroconjugates of two IgG molecules, which diffuse slowly into tissues and are rapidly removed from the circulation. Bispecific antibodies can also be produced by reduction of each of two parental monoclonal antibodies to the respective half molecules, which are then mixed and allowed to reoxidize to obtain the hybrid structure (Staerz and Bevan. *Proc Natl Acad Sci USA* 1986; 83:1453-1457). An alternative approach involves chemically cross-linking two or three separately purified Fab' fragments using appropriate linkers. All these chemical methods are undesirable for commercial development due to high manufacturing cost, laborious production process, extensive purification steps, low yields (<20%), and heterogeneous products.

Discrete $V_H$ and $V_L$ domains of antibodies produced by recombinant DNA technology may pair with each other to form a dimer (recombinant Fv fragment) with binding capability (U.S. Pat. No. 4,642,334). However, such non-covalently associated molecules are not sufficiently stable under physiological conditions to have any practical use. Cognate $V_H$ and $V_L$ domains can be joined with a peptide linker of appropriate composition and length (usually consisting of more than 12 amino acid residues) to form a single-chain Fv (scFv) with binding activity. Methods of manufacturing scFv-based agents of multivalency and multispecificity by varying the linker length were disclosed in U.S. Pat. No. 5,844,094, U.S. Pat. No. 5,837,242 and WO 98/44001. Common problems that have been frequently associated with generating scFv-based agents of multivalency and multispecificity are low expression levels, heterogeneous products, instability in solution leading to aggregates, instability in serum, and impaired affinity.

Several bispecific antibodies targeting CD3 and CD19 are in clinical development. An scFv-based bispecific antibody construct, known as BITE® (Bispecific T-cell Engager), employs a single polypeptide containing 2 antigen-binding specificities, each contributed by a cognate VH and VL, linked in tandem via a flexible linker (see, e.g., Nagorsen et al., 2009, *Leukemia & Lymphoma* 50:886-91; Amann et al., 2009, *J Immunother* 32:453-64; Baeuerle and Reinhardt, 2009, *Cancer Res* 69:4941-44). Another bispecific antibody called DART® (Dual-Affinity Re-Targeting) utilizes a dis-ulfide-stabilized diabody design (see, e.g., Moore et al., 2011, *Blood* 117:4542-51; Veri et al., 2010, *Arthritis Rheum* 62:1933-43). Both BITE® and DART® exhibit fast blood clearance due to their small size (~55 kDa), which requires frequent administration to maintain therapeutic levels of the bispecific antibodies.

Interferons are critical role players in the antitumor and antimicrobial host defense, and have been extensively explored as therapeutic agents for cancer and infectious disease (Billiau et al., 2006, *Cytokine Growth Factor Rev* 17:381-409; Pestka et al., 2004, *Immunol Rev* 202:8-32). Despite considerable efforts with type I and II interferons (IFN-α/β and γ), their use in clinic settings have been limited because of the short circulation half-life, systemic toxicity, and suboptimal responses in patients (Pestka et al., 2004, *Immunol Rev* 202:8-32; Miller et al., 2009, *Ann N Y Acad Sci* 1182:69-79). The discovery of the IFN-λ family in early 2003 brought an exciting new opportunity to develop alternative IFN agents for these unmet clinical indications (Kotenko et al., 2003, *Nat Immunol* 4:69-77; Sheppard et al., 2003, *Nat Immunol* 4:63-8).

The therapeutic effectiveness of IFNs has been validated to date by the approval of IFN-α2 for treating hairy cell leukemia, chronic myelogenous leukemia, malignant melanoma, follicular lymphoma, condylomata acuminata, AIDs-related Kaposi sarcoma, and chronic hepatitis B and C; IFN-β for treating multiple sclerosis; and IFN-γ for treating chronic granulomatous disease and malignant osteopetrosis. Despite a vast literature on this group of autocrine and paracrine cytokines, their functions in health and disease are still being elucidated, including more effective and novel forms being introduced clinically (Pestka, 2007, *J. Biol. Chem* 282:20047-51; Vilcek, 2006, *Immunity* 25:343-48). The effects of combination of various interferons with antibody-based therapies also remain under investigation.

Antibody-drug conjugates (ADCs) are a potent class of therapeutic constructs that allow targeted delivery of cytotoxic agents to target cells, such as cancer cells. Because of the targeting function, these compounds show a much higher therapeutic index compared to the same systemically delivered agents. ADCs have been developed as intact antibodies or antibody fragments, such as scFvs. The antibody or fragment is linked to one or more copies of drug via a linker that is stable under physiological conditions, but that may be cleaved once inside the target cell. ADCs approved for therapeutic use include gemtuzumab ozogamicin for AML (subsequently withdrawn from the market), brentuximab vedotin for ALCL and Hodgkin lymphoma, and trastuzumab emtansine for HER2-positive metastatic breast cancer (Verma et al., 2012, N Engl J Med 367:1783-91; Bross et al., 2001, Clin Cancer Res 7:1490-96; Francisco et al., 2003, Blood 102:1458-65). Numerous other candidate ADCs are currently in clinical testing, such as inotuzumab ozogamicin (Pfizer), glembatumomab vedotin (Celldex Therapeutics), SAR3419 (Sanofi-Aventis), SAR56658 (Sanofi-Aventis), AMG-172 (Amgen), AMG-595 (Amgen), BAY-94-9343 (Bayer), BIIB015 (Biogen Idec), BT062 (Biotest), SGN-75 (Seattle Genetics), SGN-CD19A (Seattle Genetics), vorsetuzumab mafodotin (Seattle Genetics), ABT-414 (AbbVie), ASG-5ME (Agensys), ASG-22ME (Agensys), ASG-16M8F (Agensys), IMGN-529 (ImmunoGen), IMGN-853 (ImmunoGen), MDX-1203 (Medarex), MLN-0264 (Millenium), RG-7450 (Roche/Genentech), RG-7458 (Roche/Genentech), RG-7593 (Roche/Genentech), RG-7596 (Roche/Genentech), RG-7598 (Roche/Genentech), RG-7599 (Roche/Genentech), RG-7600 (Roche/Genentech), RG-7636 (Roche/Genentech), anti-PSMA ADC (Progenics), lorvotuzumab mertansine (ImmunoGen), milatuzumab-doxorubicin (Immunomedics), IMMU-130 (Immunomedics), IMMU-132 (Immunomedics) and antibody conjugates of pro-2-pyrrolinodoxorubicin. (See, e.g., Li et al., 2013, Drug Disc Ther 7:178-84; Firer & Gellerman, J Hematol Oncol 5:70; Beck et al., 2010, Discov Med 10:329-39; Mullard, 2013, Nature Rev Drug Discovery 12:329, Provisional U.S. Patent Application 61/761,845.) Because of the potential of ADCs to act as potent anti-cancer agents with reduced systemic toxicity, they may be used either alone or as an adjunct therapy to reduce tumor burden.

Another promising approach to immunotherapy concerns use of antagonistic antibodies against immune checkpoint proteins (e.g., Pardoll, 2012, Nature Reviews Cancer 12:252-64). Immune checkpoints function as endogenous inhibitory pathways for immune system function that act to maintain self-tolerance and to modulate the duration and extent of immune response to antigenic stimulation (Pardoll, 2012). However, it appears that tumor tissues and possibly certain pathogens may co-opt the checkpoint system to reduce the effectiveness of host immune response, resulting in tumor growth and/or chronic infection (see, e.g., Pardoll, 2012, Nature Reviews Cancer 12:252-64; Nirschl & Drake, 2013, Clin Cancer Res 19:4917-24). Checkpoint molecules include CTLA4 (cytotoxic T lymphocyte antigen-4), PD1 (programmed cell death protein 1), PD-L1 (programmed cell death ligand 1), LAG-3 (lymphocyte activation gene-3), TIM-3 (T cell immunoglobulin and mucin protein-3) and several others (Pardoll, 2012, Nature Reviews Cancer 12:252-64; Nirschl & Drake, 2013, Clin Cancer Res 19:4917-24). Antibodies against several of the checkpoint proteins (CTLA4, PD1, PD-L1) are in clinical trials and has shown unexpected efficacy against tumors that were resistant to standard treatments.

A need exists for methods and compositions to generate improved bispecific antibody complexes with longer $T_{1/2}$, better pharmacokinetic properties, increased in vivo stability and/or improved in vivo efficacy. A further need exists for combination therapies to improve efficacy of treatments directed to inducing immune response against various diseases, such as cancer or infectious disease.

SUMMARY

The present invention relates to combination therapy with two or more agents selected from the group consisting of a leukocyte-redirecting complexes, interferons, checkpoint inhibitor antibodies, and antibody-drug conjugates (ADCs). The first three types of agents may be used to induce or enhance the immune response against disease-associated antigens, such as tumor-associated antigens (TAAs) or pathogen (micro-organism)-expressed antigens. ADCs may be used in combination with any or all of the immunomodulatory agents to reduce tumor burden and enhance overall efficacy of treatment.

In embodiments utilizing leukocyte-redirecting complexes, the complexes preferably are bispecific antibodies (bsAbs), with one binding site against a leukocyte expressed antigen and a second binding site that binds to a target antigen on a tumor cell or pathogen (i.e., micro-organism). Exemplary T-cell antigens are selected from the group consisting of CD2, CD3, CD4, CD5, CD6, CD8, CD25, CD28, CD30, CD40, CD40L, CD44, CD45, CD69 and CD90. Exemplary antigens expressed on NK cells are selected from the group consisting of CD8, CD16, CD56, CD57, ADAM17, KIR and CD137. Exemplary monocyte antigens are selected from the group consisting of CD74, HLA-DR alpha chain, CD14, CD16, CD64 and CD89. Exemplary neutrophil antigens are selected from the group consisting of CEACAM6, CEACAM8, CD16b, CD32a, CD89, CD177, CD11a, CD11b and SLC44A2. Preferably the T-cell antigen is CD3, or the NK cell antigen is CD16. Target antigens for the second antibody may be selected from the group consisting of alpha-fetoprotein (AFP), α4 integrin, B7, carbonic anhydrase IX, complement factors C1q, C1r, C1s, C2a, C2b, C3, C3a, C3b, C4, C4a, C4b, C5a, C5aR, C5b, C5, C6, C7, C8, C9n, CCL19, CCL21, CD1, CD1a, CD2, CD3R, CD4, CD5, CD8, CD11A, CD14, CD15, CD16, CD18, CD19, CD20, CD21, CD22, CD23, CD25, CD29, CD30, CD32b, CD33, CD37, CD38, CD40, CD40L, CD44, CD45, CD46, CD52, CD54, CD55, CD59, CD64, CD66a-e, CD67, CD70, CD74, CD79a, CD79b, CD80, CD83, CD86, CD95, CD126, CD133, CD138, CD147, CD154, CEACAM-5, CEACAM-6, CSAp, ED-B of fibronectin, EGFR, EGP-1 (TROP-2), EGP-2, ErbB2, Factor H, FHL-1, fibrin, Flt-3, folate receptor, glycoprotein IIb/IIIa, gp41, gp120, GRO-β, HLA-DR, HM1.24, HM1.24, HMGB-1, hypoxia inducible factor (HIF), Ia, ICAM-1, IFN-α, IFN-β, IFN-γ, IFN-λ, IgE, IGF-1R, IL-1, IL-1Ra, IL-2, IL-4R, IL-6, IL-6R, IL-8, IL-13R, IL-15R, IL-15, IL-17, IL-17R, IL-18, IL-18R, IL-6, IL-8, IL-12, IL-15, IL-17, IL-18, IL-25, insulin-like growth factor-1 (ILGF-1), IP-10, KIR, Le(y), lipopolysaccharide (LPS), MAGE, MCP-1, mCRP, MIF, MIP-1A, MIP-1B, MUC1, MUC2, MUC3, MUC4, MUC5ac, NCA-90, NCA-95, NF-κB, PlGF, PSMA, RANTES, T101, TAC, TAG-72, tenascin, Thomson-Friedenreich antigens, thrombin, tissue factor, Tn antigen, TNF-α, TRAIL receptor (R1 and R2), tumor necrosis antigens, VEGF, VEGFR and an oncogene product.

An exemplary design for a leukocyte redirecting bsAb disclosed in the Examples below combined an anti-CD3 scFv with an anti-CD19 F(ab)₂ to form a construct designated (19)-3s, which specifically targeted B cells. Other bsAbs combining anti-CD3 with antibody fragments against other tumor-associated antigens, discussed in more detail below, are of use in targeted leukocyte immunotherapy of various solid tumors. The advantages of this design include bivalent binding to tumor cells, a larger size (~130 kDa) to preclude rapid renal clearance, and potent leukocyte mediated cytotoxicity. The bsAbs mediate the formation of immunological synapses between leukocytes and cognate target cells, induce leukocyte activation and proliferation in the presence of target cells, redirect potent leukocyte mediated killing of target cells in vitro and inhibit growth of human tumors in vivo.

A preferred embodiment concerns leukocyte redirecting bispecific antibodies produced as trivalent DNL™ complexes, with longer $T_{1/2}$, better pharmacokinetic properties and increased in vivo stability. Methods for production and use of DNL™ complexes, comprising dimers of DDD moieties from human PKA regulatory subunits RIα, RIβ, RIIα or RIIβ, bound to AD moieties from AKAPs, are well known (see, e.g., U.S. Pat. Nos. 7,550,143; 7,521,056; 7,534,866; 7,527,787; 7,666,400; 7,906,118; 7,901,680; 8,003,111 and 8,034,352, the Examples section of each incorporated herein by reference.) By attaching different effector moieties, such as antibodies or antibody fragments, to the DDD and AD moieties, DNL™ complexes comprising virtually any combination of effectors may be constructed and used.

The antibodies of use can be of various isotypes, preferably human IgG1, IgG2, IgG3 or IgG4, more preferably comprising human IgG1 hinge and constant region sequences. The antibodies or fragments thereof can be chimeric human-mouse, humanized (human framework and murine hypervariable (CDR) regions), or fully human, as well as variations thereof, such as half-IgG4 antibodies (referred to as "unibodies"), as described by van der Neut Kolfschoten et al. (*Science* 2007; 317:1554-1557). More preferably, the antibodies or fragments thereof may be designed or selected to comprise human constant region sequences that belong to specific allotypes, which may result in reduced immunogenicity when administered to a human subject. Preferred allotypes for administration include a non-G1m1 allotype (nG1m1), such as G1m3, G1m3,1, G1m3,2 or G1m3,1,2. More preferably, the allotype is selected from the group consisting of the nG1m1, G1m3, nG1m1,2 and Km3 allotypes.

Other preferred embodiments concern compositions and/or use of leukocyte-redirecting complexes in combination with one or more checkpoint inhibitor antibodies. Such antibodies are antagonistic for checkpoint inhibitor function. Many such antibodies are known in the art, such as lambrolizumab (MK-3475, Merck), nivolumab (BMS-936558, Bristol-Myers Squibb), pidilizumab (CT-011, CureTech Ltd.), AMP-224 (Merck), MDX-1105 (Medarex), MEDI4736 (MedImmune), MPDL3280A (Genentech), BMS-936559 (Bristol-Myers Squibb), ipilimumab (Bristol-Myers Squibb) and tremelimumab (Pfizer). Anti-KIR antibodies such as lirlumab (Innate Pharma) and IPH2101 (Innate Pharma) may perform similar functions in NK cells. Any known checkpoint inhibitor antibody may be used in combination with one or more of the other agents.

Another agent that may be used in combination is an interferon. Interferons of use are known in the art and may include interferon-α, interferon-β, interferon-λ1, interferon-λ2 or interferon-λ3. Preferably, the interferon is interferon-α. The subject interferon may be administered as free interferon, PEGylated interferon, an interferon fusion protein or interferon conjugated to an antibody.

In alternative embodiments, one or more of the immunomodulatory agents discussed above may be used in combination with an antibody-drug conjugate (ADC). ADCs are particularly effective for reducing tumor burden without significant systemic toxicity and may act to improve the effectiveness of the immune response induced by leukocyte retargeting bsAb, interferon and/or checkpoint inhibitor antibody. Exemplary ADCs of use may include ADCs approved for therapeutic use include gemtuzumab ozogamicin for AML (subsequently withdrawn from the market), brentuximab vedotin for ALCL and Hodgkin lymphoma, and trastuzumab emtansine for HER2-positive metastatic breast cancer (Verma et al., 2012, N Engl J Med 367:1783-91; Bross et al., 2001, Clin Cancer Res 7:1490-96; Francisco et al., 2003, Blood 102:1458-65). Numerous other candidate ADCs are currently in clinical testing, such as inotuzumab ozogamicin (Pfizer), glembatumomab vedotin (Celldex Therapeutics), SAR3419 (Sanofi-Aventis), SAR56658 (Sanofi-Aventis), AMG-172 (Amgen), AMG-595 (Amgen), BAY-94-9343 (Bayer), BIIB015 (Biogen Idec), BT062 (Biotest), SGN-75 (Seattle Genetics), SGN-CD19A (Seattle Genetics), vorsetuzumab mafodotin (Seattle Genetics), ABT-414 (AbbVie), ASG-5ME (Agensys), ASG-22ME (Agensys), ASG-16M8F (Agensys), IMGN-529 (ImmunoGen), IMGN-853 (ImmunoGen), MDX-1203 (Medarex), MLN-0264 (Millenium), RG-7450 (Roche/Genentech), RG-7458 (Roche/Genentech), RG-7593 (Roche/Genentech), RG-7596 (Roche/Genentech), RG-7598 (Roche/Genentech), RG-7599 (Roche/Genentech), RG-7600 (Roche/Genentech), RG-7636 (Roche/Genentech), anti-PSMA ADC (Progenics), lorvotuzumab mertansine (ImmunoGen), milatuzumab-doxorubicin (Immunomedics), IMMU-130 (Immunomedics) and IMMU-132 (Immunomedics). (See, e.g., Li et al., 2013, Drug Disc Ther 7:178-84; Firer & Gellerman, J Hematol Oncol 5:70; Beck et al., 2010, Discov Med 10:329-39; Mullard, 2013, Nature Rev Drug Discovery 12:329.) Preferably, where an ADC is used in combination with an immunomodulator, the ADC is administered prior to the immunomodulator.

In certain embodiments, the subject combination therapy may be of use for treating cancer. It is anticipated that any type of tumor and any type of tumor antigen may be targeted. Exemplary types of cancers that may be targeted include acute lymphoblastic leukemia, acute myelogenous leukemia, biliary cancer, breast cancer, cervical cancer, chronic lymphocytic leukemia, chronic myelogenous leukemia, colorectal cancer, endometrial cancer, esophageal, gastric, head and neck cancer, Hodgkin's lymphoma, lung cancer, medullary thyroid cancer, non-Hodgkin's lymphoma, multiple myeloma, renal cancer, ovarian cancer, pancreatic cancer, glioma, melanoma, liver cancer, prostate cancer, and urinary bladder cancer. However, the skilled artisan will realize that tumor-associated antigens are known for virtually any type of cancer.

Tumor-associated antigens that may be targeted by leukocyte redirecting bsAbs and/or by ADCs include, but are not limited to, alpha-fetoprotein (AFP), α-actinin-4, A3, antigen specific for A33 antibody, ART-4, B7, Ba 733, BAGE, BrE3-antigen, CA125, CAMEL, CAP-1, carbonic anhydrase IX, CASP-8/m, CCL19, CCL21, CD1, CD1a, CD2, CD3, CD4, CD5, CD8, CD11A, CD14, CD15, CD16, CD18, CD19, CD20, CD21, CD22, CD23, CD25, CD29, CD30, CD32b, CD33, CD37, CD38, CD40, CD40L, CD44, CD45, CD46, CD52, CD54, CD55, CD59, CD64, CD66a-e, CD67, CD70, CD70L, CD74, CD79a, CD79b, CD80, CD83, CD95, CD126, CD132, CD133, CD138, CD147, CD154, CDC27, CDK-4/m, CDKN2A, CTLA4, CXCR4, CXCR7, CXCL12, HIF-1α, colon-specific antigen-p (CSAp), CEA (CEACAM5), CEACAM6, c-Met, DAM, EGFR, EGFRvIII, EGP-1 (TROP-2), EGP-2, ELF2-M, Ep-CAM, fibroblast growth factor (FGF), Flt-1, Flt-3, folate receptor, G250 antigen, GAGE, gp100, GRO-β, HLA-DR, HM1.24, human chorionic gonadotropin (HCG) and its subunits, HER2/neu, HMGB-1, hypoxia inducible factor (HIF-1), HSP70-2M, HST-2, Ia, IGF-1R, IFN-γ, IFN-α, IFN-β, IFN-λ, IL-4R, IL-6R, IL-13R, IL-15R, IL-17R, IL-18R, IL-2, IL-6, IL-8, IL-12, IL-15, IL-17, IL-18, IL-23, IL-25, insulin-like growth factor-1 (IGF-1), KC4-antigen, KS-1-antigen, KS1-4, Le-Y, LDR/FUT, macrophage migration inhibitory factor (MIF), MAGE, MAGE-3, MART-1, MART-2, NY-ESO-1, TRAG-3, mCRP, MCP-1, MIP-1A, MIP-1B, MIF, MUC1, MUC2, MUC3, MUC4, MUC5ac, MUC13, MUC16, MUM-1/2, MUM-3, NCA66, NCA95, NCA90, PAM4 antigen, pancreatic cancer mucin, PD1 receptor, placental growth factor, p53, PLAGL2, prostatic acid phosphatase, PSA, PRAME, PSMA, PlGF, ILGF, ILGF-1R, IL-6, IL-25, RS5, RANTES, T101, SAGE, S100, survivin, survivin-2B, TAC, TAG-72, tenascin, TRAIL receptors, TNF-α, Tn antigen, Thomson-Friedenreich antigens, tumor necrosis antigens, VEGFR, ED-B fibronectin, WT-1, 17-1A-antigen, complement factors C3, C3a, C3b, C5a, C5, an angiogenesis marker, bcl-2, bcl-6, Kras, an oncogene marker and an oncogene product (see, e.g., Sensi et al., *Clin Cancer Res* 2006, 12:5023-32; Parmiani et al., *J Immunol* 2007, 178:1975-79; Novellino et al. *Cancer Immunol Immunother* 2005, 54:187-207).

Exemplary antibodies that may be used for cancer therapy include, but are not limited to, hA19 (anti-CD19, U.S. Pat. No. 7,109,304), hR1 (anti-IGF-1R, U.S. patent application Ser. No. 13/688,812, filed Nov. 29, 2012), hPAM4 (anti-MUC5ac, U.S. Pat. No. 8,795,662), hA20 (anti-CD20, U.S. Pat. No. 7,151,164), hIMMU31 (anti-AFP, U.S. Pat. No. 7,300,655), hLL1 (anti-CD74, U.S. Pat. No. 7,312,318), hLL2 (anti-CD22, U.S. Pat. No. 5,789,554), hMu-9 (anti-CSAp, U.S. Pat. No. 7,387,772), hL243 (anti-HLA-DR, U.S. Pat. No. 7,612,180), hMN-14 (anti-CEACAM5, U.S. Pat. No. 6,676,924), hMN-15 (anti-CEACAM6, U.S. Pat. No. 8,287,865), hRS7 (anti-EGP-1, U.S. Pat. No. 7,238,785), hMN-3 (anti-CEACAM6, U.S. Pat. No. 7,541,440), Ab124 and Ab125 (anti-CXCR4, U.S. Pat. No. 7,138,496), the Examples section of each cited patent or application incorporated herein by reference.

Combination therapy with immunostimulatory antibodies has been reported to enhance efficacy, for example against tumor cells. Morales-Kastresana et al. (2013, Clin Cancer Res 19:6151-62) showed that the combination of anti-PD-L1 (10B5) antibody with anti-CD137 (1D8) and anti-OX40 (OX86) antibodies provided enhanced efficacy in a transgenic mouse model of hepatocellular carcinoma. Combination of anti-CTLA4 and anti-PD1 antibodies has also been reported to be highly efficacious (Wolchok et al., 2013, N Engl J Med 369:122-33). Combination of rituximab with anti-KIR antibody, such as lirlumab (Innate Pharma) or IPH2101 (Innate Pharma), was also more efficacious against hematopoietic tumors (Kohrt et al., 2012). The person of ordinary skill will realize that the subject combination therapy may include combinations with multiple antibodies that are immunostimulatory, anti-tumor or anti-infectious agent.

Alternative antibodies that may be used for treatment of various disease states include, but are not limited to, abciximab (anti-glycoprotein IIb/IIIa), alemtuzumab (anti-CD52), bevacizumab (anti-VEGF), cetuximab (anti-EGFR), gemtuzumab (anti-CD33), ibritumomab (anti-CD20), panitumumab (anti-EGFR), rituximab (anti-CD20), tositumomab (anti-CD20), trastuzumab (anti-ErbB2), lambrolizumab (anti-PD1 receptor), nivolumab (anti-PD1 receptor), ipilimumab (anti-CTLA4), abagovomab (anti-CA-125), adecatumumab (anti-EpCAM), atlizumab (anti-IL-6 receptor), benralizumab (anti-CD125), obinutuzumab (GA101, anti-CD20), CC49 (anti-TAG-72), AB-PG1-XG1-026 (anti-PSMA, U.S. patent application Ser. No. 11/983,372, deposited as ATCC PTA-4405 and PTA-4406), D2/B (anti-PSMA, WO 2009/130575), tocilizumab (anti-IL-6 receptor), basiliximab (anti-CD25), daclizumab (anti-CD25), efalizumab (anti-CD11a), GA101 (anti-CD20; Glycart Roche), atalizumab (anti-α4 integrin), omalizumab (anti-IgE); anti-TNF-α antibodies such as CDP571 (Ofei et al., 2011, Diabetes 45:881-85), MTNFAI, M2TNFAI, M3TNFAI, M3TNFABI, M302B, M303 (Thermo Scientific, Rockford, Ill.), infliximab (Centocor, Malvern, Pa.), certolizumab pegol (UCB, Brussels, Belgium), anti-CD40L (UCB, Brussels, Belgium), adalimumab (Abbott, Abbott Park, Ill.), BENLYSTA® (Human Genome Sciences); anti-CD38 antibodies such as MOR03087 (MorphoSys AG), MOR202 (Celgene), HuMax-CD38 (Genmab) or daratumumab (Johnson & Johnson); anti-HIV antibodies such as P4/D10 (U.S. Pat. No. 8,333,971), Ab 75, Ab 76, Ab 77 (Paulik et al., 1999, *Biochem Pharmacol* 58:1781-90), as well as the anti-HIV antibodies described and sold by Polymun (Vienna, Austria), also described in U.S. Pat. No. 5,831,034, U.S. Pat. No. 5,911,989, and Vcelar et al., *AIDS* 2007; 21(16):2161-2170 and Joos et al., *Antimicrob. Agents Chemother.* 2006; 50(5):1773-9.

In other embodiments, the subject combination therapy may be of use to treat subjects infected with pathogenic organisms, such as bacteria, viruses or fungi. Exemplary fungi that may be treated include *Microsporum, Trichophyton, Epidermophyton, Sporothrix schenckii, Cryptococcus neoformans, Coccidioides immitis, Histoplasma capsulatum, Blastomyces dermatitidis* or *Candida albican*. Exemplary viruses include human immunodeficiency virus (HIV), herpes virus, cytomegalovirus, rabies virus, influenza virus, human papilloma virus, hepatitis B virus, hepatitis C virus, Sendai virus, feline leukemia virus, Reo virus, polio virus, human serum parvo-like virus, simian virus 40, respiratory syncytial virus, mouse mammary tumor virus, Varicella-Zoster virus, dengue virus, rubella virus, measles virus, adenovirus, human T-cell leukemia viruses, Epstein-Barr virus, murine leukemia virus, mumps virus, vesicular stomatitis virus, Sindbis virus, lymphocytic choriomeningitis virus or blue tongue virus. Exemplary bacteria include *Bacillus anthracis, Streptococcus agalactiae, Legionella pneumophila, Streptococcus pyogenes, Escherichia coli, Neisseria gonorrhoeae, Neisseria meningitidis, Pneumococcus* spp., *Hemophilis influenzae B, Treponema pallidum, Lyme disease spirochetes, Pseudomonas aeruginosa, Mycobacterium leprae, Brucella abortus, Mycobacterium tuberculosis* or a *Mycoplasma*. Exemplary use of ADCs against infectious agents are disclosed in Johannson et al. (2006, AIDS 20:1911-15) and Chang et al., 2012, PLos One 7:e41235).

Known antibodies against pathogens include, but are not limited to, P4D10 (anti-HIV), CR6261 (anti-influenza), exbivirumab (anti-hepatitis B), felvizumab (anti-respiratory syncytial virus), foravirumab (anti-rabies virus), motavizumab (anti-respiratory syncytial virus), palivizumab (anti-respiratory syncytial virus), panobacumab (anti-*Pseudomonas*), rafivirumab (anti-rabies virus), regavirumab (anti-cytomegalovirus), sevirumab (anti-cytomegalovirus), tivirumab (anti-hepatitis B), and urtoxazumab (anti-*E. coli*).

The subject agents may be administered in combination with one or more other immunomodulators to enhance the immune response. Immunomodulators may include, but are not limited to, a cytokine, a chemokine, a stem cell growth factor, a lymphotoxin, an hematopoietic factor, a colony stimulating factor (CSF), erythropoietin, thrombopoietin, tumor necrosis factor-α (TNF), TNF-β, granulocyte-colony stimulating factor (G-CSF), granulocyte macrophage-colony stimulating factor (GM-CSF), interferon-α, interferon-β, interferon-γ, interferon-λ, stem cell growth factor designated "S1 factor", human growth hormone, N-methionyl human growth hormone, bovine growth hormone, parathyroid hormone, thyroxine, insulin, proinsulin, relaxin, prorelaxin, follicle stimulating hormone (FSH), thyroid stimulating hormone (TSH), luteinizing hormone (LH), hepatic growth factor, prostaglandin, fibroblast growth factor, prolactin, placental lactogen, OB protein, mullerian-inhibiting substance, mouse gonadotropin-associated peptide, inhibin, activin, vascular endothelial growth factor, integrin, NGF-β, platelet-growth factor, TGF-α, TGF-β, insulin-like growth factor-I, insulin-like growth factor-II, macrophage-CSF (M-CSF), IL-1, IL-1α, IL-2, IL-3, IL-4, IL-5, IL-6, IL-7, IL-8, IL-9, IL-10, IL-11, IL-12, IL-13, IL-14, IL-15, IL-16, IL-17, IL-18, IL-21, IL-25, LIF, FLT-3, angiostatin, thrombospondin, endostatin, or lymphotoxin. In certain embodiments, a leukocyte-redirecting bispecific antibody or antibody fragment may be attached to an immunomodulator, such as a cytokine. Cytokine complexes are disclosed, for example, in U.S. Pat. Nos. 7,906,118 and 8,034,352, the Examples section of each incorporated herein by reference.

Although in preferred embodiments the T-cell binding component of the leukocyte redirecting bsAb binds to the CD3 antigen, other antigens expressed on effector T cells are known and may be targeted by the leukocyte redirecting complex. Exemplary T-cell antigens include, but are not limited to, CD2, CD3, CD4, CD5, CD6, CD8, CD25, CD28, CD30, CD40, CD40L, CD44, CD45, CD69 and CD90. Other exemplary antigens may be selected from CD8, CD16, CD56, CD57, ADAM17, and CD137 for NK cells; CD74, HLA-DR alpha chain, CD14, CD16, CD64 and CD89 for monocytes; and CEACAM6, CEACAM8, CD16b, CD32a, CD89, CD177, CD11a, CD11b and SLC44A2 for neutrophils.

BRIEF DESCRIPTION OF THE DRAWINGS

The following drawings form part of the present specification and are included to further demonstrate certain embodiments of the present invention. The embodiments may be better understood by reference to one or more of these drawings in combination with the detailed description of specific embodiments presented herein.

FIG. 12. Summary of in vitro cytotoxicity data for T-cell redirecting bsAbs in cancer cell lines.

FIG. 14A shows untreated control.

FIG. 21. Survival curves for NOD/SCID mice with NCI-N87 gastric cancer xenografts treated with (E1)-3s with or without interferon-α (PEGASYS®). Controls were untreated or treated with PEGASYS® alone or TF12 alone.

DETAILED DESCRIPTION

Definitions

Figure 1:
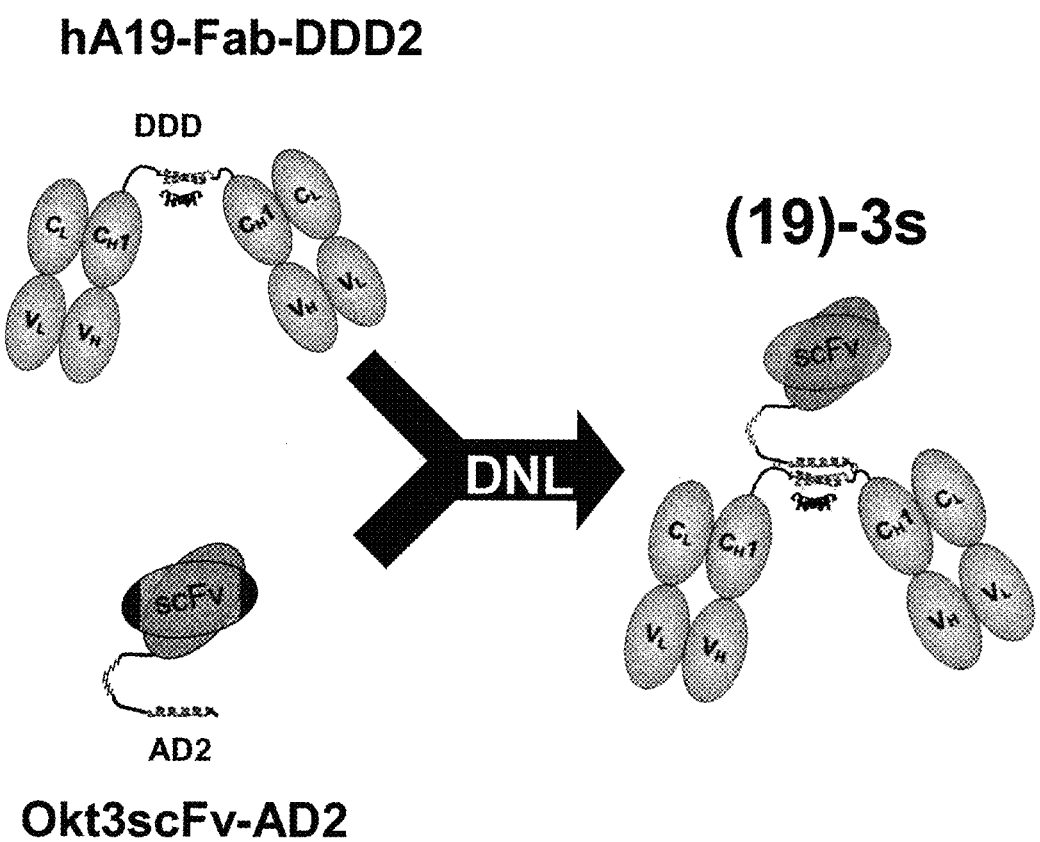
FIG. 1. Schematic diagram of formation of DOCK-AND-LOCK™ complex comprising anti-CD19 F(ab)$_2$×anti-CD3 scFv.

Unless otherwise specified, "a" or "an" means "one or more".

As used herein, the terms "and" and "or" may be used to mean either the conjunctive or disjunctive. That is, both terms should be understood as equivalent to "and/or" unless otherwise stated.

A "therapeutic agent" is an atom, molecule, or compound that is useful in the treatment of a disease. Examples of therapeutic agents include antibodies, antibody fragments, peptides, drugs, toxins, enzymes, nucleases, hormones, immunomodulators, antisense oligonucleotides, small interfering RNA (siRNA), chelators, boron compounds, photoactive agents, dyes, and radioisotopes.

An "antibody" as used herein refers to a full-length (i.e., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, like an antibody fragment. An "antibody" includes monoclonal, polyclonal, bispecific, multispecific, murine, chimeric, humanized and human antibodies.

A "naked antibody" is an antibody or antigen binding fragment thereof that is not attached to a therapeutic or diagnostic agent. The Fc portion of an intact naked antibody can provide effector functions, such as complement fixation and ADCC (see, e.g., Markrides, *Pharmacol Rev* 50:59-87, 1998). Other mechanisms by which naked antibodies induce cell death may include apoptosis. (Vaswani and Hamilton, *Ann Allergy Asthma Immunol* 81: 105-119, 1998.)

An "antibody fragment" is a portion of an intact antibody such as F(ab')$_2$, F(ab)$_2$, Fab', Fab, Fv, scFv, dAb and the like. Regardless of structure, an antibody fragment binds with the same antigen that is recognized by the full-length antibody. For example, antibody fragments include isolated fragments consisting of the variable regions, such as the "Fv" fragments consisting of the variable regions of the heavy and light chains or recombinant single chain polypeptide molecules in which light and heavy variable regions are connected by a peptide linker ("scFv proteins"). "Single-chain antibodies", often abbreviated as "scFv" consist of a polypeptide chain that comprises both a $V_H$ and a $V_L$ domain which interact to form an antigen-binding site. The $V_H$ and $V_L$ domains are usually linked by a peptide of 1 to 25 amino acid residues. Antibody fragments also include diabodies, triabodies and single domain antibodies (dAb).

A "chimeric antibody" is a recombinant protein that contains the variable domains including the complementarity determining regions (CDRs) of an antibody derived from one species, preferably a rodent antibody, while the constant domains of the antibody molecule are derived from those of a human antibody. For veterinary applications, the constant domains of the chimeric antibody may be derived from that of other species, such as a cat or dog.

A "humanized antibody" is a recombinant protein in which the CDRs from an antibody from one species; e.g., a rodent antibody, are transferred from the heavy and light variable chains of the rodent antibody into human heavy and light variable domains, including human framework region (FR) sequences. The constant domains of the antibody molecule are derived from those of a human antibody. To maintain binding activity, a limited number of FR amino acid residues from the parent (e.g., murine) antibody may be substituted for the corresponding human FR residues.

A "human antibody" is an antibody obtained from transgenic mice that have been genetically engineered to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described by Green et al., *Nature Genet.* 7:13 (1994), Lonberg et al., *Nature* 368:856 (1994), and Taylor et al., *Int. Immun.* 6:579 (1994). A human antibody also can be constructed by genetic or chromosomal transfection methods, as well as phage display technology, all of which are known in the art. (See, e.g., McCafferty et al., 1990, *Nature* 348:552-553 for the production of human antibodies and fragments thereof in vitro, from immunoglobulin variable domain gene repertoires from unimmunized donors). In this technique, antibody variable domain genes are cloned in-frame into either a major or minor coat protein gene of a filamentous bacteriophage, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. In this way, the phage mimics some of the properties of the B cell. Phage display can be performed in a variety of formats, for their review, see, e.g. Johnson and Chiswell, *Current Opinion in Structural Biology* 3:5564-571 (1993). Human antibodies may also be generated by in vitro activated B cells. (See, U.S. Pat. Nos. 5,567,610 and 5,229,275).

As used herein, the term "antibody fusion protein" is a recombinantly produced antigen-binding molecule in which an antibody or antibody fragment is linked to another protein or peptide, such as the same or different antibody or antibody fragment or a DDD or AD peptide. The fusion protein may comprise a single antibody component, a multivalent or multispecific combination of different antibody components or multiple copies of the same antibody component. The fusion protein may additionally comprise an antibody or an antibody fragment and a therapeutic agent. Examples of therapeutic agents suitable for such fusion proteins include immunomodulators and toxins. One preferred toxin comprises a ribonuclease (RNase), preferably a recombinant RNase. A preferred immunomodulator might be an interferon, such as interferon-α, interferon-β or interferon-λ.

A "multispecific antibody" is an antibody that can bind simultaneously to at least two targets that are of different structure, e.g., two different antigens, two different epitopes on the same antigen, or a hapten and/or an antigen or epitope. A "multivalent antibody" is an antibody that can bind simultaneously to at least two targets that are of the same or different structure. Valency indicates how many binding arms or sites the antibody has to a single antigen or epitope; i.e., monovalent, bivalent, trivalent or multivalent. The multivalency of the antibody means that it can take advantage of multiple interactions in binding to an antigen, thus increasing the avidity of binding to the antigen. Specificity indicates how many antigens or epitopes an antibody is able to bind; i.e., monospecific, bispecific, trispecific, multispecific. Using these definitions, a natural antibody, e.g., an IgG, is bivalent because it has two binding arms but is monospecific because it binds to one epitope. Multispecific, multivalent antibodies are constructs that have more than one binding site of different specificity.

A "bispecific antibody" is an antibody that can bind simultaneously to two targets which are of different structure. Bispecific antibodies (bsAb) and bispecific antibody fragments (bsFab) may have at least one arm that specifically binds to, for example, a T cell, an NK cell, a monocyte or a neutrophil, and at least one other arm that specifically binds to an antigen produced by or associated with a diseased cell, tissue, organ or pathogen, for example a tumor-associated antigen. A variety of bispecific antibodies can be produced using molecular engineering.

An antibody preparation, or a composition described herein, is said to be administered in a "therapeutically effective amount" if the amount administered is physiologically significant. An agent is physiologically significant if its presence results in a detectable change in the physiology of a recipient subject. In particular embodiments, an antibody preparation is physiologically significant if its presence invokes an antitumor response or mitigates the signs and symptoms of an infectious disease state. A physiologically significant effect could also be the evocation of a humoral and/or cellular immune response in the recipient subject leading to growth inhibition or death of target cells.

Leukocyte Redirecting Bispecific Antibody Complexes

Various embodiments concern bsAbs comprising an anti-leukocyte antibody or fragment thereof attached to an antibody or fragment thereof against a disease-associated antigen. Exemplary T-cell antigens include CD2, CD3, CD4, CD5, CD6, CD8, CD25, CD28, CD30, CD40, CD40L, CD44, CD45, CD69 and CD90. Other exemplary antigens may be selected from CD8, CD16, CD56, CD57, ADAM17, and CD137 for NK cells; CD74, HLA-DR alpha chain, CD14, CD16, CD64 and CD89 for monocytes; and CEACAM6, CEACAM8, CD16b, CD32a, CD89, CD177, CD11a, CD11b and SLC44A2 for neutrophils. In preferred embodiments, the anti-T-cell antibody binds to CD3, or the anti-NK antibody binds to CD16. As discussed below, many examples of disease-associated antigens, such as tumor-associated antigens (TAAs) or pathogen-expressed antigens are known. An exemplary preferred TAA is CD19.

Various bispecific anti-CD3×anti-CD19 antibodies are known in the art and presently in clinical development, such as BITE® (Bispecific T-cell Engager) (e.g., Nagorsen et al., 2009, *Leukemia & Lymphoma* 50:886-91; Amann et al., 2009, *J Immunother* 32:453-64; Baeuerle and Reinhardt, 2009, *Cancer Res* 69:4941-44) and DART® (see, e.g., Moore et al., 2011, *Blood* 117:4542-51; Veri et al., 2010, *Arthritis Rheum* 62:1933-43). Blinatumomab is a BITE® antibody comprising $V_H$ and $V_L$ domains of anti-CD3 and anti-CD19 antibody fragments, connected with a 5-amino acid linker and expressed as a single polypeptide chain that anneals to itself to form the antigen-binding sites. It is thought that blinatumomab acts by bringing the T-cell-specific CD3 and B-cell specific CD19 antigens into close proximity, to initiate a T-cell cytotoxic response against the juxtaposed B cells, which does not require T-cell specificity to the cancer cells (e.g., Portell et al., 2013, *Clin Pharmacol* 5(Suppl 1): 5-11). Due to its short half-life, blinatumomab requires continuous intravenous infusion to be effective, (Portell et al., 2013). A phase II trial of B-cell ALL patients with persistent or relapsed minimal residual disease reported an approximately 80% rate of complete remission (Portell et al., 2013).

Doses of blinatumomab as low as 0.005 mg/m²/day were reported to be effective to eliminate cancer cells in non-Hodgkin's lymphoma patients (Bargou et al., 2008, *Science* 321:974-77). Partial and complete remissions were observed starting at a dose level of 0.015 mg and all six patients tested at a dose of 0.06 mg experienced a tumor regression (Bargou et al., 2008). In vitro, blinatumomab induced 50% cell lysis of MEC-1 cells at a concentration of 10 pg/mL (Topp et al., 2012, *Blood* 120:5185-87; Bassan et al., 2012, *Blood* 120: 5094-95).

The anti-CD19 portion of blinatumomab was derived from the HD37 hybridoma (see, e.g., U.S. Pat. No. 7,575,923, the Examples section of which is incorporated herein by reference), which is publicly available (e.g., Santa Cruz Biotechnology Cat. No. sc-18894). The anti-CD3 portion of blinatumomab was derived from the TR66 hybridoma (U.S. Pat. No. 7,575,923; Traunecker et al., 1991, *EMBO J.* 10:3655-59), also publicly available (e.g., Enzo Life Sciences, catalog No. ALX-804-822-C100).

A variety of antibodies against CD3 that may be used in the claimed methods and compositions are publicly known and/or commercially available, such as from LSBio (catalog Nos. LS-B6698, LS-B8669; LS-B8765, LS-C96311, LS-058677, etc.); ABCAM® (catalog Nos. ab5690, ab16669, ab699, ab828, ab8671, etc.); Santa Cruz Biotechnology (catalog Nos. sc-20047, sc-20080, sc-19590, sc-59008, sc-101442, etc.); and many other suppliers.

In a preferred embodiment, the amino acid sequence of the anti-CD3 moiety, used as part of a DNL™ complex, is as disclosed below in SEQ ID NO:96 to SEQ ID NO:101. However, the person of ordinary skill will realize that any known anti-CD3 antibody may be utilized in the claimed methods and compositions. Preferably, the antibody moieties of use are humanized or human.

A variety of antibodies against CD19 that may be used in the claimed methods and compositions are publicly known and/or commercially available, such as from Santa Cruz Biotechnology (catalog Nos. sc-390244, sc-373897, sc-18894, sc-18896, etc.); ABCAM® (catalog Nos. ab25232, ab134114, ab140981, ab1255, etc.); ABBIOTEC™ (catalog Nos. 252262, 252248, 250585, 251063, etc.) and many other vendors.

In a preferred embodiment, the anti-CD19 antibody moiety is a humanized A19 antibody, comprising the light chain CDR sequences CDR1 KASQSVDYDGDSYLN (SEQ ID NO:90); CDR2 DASNLVS (SEQ ID NO:91); and CDR3 QQSTEDPWT (SEQ ID NO:92) and the heavy chain CDR sequences CDR1 SYWMN (SEQ ID NO:93); CDR2 QIWPGDGDTNYNGKFKG (SEQ ID NO:94) and CDR3 RETTTVGRYYYAMDY (SEQ ID NO:95).

Other anti-CD3×anti-CD19 bispecific antibodies are known, such as DART®, which also incorporates the anti-CD19 Fv sequences of HD37 and the anti-CD3 Fv sequences of TR66 (Moore et al., 2011, *Blood* 117:4542-51; Veri et al., 2010, *Arthritis Rheum* 62:1933-43). Moore et al.

(2011) reported that DART® bispecific antibodies were more potent at inducing B cell lysis than single-chain, bispecific antibodies (BITE®) bearing identical anti-CD19 and anti-CD3 variable region sequences, with $EC_{50}$ values in the pg/mL range (Moore et al., 2011). Other anti-CD3×anti-CD19 bispecific antibodies besides DART® and BITE® have been reported (see, e.g., Wei et al., 2012, *Cell Oncol* 35:423-34; Portner et al., 2012, *Cancer Immunol Immunother* 61:1869-75; Zhou et al., 2012, *Biotechnol Lett.* 34:1183-91). In certain embodiments, any known anti-CD3×anti-CD19 bispecific antibody may be used to induce an immune response against disease-associated cells or pathogens.

Catumaxomab is an anti-CD3×anti-EpCAM bispecific antibody that has been approved in Europe for treatment of malignant ascites associated with metastasizing cancer (Chames & Baty, 2009, *MAbs* 1:539-47). In a mouse model system, catumaxomab was able to kill tumor cells at a concentration range of 10 pM and was reported to lead to total eradication of melanoma tumors (Chames & Baty, 2009). Human clinical trials with ovarian cancer patients with malignant ascites also showed a statistically significant efficacy (Chames & Baty, 2009). However, the high immunogenicity of the rat/mouse hybrid bsAb may limit i.v. administration of the antibody (Chames & Baty, 2009). The use of anti-tumor bsAbs is not limited to anti-CD3×anti-CD19, but has also included anti-HER2×anti-CD64 (MDX-210, MDX-H210), anti-EGFR×anti-CD64 (MDX-447), anti-CD30×anti-CD16 (HRS-3/A9), anti-HER2×anti-CD3 (Her2Bi), anti-CD20×anti-CD3 (CD20Bi, Bi20), anti-EpCAM×anti-CD3 (catumaxomab, MT110), anti-HER2×anti-CD3 (ertumaxomab), and anti-NG2×anti-CD28 (rM28) (Chames & Baty, 2009).

In a most preferred embodiment, an anti-CD3×anti-CD19 bispecific antibody or other leukocyte redirecting bsAb is made as a DNL™ construct, as disclosed in Example 1 below. The person of ordinary skill will realize that the subject leukocyte redirecting bispecific antibodies are not limited to anti-CD3×anti-CD19 constructs, but may comprise antibodies against any known disease-associated antigens attached to an anti-CD3 antibody moiety. Alternatively, antibodies against other T-cell antigens besides CD3, or other antigens expressed on NK cells, monocytes or neutrophils may also be used. Exemplary T-cell antigens include, but are not limited to, CD2, CD3, CD4, CD5, CD6, CD8, CD25, CD28, CD30, CD40, CD40L, CD44, CD45, CD69 and CD90. Other exemplary antigens may be selected from CD8, CD16, CD56, CD57, ADAM17, KIR and CD137 for NK cells; CD74, HLA-DR alpha chain, CD14, CD16, CD64 and CD89 for monocytes; and CEACAM6, CEACAM8, CD16b, CD32a, CD89, CD177, CD11a, CD11b and SLC44A2 for neutrophils. Antibodies against each of the leukocyte antigens are publicly known and/or publicly available (see, e.g., ABCAM® catalog numbers ab131276, ab139266, ab8360, ab51312, ab846, ab133616, ab75877, ab133255, ab109217, ab93278, ab17147, ab115851, ab128955, ab13463, ab85986; Santa Cruz Biotechnology catalog numbers sc-46683, sc-59047; Enzo Life Sciences, Inc. catalog number ALX-805-037-C100; Sino Biological Inc. catalog numbers 12211-RP02, 11150-R074; Millipore catalog numbers 04-1102, 04-1102, MAB1406). These and numerous other anti-leukocyte antibodies were publicly available and could have been used in the subject leukocyte redirecting bsAbs. As discussed below, numerous antibodies against a wide variety of disease-associated antigens were publicly known and/or commercially available and could have been used in the subject leukocyte redirecting bispecific antibodies. Other exemplary leukocyte redirecting bsAbs of potential use include FBTA05 (anti-CD20×anti-CD3) and TRBS07 (anti-GD2×anti-CD3).

Interferon Therapy

In various embodiments, leukocyte redirecting bsAbs, antibody-drug conjugates and/or checkpoint inhibitor antibodies may be used in combination with one or more interferons, such as interferon-α, interferon-β or interferon-λ. Human interferons are well known in the art and the amino acid sequences of human interferons may be readily obtained from public databases (e.g., GenBank Accession Nos. AAA52716.1; AAA52724; AAC41702.1; EAW56871.1; EAW56870.1; EAW56869.1). Human interferons may also be commercially obtained from a variety of vendors (e.g., Cell Signaling Technology, Inc., Danvers, Mass.; Genentech, South San Francisco, Calif.; EMD Millipore, Billerica, Mass.).

Interferon-α (IFNα) has been reported to have anti-tumor activity in animal models of cancer (Ferrantini et al., 1994, *J Immunol* 153:4604-15) and human cancer patients (Gutterman et al., 1980, *Ann Intern Med* 93:399-406). IFNα can exert a variety of direct anti-tumor effects, including down-regulation of oncogenes, up-regulation of tumor suppressors, enhancement of immune recognition via increased expression of tumor surface MHC class I proteins, potentiation of apoptosis, and sensitization to chemotherapeutic agents (Gutterman et al., 1994, *PNAS USA* 91:1198-205; Matarrese et al., 2002, *Am J Pathol* 160:1507-20; Mecchia et al., 2000, *Gene Ther* 7:167-79; Sabaawy et al., 1999, *Int J Oncol* 14:1143-51; Takaoka et al, 2003, *Nature* 424:516-23). For some tumors, IFNα can have a direct and potent anti-proliferative effect through activation of STAT1 (Grimley et al., 1998 *Blood* 91:3017-27). Interferon-α2b has been conjugated to anti-tumor antibodies, such as the hL243 anti-HLA-DR antibody and depletes lymphoma and myeloma cells in vitro and in vivo (Rossi et al., 2011, *Blood* 118:1877-84).

Indirectly, IFNα can inhibit angiogenesis (Sidky and Borden, 1987, *Cancer Res* 47:5155-61) and stimulate host immune cells, which may be vital to the overall antitumor response but has been largely under-appreciated (Belardelli et al., 1996, *Immunol Today* 17:369-72). IFNα has a pleiotropic influence on immune responses through effects on myeloid cells (Raefsky et al, 1985, *J Immunol* 135:2507-12; Luft et al, 1998, *J Immunol* 161:1947-53), T-cells (Carrero et al, 2006, *J Exp Med* 203:933-40; Pilling et al., 1999, *Eur J Immunol* 29:1041-50), and B-cells (Le et al, 2001, *Immunity* 14:461-70). As an important modulator of the innate immune system, IFNα induces the rapid differentiation and activation of dendritic cells (Belardelli et al, 2004, *Cancer Res* 64:6827-30; Paquette et al., 1998, *J Leukoc Biol* 64:358-67; Santini et al., 2000, *J Exp Med* 191:1777-88) and enhances the cytotoxicity, migration, cytokine production and antibody-dependent cellular cytotoxicity (ADCC) of NK cells (Biron et al., 1999, *Ann Rev Immunol* 17:189-220; Brunda et al. 1984, *Cancer Res* 44:597-601).

Interferon-β has been reported to be efficacious for therapy of a variety of solid tumors. Patients treated with 6 million units of IFN-β twice a week for 36 months showed a decreased recurrence of hepatocellular carcinoma after complete resection or ablation of the primary tumor in patients with HCV-related liver cancer (Ikeda et al., 2000, *Hepatology* 32:228-32). Gene therapy with interferon-β induced apoptosis of glioma, melanoma and renal cell carcinoma (Yoshida et al., 2004, *Cancer Sci* 95:858-65). Endogenous IFN-β has been observed to inhibit tumor growth by inhibiting angiogenesis in vivo (Jablonska et al., 2010, *J Clin Invest.* 120:1151-64.)

IFN-λs, designated as type III interferons, are a newly described group of cytokines that consist of IFN-λ1, 2, 3 (also referred to as interleukin-29, 28A, and 28B, respectively), that are genetically encoded by three different genes located on chromosome 19 (Kotenko et al., 2003, *Nat Immunol* 4:69-77; Sheppard et al., 2003, *Nat Immunol* 4:63-8). At the protein level, IFN-λ2 and -λ3 are is highly homologous, with 96% amino acid identity, while IFN-λ1 shares approximately 81% homology with IFN-λ2 and -λ3 (Sheppard et al., 2003, *Nat Immunol* 4:63-8). IFN-λs activate signal transduction via the JAK/STAT pathway similar to that induced by type I IFN, including the activation of JAK1 and TYK2 kinases, the phosphorylation of STAT proteins, and the activation of the transcription complex of IFN-stimulated gene factor 3 (ISGF3) (Witte et al., 2010, *Cytokine Growth Factor Rev* 21:237-51; Zhou et al., 2007, *J Virol* 81:7749-58).

A major difference between type III and type I IFN systems is the distribution of their respective receptor complexes. IFN-α/β signals through two extensively expressed type I interferon receptors, and the resulting systemic toxicity associated with IFN-α/β administration has limited their use as therapeutic agents (Pestka et al., 2007, *J Biol Chem* 282:20047-51). In contrast, IFN-λs signal through a heterodimeric receptor complex consisting of unique IFN-λ receptor 1 (IFN-λR1) and IL-10 receptor 2 (IL-10R2). As previously reported (Witte et al., 2009, *Genes Immun* 10:702-14), IFN-λR1 has a very restricted expression pattern with the highest levels in epithelial cells, melanocytes, and hepatocytes, and the lowest level in primary central nervous system (CNS) cells. Blood immune system cells express high levels of a short IFN-λ receptor splice variant (sIFN-λR1) that inhibits IFN-λ action. The limited responsiveness of neuronal cells and immune cells implies that the severe toxicity frequently associated with IFN-α therapy may be absent or significantly reduced with IFN-λs (Witte et al., 2009, *Genes Immun* 10:702-14; Witte et al., 2010, *Cytokine Growth Factor Rev* 21:237-51). A recent publication reported that while IFN-α and IFN-λ induce expression of a common set of ISGs (interferon-stimulated genes) in hepatocytes, unlike IFN-α, administration of IFN-λ did not induce STAT activation or ISG expression in purified lymphocytes or monocytes (Dickensheets et al., 2013, *J Leukoc Biol.* 93, published online 12/20/12). It was suggested that IFN-λ may be superior to IFN-α for treatment of chronic HCV infection, as it is less likely to induce leukopenias that are often associated with IFN-α therapy (Dickensheets et al., 2013).

IFN-λs display structural features similar to IL-10-related cytokines, but functionally possess type I IFN-like anti-viral and anti-proliferative activity (Witte et al., 2009, *Genes Immun* 10:702-14; Ank et al., 2006, *J Virol* 80:4501-9; Robek et al., 2005, *J Virol* 79:3851-4). IFN-λ1 and -λ2 have been demonstrated to reduce viral replication or the cytopathic effect of various viruses, including DNA viruses (hepatitis B virus (Robek et al., 2005, *J Virol* 79:3851-4, Doyle et al., 2006, *Hepatology* 44:896-906) and herpes simplex virus 2 (Ank et al., 2008, *J Immunol* 180:2474-85)), ss (+) RNA viruses (EMCV; Sheppard et al., 2003, *Nat Immunol* 4:63-8) and hepatitis C virus (Robek et al., 2005, *J Virol* 79:3851-4, Doyle et al., 2006, *Hepatology* 44:896-906; Marcello et al., 2006, *Gastroenterol* 131:1887-98; Pagliaccetti et al., 2008, *J Biol Chem* 283:30079-89), ss (−) RNA viruses (vesicular stomatitis virus; Pagliaccetti et al., 2008, *J Biol Chem* 283:30079-89) and influenza-A virus (Jewell et al., 2010, *J Virol* 84:11515-22) and double-stranded RNA viruses, such as rotavirus (Pott et al., 2011, *PNAS USA* 108:7944049). IFN-λ3 has been identified from genetic studies as a key cytokine in HCV infection (Ge et al., 2009, *Nature* 461:399-401), and has also shown potent activity against EMCV (Dellgren et al., 2009, *Genes Immun* 10:125-31). A deficiency of rhinovirus-induced IFN-λ production was reported to be highly correlated with the severity of rhinovirus-induced asthma exacerbation (Controli et al., 2006, *Nature Med* 12:1023-26) and IFN-λ therapy has been suggested as a new approach for treatment of allergic asthma (Edwards and Johnston, 2011, *EMBO Mol Med* 3:306-8; Koltsida et al., 2011, *EMBO Mol Med* 3:348-61).

The anti-proliferative activity of IFN-λs has been established in several human cancer cell lines, including neuroendocrine carcinoma BON1 (Zitzmann et al., 2006, *Biochem Biophys Res Commun* 344:1334-41), glioblastoma LN319 (Meager et al., 2005, *Cytokine* 31:109-18), immortalized keratinocyte HaCaT (Maher et al., 2008, *Cancer Biol Ther* 7:1109-15), melanoma F01 (Guenterberg et al., 2010, *Mol Cancer Ther* 9:510-20), and esophageal carcinoma TE-11 (Li et al., 2010, *Eur J Cancer* 46:180-90). In animal models, IFN-λs induce both tumor apoptosis and destruction through innate and adaptive immune responses, suggesting that local delivery of IFN-λ might be a useful adjunctive strategy in the treatment of human malignancies (Numasaki et al., 2007, *J Immunol* 178:5086-98). A Fab-linked interferon-λ was demonstrated to have potent anti-tumor and anti-viral activity in targeted cells (Liu et al., 2013, *PLoS One* 8:e63940).

In clinical settings, PEGylated IFN-λ1 (PEG-IFN-λ1) has been provisionally used for patients with chronic hepatitis C virus infection. In a phase Ib study (n=56), antiviral activity was observed at all dose levels (0.5-3.0 μg/kg), and viral load reduced 2.3 to 4.0 logs when PEG-IFN-λ1 was administrated to genotype 1 HCV patients who relapsed after IFN-α therapy (Muir et al., 2010, *Hepatology* 52:822-32). A phase 11b study (n=526) showed that patients with HCV genotypes 1 and 4 had significantly higher response rates to treatment with PEG-IFN-λ1 compared to PEG-IFN-α. At the same time, rates of adverse events commonly associated with type I interferon treatment were lower with PEG-IFN-λ1 than with PEG-IFN-α. Neutropenia and thrombocytopenia were infrequently observed and the rates of flu-like symptoms, anemia, and musculoskeletal symptoms decreased to about ⅓ of that seen with PEG-IFN-α treatment. However, rates of serious adverse events, depression and other common adverse events (≥10%) were similar between PEG-IFN-λ1 and PEG-IFN-α. Higher rates of hepatotoxicity were seen in the highest-dose PEG-IFN-λ1 compared with PEG-IFN-α ("Investigational Compound PEG-Interferon Lambda Achieved Higher Response Rates with Fewer Flu-like and Musculoskeletal Symptoms and Cytopenias Than PEG-Interferon Alfa in Phase IIb Study of 526 Treatment-Naive Hepatitis C Patients," Apr. 2, 2011, Press Release from Bristol-Myers Squibb).

In various embodiments, the subject leukocyte redirecting bispecific antibodies, ADCs and/or checkpoint inhibitor mAbs may be used in combination with one or more interferons, such as interferon-α, interferon-β, interferon-λ1, interferon-λ2, or interferon-λ3. When used with other agents, the interferon may be administered prior to, concurrently with, or after the other agent. When administered concurrently, the interferon may be either conjugated to or separate from the other agent.

Checkpoint Inhibitor Antibodies

Studies with checkpoint inhibitor antibodies for cancer therapy have generated unprecedented response rates in cancers previously thought to be resistant to cancer treatment (see, e.g., Ott & Bhardwaj, 2013, Frontiers in Immunology 4:346; Menzies & Long, 2013, Ther Adv Med Oncol 5:278-85; Pardoll, 2012, Nature Reviews Cancer 12:252-64; Mavilio & Lugli,). Therapy with antagonistic checkpoint blocking antibodies against immune system checkpoints such as CTLA4, PD1 and PD-L1 are one of the most promising new avenues of immunotherapy for cancer and other diseases. In contrast to the majority of anti-cancer agents, checkpoint inhibitors do not target tumor cells directly, but rather target lymphocyte receptors or their ligands in order to enhance the endogenous antitumor activity of the immune system. (Pardoll, 2012, Nature Reviews Cancer 12:252-264) Because such antibodies act primarily by regulating the immune response to diseased cells, tissues or pathogens, they may be used in combination with other therapeutic modalities, such as the subject leukocyte redirecting bispecific antibodies, ADCs and/or interferons to enhance the anti-tumor effect of such agents. Because checkpoint activation may also be associated with chronic infections (Nirschl & Drake, 2013, Clin Cancer Res 19:4917-24), such combination therapies may also be of use to treat infectious disease.

It is now clear that tumors can escape immune surveillance by co-opting certain immune-checkpoint pathways, particularly in T cells that are specific for tumor antigens (Pardoll, 2012, Nature Reviews Cancer 12:252-264). Because many such immune checkpoints are initiated by ligand-receptor interactions, they can be readily blocked by antibodies against the ligands and/or their receptors (Pardoll, 2012, Nature Reviews Cancer 12:252-264). Although checkpoint inhibitor antibodies against CTLA4, PD1 and PD-L1 are the most clinically advanced, other potential checkpoint antigens are known and may be used as the target of therapeutic antibodies, such as LAG3, B7-H3, B7-H4 and TIM3 (Pardoll, 2012, Nature Reviews Cancer 12:252-264).

Programmed cell death protein 1 (PD1, also known as CD279) encodes a cell surface membrane protein of the immunoglobulin superfamily, which is expressed in B cells and NK cells (Shinohara et al., 1995, Genomics 23:704-6; Blank et al., 2007, Cancer Immunol Immunother 56:739-45; Finger et al., 1997, Gene 197:177-87; Pardoll, 2012, Nature Reviews Cancer 12:252-264). The major role of PD1 is to limit the activity of T cells in peripheral tissues during inflammation in response to infection, as well as to limit autoimmunity (Pardoll, 2012, Nature Reviews Cancer 12:252-264). PD1 expression is induced in activated T cells and binding of PD1 to one of its endogenous ligants acts to inhibit T-cell activation by inhibiting stimulatory kinases (Pardoll, 2012, Nature Reviews Cancer 12:252-264). PD1 also acts to inhibit the TCR "stop signal" (Pardoll, 2012, Nature Reviews Cancer 12:252-264). PD1 is highly expressed on $T_{reg}$ cells and may increase their proliferation in the presence of ligand (Pardoll, 2012, Nature Reviews Cancer 12:252-264).

Anti-PD1 antibodies have been used for treatment of melanoma, non-small-cell lung cancer, bladder cancer, prostate cancer, colorectal cancer, head and neck cancer, triple-negative breast cancer, leukemia, lymphoma and renal cell cancer (Topalian et al., 2012, N Engl J Med 366:2443-54; Lipson et al., 2013, Clin Cancer Res 19:462-8; Berger et al., 2008, Clin Cancer Res 14:3044-51; Gildener-Leapman et al., 2013, Oral Oncol 49:1089-96; Menzies & Long, 2013, Ther Adv Med Oncol 5:278-85). Because PD1/PD-L1 and CTLA4 act by different pathways, it is possible that combination therapy with checkpoint inhibitor antibodies against each may provide an enhanced immune response.

Exemplary anti-PD1 antibodies include lambrolizumab (MK-3475, MERCK), nivolumab (BMS-936558, BRISTOL-MYERS SQUIBB), AMP-224 (MERCK), and pidilizumab (CT-011, CURETECH LTD.). Anti-PD1 antibodies are commercially available, for example from ABCAM® (AB137132), BIOLEGEND® (EH12.2H7, RMP1-14) and AFFYMETRIX EBIOSCIENCE (J105, J116, MIH4).

Programmed cell death 1 ligand 1 (PD-L1, also known as CD274 and B7-H1) is a ligand for PD1, found on activated T cells, B cells, myeloid cells and macrophages. Although there are two endogenous ligands for PD1-PD-L1 and PD-L2, anti-tumor therapies have focused on anti-PD-L1 antibodies. The complex of PD1 and PD-L1 inhibits proliferation of CD8+ T cells and reduces the immune response (Topalian et al., 2012, N Engl J Med 366:2443-54; Brahmer et al., 2012, N Eng J Med 366:2455-65). Anti-PD-L1 antibodies have been used for treatment of non-small cell lung cancer, melanoma, colorectal cancer, renal-cell cancer, pancreatic cancer, gastric cancer, ovarian cancer, breast cancer, and hematologic malignancies (Brahmer et al., N Eng J Med 366:2455-65; Ott et al., 2013, Clin Cancer Res 19:5300-9; Radvanyi et al., 2013, Clin Cancer Res 19:5541; Menzies & Long, 2013, Ther Adv Med Oncol 5:278-85; Berger et al., 2008, Clin Cancer Res 14:13044-51).

Exemplary anti-PD-L1 antibodies include MDX-1105 (MEDAREX), MEDI4736 (MEDIMMUNE) MPDL3280A (GENENTECH) and BMS-936559 (BRISTOL-MYERS SQUIBB). Anti-PD-L1 antibodies are also commercially available, for example from AFFYMETRIX EBIOSCIENCE (MIH1).

Cytotoxic T-lymphocyte antigen 4 (CTLA4, also known as CD152) is also a member of the immunoglobulin superfamily that is expressed exclusively on T-cells. CTLA4 acts to inhibit T-cell activation and is reported to inhibit helper T-cell activity and enhance regulatory T-cell immunosuppressive activity (Pardoll, 2012, Nature Reviews Cancer 12:252-264). Although the precise mechanism of action of CTL4-A remains under investigation, it has been suggested that it inhibits T cell activation by outcompeting CD28 in binding to CD80 and CD86, as well as actively delivering inhibitor signals to the T cell (Pardoll, 2012, Nature Reviews Cancer 12:252-264). Anti-CTL4A antibodies have been used in clinical trials for treatment of melanoma, prostate cancer, small cell lung cancer, non-small cell lung cancer (Robert & Ghiringhelli, 2009, Oncologist 14:848-61; Ott et al., 2013, Clin Cancer Res 19:5300; Weber, 2007, Oncologist 12:864-72; Wada et al., 2013, J Transl Med 11:89). A significant feature of anti-CTL4A is the kinetics of anti-tumor effect, with a lag period of up to 6 months after initial treatment required for physiologic response (Pardoll, 2012, Nature Reviews Cancer 12:252-264). In some cases, tumors may actually increase in size after treatment initiation, before a reduction is seen (Pardoll, 2012, Nature Reviews Cancer 12:252-264).

Exemplary anti-CTLA4 antibodies include ipilimumab (Bristol-Myers Squibb) and tremelimumab (PFIZER). Anti-PD1 antibodies are commercially available, for example from ABCAM® (AB134090), SINO BIOLOGICAL INC. (11159-H03H, 11159-H08H), and THERMO SCIENTIFIC PIERCE (PA5-29572, PA5-23967, PA5-26465, MA1-12205, MA1-35914). Ipilimumab has recently received FDA approval for treatment of metastatic melanoma (Wada et al., 2013, J Transl Med 11:89).

The person of ordinary skill will realize that methods of determining optimal dosages of checkpoint inhibitor antibodies to administer to a patient in need thereof, either alone or in combination with one or more other agents, may be determined by standard dose-response and toxicity studies that are well known in the art. In an exemplary embodiment, a checkpoint inhibitor antibody may preferably be administered at about 0.3-10 mg/kg, or the maximum tolerated dose, administered about every three weeks or about every six weeks. Alternatively, the checkpoint inhibitor antibody may be administered by an escalating dosage regimen including administering a first dosage at about 3 mg/kg, a second dosage at about 5 mg/kg, and a third dosage at about 9 mg/kg. Alternatively, the escalating dosage regimen includes administering a first dosage of checkpoint inhibitor antibody at about 5 mg/kg and a second dosage at about 9 mg/kg. Another stepwise escalating dosage regimen may include administering a first dosage of checkpoint inhibitor antibody about 3 mg/kg, a second dosage of about 3 mg/kg, a third dosage of about 5 mg/kg, a fourth dosage of about 5 mg/kg, and a fifth dosage of about 9 mg/kg. In another aspect, a stepwise escalating dosage regimen may include administering a first dosage of 5 mg/kg, a second dosage of 5 mg/kg, and a third dosage of 9 mg/kg. Exemplary reported dosages of checkpoint inhibitor mAbs include 3 mg/kg ipilimumab administered every three weeks for four doses; 10 mg/kg ipilimumab every three weeks for eight cycles; 10 mg/kg every three weeks for four cycles then every 12 weeks for a total of three years; 10 mg/kg MK-3475 every two or every three weeks; 2 mg/kg MK-3475 every three weeks; 15 mg/kg tremilimumab every three months; 0.1, 0.3, 1, 3 or 10 mg/kg nivolumab every two weeks for up to 96 weeks; 0.3, 1, 3, or 10 mg/kg BMS-936559 every two weeks for up to 96 weeks (Kyi & Postow, Oct. 23, 2013, FEBS Lett [Epub ahead of print]; Callahan & Wolchok, 2013, J Leukoc Biol 94:41-53).

These and other known agents that stimulate immune response to tumors and/or pathogens may be used in combination with leukocyte redirecting bispecific antibodies alone or in further combination with an interferon, such as interferon-α, and/or an antibody-drug conjugate for improved cancer therapy. Other known co-stimulatory pathway modulators that may be used in combination include, but are not limited to, agatolimod, belatacept, blinatumomab, CD40 ligand, anti-B7-1 antibody, anti-B7-2 antibody, anti-B7-H4 antibody, AG4263, eritoran, anti-OX40 antibody, ISF-154, and SGN-70; B7-1, B7-2, ICAM-1, ICAM-2, ICAM-3, CD48, LFA-3, CD30 ligand, CD40 ligand, heat stable antigen, B7h, OX40 ligand, LIGHT, CD70 and CD24.

In certain embodiments, anti-KIR antibodies may also be used in combination with leukocyte-redirecting bsAbs, interferons, ADCs and/or checkpoint inhibitor antibodies. NK cells mediate anti-tumor and anti-infectious agent activity by spontaneous cytotoxicity and by ADCC when activated by antibodies (Kohrt et al., 2013, Blood, [Epub ahead of print 12/10/13]). The degree of cytotoxic response is determined by a balance of inhibitory and activating signals received by the NK cells (Kohrt et al., 2013). The killer cell immunoglobulin-like receptor (KIR) mediates an inhibitory signal that decreases NK cell response. Anti-KIR antibodies, such as lirlumab (Innate Pharma) and IPH2101 (Innate Pharma) have demonstrated anti-tumor activity in multiple myeloma (Benson et al., 2012, Blood 120:4324-33). In vitro, anti-KIR antibodies prevent the tolerogenic interaction of NK cells with target cells and augments the NK cell cytotoxic response to tumor cells (Kohrt et al., 2013). In vivo, in combination with rituximab (anti-CD20), anti-KIR antibodies at a dose of 0.5 mg/kg induced enhanced NK cell-mediated, rituximab-dependent cytotoxicity against lymphoma tumors (Kohrt et al., 2013). Anti-KIR mAbs may be combined with ADCs, leukocyte-redirecting bsAbs, interferons and/or checkpoint inhibitor antibodies to potentiate cytotoxicity to tumor cells or pathogenic organisms.

General Antibody Techniques

Techniques for preparing monoclonal antibodies against virtually any target antigen are well known in the art. See, for example, Kohler and Milstein, *Nature* 256: 495 (1975), and Coligan et al. (eds.), CURRENT PROTOCOLS IN IMMUNOLOGY, VOL. 1, pages 2.5.1-2.6.7 (John Wiley & Sons 1991). Briefly, monoclonal antibodies can be obtained by injecting mice with a composition comprising an antigen, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

MAbs can be isolated and purified from hybridoma cultures by a variety of well-established techniques. Such isolation techniques include affinity chromatography with Protein-A Sepharose, size-exclusion chromatography, and ion-exchange chromatography. See, for example, Coligan at pages 2.7.1-2.7.12 and pages 2.9.1-2.9.3. Also, see Baines et al., "Purification of Immunoglobulin G (IgG)," in *METHODS IN MOLECULAR BIOLOGY*, VOL. 10, pages 79-104 (The Humana Press, Inc. 1992).

After the initial raising of antibodies to the immunogen, the antibodies can be sequenced and subsequently prepared by recombinant techniques. Humanization and chimerization of murine antibodies and antibody fragments are well known to those skilled in the art. The use of antibody components derived from humanized, chimeric or human antibodies obviates potential problems associated with the immunogenicity of murine constant regions.

Chimeric Antibodies

A chimeric antibody is a recombinant protein in which the variable regions of a human antibody have been replaced by the variable regions of, for example, a mouse antibody, including the complementarity-determining regions (CDRs) of the mouse antibody. Chimeric antibodies exhibit decreased immunogenicity and increased stability when administered to a subject. General techniques for cloning murine immunoglobulin variable domains are disclosed, for example, in Orlandi et al., *Proc. Nat'l Acad. Sci. USA* 86: 3833 (1989). Techniques for constructing chimeric antibodies are well known to those of skill in the art. As an example, Leung et al., *Hybridoma* 13:469 (1994), produced an LL2 chimera by combining DNA sequences encoding the $V_\kappa$ and $V_H$ domains of murine LL2, an anti-CD22 monoclonal antibody, with respective human κ and $IgG_1$ constant region domains.

Humanized Antibodies

Techniques for producing humanized MAbs are well known in the art (see, e.g., Jones et al., *Nature* 321: 522 (1986), Riechmann et al., *Nature* 332: 323 (1988), Verhoeyen et al., *Science* 239: 1534 (1988), Carter et al., *Proc. Nat'l Acad. Sci. USA* 89: 4285 (1992), Sandhu, *Crit. Rev. Biotech.* 12: 437 (1992), and Singer et al., *J. Immun.* 150: 2844 (1993)). A chimeric or murine monoclonal antibody may be humanized by transferring the mouse CDRs from the heavy and light variable chains of the mouse immunoglobulin into the corresponding variable domains of a human antibody. The mouse framework regions (FR) in the chimeric monoclonal antibody are also replaced with human FR sequences. As simply transferring mouse CDRs into human FRs often results in a reduction or even loss of antibody affinity, additional modification might be required in order to restore the original affinity of the murine antibody. This can be accomplished by the replacement of one or more human residues in the FR regions with their murine counterparts to obtain an antibody that possesses good binding affinity to its epitope. See, for example, Tempest et al., *Biotechnology* 9:266 (1991) and Verhoeyen et al., *Science* 239: 1534 (1988). Generally, those human FR amino acid residues that differ from their murine counterparts and are located close to or touching one or more CDR amino acid residues would be candidates for substitution.

Human Antibodies

Methods for producing fully human antibodies using either combinatorial approaches or transgenic animals transformed with human immunoglobulin loci are known in the art (e.g., Mancini et al., 2004, *New Microbiol.* 27:315-28; Conrad and Scheller, 2005, *Comb. Chem. High Throughput Screen.* 8:117-26; Brekke and Loset, 2003, *Curr. Opin. Phamacol.* 3:544-50). A fully human antibody also can be constructed by genetic or chromosomal transfection methods, as well as phage display technology, all of which are known in the art. See for example, McCafferty et al., *Nature* 348:552-553 (1990). Such fully human antibodies are expected to exhibit even fewer side effects than chimeric or humanized antibodies and to function in vivo as essentially endogenous human antibodies. In certain embodiments, the claimed methods and procedures may utilize human antibodies produced by such techniques.

In one alternative, the phage display technique may be used to generate human antibodies (e.g., Dantas-Barbosa et al., 2005, *Genet. Mol. Res.* 4:126-40). Human antibodies may be generated from normal humans or from humans that exhibit a particular disease state, such as cancer (Dantas-Barbosa et al., 2005). The advantage to constructing human antibodies from a diseased individual is that the circulating antibody repertoire may be biased towards antibodies against disease-associated antigens.

In one non-limiting example of this methodology, Dantas-Barbosa et al. (2005) constructed a phage display library of human Fab antibody fragments from osteosarcoma patients. Generally, total RNA was obtained from circulating blood lymphocytes (Id.). Recombinant Fab were cloned from the μ, γ and κ chain antibody repertoires and inserted into a phage display library (Id.). RNAs were converted to cDNAs and used to make Fab cDNA libraries using specific primers against the heavy and light chain immunoglobulin sequences (Marks et al., 1991, *J. Mol. Biol.* 222:581-97). Library construction was performed according to Andris-Widhopf et al. (2000, In: PHAGE DISPLAY LABORATORY MANUAL, Barbas et al. (eds), $1^{st}$ edition, Cold Spring Harbor Laboratory Press, Cold Spring Harbor, N.Y. pp. 9.1 to 9.22). The final Fab fragments were digested with restriction endonucleases and inserted into the bacteriophage genome to make the phage display library. Such libraries may be screened by standard phage display methods, as known in the art (see, e.g., Pasqualini and Ruoslahti, 1996, *Nature* 380:364-366; Pasqualini, 1999, *The Quart. J. Nucl. Med.* 43:159-162).

Phage display can be performed in a variety of formats, for their review, see e.g. Johnson and Chiswell, *Current Opinion in Structural Biology* 3:5564-571 (1993). Human antibodies may also be generated by in vitro activated B cells. See U.S. Pat. Nos. 5,567,610 and 5,229,275, incorporated herein by reference in their entirety. The skilled artisan will realize that these techniques are exemplary and any known method for making and screening human antibodies or antibody fragments may be utilized.

In another alternative, transgenic animals that have been genetically engineered to produce human antibodies may be used to generate antibodies against essentially any immunogenic target, using standard immunization protocols. Methods for obtaining human antibodies from transgenic mice are disclosed by Green et al., *Nature Genet.* 7:13 (1994), Lonberg et al., *Nature* 368:856 (1994), and Taylor et al., *Int. Immun.* 6:579 (1994). A non-limiting example of such a system is the XENOMOUSE® (e.g., Green et al., 1999, *J. Immunol. Methods* 231:11-23) from Abgenix (Fremont, Calif.). In the XENOMOUSE® and similar animals, the mouse antibody genes have been inactivated and replaced by functional human antibody genes, while the remainder of the mouse immune system remains intact.

The XENOMOUSE® was transformed with germline-configured YACs (yeast artificial chromosomes) that contained portions of the human IgH and Igkappa loci, including the majority of the variable region sequences, along accessory genes and regulatory sequences. The human variable region repertoire may be used to generate antibody producing B cells, which may be processed into hybridomas by known techniques. A XENOMOUSE® immunized with a target antigen will produce human antibodies by the normal immune response, which may be harvested and/or produced by standard techniques discussed above. A variety of strains of XENOMOUSE® are available, each of which is capable of producing a different class of antibody. Transgenically produced human antibodies have been shown to have therapeutic potential, while retaining the pharmacokinetic properties of normal human antibodies (Green et al., 1999). The skilled artisan will realize that the claimed compositions and methods are not limited to use of the XENOMOUSE® system but may utilize any transgenic animal that has been genetically engineered to produce human antibodies.

Antibody Cloning and Production

Various techniques, such as production of chimeric or humanized antibodies, may involve procedures of antibody cloning and construction. The antigen-binding Vκ (variable light chain) and $V_H$ (variable heavy chain) sequences for an antibody of interest may be obtained by a variety of molecular cloning procedures, such as RT-PCR, 5'-RACE, and cDNA library screening. The V genes of an antibody from a cell that expresses a murine antibody can be cloned by PCR amplification and sequenced. To confirm their authenticity, the cloned $V_L$ and $V_H$ genes can be expressed in cell culture as a chimeric Ab as described by Orlandi et al., (*Proc. Natl. Acad. Sci. USA*, 86: 3833 (1989)). Based on the V gene sequences, a humanized antibody can then be designed and constructed as described by Leung et al. (*Mol. Immunol.*, 32: 1413 (1995)).

cDNA can be prepared from any known hybridoma line or transfected cell line producing a murine antibody by general molecular cloning techniques (Sambrook et al., *Molecular Cloning, A laboratory manual*, $2^{nd}$ Ed (1989)). The Vκ sequence for the antibody may be amplified using the primers VK1BACK and VK1FOR (Orlandi et al., 1989) or the extended primer set described by Leung et al. (*BioTechniques*, 15: 286 (1993)). The $V_H$ sequences can be amplified using the primer pair VH1BACK/VH1FOR (Orlandi et al., 1989) or the primers annealing to the constant region of murine IgG described by Leung et al. (*Hybridoma*, 13:469 (1994)). Humanized V genes can be constructed by a combination of long oligonucleotide template syntheses and PCR amplification as described by Leung et al. (*Mol. Immunol.*, 32: 1413 (1995)).

PCR products for Vκ can be subcloned into a staging vector, such as a pBR327-based staging vector, VKpBR, that contains an Ig promoter, a signal peptide sequence and convenient restriction sites. PCR products for $V_H$ can be subcloned into a similar staging vector, such as the pBluescript-based VHpBS. Expression cassettes containing the Vκ and $V_H$ sequences together with the promoter and signal peptide sequences can be excised from VKpBR and VHpBS and ligated into appropriate expression vectors, such as pKh and pG1g, respectively (Leung et al., *Hybridoma*, 13:469 (1994)). The expression vectors can be co-transfected into an appropriate cell and supernatant fluids monitored for production of a chimeric, humanized or human antibody. Alternatively, the Vκ and $V_H$ expression cassettes can be excised and subcloned into a single expression vector, such as pdHL2, as described by Gillies et al. (*J. Immunol. Methods* 125:191 (1989) and also shown in Losman et al., *Cancer*, 80:2660 (1997)).

In an alternative embodiment, expression vectors may be transfected into host cells that have been pre-adapted for transfection, growth and expression in serum-free medium. Exemplary cell lines that may be used include the Sp/EEE, Sp/ESF and Sp/ESF-X cell lines (see, e.g., U.S. Pat. Nos. 7,531,327; 7,537,930 and 7,608,425; the Examples section of each of which is incorporated herein by reference). These exemplary cell lines are based on the Sp2/0 myeloma cell line, transfected with a mutant Bcl-EEE gene, exposed to methotrexate to amplify transfected gene sequences and pre-adapted to serum-free cell line for protein expression.

Antibody Fragments

Antibody fragments which recognize specific epitopes can be generated by known techniques. Antibody fragments are antigen binding portions of an antibody, such as F(ab')₂, Fab', F(ab)₂, Fab, Fv, scFv and the like. F(ab')₂ fragments can be produced by pepsin digestion of the antibody molecule and Fab' fragments can be generated by reducing disulfide bridges of the F(ab')₂ fragments. Alternatively, Fab' expression libraries can be constructed (Huse et al., 1989, *Science*, 246:1274-1281) to allow rapid and easy identification of monoclonal Fab' fragments with the desired specificity. F(ab)₂ fragments may be generated by papain digestion of an antibody.

A single chain Fv molecule (scFv) comprises a VL domain and a VH domain. The VL and VH domains associate to form a target binding site. These two domains are further covalently linked by a peptide linker (L). Methods for making scFv molecules and designing suitable peptide linkers are described in U.S. Pat. No. 4,704,692; U.S. Pat. No. 4,946,778; Raag and Whitlow, *FASEB* 9:73-80 (1995) and Bird and Walker, *TIBTECH*, 9: 132-137 (1991).

Techniques for producing single domain antibodies (DABs or VHH) are also known in the art, as disclosed for example in Cossins et al. (2006, *Prot Express Purif* 51:253-259), incorporated herein by reference. Single domain antibodies may be obtained, for example, from camels, alpacas or llamas by standard immunization techniques. (See, e.g., Muyldermans et al., *TIBS* 26:230-235, 2001; Yau et al., *J Immunol Methods* 281:161-75, 2003; Maass et al., *J Immunol Methods* 324:13-25, 2007). The VHH may have potent antigen-binding capacity and can interact with novel epitopes that are inaccessible to conventional VH-VL pairs. (Muyldermans et al., 2001). Alpaca serum IgG contains about 50% camelid heavy chain only IgG antibodies (HCAbs) (Maass et al., 2007). Alpacas may be immunized with known antigens, such as TNF-α, and VHHs can be isolated that bind to and neutralize the target antigen (Maass et al., 2007). PCR primers that amplify virtually all alpaca VHH coding sequences have been identified and may be used to construct alpaca VHH phage display libraries, which can be used for antibody fragment isolation by standard biopanning techniques well known in the art (Maass et al., 2007). In certain embodiments, anti-pancreatic cancer VHH antibody fragments may be utilized in the claimed compositions and methods.

An antibody fragment can be prepared by proteolytic hydrolysis of the full length antibody or by expression in *E. coli* or another host of the DNA coding for the fragment. An antibody fragment can be obtained by pepsin or papain digestion of full length antibodies by conventional methods. These methods are described, for example, by Goldenberg, U.S. Pat. Nos. 4,036,945 and 4,331,647 and references contained therein. Also, see Nisonoff et al., *Arch Biochem. Biophys.* 89: 230 (1960); Porter, *Biochem. J.* 73: 119 (1959), Edelman et al., in *METHODS IN ENZYMOLOGY* VOL. 1, page 422 (Academic Press 1967), and Coligan at pages 2.8.1-2.8.10 and 2.10.-2.10.4.

Antibody Allotypes

Immunogenicity of therapeutic antibodies is associated with increased risk of infusion reactions and decreased duration of therapeutic response (Baert et al., 2003, *N Engl J Med* 348:602-08). The extent to which therapeutic antibodies induce an immune response in the host may be determined in part by the allotype of the antibody (Stickler et al., 2011, *Genes and Immunity* 12:213-21). Antibody allotype is related to amino acid sequence variations at specific locations in the constant region sequences of the antibody. The allotypes of IgG antibodies containing a heavy chain γ-type constant region are designated as Gm allotypes (1976, *J Immunol* 117:1056-59).

For the common IgG1 human antibodies, the most prevalent allotype is G1m1 (Stickler et al., 2011, *Genes and Immunity* 12:213-21). However, the G1m3 allotype also occurs frequently in Caucasians (Stickler et al., 2011). It has been reported that G1m1 antibodies contain allotypic sequences that tend to induce an immune response when administered to non-G1m1 (nG1m1) recipients, such as G1m3 patients (Stickler et al., 2011). Non-G1m1 allotype antibodies are not as immunogenic when administered to G1m1 patients (Stickler et al., 2011).

The human G1m1 allotype comprises the amino acids aspartic acid at Kabat position 356 and leucine at Kabat position 358 in the CH3 sequence of the heavy chain IgG1. The nG1m1 allotype comprises the amino acids glutamic acid at Kabat position 356 and methionine at Kabat position 358. Both G1m1 and nG1m1 allotypes comprise a glutamic acid residue at Kabat position 357 and the allotypes are sometimes referred to as DEL and EEM allotypes. A non-limiting example of the heavy chain constant region sequences for G1m1 and nG1m1 allotype antibodies is shown for the exemplary antibodies rituximab (SEQ ID NO:85) and veltuzumab (SEQ ID NO:86).

Rituximab heavy chain variable region sequence
(SEQ ID NO: 85)
ASTKGPSVFPLAPSSKSTSGGTAALGCLVKDYFPEPVTVSWNSGALTSGVHTFPAVLQSS

GLYSLSSVVTVPSSSLGTQTYICNVNHKPSNTKVDKKAEPKSCDKTHTCPPCPAPELLGG

PSVFLFPPKPKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREPQVYTLPPSR

DELTKNQVSLTCLVKGFYPSDIAVEWESNGQPENNYKTTPPVLDSDGSFFLYSKLTVDK

SRWQQGNVFSCSVMHEALHNHYTQKSLSLSPGK

Veltuzumab heavy chain variable region
(SEQ ID NO: 86)
ASTKGPSVFPLAPSSKSTSGGTAALGCLVKDYFPEPVTVSWNSGALTSGVHTFPAVLQSS

GLYSLSSVVTVPSSSLGTQTYICNVNHKPSNTKVDKRVEPKSCDKTHTCPPCPAPELLGG

PSVFLFPPKPKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREPQVYTLPPSR

EEMTKNQVSLTCLVKGFYPSDIAVEWESNGQPENNYKTTPPVLDSDGSFFLYSKLTVDK

SRWQQGNVFSCSVMHEALHNHYTQKSLSLSPGK

Jefferis and Lefranc (2009, *mAbs* 1:1-7) reviewed sequence variations characteristic of IgG allotypes and their effect on immunogenicity. They reported that the G1m3 allotype is characterized by an arginine residue at Kabat position 214, compared to a lysine residue at Kabat 214 in the G1 m17 allotype. The nG1m1,2 allotype was characterized by glutamic acid at Kabat position 356, methionine at Kabat position 358 and alanine at Kabat position 431. The G1m1,2 allotype was characterized by aspartic acid at Kabat position 356, leucine at Kabat position 358 and glycine at Kabat position 431. In addition to heavy chain constant region sequence variants, Jefferis and Lefranc (2009) reported allotypic variants in the kappa light chain constant region, with the Km1 allotype characterized by valine at Kabat position 153 and leucine at Kabat position 191, the Km1,2 allotype by alanine at Kabat position 153 and leucine at Kabat position 191, and the Km3 allotype characterized by alanine at Kabat position 153 and valine at Kabat position 191.

With regard to therapeutic antibodies, veltuzumab and rituximab are, respectively, humanized and chimeric IgG1 antibodies against CD20, of use for therapy of a wide variety of hematological malignancies and/or autoimmune diseases. Table 1 compares the allotype sequences of rituximab vs. veltuzumab. As shown in Table 1, rituximab (G1m17,1) is a DEL allotype IgG1, with an additional sequence variation at Kabat position 214 (heavy chain CH1) of lysine in rituximab vs. arginine in veltuzumab. It has been reported that veltuzumab is less immunogenic in subjects than rituximab (see, e.g., Morchhauser et al., 2009, *J Clin Oncol* 27:3346-53; Goldenberg et al., 2009, *Blood* 113:1062-70; Robak & Robak, 2011, *BioDrugs* 25:13-25), an effect that has been attributed to the difference between humanized and chimeric antibodies. However, the difference in allotypes between the EEM and DEL allotypes likely also accounts for the lower immunogenicity of veltuzumab.

TABLE 1

Allotypes of Rituximab vs. Veltuzumab

| | Complete allotype | Heavy chain position and associated allotypes | | | |
| --- | --- | --- | --- | --- | --- |
| | | 214 (allotype) | | 356/358 (allotype) | 431 (allotype) |
| Rituximab | G1m17,1 | K | 17 | D/L 1 | A — |
| Veltuzumab | G1m3 | R | 3 | E/M — | A — |

In order to reduce the immunogenicity of therapeutic antibodies in individuals of nG1m1 genotype, it is desirable to select the allotype of the antibody to correspond to the G1m3 allotype, characterized by arginine at Kabat 214, and the nG1m1,2 null-allotype, characterized by glutamic acid at Kabat position 356, methionine at Kabat position 358 and alanine at Kabat position 431. Surprisingly, it was found that repeated subcutaneous administration of G1m3 antibodies over a long period of time did not result in a significant immune response. In alternative embodiments, the human IgG4 heavy chain in common with the G1m3 allotype has arginine at Kabat 214, glutamic acid at Kabat 356, methionine at Kabat 359 and alanine at Kabat 431. Since immunogenicity appears to relate at least in part to the residues at those locations, use of the human IgG4 heavy chain constant region sequence for therapeutic antibodies is also a preferred embodiment. Combinations of G1m3 IgG1 antibodies with IgG4 antibodies may also be of use for therapeutic administration.

Known Antibodies
Target Antigens and Exemplary Antibodies

In a preferred embodiment, antibodies are used that recognize and/or bind to antigens that are expressed at high levels on target cells and that are expressed predominantly or exclusively on diseased cells versus normal tissues. Exemplary antibodies of use for therapy of, for example, cancer include but are not limited to LL1 (anti-CD74), LL2 or RFB4 (anti-CD22), veltuzumab (hA20, anti-CD20), rituxumab (anti-CD20), obinutuzumab (GA101, anti- CD20), lambrolizumab (anti-PD1), nivolumab (anti-PD1), MK-3475 (anti-PD1), AMP-224 (anti-PD1), pidilizumab (anti-PD1), MDX-1105 (anti-PD-L1), MEDI4736 (anti-PD-L1), MPDL3280A (anti-PD-L1), BMS-936559 (anti-PD-L1), ipilimumab (anti-CTLA4), trevilizumab (anti-CTL4A), RS7 (anti-epithelial glycoprotein-1 (EGP-1, also known as TROP-2)), PAM4 or KC4 (both anti-mucin), MN-14 (anti-carcinoembryonic antigen (CEA, also known as CD66e or CEACAM5), MN-15 or MN-3 (anti-CEACAM6), Mu-9 (anti-colon-specific antigen-p), Immu 31 (an anti-alpha-fetoprotein), R1 (anti-IGF-1R), A19 (anti-CD19), TAG-72 (e.g., CC49), Tn, J591 or HuJ591 (anti-PSMA (prostate-specific membrane antigen)), AB-PG1-XG1-026 (anti-PSMA dimer), D2/B (anti-PSMA), G250 (an anti-carbonic anhydrase IX MAb), L243 (anti-HLA-DR) alemtuzumab (anti-CD52), bevacizumab (anti-VEGF), cetuximab (anti-EGFR), gemtuzumab (anti-CD33), ibritumomab tiuxetan (anti-CD20); panitumumab (anti-EGFR); tositumomab (anti-CD20); PAM4 (aka clivatuzumab, anti-mucin), BWA-3 (anti-histone H2A/H4), LG2-1 (anti-histone H3), MRA12 (anti-histone H1), PR1-1 (anti-histone H2B), LG11-2 (anti-histone H2B), LG2-2 (anti-histone H2B), and trastuzumab (anti-ErbB2). Such antibodies are known in the art (e.g., U.S. Pat. Nos. 5,686,072; 5,874,540; 6,107,090; 6,183,744; 6,306,393; 6,653,104; 6,730.300; 6,899,864; 6,926,893; 6,962,702; 7,074,403; 7,230,084; 7,238,785; 7,238,786; 7,256,004; 7,282,567; 7,300,655; 7,312,318; 7,585,491; 7,612,180; 7,642,239; and U.S. Patent Application Publ. No. 20050271671; 20060193865; 20060210475; 20070087001; the Examples section of each incorporated herein by reference.) Specific known antibodies of use include hPAM4 (U.S. Pat. No. 7,282,567), hA20 (U.S. Pat. No. 7,251,164), hA19 (U.S. Pat. No. 7,109,304), hIMMU-31 (U.S. Pat. No. 7,300,655), hLL1 (U.S. Pat. No. 7,312,318), hLL2 (U.S. Pat. No. 7,074,403), hMu-9 (U.S. Pat. No. 7,387,773), hL243 (U.S. Pat. No. 7,612,180), hMN-14 (U.S. Pat. No. 6,676,924), hMN-15 (U.S. Pat. No. 7,541,440), hR1 (U.S. patent application Ser. No. 12/772,645), hRS7 (U.S. Pat. No. 7,238,785), hMN-3 (U.S. Pat. No. 7,541,440), AB-PG1-XG1-026 (U.S. patent application Ser. No. 11/983, 372, deposited as ATCC PTA-4405 and PTA-4406) and D2/B (WO 2009/130575) the text of each recited patent or application is incorporated herein by reference with respect to the Figures and Examples sections.

Other useful antigens that may be targeted using the described conjugates include carbonic anhydrase IX, B7, CCL19, CCL21, CSAp, HER-2/neu, BrE3, CD1, CD1a, CD2, CD3, CD4, CD5, CD8, CD11A, CD14, CD15, CD16, CD18, CD19, CD20 (e.g., C2B8, hA20, 1F5 MAbs), CD21, CD22, CD23, CD25, CD29, CD30, CD32b, CD33, CD37, CD38, CD40, CD40L, CD44, CD45, CD46, CD52, CD54, CD55, CD59, CD64, CD67, CD70, CD74, CD79a, CD80, CD83, CD95, CD126, CD133, CD138, CD147, CD154, CEACAM5, CEACAM6, CTLA4, alpha-fetoprotein (AFP), VEGF (e.g., AVASTIN®, fibronectin splice variant), ED-B fibronectin (e.g., L19), EGP-1 (TROP-2), EGP-2 (e.g., 17-1A), EGF receptor (ErbB1) (e.g., ERBITUX®), ErbB2, ErbB3, Factor H, FHL-1, Flt-3, folate receptor, Ga 733, GRO-β, HMGB-1, hypoxia inducible factor (HIF), HM1.24, HER-2/neu, insulin-like growth factor (ILGF), IFN-γ, IFN-α, IFN-β, IFN-λ, IL-2R, IL-4R, IL-6R, IL-13R, IL-15R, IL-17R, IL-18R, IL-2, IL-6, IL-8, IL-12, IL-15, IL-17, IL-18, IL-25, IP-10, IGF-1R, Ia, HM1.24, gangliosides, HCG, the HLA-DR antigen to which L243 binds, CD66 antigens, i.e., CD66a-d or a combination thereof, MAGE, mCRP, MCP-1, MIP-1A, MIP-1B, macrophage migration-inhibitory factor (MIF), MUC1, MUC2, MUC3, MUC4, MUC5ac, placental growth factor (PlGF), PSA (prostate-specific antigen), PSMA, PAM4 antigen, PD1 receptor, NCA-95, NCA-90, A3, A33, Ep-CAM, KS-1, Le(y), mesothelin, S100, tenascin, TAC, Tn antigen, Thomas-Friedenreich antigens, tumor necrosis antigens, tumor angiogenesis antigens, TNF-α, TRAIL receptor (R1 and R2), TROP-2, VEGFR, RANTES, T101, as well as cancer stem cell antigens, complement factors C3, C3a, C3b, C5a, C5, and an oncogene product.

A comprehensive analysis of suitable antigen (Cluster Designation, or CD) targets on hematopoietic malignant cells, as shown by flow cytometry and which can be a guide to selecting suitable antibodies for immunotherapy, is Craig and Foon, *Blood* prepublished online Jan. 15, 2008; DOL 10.1182/blood-2007-11-120535.

The CD66 antigens consist of five different glycoproteins with similar structures, CD66a-e, encoded by the carcinoembryonic antigen (CEA) gene family members, BCG, CGM6, NCA, CGM1 and CEA, respectively. These CD66 antigens (e.g., CEACAM6) are expressed mainly in granulocytes, normal epithelial cells of the digestive tract and tumor cells of various tissues. Also included as suitable targets for cancers are cancer testis antigens, such as NY-ESO-1 (Theurillat et al., *Int. J. Cancer* 2007; 120(11):2411-7), as well as CD79a in myeloid leukemia (Kozlov et al., *Cancer Genet. Cytogenet.* 2005; 163(1):62-7) and also B-cell diseases, and CD79b for non-Hodgkin's lymphoma (Poison et al., *Blood* 110(2):616-623). A number of the aforementioned antigens are disclosed in U.S. Provisional Application Ser. No. 60/426,379, entitled "Use of Multi-specific, Non-covalent Complexes for Targeted Delivery of Therapeutics," filed Nov. 15, 2002. Cancer stem cells, which are ascribed to be more therapy-resistant precursor malignant cell populations (Hill and Perris, *J. Natl. Cancer Inst.* 2007; 99:1435-40), have antigens that can be targeted in certain cancer types, such as CD133 in prostate cancer (Maitland et al., *Ernst Schering Found. Sympos. Proc.* 2006; 5:155-79), non-small-cell lung cancer (Donnenberg et al., *J. Control Release* 2007; 122(3):385-91), and glioblastoma (Beier et al., *Cancer Res.* 2007; 67(9):4010-5), and CD44 in colorectal cancer (Dalerba er al., *Proc. Natl. Acad. Sci. USA* 2007; 104(24)10158-63), pancreatic cancer (Li et al., *Cancer Res.* 2007; 67(3):1030-7), and in head and neck squamous cell carcinoma (Prince et al., *Proc. Natl. Acad. Sci. USA* 2007; 104(3)973-8).

Anti-cancer antibodies have been demonstrated to bind to histones in some case. Kato et al. (1991, Hum Antibodies Hybridomas 2:94-101) reported that the lung cancer-specific human monoclonal antibody HB4C5 binds to histone H2B. Garzelli et al. (1994, Immunol Lett 39:277-82) observed that Epstein-Barr virus-transformed human B lymphocytes produce natural antibodies to histones. In certain embodiments, antibodies against histones may be of use in the subject combinations. Known anti-histone antibodies include, but are not limited to, BWA-3 (anti-histone H2A/H4), LG2-1 (anti-histone H3), MRA12 (anti-histone H1), PR1-1 (anti-histone H2B), LG11-2 (anti-histone H2B), and LG2-2 (anti-histone H2B) (see, e.g., Monestier et al., 1991, Eur J Immunol 21:1725-31; Monestier et al., 1993, Molec Immunol 30:1069-75).

For multiple myeloma therapy, suitable targeting antibodies have been described against, for example, CD38 and CD138 (Stevenson, *Mol Med* 2006; 12(11-12):345-346; Tassone et al., *Blood* 2004; 104(12):3688-96), CD74 (Stein et al., ibid.), CS1 (Tai et al., *Blood* 2008; 112(4):1329-37, and CD40 (Tai et al., 2005; *Cancer Res.* 65(13):5898-5906).

Macrophage migration inhibitory factor (MIF) is an important regulator of innate and adaptive immunity and apoptosis. It has been reported that CD74 is the endogenous receptor for MIF (Leng et al., 2003, *J Exp Med* 197:1467-76). The therapeutic effect of antagonistic anti-CD74 antibodies on MIF-mediated intracellular pathways may be of use for treatment of a broad range of disease states, such as cancers of the bladder, prostate, breast, lung, colon and chronic lymphocytic leukemia (e.g., Meyer-Siegler et al., 2004, *BMC Cancer* 12:34; Shachar & Haran, 2011, *Leuk Lymphoma* 52:1446-54). Milatuzumab (hLL1) is an exemplary anti-CD74 antibody of therapeutic use for treatment of MIF-mediated diseases.

An example of a most-preferred antibody/antigen pair is LL1, an anti-CD74 MAb (invariant chain, class II-specific chaperone, Ii) (see, e.g., U.S. Pat. Nos. 6,653,104; 7,312,318; the Examples section of each incorporated herein by reference). The CD74 antigen is highly expressed on B-cell lymphomas (including multiple myeloma) and leukemias, certain T-cell lymphomas, melanomas, colonic, lung, and renal cancers, glioblastomas, and certain other cancers (Ong et al., *Immunology* 98:296-302 (1999)). A review of the use of CD74 antibodies in cancer is contained in Stein et al., *Clin Cancer Res.* 2007 Sep. 15; 13(18 Pt 2):5556s-5563s, incorporated herein by reference. The diseases that are preferably treated with anti-CD74 antibodies include, but are not limited to, non-Hodgkin's lymphoma, Hodgkin's disease, melanoma, lung, renal, colonic cancers, glioblastome multiforme, histiocytomas, myeloid leukemias, and multiple myeloma.

In another preferred embodiment, the therapeutic combinations can be used against pathogens, since antibodies against pathogens are known. For example, antibodies and antibody fragments which specifically bind markers produced by or associated with infectious lesions, including viral, bacterial, fungal and parasitic infections, for example caused by pathogens such as bacteria, rickettsia, mycoplasma, protozoa, fungi, and viruses, and antigens and products associated with such microorganisms have been disclosed, inter alia, in Hansen et al., U.S. Pat. No. 3,927,193 and Goldenberg U.S. Pat. Nos. 4,331,647, 4,348,376, 4,361,544, 4,468,457, 4,444,744, 4,818,709 and 4,624,846, the Examples section of each incorporated herein by reference, and in Reichert and Dewitz (Nat Rev Drug Discovery 2006; 5:191-195). A review listing antibodies against infectious organisms (antitoxin and antiviral antibodies), as well as other targets, is contained in Casadevall, *Clin Immunol* 1999; 93(1):5-15, incorporated herein by reference. Commercially antibodies (e.g., KPL, Inc., Gaithersburg, Md.) are available against a wide variety of human pathogens including *Staphylococcus aureaus* (Cat. #011-90-05), *Streptococcus agalactiae* (Cat. #011-90-08), *Streptococcus pyogenes* (Cat. #01-90-07), *Helicobacter pylori* (Cat. #01-93-94), *Borrelia burgdorferi* (Cat. #05-97-91), *Escherichia coli* (Cat. #01-95-91; 01-95-96), *Legionella* spp. (Cat. #01-90-03), *Listeria* spp. (Cat. #01-90-90), *Vibrio cholera* (Cat. #01-90-50), *Shigella* spp. (Cat. #16-90-01), and *Campylobacter* spp. (Cat. #01-92-93).

In a preferred embodiment, the pathogens are selected from the group consisting of HIV virus, *Mycobacterium tuberculosis, Streptococcus agalactiae*, methicillin-resistant *Staphylococcus aureus, Legionella pneumophilia, Streptococcus pyogenes, Escherichia coli, Neisseria gonorrhoeae, Neisseria meningitidis, Pneumococcus, Cryptococcus neoformans, Histoplasma capsulatum*, Hemophilis influenzae B, *Treponema pallidum*, Lyme disease spirochetes, *Pseudomonas aeruginosa, Mycobacterium leprae, Brucella abortus*, rabies virus, influenza virus, cytomegalovirus, herpes simplex virus I, herpes simplex virus II, human serum parvo-like virus, respiratory syncytial virus, varicella-zoster virus, hepatitis B virus, hepatitis C virus, measles virus, adenovirus, human T-cell leukemia viruses, Epstein-Barr virus, murine leukemia virus, mumps virus, vesicular stomatitis virus, sindbis virus, lymphocytic choriomeningitis virus, wart virus, blue tongue virus, Sendai virus, feline leukemia virus, reovirus, polio virus, simian virus 40, mouse mammary tumor virus, dengue virus, rubella virus, West Nile virus, *Plasmodium falciparum, Plasmodium vivax, Toxoplasma gondii, Trypanosoma rangeli, Trypanosoma cruzi, Trypanosoma rhodesiensei, Trypanosoma brucei, Schistosoma mansoni, Schistosoma japonicum, Babesia bovis, Elmeria tenella, Onchocerca volvulus, Leishmania tropica, Trichinella spiralis, Theileria parva, Taenia hydatigena, Taenia ovis, Taenia saginata, Echinococcus granulosus, Mesocestoides corti, Mycoplasma arthritidis, M. hyorhinis, M. orale, M. arginini, Acholeplasma laidlawii, M. salivarium* and *M. pneumoniae*, as disclosed in U.S. Pat. No. 6,440,416, the Examples section of which is incorporated herein by reference.

In various embodiments, the claimed methods and compositions may utilize any of a variety of antibodies known in the art. Antibodies of use may be commercially obtained from a number of known sources. For example, a variety of antibody secreting hybridoma lines are available from the American Type Culture Collection (ATCC, Manassas, Va.). A large number of antibodies against various disease targets, including but not limited to tumor-associated antigens, have been deposited at the ATCC and/or have published variable region sequences and are available for use in the claimed methods and compositions. See, e.g., U.S. Pat. Nos. 7,312,318; 7,282,567; 7,151,164; 7,074,403; 7,060,802; 7,056,509; 7,049,060; 7,045,132; 7,041,803; 7,041,802; 7,041,293; 7,038,018; 7,037,498; 7,012,133; 7,001,598; 6,998,468; 6,994,976; 6,994,852; 6,989,241; 6,974,863; 6,965,018; 6,964,854; 6,962,981; 6,962,813; 6,956,107; 6,951,924; 6,949,244; 6,946,129; 6,943,020; 6,939,547; 6,921,645; 6,921,645; 6,921,533; 6,919,433; 6,919,078; 6,916,475; 6,905,681; 6,899,879; 6,893,625; 6,887,468; 6,887,466; 6,884,594; 6,881,405; 6,878,812; 6,875,580; 6,872,568; 6,867,006; 6,864,062; 6,861,511; 6,861,227; 6,861,226; 6,838,282; 6,835,549; 6,835,370; 6,824,780; 6,824,778; 6,812,206; 6,793,924; 6,783,758; 6,770,450; 6,767,711; 6,764,688; 6,764,681; 6,764,679; 6,743,898; 6,733,981; 6,730,307; 6,720,155; 6,716,966; 6,709,653; 6,693,176; 6,692,908; 6,689,607; 6,689,362; 6,689,355; 6,682,737; 6,682,736; 6,682,734; 6,673,344; 6,653,104; 6,652,852; 6,635,482; 6,630,144; 6,610,833; 6,610,294; 6,605,441; 6,605,279; 6,596,852; 6,592,868; 6,576,745; 6,572,856; 6,566,076; 6,562,618; 6,545,130; 6,544,749; 6,534,058; 6,528,625; 6,528,269; 6,521,227; 6,518,404; 6,511,665; 6,491,915; 6,488,930; 6,482,598; 6,482,408; 6,479,247; 6,468,531; 6,468,529; 6,465,173; 6,461,823; 6,458,356; 6,455,044; 6,455,040; 6,451,310; 6,444,206; 6,441,143; 6,432,404; 6,432,402; 6,419,928; 6,413,726; 6,406,694; 6,403,770; 6,403,091; 6,395,276; 6,395,274; 6,387,350; 6,383,759; 6,383,484; 6,376,654; 6,372,215; 6,359,126; 6,355,481; 6,355,444; 6,355,245; 6,355,244; 6,346,246; 6,344,198; 6,340,571; 6,340,459; 6,331,175; 6,306,393; 6,254,868; 6,187,287; 6,183,744; 6,129,914; 6,120,767; 6,096,289; 6,077,499; 5,922,302; 5,874,540; 5,814,440; 5,798,229; 5,789,554; 5,776,456; 5,736,119; 5,716,595; 5,677,136; 5,587,459; 5,443,953, 5,525,338, the Examples section of each of which is incorporated herein by reference. These are exemplary only and a wide variety of other antibodies and their hybridomas are known in the art. The skilled artisan will realize that antibody sequences or antibody-secreting hybridomas against almost any disease-associated antigen may be obtained by a simple search of the ATCC, NCBI and/or USPTO databases for antibodies against a selected disease-associated target of interest. The antigen binding domains of the cloned antibodies may be amplified, excised, ligated into an expression vector, transfected into an adapted host cell and used for protein production, using standard techniques well known in the art (see, e.g., U.S. Pat. Nos. 7,531,327; 7,537,930; 7,608,425 and 7,785,880, the Examples section of each of which is incorporated herein by reference).

In other embodiments, the antibody complexes bind to a MHC class I, MHC class II or accessory molecule, such as CD40, CD54, CD80 or CD86. The antibody complex also may bind to a leukocyte activation cytokine, or to a cytokine mediator, such as NF-κB.

In certain embodiments, one of the two different targets may be a cancer cell receptor or cancer-associated antigen, particularly one that is selected from the group consisting of B-cell lineage antigens (CD19, CD20, CD21, CD22, CD23, etc.), VEGF, VEGFR, EGFR, carcinoembryonic antigen (CEA), placental growth factor (PlGF), tenascin, HER-2/neu, EGP-1, EGP-2, CD25, CD30, CD33, CD38, CD40, CD45, CD52, CD74, CD80, CD138, NCA66, CEACAM1, CEACAM6 (carcinoembryonic antigen-related cellular adhesion molecule 6), MUC1, MUC2, MUC3, MUC4, MUC16, IL-6, α-fetoprotein (AFP), A3, CA125, colon-specific antigen-p (CSAp), folate receptor, HLA-DR, human chorionic gonadotropin (HCG), Ia, EL-2, insulin-like growth factor (IGF) and IGF receptor, KS-1, Le(y), MAGE, necrosis antigens, PAM-4, prostatic acid phosphatase (PAP), Prl, prostate specific antigen (PSA), prostate specific membrane antigen (PSMA), S100, T101, TAC, TAG72, TRAIL receptors, and carbonic anhydrase IX.

Other antibodies that may be used include antibodies against infectious disease agents, such as bacteria, viruses, mycoplasma or other pathogens. Many antibodies against such infectious agents are known in the art and any such known antibody may be used in the claimed methods and compositions. For example, antibodies against the gp120 glycoprotein antigen of human immunodeficiency virus (HIV-1) are known, and certain of such antibodies can have an immunoprotective role in humans. See, e.g., Rossi et al., *Proc. Natl. Acad. Sci. USA.* 86:8055-8058, 1990. Known anti-HIV antibodies include the anti-envelope antibody described by Johansson et al. (*AIDS,* 2006 Oct. 3; 20(15): 1911-5), as well as the anti-HIV antibodies described and sold by Polymun (Vienna, Austria), also described in U.S. Pat. No. 5,831,034, U.S. Pat. No. 5,911,989, and Vcelar et al., *AIDS* 2007; 21(16):2161-2170 and Joos et al., *Antimicrob. Agents Chemother.* 2006; 50(5):1773-9, all incorporated herein by reference.

Antibodies against malaria parasites can be directed against the sporozoite, merozoite, schizont and gametocyte stages. Monoclonal antibodies have been generated against sporozoites (cirumsporozoite antigen), and have been shown to neutralize sporozoites in vitro and in rodents (N. Yoshida et al., *Science* 207:71-73, 1980). Several groups have developed antibodies to *T. gondii*, the protozoan parasite involved in toxoplasmosis (Kasper et al., *J. Immunol.* 129:1694-1699, 1982; Id., 30:2407-2412, 1983). Antibodies have been developed against schistosomular surface antigens and have been found to act against schistosomulae in vivo or in vitro (Simpson et al., *Parasitology,* 83:163-177, 1981; Smith et al., *Parasitology,* 84:83-91, 1982: Gryzch et al., *J. Immunol.,* 129:2739-2743, 1982; Zodda et al., *J. Immunol.* 129:2326-2328, 1982; Dissous et al., *J. Immunol.,* 129:2232-2234, 1982)

*Trypanosoma cruzi* is the causative agent of Chagas' disease, and is transmitted by blood-sucking reduviid insects. An antibody has been generated that specifically inhibits the differentiation of one form of the parasite to another (epimastigote to trypomastigote stage) in vitro, and which reacts with a cell-surface glycoprotein; however, this antigen is absent from the mammalian (bloodstream) forms of the parasite (Sher et al., *Nature,* 300:639-640, 1982).

Anti-fungal antibodies are known in the art, such as anti-Sclerotinia antibody (U.S. Pat. No. 7,910,702); antiglucuronoxylomannan antibody (Zhong and Priofski, 1998, *Clin Diag Lab Immunol* 5:58-64); anti-*Candida* antibodies (Matthews and Burnie, 2001, *Curr Opin Investig Drugs* 2:472-76); and anti-glycosphingolipid antibodies (Toledo et al., 2010, *BMC Microbiol* 10:47).

Suitable antibodies have been developed against most of the microorganism (bacteria, viruses, protozoa, fungi, other parasites) responsible for the majority of infections in humans, and many have been used previously for in vitro diagnostic purposes. These antibodies, and newer antibodies that can be generated by conventional methods, are appropriate for use in the present invention.

Immunoconjugates

In certain embodiments, the antibodies or fragments thereof may be conjugated to one or more therapeutic or diagnostic agents. The therapeutic agents do not need to be the same but can be different, e.g. a drug and a radioisotope. For example, $^{131}I$ can be incorporated into a tyrosine of an antibody or fusion protein and a drug attached to an epsilon amino group of a lysine residue. Therapeutic and diagnostic agents also can be attached, for example to reduced SH groups and/or to carbohydrate side chains. Many methods for making covalent or non-covalent conjugates of therapeutic or diagnostic agents with antibodies or fusion proteins are known in the art and any such known method may be utilized.

A therapeutic or diagnostic agent can be attached at the hinge region of a reduced antibody component via disulfide bond formation. Alternatively, such agents can be attached using a heterobifunctional cross-linker, such as N-succinyl 3-(2-pyridyldithio)propionate (SPDP). Yu et al., *Int. J. Cancer* 56: 244 (1994). General techniques for such conjugation are well-known in the art. See, for example, Wong, CHEMISTRY OF PROTEIN CONJUGATION AND CROSS-LINKING (CRC Press 1991); Upeslacis et al., "Modification of Antibodies by Chemical Methods," in MONOCLONAL ANTIBODIES: PRINCIPLES AND APPLICATIONS, Birch et al. (eds.), pages 187-230 (Wiley-Liss, Inc. 1995); Price, "Production and Characterization of Synthetic Peptide-Derived Antibodies," in MONOCLONAL ANTIBODIES: PRODUCTION, ENGINEERING AND CLINICAL APPLICATION, Ritter et al. (eds.), pages 60-84 (Cambridge University Press 1995). Alternatively, the therapeutic or diagnostic agent can be conjugated via a carbohydrate moiety in the Fc region of the antibody. The carbohydrate group can be used to increase the loading of the same agent that is bound to a thiol group, or the carbohydrate moiety can be used to bind a different therapeutic or diagnostic agent.

Methods for conjugating peptides to antibody components via an antibody carbohydrate moiety are well-known to those of skill in the art. See, for example, Shih et al., *Int. J. Cancer* 41: 832 (1988); Shih et al., *Int. J. Cancer* 46: 1101 (1990); and Shih et al., U.S. Pat. No. 5,057,313, incorporated herein in their entirety by reference. The general method involves reacting an antibody component having an oxidized carbohydrate portion with a carrier polymer that has at least one free amine function. This reaction results in an initial Schiff base (imine) linkage, which can be stabilized by reduction to a secondary amine to form the final conjugate.

The Fc region may be absent if the antibody used as the antibody component of the immunoconjugate is an antibody fragment. However, it is possible to introduce a carbohydrate moiety into the light chain variable region of a full length antibody or antibody fragment. See, for example, Leung et al., *J. Immunol.* 154: 5919 (1995); Hansen et al., U.S. Pat. No. 5,443,953 (1995), Leung et al., U.S. Pat. No. 6,254,868, incorporated herein by reference in their entirety. The engineered carbohydrate moiety is used to attach the therapeutic or diagnostic agent.

In some embodiments, a chelating agent may be attached to an antibody, antibody fragment or fusion protein and used to chelate a therapeutic or diagnostic agent, such as a radionuclide. Exemplary chelators include but are not limited to DTPA (such as Mx-DTPA), DOTA, TETA, NETA or NOTA. Methods of conjugation and use of chelating agents to attach metals or other ligands to proteins are well known in the art (see, e.g., U.S. Pat. No. 7,563,433, the Examples section of which is incorporated herein by reference).

In certain embodiments, radioactive metals or paramagnetic ions may be attached to proteins or peptides by reaction with a reagent having a long tail, to which may be attached a multiplicity of chelating groups for binding ions. Such a tail can be a polymer such as a polylysine, polysaccharide, or other derivatized or derivatizable chains having pendant groups to which can be bound chelating groups such as, e.g., ethylenediaminetetraacetic acid (EDTA), diethylenetriaminepentaacetic acid (DTPA), porphyrins, polyamines, crown ethers, bis-thiosemicarbazones, polyoximes, and like groups known to be useful for this purpose.

Chelates may be directly linked to antibodies or peptides, for example as disclosed in U.S. Pat. No. 4,824,659, incorporated herein in its entirety by reference. Particularly useful metal-chelate combinations include 2-benzyl-DTPA and its monomethyl and cyclohexyl analogs, used with diagnostic isotopes in the general energy range of 60 to 4,000 keV, such as $^{125}$I, $^{131}$I, $^{123}$I, $^{124}$I, $^{62}$Cu, $^{64}$Cu, $^{18}$F, $^{111}$In, $^{67}$Ga, $^{68}$Ga, $^{99m}$Tc, $^{94m}$Tc, $^{11}$C, $^{13}$N, $^{15}$O, $^{76}$Br, for radioimaging. The same chelates, when complexed with non-radioactive metals, such as manganese, iron and gadolinium are useful for MRI. Macrocyclic chelates such as NOTA, DOTA, and TETA are of use with a variety of metals and radiometals, most particularly with radionuclides of gallium, yttrium and copper, respectively. Such metal-chelate complexes can be made very stable by tailoring the ring size to the metal of interest. Other ring-type chelates such as macrocyclic polyethers, which are of interest for stably binding nuclides, such as $^{223}$Ra for RAIT are encompassed.

More recently, methods of $^{18}$F-labeling of use in PET scanning techniques have been disclosed, for example by reaction of F-18 with a metal or other atom, such as aluminum. The $^{18}$F-Al conjugate may be complexed with chelating groups, such as DOTA, NOTA or NETA that are attached directly to antibodies or used to label targetable constructs in pre-targeting methods. Such F-18 labeling techniques are disclosed in U.S. Pat. No. 7,563,433, the Examples section of which is incorporated herein by reference.

Another exemplary immunoconjugate was disclosed in Johannson et al. (2006, AIDS 20:1911-15), in which a doxorubicin-conjugated P4/D10 (anti-gp120) antibody was found to be highly efficacious in treating cells infected with HIV.

Camptothecin Conjugates

In certain preferred embodiments, the immunoconjugate may comprise a camptothecin drug, such as SN-38. Camptothecin (CPT) and its derivatives are a class of potent antitumor agents. Irinotecan (also referred to as CPT-11) and topotecan are CPT analogs that are approved cancer therapeutics (Iyer and Ratain, *Cancer Chemother. Phamacol.* 42: S31-S43 (1998)). CPTs act by inhibiting topoisomerase I enzyme by stabilizing topoisomerase I-DNA complex (Liu, et al. in *The Camptothecins: Unfolding Their Anticancer Potential*, Liehr J. G., Giovanella, B. C. and Verschraegen (eds), NY Acad. Sci., NY 922:1-10 (2000)).

Preferred optimal dosing of immunoconjugates may include a dosage of between 3 mg/kg and 20 mg/kg, preferably given either weekly, twice weekly or every other week. The optimal dosing schedule may include treatment cycles of two consecutive weeks of therapy followed by one, two, three or four weeks of rest, or alternating weeks of therapy and rest, or one week of therapy followed by two, three or four weeks of rest, or three weeks of therapy followed by one, two, three or four weeks of rest, or four weeks of therapy followed by one, two, three or four weeks of rest, or five weeks of therapy followed by one, two, three, four or five weeks of rest, or administration once every two weeks, once every three weeks or once a month. Treatment may be extended for any number of cycles, preferably at least 2, at least 4, at least 6, at least 8, at least 10, at least 12, at least 14, or at least 16 cycles. The dosage may be up to 24 mg/kg. Exemplary dosages of use may include 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 22 mg/kg and 24 mg/kg. Preferred dosages are 4, 6, 8, 9, 10, 12, 14, 16 or 18 mg/kg. The person of ordinary skill will realize that a variety of factors, such as age, general health, specific organ function or weight, as well as effects of prior therapy on specific organ systems (e.g., bone marrow) may be considered in selecting an optimal dosage of immunoconjugate, and that the dosage and/or frequency of administration may be increased or decreased during the course of therapy. The dosage may be repeated as needed, with evidence of tumor shrinkage observed after as few as 4 to 8 doses. The optimized dosages and schedules of administration disclosed herein show unexpected superior efficacy and reduced toxicity in human subjects, which could not have been predicted from animal model studies. Surprisingly, the superior efficacy allows treatment of tumors that were previously found to be resistant to one or more standard anti-cancer therapies, including the parental compound, CPT-11, from which SN-38 is derived in vivo.

An exemplary preferred embodiment is directed to a conjugate of a drug derivative and an antibody of the general formula 1,

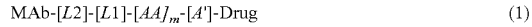

MAb-[L2]-[L1]-[AA]$_m$-[A']-Drug    (1)

where MAb is a disease-targeting antibody; L2 is a component of the cross-linker comprising an antibody-coupling moiety and one or more of acetylene (or azide) groups; L1 comprises a defined PEG with azide (or acetylene) at one end, complementary to the acetylene (or azide) moiety in L2, and a reactive group such as carboxylic acid or hydroxyl group at the other end; AA is an L-amino acid; m is an integer with values of 0, 1, 2, 3, or 4; and A' is an additional spacer, selected from the group of ethanolamine, 4-hydroxybenzyl alcohol, 4-aminobenzyl alcohol, or substituted or unsubstituted ethylenediamine. The L amino acids of 'AA' are selected from alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. If the A' group contains hydroxyl, it is linked to the hydroxyl group or amino group of the drug in the form of a carbonate or carbamate, respectively.

In a preferred embodiment of formula 1, A' is a substituted ethanolamine derived from an L-amino acid, wherein the carboxylic acid group of the amino acid is replaced by a hydroxymethyl moiety. A' may be derived from any one of the following L-amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine.

In an example of the conjugate of the preferred embodiment of formula 1, m is 0, A' is L-valinol, and the drug is exemplified by SN-38. The resultant structure is shown in formula 2.

group on the side chain of lysine intact, and the N-terminus is coupled to the carboxyl group on the defined PEG with azide (or acetylene) at the other end. The hydroxyl group of valinol is then attached to the 20-chloroformate derivative of 10-hydroxy-protected SN-38, and this intermediate is coupled to an L2 component carrying the antibody-binding moiety as well as the complementary acetylene (or azide) group involved in the click cycloaddition chemistry. Finally, removal of protecting groups at both lysine side chain and SN-38 gives the product of this example, shown in formula 2.

In another preferred embodiment, A' of the general formula 2 is A-OH, whereby A-OH is a collapsible moiety such as 4-aminobenzyl alcohol or a substituted 4-aminobenzyl alcohol substituted with a $C_1$-$C_{10}$ alkyl group at the benzylic position, and the latter, via its amino group, is attached to an L-amino acid or a polypeptide comprising up to four L-amino acid moieties; wherein the N-terminus is attached to a cross-linker terminating in the antibody-binding group.

An example of a preferred embodiment is given below, wherein the A-OH embodiment of A' of general formula (I) is derived from substituted 4-aminobenzyl alcohol, and 'AA' is comprised of a single L-amino acid with m=1 in the general formula (I), and the drug is exemplified with SN-38.

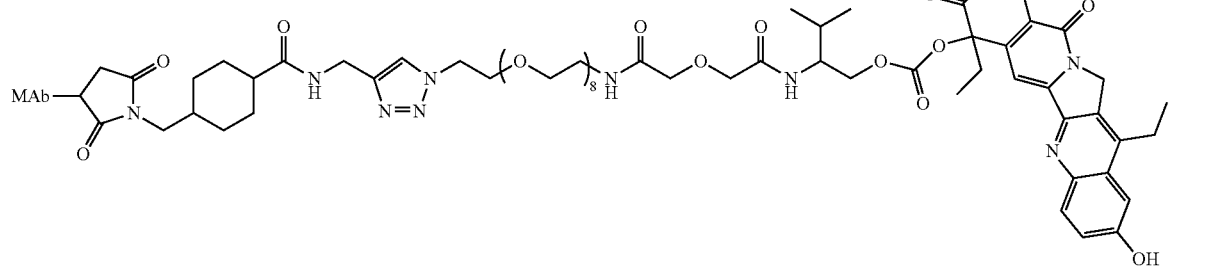

(2)

In another example of the conjugate of the preferred embodiment of formula 1, m is 1 and represented by a derivatized L-lysine, A' is L-valinol, and the drug is exemplified by SN-38. The structure is shown in formula 3.

The structure is represented below (formula 2, referred to as MAb-CLX-SN-38). Single amino acid of AA is selected from any one of the following L-amino acids: alanine, arginine, asparagine, aspartic acid, cysteine, glutamine, glu-

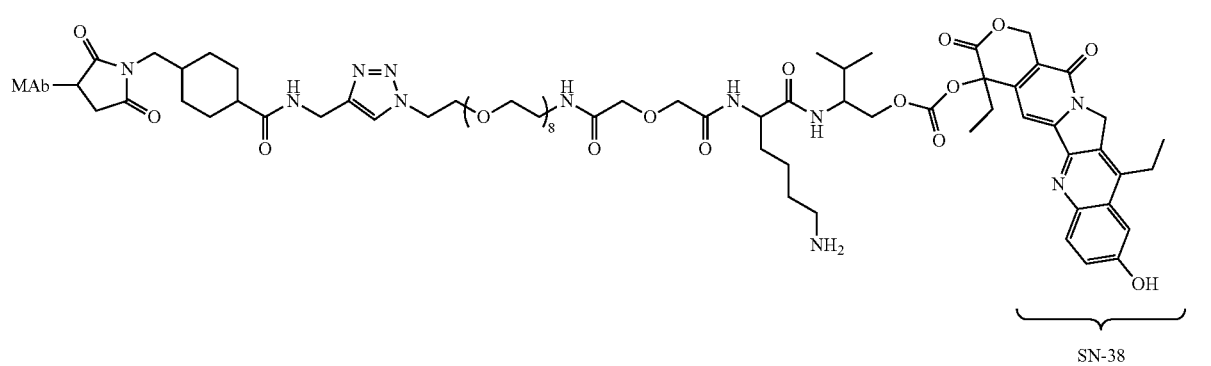

(3)

SN-38

In this embodiment, an amide bond is first formed between the carboxylic acid of an amino acid such as lysine and the amino group of valinol, using orthogonal protecting groups for the lysine amino groups. The protecting group on the N-terminus of lysine is removed, keeping the protecting tamic acid, glycine, histidine, isoleucine, leucine, lysine, methionine, phenylalanine, proline, serine, threonine, tryptophan, tyrosine, and valine. The substituent R on 4-aminobenzyl alcohol moiety (A-OH embodiment of A') is hydrogen or an alkyl group selected from $C_1$-$C_{10}$ alkyl groups.

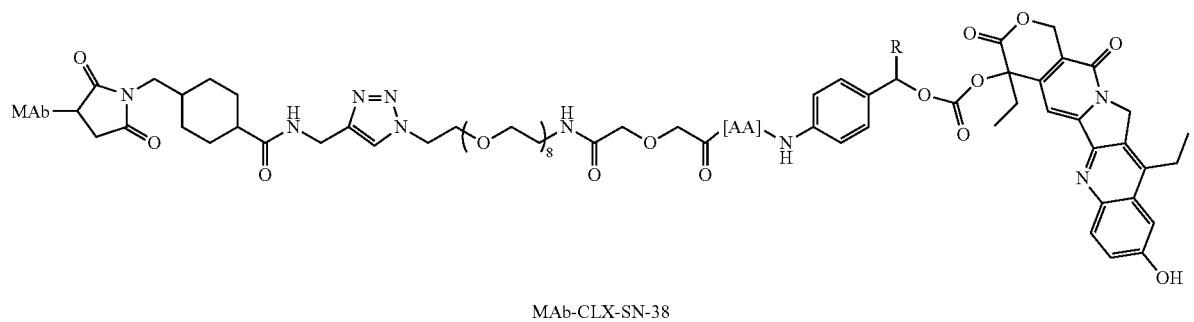

MAb-CLX-SN-38

(4)

An embodiment of MAb-CLX-SN-38 of formula 4, wherein the single amino acid AA is L-lysine and R=H, and the drug is exemplified by SN-38 (formula 5; referred to as MAb-CL2A-SN-38). Methods of preparing CL2A-SN-38 and for making and using antibody conjugates thereof are known in the art (see, e.g., U.S. Pat. Nos. 7,999,083 and 8,080,250, the Examples sections of each incorporated herein by reference).

Pro-2-Pyrrolinodoxorubicin Conjugates

The compound 2-pyrrolinodoxorubicin was described first in 1996 by Schally's group, who later used it for conjugating to a number of receptor-targeted peptides for preclinical explorations (Nagy et al., 1996, Proc Natl Aad Sci USA 93:7269-73; Nagy et al., 1996, Proc Natl Acad Sci USA 96:2464-29). This is a derivative of doxorubicin, with the daunosamine nitrogen incorporated into a 5-membered

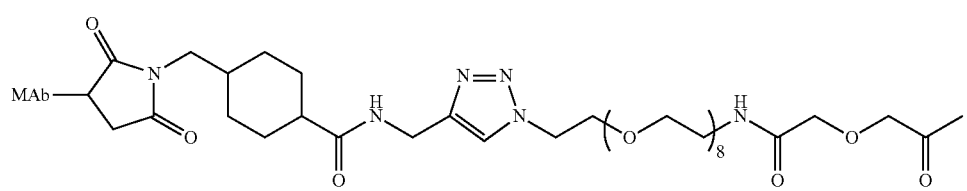

(5)

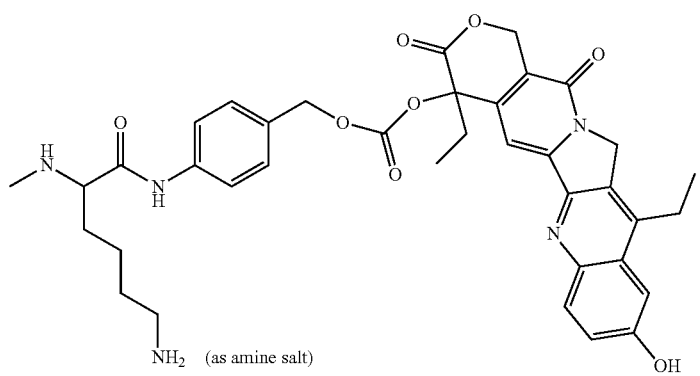

MAb-CL2A-SN-38 enamine, making it a highly potent alkylating agent, with cytotoxicity 500-1000 times that of doxorubicin. The drug's ultratoxicity necessitates special handling in isolators, for safety. A prodrug form of the same is N-(4,4-diacetoxybutyl) doxorubicin, which is converted to 2-pyrrolinodoxorubicin in vivo. Pro-2-pyrrolinodoxorubicin (Pro-2-P-Dox) may be prepared as disclosed herein and conjugated to antibodies or antibody fragments for use in ADC therapy.

The scheme below shows the structures of Dox, 2-PDox, Pro-2-P-Dox (P2PDox), and activated Pro-2-P-Dox. For coupling to IgG, Pro-2-P-Dox may be activated with SMCC-hydrazide, a procedure that introduces acid-labile hydrazone as well as the maleimide group, the latter for conjugation to thiols of mildly reduced antibody.

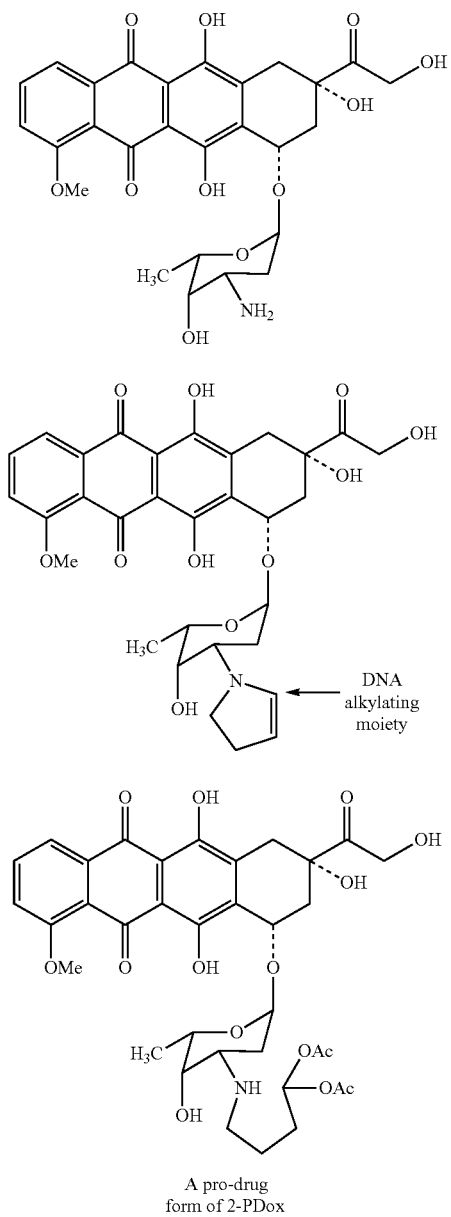

A pro-drug form of 2-PDox

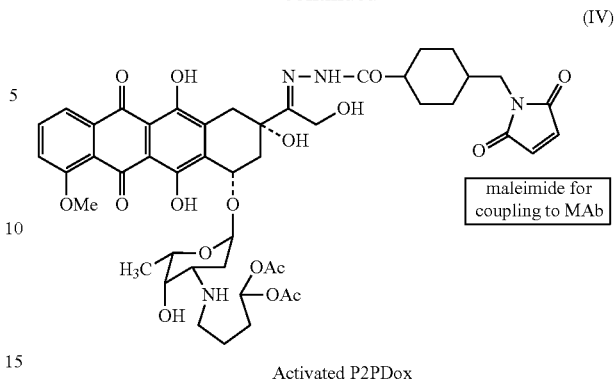

Activated P2PDox

Most of the ADCs currently being clinically examined incorporate tubulin-acting, ultratoxic, maytansinoids and auristatins, which are cell-cycle-phase-specific. Anecdotally, except for trastuzumab-DM1, these ADCs appear to exhibit a relatively narrow therapeutic index clinically in solid cancers. A DNA-alkylating agent, such as 2-PDox, is cell-cycle-phase-nonspecific and should provide an improved therapeutic index. Preliminary studies (not shown) in 2 aggressive xenograft models of pancreatic and gastric cancers showed the hRS7-6 conjugate to be very active at low and safe doses (e.g., 2.25 mg/kg protein dose, or 0.064 mg/kg of drug dose), leading to complete regressions.

Reductive alkylation of doxorubicin with 4,4-diacetoxybutyraldehyde, using sodium cyanoborohydride yields P2PDox (scheme below). Diacetoxylation of commercially available 4-benzyloxybutyraldehyde, followed by hydrogenolysis and oxidation furnished the aldehyde, which was reductively coupled to doxorubicin to obtain P2PDox. The latter was activated with SMCC-hydrazide.

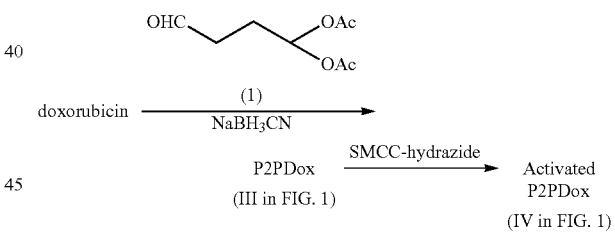

The conjugate preparation mixed mildly reducing interchain disulfides of IgG with TCEP in PBS, followed by coupling to a 10-fold excess of activated P2PDox. The conjugates were purified on centrifuged SEC on SEPHADEX® equilibrated in 25 mM histidine, pH 7, followed by passage over a hydrophobic column. The products were formulated with trehalose and Tween 80, and lyophilized. The conjugated product, with a typical substitution of 6-7 drug/IgG, eluted as a single peak by size-exclusion HPLC, and contained typically <1% of unconjugated free drug by reversed-phase HPLC.

The person of ordinary skill will realize that P2PDox may be conjugated to any known antibody or fragment thereof, for use in ADC treatment of tumors and/or infectious disease, in combination with immunomodulating agents discussed herein.

Bispecific Antibodies

In various embodiments, the subject combination therapy may utilize one or more bispecific antibodies (bsAbs), such as a leukocyte redirecting bsAb. While the section below discusses a preferred embodiment, in which the bsAb is made as a DOCK-AND-LOCK™ (DNL™) construct, numerous other types of bsAbs are known in the art and may be used within the scope of the claimed combination therapy. A bispecific antibody as used herein is an antibody that contains binding sites for two different antigens, or two different epitopes on the same antigen. An antibody that can only bind to a single epitope on a single antigen is monospecific, regardless of the number of antigen-binding sites on the antibody molecule.

As discussed in the Background section, early attempts at bispecific antibody construction either utilized chemical cross-linking or hybrid hybridomas or quadromas to join the two halves of two different antibodies together (e.g., Staerz et al., 1985, Nature 314:628-31; Milstein and Cuello, Nature 1983; 305:537-540; Karpovsky et al., 1984, J Exp Med 160:1686-701). Although the techniques work to make bsAbs, various production problems made use of such complexes difficult, such as the production of mixed populations containing different combinations of antigen-binding sites, difficulty in protein expression, the need to purify the bsAb of interest, low yields, expense of production, etc.

More recent approaches have utilized genetically engineered constructs that are capable of producing homogeneous products of single bsAbs, without the need for extensive purification to remove unwanted byproducts. Such constructs have included tandem scFv, diabodies, tandem diabodies, dual variable domain antibodies and heterodimerization using a motif such as Ch1/Ck domain or DNL™ (Chames & Baty, 2009, Curr Opin Drug Discov Devel 12:276-83; Chames & Baty, mAbs 1:539-47).

Triomabs is a variation on the quadroma approach that use a combination of mouse IgG2a and rat IgG2b antibodies to preferentially produce the recombinant antibody, compared to the random pairing typically seen in rat/rat or mouse/mouse quadromas (Chames & Baty, mAbs 1:539-47). An anti-CD3×anti-EpCAM bsAb (catumaxomab) created by this technique was able to efficiently recruit macrophages and NK cells and to activate T cells (Chames & Baty, mAbs 1:539-47). As discussed above, catumaxomab has been approved in Europe for treatment of malignant ascites in patients with EpCAM positive carcinomas (Chames & Baty, mAbs 1:539-47). Surprisingly, the recombinant bsAb was reported to induce only moderate anti-mouse and anti-rat responses in humans (Chames & Baty, mAbs 1:539-47), probably due at least in part to the i.p. route of administration for ascites. Ertumaxomab is another triomab targeting HER2, which may be of use for metastatic breast cancer. Bi20 is another triomab that targets CD20. In vitro, Bi20 exibited efficient lyis of B cells from CLL patients (Chames & Baty, mAbs 1:539-47).

BITE® refers to tandem scFvs that are joined by a short peptide linker (Chames & Baty, mAbs 1:539-47). Blinatumomab is an anti-CD19×anti-CD3 BITE® with reported efficacy in hematologic cancers, such as non-Hodgkin's lymphoma and ALL, at very low concentrations (Nagorsen et al., 2009, Leukemia & Lymphoma 50:886-91; Chames & Baty, mAbs 1:539-47; Topp et al., 2012, Blood 120:5185-87; Bargou et al., 2008, Science 321:974-77). Another BITE® with specificity for EpCAM has been used in gastrointestinal, ovarian, colorectal and lung cancer (Amann et al., 2009, J Immunother 32:452-64; Chames & Baty, mAbs 1:539-47). Another BITE® (MEDI-565) targeted to CEACAM5 has been proposed for use in melanoma, colorectal, lung, pancreatic, stomach, ovarian, uterine, and breast cancers (Sanders et al., 1994, J Pathol 172:343-8). BITE® has been reported to exhibit anti-tumor activity at picomolar or even femtomolar concentrations (Chames & Baty, mAbs 1:539-47).

Another method of bsAb formation, involving assembly of two heavy and two light chains derived from two different pre-existing antibodies, is based on a knobs-into-holes approach that facilitates heterodimer formation and prevents homodimer formation (Schaefer et al., 2011, Proc Natl. Acad Sci USA 108:11187-92). The "CrossMab" technique further involves the exchange of heavy and light chain domains within the Fab of one half of the bispecific antibody, making the two arms so different that light-heavy chain mispairing can not occur (Schaefer et al., 2011). The knobs-into-holes approach introduces amino acids with bulky side chains into the CH3 domain of one heavy chain that fit into appropriately designed cavities in the CH3 domain of the other heavy chain. The combination of approaches prevents mis-match of both heavy chain to heavy chain and heavy chain to light chain interactions, resulting in primarily a single product. The initial CrossMab, generated against angiopoietin-2 (Ang-2) and VEGF-A, exhibited binding characteristics comparable to the parent mAbs, with potent anti-angiogenic and anti-tumoral activity (Schaefer et al., 2011, Proc Natl. Acad Sci USA 108:11187-92; Kienast et al., Clin Cancer Res, Oct. 25, 2013, Epub ahead of print).

In addition to the DART™ technology discussed above, other approaches to bsAb production have included tetravalent IgG-scFv fusions (Dong et al., 2011, MAbs 3:273-88); dual-acting Fab (DAF) antibodies (Bostrom et al., 2009, Science 323:1610-14); Igg-like dual-variable domain antibodies (DVD-Ig) (Wu et al., 2007, Nat Biotechnol 25:1290-97); and use of dynamic exchange between IgG4 molecules (van der Neut Kolfschoten et al., 2007, Science 317:1554-57). Although the DNL™ technology discussed below is preferred for formation of leukocyte redirecting bsAbs, the person of ordinary skill will realize that other types of bsAbs may be used in the claimed methods and compositions.

DOCK-AND-LOCK™ (DNL™)

In preferred embodiments, a bispecific antibody, either alone or else complexed to one or more effectors such as cytokines, is formed as a DOCK-AND-LOCK™ (DNL™) complex (see, e.g., U.S. Pat. Nos. 7,521,056; 7,527,787; 7,534,866; 7,550,143; 7,666,400; 7,901,680; 7,906,118; 7,981,398; 8,003,111, the Examples section of each of which is incorporated herein by reference.) Generally, the technique takes advantage of the specific and high-affinity binding interactions that occur between a dimerization and docking domain (DDD) sequence of the regulatory (R) subunits of cAMP-dependent protein kinase (PKA) and an anchor domain (AD) sequence derived from any of a variety of AKAP proteins (Baillie et al., *FEBS Letters.* 2005; 579: 3264. Wong and Scott, *Nat. Rev. Mol. Cell. Biol.* 2004; 5: 959). The DDD and AD peptides may be attached to any protein, peptide or other molecule. Because the DDD sequences spontaneously dimerize and bind to the AD sequence, the technique allows the formation of complexes between any selected molecules that may be attached to DDD or AD sequences.

Although the standard DNL™ complex comprises a trimer with two DDD-linked molecules attached to one AD-linked molecule, variations in complex structure allow the formation of dimers, trimers, tetramers, pentamers, hexamers and other multimers. In some embodiments, the DNL™ complex may comprise two or more antibodies, antibody fragments or fusion proteins which bind to the same antigenic determinant or to two or more different antigens. The DNL™ complex may also comprise one or more other effectors, such as proteins, peptides, immunomodulators, cytokines, interleukins, interferons, binding proteins, peptide ligands, carrier proteins, toxins, ribonucleases such as onconase, inhibitory oligonucleotides such as siRNA, antigens or xenoantigens, polymers such as PEG, enzymes, therapeutic agents, hormones, cytotoxic agents, anti-angiogenic agents, pro-apoptotic agents or any other molecule or aggregate.

PKA, which plays a central role in one of the best studied signal transduction pathways triggered by the binding of the second messenger cAMP to the R subunits, was first isolated from rabbit skeletal muscle in 1968 (Walsh et al., *J. Biol. Chem.* 1968; 243:3763). The structure of the holoenzyme consists of two catalytic subunits held in an inactive form by the R subunits (Taylor, *J. Biol. Chem.* 1989; 264:8443). Isozymes of PKA are found with two types of R subunits (R1 and RII), and each type has $\alpha$ and $\beta$ isoforms (Scott, *Pharmacol. Ther.* 1991; 50:123). Thus, the four isoforms of PKA regulatory subunits are RI$\alpha$, RI$\beta$, RII$\alpha$ and RII$\beta$, each of which comprises a DDD moiety amino acid sequence. The R subunits have been isolated only as stable dimers and the dimerization domain has been shown to consist of the first 44 amino-terminal residues of RII$\alpha$ (Newlon et al., *Nat. Struct. Biol.* 1999; 6:222). As discussed below, similar portions of the amino acid sequences of other regulatory subunits are involved in dimerization and docking, each located near the N-terminal end of the regulatory subunit. Binding of cAMP to the R subunits leads to the release of active catalytic subunits for a broad spectrum of serine/threonine kinase activities, which are oriented toward selected substrates through the compartmentalization of PKA via its docking with AKAPs (Scott et al., *J. Biol. Chem.* 1990; 265; 21561)

Since the first AKAP, microtubule-associated protein-2, was characterized in 1984 (Lohmann et al., *Proc. Natl. Acad. Sci. USA* 1984; 81:6723), more than 50 AKAPs that localize to various sub-cellular sites, including plasma membrane, actin cytoskeleton, nucleus, mitochondria, and endoplasmic reticulum, have been identified with diverse structures in species ranging from yeast to humans (Wong and Scott, *Nat. Rev. Mol. Cell. Biol.* 2004; 5:959). The AD of AKAPs for PKA is an amphipathic helix of 14-18 residues (Can et al., *J. Biol. Chem.* 1991; 266:14188). The amino acid sequences of the AD are varied among individual AKAPs, with the binding affinities reported for RII dimers ranging from 2 to 90 nM (Alto et al., *Proc. Natl. Acad. Sci. USA* 2003; 100:4445). AKAPs will only bind to dimeric R subunits. For human RII$\alpha$, the AD binds to a hydrophobic surface formed by the 23 amino-terminal residues (Colledge and Scott, *Trends Cell Biol.* 1999; 6:216). Thus, the dimerization domain and AKAP binding domain of human RII$\alpha$ are both located within the same N-terminal 44 amino acid sequence (Newlon et al., *Nat. Struct. Biol.* 1999; 6:222; Newlon et al., *EMBO J.* 2001; 20:1651), which is termed the DDD herein.

We have developed a platform technology to utilize the DDD of human PKA regulatory subunits and the AD of AKAP as an excellent pair of linker modules for docking any two entities, referred to hereafter as A and B, into a noncovalent complex, which could be further locked into a DNL™ complex through the introduction of cysteine residues into both the DDD and AD at strategic positions to facilitate the formation of disulfide bonds. The general methodology of the approach is as follows. Entity A is constructed by linking a DDD sequence to a precursor of A, resulting in a first component hereafter referred to as a. Because the DDD sequence would effect the spontaneous formation of a dimer, A would thus be composed of $a_2$. Entity B is constructed by linking an AD sequence to a precursor of B, resulting in a second component hereafter referred to as b. The dimeric motif of DDD contained in $a_2$ will create a docking site for binding to the AD sequence contained in b, thus facilitating a ready association of $a_2$ and b to form a binary, trimeric complex composed of $a_2b$. This binding event is stabilized with a subsequent reaction to covalently secure the two entities via disulfide bridges, which occurs very efficiently based on the principle of effective local concentration because the initial binding interactions should bring the reactive thiol groups placed onto both the DDD and AD into proximity (Chmura et al., *Proc. Natl. Acad. Sci. USA* 2001; 98:8480) to ligate site-specifically. Using various combinations of linkers, adaptor modules and precursors, a wide variety of DNL™ constructs of different stoichiometry may be produced and used (see, e.g., U.S. Pat. Nos. 7,550,143; 7,521,056; 7,534,866; 7,527,787 and 7,666,400.)

By attaching the DDD and AD away from the functional groups of the two precursors, such site-specific ligations are also expected to preserve the original activities of the two precursors. This approach is modular in nature and potentially can be applied to link, site-specifically and covalently, a wide range of substances, including peptides, proteins, antibodies, antibody fragments, and other effector moieties with a wide range of activities. Utilizing the fusion protein method of constructing AD and DDD conjugated effectors described in the Examples below, virtually any protein or peptide may be incorporated into a DNL™ construct. However, the technique is not limiting and other methods of conjugation may be utilized.

A variety of methods are known for making fusion proteins, including nucleic acid synthesis, hybridization and/or amplification to produce a synthetic double-stranded nucleic acid encoding a fusion protein of interest. Such double-stranded nucleic acids may be inserted into expression vectors for fusion protein production by standard molecular biology techniques (see, e.g. Sambrook et al., MOLECULAR CLONING, A LABORATORY MANUAL, $2^{nd}$Ed, 1989). In such preferred embodiments, the AD and/or DDD moiety may be attached to either the N-terminal or C-terminal end of an effector protein or peptide. However, the skilled artisan will realize that the site of attachment of an AD or DDD moiety to an effector moiety may vary, depending on the chemical nature of the effector moiety and the part(s) of the effector moiety involved in its physiological activity. Site-specific attachment of a variety of effector moieties may be performed using techniques known in the art, such as the use of bivalent cross-linking reagents and/or other chemical conjugation techniques.

Dock-and-Lock™ (DNL™) technology has been used to produce a variety of complexes in assorted formats (Rossi et al., 2012, *Bioconjug Chem* 23:309-23). Bispecific hexavalent antibodies (bsHexAbs) based on veltuzumab (anti-CD20) and epratuzumab (anti-CD22) were constructed by combining a stabilized $(Fab)_2$ fused to a dimerization and docking domain (DDD) with an IgG containing an anchor domain (AD) appended at the C-terminus of each heavy chain ($C_H3$-AD2-IgG) (Rossi et al., 2009, *Blood* 113, 6161-71). Compared to mixtures of their parental mAbs, these Fc-based bsHexAbs, referred to henceforth as "Fc-bsHexAbs", induced unique signaling events (Gupta et al., 2010, *Blood* 116:3258-67), and exhibited potent cytotoxicity in vitro. However, the Fc-bsHexAbs were cleared from circulation of mice approximately twice as fast as the parental mAbs (Rossi et al., 2009, *Blood* 113, 6161-71). Although the Fc-bsHexAbs are highly stable ex vivo, it is possible that some dissociation occurs in vivo, for example by intracellular processing. Further, the Fc-bsHexAbs lack CDC activity.

Fc-based immunocytokines have also been assembled as DNL™ complexes, comprising two or four molecules of interferon-alpha 2b (IFNα2b) fused to the C-terminal end of the $C_H3$-AD2-IgG Fc (Rossi et al., 2009, *Blood* 114:3864-71; Rossi et al., 2010, *Cancer Res* 70:7600-09; Rossi et al., 2011, *Blood* 118:1877-84). The Fc-IgG-IFNα maintained high specific activity, approaching that of recombinant IFNα, and were remarkably potent in vitro and in vivo against non-Hodgkin lymphoma (NHL) xenografts. The $T_{1/2}$ of the Fc-IgG-IFNα in mice was longer than PEGylated IFNα, but half as long as the parental mAbs. Similar to the Fc-bsHexAbs, the Fc-IgG-IFNα dissociated in vivo over time and exhibited diminished CDC, but ADCC was enhanced.

Structure-Function Relationships in AD and DDD Moieties

For different types of DNL™ constructs, different AD or DDD sequences may be utilized. Exemplary DDD and AD sequences are provided below.

```
DDD1
                                              (SEQ ID NO: 1)
SHIQIPPGLTELLQGYTVEVLRQQPPDLVEFAVEYFTRLREARA

DDD2
                                              (SEQ ID NO: 2)
CGHIQIPPGLTELLQGYTVEVLRQQPPDLVEFAVEYFTRLREARA

AD1
                                              (SEQ ID NO: 3)
QIEYLAKQIVDNAIQQA

AD2
                                              (SEQ ID NO: 4)
CGQIEYLAKQIVDNAIQQAGC
```

The skilled artisan will realize that DDD1 and DDD2 are based on the DDD sequence of the human RIIα isoform of protein kinase A. However, in alternative embodiments, the DDD and AD moieties may be based on the DDD sequence of the human RIα form of protein kinase A and a corresponding AKAP sequence, as exemplified in DDD3, DDD3C and AD3 below.

```
DDD3
                                              (SEQ ID NO: 5)
SLRECELYVQKHNIQALLKDSIVQLCTARPERPMAFLREYFERLEKEEAK

DDD3C
                                              (SEQ ID NO: 6)
MSCGGSLRECELYVQKHNIQALLKDSIVQLCTARPERPMAFLREYFERLE
KEEAK

AD3
                                              (SEQ ID NO: 7)
CGFEELAWKIAKMIWSDVFQQGC
```

In other alternative embodiments, other sequence variants of AD and/or DDD moieties may be utilized in construction of the DNL™ complexes. For example, there are only four variants of human PKA DDD sequences, corresponding to the DDD moieties of PKA RIα, RIIα, RIβ and RIIβ. The RIIα DDD sequence is the basis of DDD1 and DDD2 disclosed above. The four human PKA DDD sequences are shown below. The DDD sequence represents residues 1-44 of RIIα, 1-44 of RIIβ, 12-61 of RIα and 13-66 of RIIβ. (Note that the sequence of DDD1 is modified slightly from the human PKA RIIα DDD moiety.)

```
PKA RIα
                                              (SEQ ID NO: 8)
SLRECELYVQKHNIQALLKDVSIVQLCTARPERPMAFLREYFEKLEKEEA
K

PKA RIβ
                                              (SEQ ID NO: 9)
SLKGCELYVQLHGIQQVLKDCIVHLCISKPERPMKFLREHFEKLEKEENR
QILA

PKA RIIα
                                              (SEQ ID NO: 10)
SHIQIPPGLTELLQGYTVEVGQQPPDLVDFAVEYFTRLREARRQ

PKA RIIβ
                                              (SEQ ID NO: 11)
SIEIPAGLTELLQGFTVEVLRHQPADLLEFALQHFTRLQQENER
```

The structure-function relationships of the AD and DDD domains have been the subject of investigation. (See, e.g., Burns-Hamuro et al., 2005, *Protein Sci* 14:2982-92; Carr et al., 2001, *J Biol Chem* 276:17332-38; Alto et al., 2003, *Proc Natl Acad Sci USA* 100:4445-50; Hundsrucker et al., 2006, *Biochem J*396:297-306; Stokka et al., 2006, Biochem J400: 493-99; Gold et al., 2006, *Mol Cell* 24:383-95; Kinderman et al., 2006, *Mol Cell* 24:397-408, the entire text of each of which is incorporated herein by reference.)

For example, Kinderman et al. (2006, *Mol Cell* 24:397-408) examined the crystal structure of the AD-DDD binding interaction and concluded that the human DDD sequence contained a number of conserved amino acid residues that were important in either dimer formation or AKAP binding, underlined in SEQ ID NO:1 below. (See FIG. 1 of Kinderman et al., 2006, incorporated herein by reference.) The skilled artisan will realize that in designing sequence variants of the DDD sequence, one would desirably avoid changing any of the underlined residues, while conservative amino acid substitutions might be made for residues that are less critical for dimerization and AKAP binding.

```
                                              (SEQ ID NO: 1)
SHIQIPPGLTELLQGYTVEVLRQQPPDLVEFAVEYFTRLREARA
```

As discussed in more detail below, conservative amino acid substitutions have been characterized for each of the twenty common L-amino acids. Thus, based on the data of Kinderman (2006) and conservative amino acid substitutions, potential alternative DDD sequences based on SEQ ID NO:1 are shown in Table 2. In devising Table 2, only highly conservative amino acid substitutions were considered. For example, charged residues were only substituted for residues of the same charge, residues with small side chains were substituted with residues of similar size, hydroxyl side chains were only substituted with other hydroxyls, etc. Because of the unique effect of proline on amino acid secondary structure, no other residues were substituted for proline. A limited number of such potential alternative DDD moiety sequences are shown in SEQ ID NO:12 to SEQ ID NO:31 below. The skilled artisan will realize that alternative species within the genus of DDD moieties can be constructed by standard techniques, for example using a commercial peptide synthesizer or well known site-directed mutagenesis techniques. The effect of the amino acid substitutions on AD moiety binding may also be readily determined by standard binding assays, for example as disclosed in Alto et al. (2003, *Proc Natl Acad Sci USA* 100:4445-50).

TABLE 2

Conservative Amino Acid Substitutions in DDD1 (SEQ ID NO: 1). Consensus sequence disclosed as SEQ ID NO: 87.

| S | H | I | Q | I | P | P | G | L | T | E | L | L | Q | G | Y | T | V | E | V | L | R |
|---|---|---|---|---|---|---|---|---|---|---|---|---|---|---|---|---|---|---|---|---|---|
| T | K |   | N |   | A |   | S | D |   | N | A | S |   | D |   |   |   |   |   | K |   |
| R |   |   |   |   |   |   |   |   |   |   |   |   |   |   |   |   |   |   |   |   |   |

| Q | Q | P | P | D | L | V | E | F | A | V | E | Y | F | T | R | L | R | E | A | R | A |
|---|---|---|---|---|---|---|---|---|---|---|---|---|---|---|---|---|---|---|---|---|---|
| N | N |   |   | E |   | D |   | L |   | D |   |   | S | K |   | K | D | L | K | L |   |
|   |   |   |   |   |   | I |   |   |   |   |   |   |   |   |   | I |   | I |   |   |   |
|   |   |   |   |   |   | V |   |   |   |   |   |   |   |   |   | V |   | V |   |   |   |

```
THIQIPPGLTELLQGYTVEVLRQQPPDLVEFAVEYFTRLREARA (SEQ ID NO: 12)
SKIQIPPGLTELLQGYTVEVLRQQPPDLVEFAVEYFTRLREARA (SEQ ID NO: 13)
SRIQIPPGLTELLQGYTVEVLRQQPPDLVEFAVEYFTRLREARA (SEQ ID NO: 14)
SHINIPPGLTELLQGYTVEVLRQQPPDLVEFAVEYFTRLREARA (SEQ ID NO: 15)
SHIQIPPALTELLQGYTVEVLRQQPPDLVEFAVEYFTRLREARA (SEQ ID NO: 16)
SHIQIPPGLSELLQGYTVEVLRQQPPDLVEFAVEYFTRLREARA (SEQ ID NO: 17)
SHIQIPPGLTDLLQGYTVEVLRQQPPDLVEFAVEYFTRLREARA (SEQ ID NO: 18)
SHIQIPPGLTELLNGYTVEVLRQQPPDLVEFAVEYFTRLREARA (SEQ ID NO: 19)
SHIQIPPGLTELLQAYTVEVLRQQPPDLVEFAVEYFTRLREARA (SEQ ID NO: 20)
SHIQIPPGLTELLQGYSVEVLRQQPPDLVEFAVEYFTRLREARA (SEQ ID NO: 21)
SHIQIPPGLTELLQGYTVDVLRQQPPDLVEFAVEYFTRLREARA (SEQ ID NO: 22)
SHIQIPPGLTELLQGYTVEVLKQQPPDLVEFAVEYFTRLREARA (SEQ ID NO: 23)
SHIQIPPGLTELLQGYTVEVLRNQPPDLVEFAVEYFTRLREARA (SEQ ID NO: 24)
SHIQIPPGLTELLQGYTVEVLRQNPPDLVEFAVEYFTRLREARA (SEQ ID NO: 25)
SHIQIPPGLTELLQGYTVEVLRQQPPELVEFAVEYFTRLREARA (SEQ ID NO: 26)
SHIQIPPGLTELLQGYTVEVLRQQPPDLVDFAVEYFTRLREARA (SEQ ID NO: 27)
SHIQIPPGLTELLQGYTVEVLRQQPPDLVEFLVEYFTRLREARA (SEQ ID NO: 28)
SHIQIPPGLTELLQGYTVEVLRQQPPDLVEFIVEYFTRLREARA (SEQ ID NO: 29)
SHIQIPPGLTELLQGYTVEVLRQQPPDLVEFVVEYFTRLREARA (SEQ ID NO: 30)
SHIQIPPGLTELLQGYTVEVLRQQPPDLVEFAVDYFTRLREARA (SEQ ID NO: 31)
```

Alto et al. (2003, *Proc Natl Acad Sci USA* 100:4445-50) performed a bioinformatic analysis of the AD sequence of various AKAP proteins to design an RII selective AD sequence called AKAP-IS (SEQ ID NO:3), with a binding constant for DDD of 0.4 nM. The AKAP-IS sequence was designed as a peptide antagonist of AKAP binding to PKA. Residues in the AKAP-IS sequence where substitutions tended to decrease binding to DDD are underlined in SEQ ID NO:3 below. The skilled artisan will realize that in designing sequence variants of the AD sequence, one would desirably avoid changing any of the underlined residues, while conservative amino acid substitutions might be made for residues that are less critical for DDD binding. Table 3 shows potential conservative amino acid substitutions in the sequence of AKAP-IS (AD1, SEQ ID NO:3), similar to that shown for DDD1 (SEQ ID NO:1) in Table 2 above.

A limited number of such potential alternative AD moiety sequences are shown in SEQ ID NO:32 to SEQ ID NO:49 below. Other species within the genus of possible AD moiety sequences could be made, tested and used by the skilled artisan, based on the data of Alto et al. (2003). It is noted that FIG. 2 of Alto (2003) shows a number of amino acid substitutions that may be made, while retaining binding activity to DDD moieties, based on actual binding experiments.

```
AKAP-IS
                              (SEQ ID NO: 3)
QIEYLAKQIVDNAIQQA
```

TABLE 3

Conservative Amino Acid Substitutions in AD1 (SEQ ID NO: 3). Consensus sequence disclosed as SEQ ID NO: 88.

| Q | I | E | Y | L | A | K | Q | I | V | D | N | A | I | Q | Q | A |
|---|---|---|---|---|---|---|---|---|---|---|---|---|---|---|---|---|
| N | L | D | F | I |   | R | N |   | E | Q |   |   | N | N | L |   |
|   | V |   |   | T | V |   |   |   |   |   |   |   | I |   |   |   |
|   |   |   |   | S |   |   |   |   |   |   |   |   |   |   | V |   |

```
NIEYLAKQIVDNAIQQA (SEQ ID NO: 32)
QLEYLAKQIVDNAIQQA (SEQ ID NO: 33)
QVEYLAKQIVDNAIQQA (SEQ ID NO: 34)
QIDYLAKQIVDNAIQQA (SEQ ID NO: 35)
QIEFLAKQIVDNAIQQA (SEQ ID NO: 36)
QIETLAKQIVDNAIQQA (SEQ ID NO: 37)
QIESLAKQIVDNAIQQA (SEQ ID NO: 38)
QIEYIAKQIVDNAIQQA (SEQ ID NO: 39)
QIEYVAKQIVDNAIQQA (SEQ ID NO: 40)
QIEYLARQIVDNAIQQA (SEQ ID NO: 41)
QIEYLAKNIVDNAIQQA (SEQ ID NO: 42)
QIEYLAKQIVENAIQQA (SEQ ID NO: 43)
QIEYLAKQIVDQAIQQA (SEQ ID NO: 44)
QIEYLAKQIVDNAINQA (SEQ ID NO: 45)
QIEYLAKQIVDNAIQNA (SEQ ID NO: 46)
QIEYLAKQIVDNAIQQL (SEQ ID NO: 47)
QIEYLAKQIVDNAIQQI (SEQ ID NO: 48)
QIEYLAKQIVDNAIQQV (SEQ ID NO: 49)
```

Gold et al. (2006, *Mol Cell* 24:383-95) utilized crystallography and peptide screening to develop a SuperAKAP-IS sequence (SEQ ID NO:50), exhibiting a five order of magnitude higher selectivity for the RII isoform of PKA compared with the R1 isoform. Underlined residues indicate the positions of amino acid substitutions, relative to the AKAP-IS sequence, which increased binding to the DDD moiety of RIIα. In this sequence, the N-terminal Q residue is numbered as residue number 4 and the C-terminal A residue is residue number 20. Residues where substitutions could be made to affect the affinity for RIIα were residues 8, 11, 15, 16, 18, 19 and 20 (Gold et al., 2006). It is contemplated that in certain alternative embodiments, the SuperAKAP-IS sequence may be substituted for the AKAP-IS AD moiety sequence to prepare DNL™ constructs. Other alternative sequences that might be substituted for the AKAP-IS AD sequence are shown in SEQ ID NO:51-53. Substitutions relative to the AKAP-IS sequence are underlined. It is anticipated that, as with the AD2 sequence shown in SEQ ID NO:4, the AD moiety may also include the additional N-terminal residues cysteine and glycine and C-terminal residues glycine and cysteine.

```
SuperAKAP-IS
                              (SEQ ID NO: 50)
QIEYVAKQIVDYAIHQA Alternative AKAP sequences
                              (SEQ ID NO: 51)
QIEYKAKQIVDHAIHQA (SEQ ID NO: 52)
QIEYHAKQIVDHAIHQA (SEQ ID NO: 53)
QIEYVAKQIVDHAIHQA
```

Figure 2:
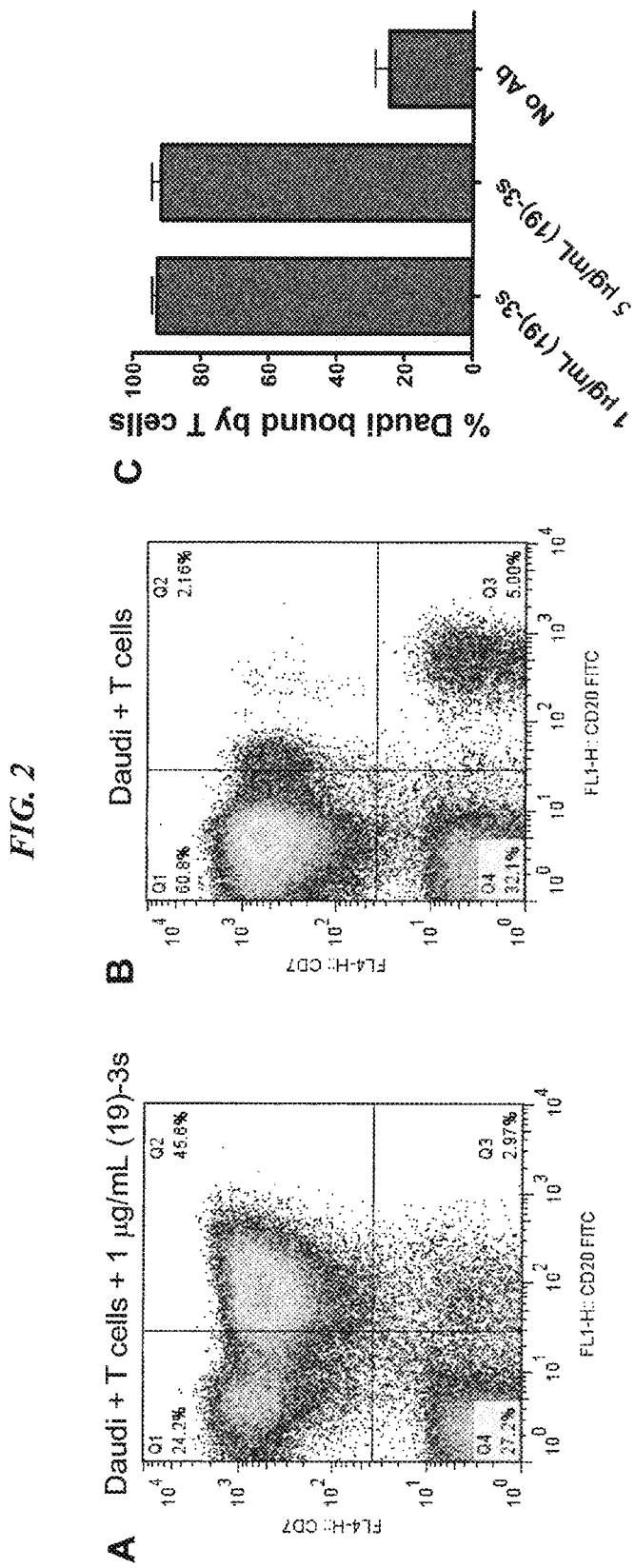
FIG. 2A. Immune synapse formation between Daudi Burkitt lymphoma and T cells, mediated by (19)-3s. Freshly isolated T cells were combined with Daudi cells at an E:T ratio of 2.5:1. Cells were treated with 0, 1 or 5 µg/mL of (19)-3s for 30 min at room temperature prior to analysis by flow cytometry. Anti-CD20-FITC and anti-CD7-APC were used to identify Daudi and T cells, respectively. Co-binding was indicated as the % of CD20$^+$/CD7$^+$ events. After treatment with (19)-3s, 45.5% of flow events were CD20/CD7 dual-positive, indicating synapsed Daudi and T cells.
FIG. 2B. Conditions were as in FIG. 2(A), except for the absence of (19)-3s antibody. Compared to FIG. 2(A), only 2% of flow events were CD20/CD7 dual-positive without antibody.
FIG. 2C. Addition of (19)-3s resulted in association of >90% of the Daudi with T cells.

FIG. 2 of Gold et al. disclosed additional DDD-binding sequences from a variety of AKAP proteins, shown below.

RII-Specific AKAPs
AKAP-KL
                                                                                   (SEQ ID NO: 54)
PLEYQAGLLVQNAIQQAI AKAP79
                                                                                    (SEQ ID NO: 55)
LLIETASSLVKNAIQLSI AKAP-Lbc
                                                                                    (SEQ ID NO: 56)
LIEEAASRIVDAVIEQVK RI-Specific AKAPs
AKAPce
                                                                                    (SEQ ID NO: 57)
ALYQFADRFSELVISEAL RIAD
                                                                                    (SEQ ID NO: 58)
LEQVANQLADQIIKEAT PV38
                                                                                    (SEQ ID NO: 59)
FEELAWKIAKMIWSDVF Dual-Specificity AKAPs
AKAP7
                                                                                    (SEQ ID NO: 60)
ELVRLSKRLVENAVLKAV MAP2D
                                                                                    (SEQ ID NO: 61)
TAEEVSARIVQVVTAEAV DAKAP1
                                                                                    (SEQ ID NO: 62)
QIKQAAFQLISQVILEAT DAKAP2
                                                                                    (SEQ ID NO: 63)
LAWKIAKMIVSDVMQQ Stokka et al. (2006, *Biochem J* 400:493-99) also developed peptide competitors of AKAP binding to PKA, shown in SEQ ID NO:64-66. The peptide antagonists were designated as Ht31 (SEQ ID NO:64), RIAD (SEQ ID NO:65) and PV-38 (SEQ ID NO:66). The Ht-31 peptide exhibited a greater affinity for the RII isoform of PKA, while the RIAD and PV-38 showed higher affinity for RI.

Ht31
                                                                                    (SEQ ID NO: 64)
DLIEEAASRIVDAVIEQVKAAGAY

RIAD
                                                                                    (SEQ ID NO: 65)
LEQYANQLADQIIKEATE

PV-38
                                                                                 (SEQ ID NO: 66)
FEELAWKIAKMIWSDVFQQC

Hundsrucker et al. (2006, *Biochem J* 396:297-306) developed still other peptide competitors for AKAP binding to PKA, with a binding constant as low as 0.4 nM to the DDD of the RII form of PKA. The sequences of various AKAP antagonistic peptides are provided in Table 1 of Hundsrucker et al., reproduced in Table 4 below. AKAPIS represents a synthetic RII subunit-binding peptide. All other peptides are derived from the RII-binding domains of the indicated AKAPs.

TABLE 4

| AKAP Peptide sequences | |
|---|---|
| | Peptide Sequence |
| AKAPIS | QIEYLAKQIVDNAIQQA (SEQ ID NO: 3) |
| AKAPIS-P | QIEYLAKQIPDNAIQQA (SEQ ID NO: 67) |
| Ht31 | KGADLIEEAASRIVDAVIEQVKAAG (SEQ ID NO: 68) |
| Ht31-P | KGADLIEEAASRIPDAPIEQVKAAG (SEQ ID NO: 69) |
| AKAP7δ-wt-pep | PEDAELVRLSKRLVENAVLKAVQQY (SEQ ID NO: 70) |
| AKAP7δ-L304T-pep | PEDAELVRTSKRLVENAVLKAVQQY (SEQ ID NO: 71) |
| AKAP7δ-L308D-pep | PEDAELVRLSKRDVENAVLKAVQQY (SEQ ID NO: 72) |
| AKAP7δ-P-pep | PEDAELVRLSKRLPENAVLKAVQQY (SEQ ID NO: 73) |
| AKAP7δ-PP-pep | PEDAELVRLSKRLPENAPLKAVQQY (SEQ ID NO: 74) |
| AKAP7δ-L314E-pep | PEDAELVRLSKRLVENAVEKAVQQY (SEQ ID NO: 75) |
| AKAP1-pep | EEGLDRNEEIKRAAFQIISQVISEA (SEQ ID NO: 76) |
| AKAP2-pep | LVDDPLEYQAGLLVQNAIQQAIAEQ (SEQ ID NO: 77) |
| AKAP5-pep | QYETLLIETASSLVKNAIQLSIEQL (SEQ ID NO: 78) |
| AKAP9-pep | LEKQYQEQLEEEVAKVIVSMSIAFA (SEQ ID NO: 79) |
| AKAP10-pep | NTDEAQEELAWKIAKMIVSDIMQQA (SEQ ID NO: 80) |
| AKAP11-pep | VNLDKKAVLAEKIVAEAIEKAEREL (SEQ ID NO: 81) |
| AKAP12-pep | NGILELETKSSKLVQNIIQTAVDQF (SEQ ID NO: 82) |
| AKAP14-pep | TQDKNYEDELTQVALALVEDVINYA (SEQ ID NO: 83) |
| Rab32-pep | ETSAKDNINIEEAARFLVEKILVNH (SEQ ID NO: 84) |

Residues that were highly conserved among the AD domains of different AKAP proteins are indicated below by underlining with reference to the AKAP IS sequence (SEQ ID NO:3). The residues are the same as observed by Alto et al. (2003), with the addition of the C-terminal alanine residue. (See FIG. 4 of Hundsrucker et al. (2006), incorporated herein by reference.) The sequences of peptide antagonists with particularly high affinities for the RII DDD sequence were those of AKAP-IS, AKAP7δ-wt-pep, AKAP7δ-L304T-pep and AKAP7δ-L308D-pep.

AKAP-IS
                                                          (SEQ ID NO: 3)
QIEYLAKQIVDNAIQQA

Can et al. (2001, *J Biol Chem* 276:17332-38) examined the degree of sequence homology between different AKAP-binding DDD sequences from human and non-human proteins and identified residues in the DDD sequences that appeared to be the most highly conserved among different DDD moieties. These are indicated below by underlining with reference to the human PKA RIIα DDD sequence of SEQ ID NO:1. Residues that were particularly conserved are further indicated by italics. The residues overlap with, but are not identical to those suggested by Kinderman et al. (2006) to be important for binding to AKAP proteins. The skilled artisan will realize that in designing sequence variants of DDD, it would be most preferred to avoid changing the most conserved residues (italicized), and it would be preferred to also avoid changing the conserved residues (underlined), while conservative amino acid substitutions may be considered for residues that are neither underlined nor italicized.

(SEQ ID NO: 1)
SH*IQ*IPP*GL*TE*LL*QGY*TV*EVLRQQPP*DL*VEF*AV*E*YF*TR*LR*EA*RA

A modified set of conservative amino acid substitutions for the DDD1 (SEQ ID NO:1) sequence, based on the data of Carr et al. (2001) is shown in Table 5. Even with this reduced set of substituted sequences, there are over 65,000 possible alternative DDD moiety sequences that may be produced, tested and used by the skilled artisan without undue experimentation. The skilled artisan could readily derive such alternative DDD amino acid sequences as disclosed above for Table 2 and Table 3.

properties of the various amino acids and effect of amino acid substitution on protein structure and function have been the subject of extensive study and knowledge in the art.

For example, the hydropathic index of amino acids may be considered (Kyte & Doolittle, 1982, *J. Mol. Biol.*, 157: 105-132). The relative hydropathic character of the amino acid contributes to the secondary structure of the resultant protein, which in turn defines the interaction of the protein with other molecules. Each amino acid has been assigned a hydropathic index on the basis of its hydrophobicity and charge characteristics (Kyte & Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). In making conservative substitutions, the use of amino acids whose hydropathic indices are within ±2 is preferred, within ±1 are more preferred, and within ±0.5 are even more preferred.

Amino acid substitution may also take into account the hydrophilicity of the amino acid residue (e.g., U.S. Pat. No. 4,554,101). Hydrophilicity values have been assigned to amino acid residues: arginine (+3.0); lysine (+3.0); aspartate (+3.0); glutamate (+3.0); serine (+0.3); asparagine (+0.2); glutamine (+0.2); glycine (0); threonine (−0.4); proline (−0.5+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5);

TABLE 5

Conservative Amino Acid Substitutions in DDD1 (SEQ ID NO: 1).
Consensus sequence disclosed as SEQ ID NO: 89.

| S | H | I | Q | *I* | *P* | P | *G* | *L* | T | *E* | *L* | *L* | Q | *G* | *Y* | *T* | V | *E* | *V* | *L* | *R* |
|---|---|---|---|---|---|---|---|---|---|---|---|---|---|---|---|---|---|---|---|---|---|
| T |   | N |   |   |   |   |   |   | S |   |   |   |   |   |   | I |   |   |   |   |   |
|   |   |   |   |   |   |   |   |   |   |   |   |   |   |   |   | L |   |   |   |   |   |
|   |   |   |   |   |   |   |   |   |   |   |   |   |   |   |   | A |   |   |   |   |   |

| Q | *Q* | *P* | P | *D* | *L* | *V* | E | *F* | *A* | V | E | *Y* | *F* | T | R | *L* | R | *E* | A | *R* | A |
|---|---|---|---|---|---|---|---|---|---|---|---|---|---|---|---|---|---|---|---|---|---|
| N |   |   |   |   |   |   | I | D |   |   |   | S | K |   |   | K |   | L |   | L |   |
|   |   |   |   |   |   |   | L |   |   |   |   |   |   |   |   | I |   |   |   | I |   |
|   |   |   |   |   |   |   | A |   |   |   |   |   |   |   |   | V |   |   |   | V |   |

The skilled artisan will realize that these and other amino acid substitutions in the DDD or AD amino acid sequences may be utilized to produce alternative species within the genus of AD or DDD moieties, using techniques that are standard in the field and only routine experimentation.

Amino Acid Substitutions

In alternative embodiments, the disclosed methods and compositions may involve production and use of proteins or peptides with one or more substituted amino acid residues. For example, the DDD and/or AD sequences used to make DNL™ constructs may be modified as discussed above.

The skilled artisan will be aware that, in general, amino acid substitutions typically involve the replacement of an amino acid with another amino acid of relatively similar properties (i.e., conservative amino acid substitutions). The tryptophan (−3.4). Replacement of amino acids with others of similar hydrophilicity is preferred.

Other considerations include the size of the amino acid side chain. For example, it would generally not be preferred to replace an amino acid with a compact side chain, such as glycine or serine, with an amino acid with a bulky side chain, e.g., tryptophan or tyrosine. The effect of various amino acid residues on protein secondary structure is also a consideration. Through empirical study, the effect of different amino acid residues on the tendency of protein domains to adopt an alpha-helical, beta-sheet or reverse turn secondary structure has been determined and is known in the art (see, e.g., Chou & Fasman, 1974, *Biochemistry*, 13:222-245; 1978, *Ann. Rev. Biochem.*, 47: 251-276; 1979, *Biophys. J.*, 26:367-384).

Based on such considerations and extensive empirical study, tables of conservative amino acid substitutions have been constructed and are known in the art. For example: arginine and lysine; glutamate and aspartate; serine and threonine; glutamine and asparagine; and valine, leucine and isoleucine. Alternatively: Ala (A) leu, ile, val; Arg (R) gln, asn, lys; Asn (N) his, asp, lys, arg, gln; Asp (D) asn, glu; Cys (C) ala, ser; Gln (Q) glu, asn; Glu (E) gln, asp; Gly (G) ala; His (H) asn, gln, lys, arg; Ile (I) val, met, ala, phe, leu; Leu (L) val, met, ala, phe, ile; Lys (K) gln, asn, arg; Met (M) phe, ile, leu; Phe (F) leu, val, ile, ala, tyr; Pro (P) ala; Ser (S), thr; Thr (T) ser; Trp (W) phe, tyr; Tyr (Y) trp, phe, thr, ser; Val (V) ile, leu, met, phe, ala.

Other considerations for amino acid substitutions include whether or not the residue is located in the interior of a protein or is solvent exposed. For interior residues, conservative substitutions would include: Asp and Asn; Ser and Thr; Ser and Ala; Thr and Ala; Ala and Gly; Ile and Val; Val and Leu; Leu and Ile; Leu and Met; Phe and Tyr; Tyr and Trp. (See, e.g., PROWL website at rockefeller.edu) For solvent exposed residues, conservative substitutions would include: Asp and Asn; Asp and Glu; Glu and Gln; Glu and Ala; Gly and Asn; Ala and Pro; Ala and Gly; Ala and Ser; Ala and Lys; Ser and Thr; Lys and Arg; Val and Leu; Leu and Ile; Ile and Val; Phe and Tyr. (Id.) Various matrices have been constructed to assist in selection of amino acid substitutions, such as the PAM250 scoring matrix, Dayhoff matrix, Grantham matrix, McLachlan matrix, Doolittle matrix, Henikoff matrix, Miyata matrix, Fitch matrix, Jones matrix, Rao matrix, Levin matrix and Risler matrix (Idem.) In determining amino acid substitutions, one may also consider the existence of intermolecular or intramolecular bonds, such as formation of ionic bonds (salt bridges) between positively charged residues (e.g., His, Arg, Lys) and negatively charged residues (e.g., Asp, Glu) or disulfide bonds between nearby cysteine residues.

Methods of substituting any amino acid for any other amino acid in an encoded protein sequence are well known and a matter of routine experimentation for the skilled artisan, for example by the technique of site-directed mutagenesis or by synthesis and assembly of oligonucleotides encoding an amino acid substitution and splicing into an expression vector construct.

Therapeutic Agents

In alternative embodiments, therapeutic agents such as cytotoxic agents, anti-angiogenic agents, pro-apoptotic agents, antibiotics, hormones, hormone antagonists, chemokines, drugs, prodrugs, toxins, enzymes or other agents may be used, either conjugated to the subject bsAbs, ADCs and/or antibodies or separately administered before, simultaneously with, or after the bsAbs, ADCs and/or antibodies. Drugs of use may possess a pharmaceutical property selected from the group consisting of antimitotic, antikinase, alkylating, antimetabolite, antibiotic, alkaloid, anti-angiogenic, pro-apoptotic agents and combinations thereof.

Exemplary drugs of use may include, but are not limited to, 5-fluorouracil, afatinib, aplidin, azaribine, anastrozole, anthracyclines, axitinib, AVL-101, AVL-291, bendamustine, bleomycin, bortezomib, bosutinib, bryostatin-1, busulfan, calicheamycin, camptothecin, carboplatin, 10-hydroxycamptothecin, carmustine, celebrex, chlorambucil, cisplatin (CDDP), Cox-2 inhibitors, irinotecan (CPT-11), SN-38, carboplatin, cladribine, camptothecans, crizotinib, cyclophosphamide, cytarabine, dacarbazine, dasatinib, dinaciclib, docetaxel, dactinomycin, daunorubicin, doxorubicin, 2-pyrrolinodoxorubicine (2P-DOX), cyano-morpholino doxorubicin, doxorubicin glucuronide, epirubicin glucuronide, erlotinib, estramustine, epidophyllotoxin, erlotinib, entinostat, estrogen receptor binding agents, etoposide (VP16), etoposide glucuronide, etoposide phosphate, exemestane, fingolimod, floxuridine (FUdR), 3',5'-O-dioleoyl-FudR (FUdR-dO), fludarabine, flutamide, farnesyl-protein transferase inhibitors, flavopiridol, fostamatinib, ganetespib, GDC-0834, GS-1101, gefitinib, gemcitabine, hydroxyurea, ibrutinib, idarubicin, idelalisib, ifosfamide, imatinib, L-asparaginase, lapatinib, lenolidamide, leucovorin, LFM-A13, lomustine, mechlorethamine, melphalan, mercaptopurine, 6-mercaptopurine, methotrexate, mitoxantrone, mithramycin, mitomycin, mitotane, navelbine, neratinib, nilotinib, nitrosurea, olaparib, plicomycin, procarbazine, paclitaxel, PCI-32765, pentostatin, PSI-341, raloxifene, semustine, sorafenib, streptozocin, SU11248, sunitinib, tamoxifen, temazolomide (an aqueous form of DTIC), transplatinum, thalidomide, thioguanine, thiotepa, teniposide, topotecan, uracil mustard, vatalanib, vinorelbine, vinblastine, vincristine, vinca alkaloids and ZD1839.

Toxins of use may include ricin, abrin, alpha toxin, saporin, ribonuclease (RNase), e.g., onconase, DNase I, Staphylococcal enterotoxin-A, pokeweed antiviral protein, gelonin, diphtheria toxin, *Pseudomonas* exotoxin, and *Pseudomonas* endotoxin.

Chemokines of use may include RANTES, MCAF, MIP1-alpha, MIP1-Beta and IP-10.

In certain embodiments, anti-angiogenic agents, such as angiostatin, baculostatin, canstatin, maspin, anti-VEGF antibodies, anti-PlGF peptides and antibodies, anti-vascular growth factor antibodies, anti-Flk-1 antibodies, anti-Flt-1 antibodies and peptides, anti-Kras antibodies, anti-cMET antibodies, anti-MIF (macrophage migration-inhibitory factor) antibodies, laminin peptides, fibronectin peptides, plasminogen activator inhibitors, tissue metalloproteinase inhibitors, interferons, interleukin-12, IP-10, Gro-β, thrombospondin, 2-methoxyoestradiol, proliferin-related protein, carboxiamidotriazole, CM101, Marimastat, pentosan polysulphate, angiopoietin-2, interferon-alpha, herbimycin A, PNU145156E, 16K prolactin fragment, Linomide (roquinimex), thalidomide, pentoxifylline, genistein, TNP-470, endostatin, paclitaxel, accutin, angiostatin, cidofovir, vincristine, bleomycin, AGM-1470, platelet factor 4 or minocycline may be of use.

Immunomodulators of use may be selected from a cytokine, a stem cell growth factor, a lymphotoxin, a hematopoietic factor, a colony stimulating factor (CSF), an interferon (IFN), erythropoietin, thrombopoietin and a combination thereof. Specifically useful are lymphotoxins such as tumor necrosis factor (TNF), hematopoietic factors, such as interleukin (IL), colony stimulating factor, such as granulocyte-colony stimulating factor (G-CSF) or granulocyte macrophage-colony stimulating factor (GM-CSF), interferon, such as interferons-α, -β or -λ, and stem cell growth factor, such as that designated "S1 factor". Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; prostaglandin, fibroblast growth factor; prolactin; placental lactogen, OB protein; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); interleukins (ILs) such as IL-1, IL-1α, IL-2, IL-3, IL-4, IL-5, IL-6, IL-7, IL-8, IL-9, IL-10, IL-11, IL-12; IL-13, IL-14, IL-15, IL-16, IL-17, IL-18, IL-21, IL-25, LIF, kit-ligand or FLT-3, angiostatin, thrombospondin, endostatin, tumor necrosis factor and LT.

Radionuclides of use include, but are not limited to—$^{111}$In, $^{177}$Lu, $^{212}$Bi, $^{213}$Bi $^{211}$At, $^{62}$Cu, $^{67}$Cu, $^{90}$Y, $^{125}$I, $^{131}$I, $^{32}$P, $^{33}$P, $^{47}$Sc, $^{111}$Ag, $^{67}$Ga, $^{142}$Pr, $^{153}$Sm, $^{161}$Tb, $^{166}$Dy, $^{166}$Ho, $^{186}$Re, $^{188}$Re, $^{189}$Re, $^{212}$Pb, $^{223}$Ra, $^{225}$Ac, $^{59}$Fe, $^{75}$Se, $^{77}$As, $^{89}$Sr, $^{99}$Mo, $^{105}$Rh, $^{109}$Pd, $^{143}$Pr, $^{149}$Pm, $^{169}$Er, $^{194}$Ir, $^{198}$Au, $^{199}$Au, $^{211}$Pb, and $^{227}$Th. The therapeutic radionuclide preferably has a decay-energy in the range of 20 to 6,000 keV, preferably in the ranges 60 to 200 keV for an Auger emitter, 100-2,500 keV for a beta emitter, and 4,000-6,000 keV for an alpha emitter. Maximum decay energies of useful beta-particle-emitting nuclides are preferably 20-5,000 keV, more preferably 100-4,000 keV, and most preferably 500-2,500 keV. Also preferred are radionuclides that substantially decay with Auger-emitting particles. For example, Co-58, Ga-67, Br-80m, Tc-99m, Rh-103m, Pt-109, In-111, Sb-119, 1-125, Ho-161, Os-189m and Ir-192. Decay energies of useful beta-particle-emitting nuclides are preferably <1,000 keV, more preferably <100 keV, and most preferably <70 keV. Also preferred are radionuclides that substantially decay with generation of alpha-particles. Such radionuclides include, but are not limited to: Dy-152, At-211, Bi-212, Ra-223, Rn-219, Po-215, Bi-211, Ac-225, Fr-221, At-217, Bi-213, Th-227 and Fm-255. Decay energies of useful alpha-particle-emitting radionuclides are preferably 2,000-10,000 keV, more preferably 3,000-8,000 keV, and most preferably 4,000-7,000 keV. Additional potential radioisotopes of use include $^{11}$C, 13N, $^{15}$O, $^{75}$Br, $^{198}$Au, $^{224}$Ac, $^{126}$I, $^{133}$I, $^{103}$Ru, $^{105}$Ru, $^{107}$Hg, $^{203}$Hg, $^{121m}$Te, $^{122m}$Te, $^{125m}$Te, $^{165}$Tm, $^{167}$Tm, $^{77}$Br, $^{113m}$In, $^{95}$Ru, $^{97}$Ru, $^{168}$Tm, $^{197}$Pt, $^{109}$Pd, $^{105}$Rh, $^{142}$Pr, $^{143}$Pr, $^{161}$Tb, $^{166}$Ho, $^{199}$Au, $^{57}$Co, $^{58}$Co, $^{51}$Cr, $^{59}$Fe, $^{75}$Se, $^{201}$Tl, $^{225}$Ac, $^{76}$Br, $^{169}$Yb, and the like. Some useful diagnostic nuclides may include $^{18}$F, $^{52}$Fe, $^{62}$Cu, $^{64}$Cu, $^{67}$Cu, $^{67}$Ga, $^{68}$Ga, $^{86}$Y, $^{89}$Zr, $^{94}$Tc, $^{94m}$Tc, $^{99m}$Tc, or $^{111}$In.

Therapeutic agents may include a photoactive agent or dye. Fluorescent compositions, such as fluorochrome, and other chromogens, or dyes, such as porphyrins sensitive to visible light, have been used to detect and to treat lesions by directing the suitable light to the lesion. In therapy, this has been termed photoradiation, phototherapy, or photodynamic therapy. See Joni et al. (eds.), PHOTODYNAMIC THERAPY OF TUMORS AND OTHER DISEASES (Liberia Progetto 1985); van den Bergh, Chem. Britain (1986), 22:430. Moreover, monoclonal antibodies have been coupled with photoactivated dyes for achieving phototherapy. See Mew et al., *J. Immunol.* (1983), 130:1473; idem., *Cancer Res.* (1985), 45:4380; Oseroff et al., *Proc. Natl. Acad. Sci. USA* (1986), 83:8744; idem., *Photochem. Photobiol.* (1987), 46:83; Hasan et al., *Prog. Clin. Biol. Res.* (1989), 288:471; Tatsuta et al., *Lasers Surg. Med.* (1989), 9:422; Pelegrin et al., *Cancer* (1991), 67:2529.

Other useful therapeutic agents may comprise oligonucleotides, especially antisense oligonucleotides that preferably are directed against oncogenes and oncogene products, such as bcl-2 or p53. A preferred form of therapeutic oligonucleotide is siRNA. The skilled artisan will realize that any siRNA or interference RNA species may be attached to an antibody or fragment thereof for delivery to a targeted tissue. Many siRNA species against a wide variety of targets are known in the art, and any such known siRNA may be utilized in the claimed methods and compositions.

Known siRNA species of potential use include those specific for IKK-gamma (U.S. Pat. No. 7,022,828); VEGF, Flt-1 and Flk-1/KDR (U.S. Pat. No. 7,148,342); Bcl2 and EGFR (U.S. Pat. No. 7,541,453); CDC20 (U.S. Pat. No. 7,550,572); transducin (beta)-like 3 (U.S. Pat. No. 7,576, 196); KRAS (U.S. Pat. No. 7,576,197); carbonic anhydrase II (U.S. Pat. No. 7,579,457); complement component 3 (U.S. Pat. No. 7,582,746); interleukin-1 receptor-associated kinase 4 (IRAK4) (U.S. Pat. No. 7,592,443); survivin (U.S. Pat. No. 7,608,7070); superoxide dismutase 1 (U.S. Pat. No. 7,632,938); MET proto-oncogene (U.S. Pat. No. 7,632,939); amyloid beta precursor protein (APP) (U.S. Pat. No. 7,635, 771); IGF-1R (U.S. Pat. No. 7,638,621); ICAM1 (U.S. Pat. No. 7,642,349); complement factor B (U.S. Pat. No. 7,696, 344); p53 (U.S. Pat. No. 7,781,575), and apolipoprotein B (U.S. Pat. No. 7,795,421), the Examples section of each referenced patent incorporated herein by reference.

Additional siRNA species are available from known commercial sources, such as Sigma-Aldrich (St Louis, Mo.), Invitrogen (Carlsbad, Calif.), Santa Cruz Biotechnology (Santa Cruz, Calif.), Ambion (Austin, Tex.), Dharmacon (Thermo Scientific, Lafayette, Colo.), Promega (Madison, Wis.), Mims Bio (Madison, Wis.) and Qiagen (Valencia, Calif.), among many others. Other publicly available sources of siRNA species include the siRNAdb database at the Stockholm Bioinformatics Centre, the MIT/ICBP siRNA Database, the RNAi Consortium shRNA Library at the Broad Institute, and the Probe database at NCBI. For example, there are 30,852 siRNA species in the NCBI Probe database. The skilled artisan will realize that for any gene of interest, either a siRNA species has already been designed, or one may readily be designed using publicly available software tools. Any such siRNA species may be delivered using the subject DNL™ complexes.

Methods of Therapeutic Treatment

Various embodiments concern methods of treating a cancer in a subject, such as a mammal, including humans, domestic or companion pets, such as dogs and cats, comprising administering to the subject a therapeutically effective amount of a combination of cytotoxic and/or immunomodulatory agents.

The administration of the cytotoxic bsAbs, ADCs and/or checkpoint inhibitor antibodies can be supplemented by administering concurrently or sequentially a therapeutically effective amount of another antibody that binds to or is reactive with another antigen on the surface of the target cell. Preferred additional MAbs comprise at least one humanized, chimeric or human MAb selected from the group consisting of a MAb reactive with CD4, CD5, CD8, CD14, CD15, CD16, CD19, IGF-1R, CD20, CD21, CD22, CD23, CD25, CD30, CD32b, CD33, CD37, CD38, CD40, CD40L, CD45, CD46, CD52, CD54, CD70, CD74, CD79a, CD79b, CD80, CD95, CD126, CD133, CD138, CD154, CEACAM5, CEACAM6, B7, AFP, PSMA, EGP-1, EGP-2, carbonic anhydrase IX, PAM4 antigen, MUC1, MUC2, MUC3, MUC4, MUC5, Ia, MIF, HM1.24, HLA-DR, tenascin, Flt-3, VEGFR, PlGF, ILGF, IL-6, IL-25, tenascin, TRAIL-R1, TRAIL-R2, complement factor C5, oncogene product, or a combination thereof. Various antibodies of use, such as anti-CD19, anti-CD20, and anti-CD22 antibodies, are known to those of skill in the art. See, for example, Ghetie et al., *Cancer Res.* 48:2610 (1988); Hekman et al., *Cancer Immunol. Immunother.* 32:364 (1991); Longo, *Curr. Opin. Oncol.* 8:353 (1996), U.S. Pat. Nos. 5,798,554; 6,187,287; 6,306,393; 6,676,924; 7,109,304; 7,151,164; 7,230,084;

7,230,085; 7,238,785; 7,238,786; 7,282,567; 7,300,655; 7,312,318; 7,501,498; 7,612,180; 7,670,804; and U.S. Patent Application Publ. Nos. 20080131363; 20070172920; 20060193865; and 20080138333, the Examples section of each incorporated herein by reference.

The combination therapy can be further supplemented with the administration, either concurrently or sequentially, of at least one therapeutic agent. For example, "CVB" (1.5 g/m² cyclophosphamide, 200-400 mg/m² etoposide, and 150-200 mg/m² carmustine) is a regimen used to treat non-Hodgkin's lymphoma. Patti et al., *Eur. J. Haematol.* 51: 18 (1993). Other suitable combination chemotherapeutic regimens are well-known to those of skill in the art. See, for example, Freedman et al., "Non-Hodgkin's Lymphomas," in CANCER MEDICINE, VOLUME 2, 3rd Edition, Holland et al. (eds.), pages 2028-2068 (Lea & Febiger 1993). As an illustration, first generation chemotherapeutic regimens for treatment of intermediate-grade non-Hodgkin's lymphoma (NHL) include C-MOPP (cyclophosphamide, vincristine, procarbazine and prednisone) and CHOP (cyclophosphamide, doxorubicin, vincristine, and prednisone). A useful second generation chemotherapeutic regimen is m-BACOD (methotrexate, bleomycin, doxorubicin, cyclophosphamide, vincristine, dexamethasone and leucovorin), while a suitable third generation regimen is MACOP-B (methotrexate, doxorubicin, cyclophosphamide, vincristine, prednisone, bleomycin and leucovorin). Additional useful drugs include phenyl butyrate, bendamustine, and bryostatin-1.

The combinations of therapeutic agents can be formulated according to known methods to prepare pharmaceutically useful compositions, whereby the bsAb, ADC, interferon and/or checkpoint inhibitor antibody is combined in a mixture with a pharmaceutically suitable excipient. Sterile phosphate-buffered saline is one example of a pharmaceutically suitable excipient. Other suitable excipients are well-known to those in the art. See, for example, Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The subject bsAbs, ADCs, interferons and/or antibodies can be formulated for intravenous administration via, for example, bolus injection or continuous infusion. Preferably, the bsAb, ADC and/or antibody is infused over a period of less than about 4 hours, and more preferably, over a period of less than about 3 hours. For example, the first bolus could be infused within 30 minutes, preferably even 15 min, and the remainder infused over the next 2-3 hrs. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

Additional pharmaceutical methods may be employed to control the duration of action of the therapeutic combinations. Control release preparations can be prepared through the use of polymers to complex or adsorb the agents to be administered. For example, biocompatible polymers include matrices of poly(ethylene-co-vinyl acetate) and matrices of a polyanhydride copolymer of a stearic acid dimer and sebacic acid. Sherwood et al., *Bio/Technology* 10: 1446 (1992). The rate of release from such a matrix depends upon the molecular weight of the therapeutic agent, the amount of agent within the matrix, and the size of dispersed particles. Saltzman et al., *Biophys. J.* 55: 163 (1989); Sherwood et al., supra. Other solid dosage forms are described in Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The bsAbs, interferons and/or checkpoint inhibitor antibodies may be administered to a mammal subcutaneously or even by other parenteral routes, such as intravenously, intramuscularly, intraperitoneally or intravascularly. ADCs may be administered intravenously, intraperitoneally or intravascularly. Moreover, the administration may be by continuous infusion or by single or multiple boluses. Preferably, the bsAb, ADC, interferon and/or checkpoint inhibitor antibody is infused over a period of less than about 4 hours, and more preferably, over a period of less than about 3 hours.

More generally, the dosage of an administered bsAb, ADC, interferon and/or checkpoint inhibitor antibody for humans will vary depending upon such factors as the patient's age, weight, height, sex, general medical condition and previous medical history. It may be desirable to provide the recipient with a dosage of bsAb, ADC and/or antibody that is in the range of from about 1 mg/kg to 25 mg/kg as a single intravenous infusion, although a lower or higher dosage also may be administered as circumstances dictate. A dosage of 1-20 mg/kg for a 70 kg patient, for example, is 70-1,400 mg, or 41-824 mg/m² for a 1.7-m patient. The dosage may be repeated as needed, for example, once per week for 4-10 weeks, once per week for 8 weeks, or once per week for 4 weeks. It may also be given less frequently, such as every other week for several months, or monthly or quarterly for many months, as needed in a maintenance therapy.

Alternatively, a bsAb, ADC, and/or checkpoint inhibitor antibody may be administered as one dosage every 2 or 3 weeks, repeated for a total of at least 3 dosages. Or, the combination may be administered twice per week for 4-6 weeks. If the dosage is lowered to approximately 200-300 mg/m² (340 mg per dosage for a 1.7-m patient, or 4.9 mg/kg for a 70 kg patient), it may be administered once or even twice weekly for 4 to 10 weeks. Alternatively, the dosage schedule may be decreased, namely every 2 or 3 weeks for 2-3 months. It has been determined, however, that even higher doses, such as 20 mg/kg once weekly or once every 2-3 weeks can be administered by slow i.v. infusion, for repeated dosing cycles. The dosing schedule can optionally be repeated at other intervals and dosage may be given through various parenteral routes, with appropriate adjustment of the dose and schedule.

The person of ordinary skill will realize that while the dosage schedules discussed above are relevant for ADCs, bsAbs and/or mAbs, the interferon agents should be administered at substantially lower dosages to avoid systemic toxicity. Dosages of interferons (such as PEGINTERFERON) for humans are more typically in the microgram range, for example 180 μg s.c. once per week, or 100 to 180 μg, or 135 μg, or 135 μg/1.73 m², or 90 μg/1.73 m², or 250 μg s.c. every other day may be of use, depending on the type of interferon.

While the bsAbs, interferons, ADCs and/or checkpoint inhibitor antibodies may be administered as a periodic bolus injection, in alternative embodiments the bsAbs, ADCs, interferons and/or checkpoint inhibitor antibodies may be administered by continuous infusion. In order to increase the Cmax and extend the PK of the therapeutic agents in the blood, a continuous infusion may be administered for example by indwelling catheter. Such devices are known in the art, such as HICKMAN®, BROVIAC® or PORT-A-CATH® catheters (see, e.g., Skolnik et al., *Ther Drug Monit* 32:741-48, 2010) and any such known indwelling catheter may be used. A variety of continuous infusion pumps are also known in the art and any such known infusion pump may be used. The dosage range for continuous infusion may be between 0.1 and 3.0 mg/kg per day. More preferably, the bsAbs, ADCs, interferons and/or checkpoint inhibitor antibodies can be administered by intravenous infusions over relatively short periods of 2 to 5 hours, more preferably 2-3 hours.

In preferred embodiments, the combination of agents is of use for therapy of cancer. Examples of cancers include, but are not limited to, carcinoma, lymphoma, glioblastoma, melanoma, sarcoma, and leukemia, myeloma, or lymphoid malignancies. More particular examples of such cancers are noted below and include: squamous cell cancer (e.g., epithelial squamous cell cancer), Ewing sarcoma, Wilms tumor, astrocytomas, lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma multiforme, cervical cancer, ovarian cancer, liver cancer, bladder cancer, hepatoma, hepatocellular carcinoma, neuroendocrine tumors, medullary thyroid cancer, differentiated thyroid carcinoma, breast cancer, ovarian cancer, colon cancer, rectal cancer, endometrial cancer or uterine carcinoma, salivary gland carcinoma, kidney or renal cancer, prostate cancer, vulvar cancer, anal carcinoma, penile carcinoma, as well as head-and-neck cancer. The term "cancer" includes primary malignant cells or tumors (e.g., those whose cells have not migrated to sites in the subject's body other than the site of the original malignancy or tumor) and secondary malignant cells or tumors (e.g., those arising from metastasis, the migration of malignant cells or tumor cells to secondary sites that are different from the site of the original tumor). Cancers conducive to treatment methods of the present invention involves cells which express, over-express, or abnormally express IGF-1R.

Other examples of cancers or malignancies include, but are not limited to: Acute Childhood Lymphoblastic Leukemia, Acute Lymphoblastic Leukemia, Acute Lymphocytic Leukemia, Acute Myeloid Leukemia, Adrenocortical Carcinoma, Adult (Primary) Hepatocellular Cancer, Adult (Primary) Liver Cancer, Adult Acute Lymphocytic Leukemia, Adult Acute Myeloid Leukemia, Adult Hodgkin's Lymphoma, Adult Lymphocytic Leukemia, Adult Non-Hodgkin's Lymphoma, Adult Primary Liver Cancer, Adult Soft Tissue Sarcoma, AIDS-Related Lymphoma, AIDS-Related Malignancies, Anal Cancer, Astrocytoma, Bile Duct Cancer, Bladder Cancer, Bone Cancer, Brain Stem Glioma, Brain Tumors, Breast Cancer, Cancer of the Renal Pelvis and Ureter, Central Nervous System (Primary) Lymphoma, Central Nervous System Lymphoma, Cerebellar Astrocytoma, Cerebral Astrocytoma, Cervical Cancer, Childhood (Primary) Hepatocellular Cancer, Childhood (Primary) Liver Cancer, Childhood Acute Lymphoblastic Leukemia, Childhood Acute Myeloid Leukemia, Childhood Brain Stem Glioma, Childhood Cerebellar Astrocytoma, Childhood Cerebral Astrocytoma, Childhood Extracranial Germ Cell Tumors, Childhood Hodgkin's Disease, Childhood Hodgkin's Lymphoma, Childhood Hypothalamic and Visual Pathway Glioma, Childhood Lymphoblastic Leukemia, Childhood Medulloblastoma, Childhood Non-Hodgkin's Lymphoma, Childhood Pineal and Supratentorial Primitive Neuroectodermal Tumors, Childhood Primary Liver Cancer, Childhood Rhabdomyosarcoma, Childhood Soft Tissue Sarcoma, Childhood Visual Pathway and Hypothalamic Glioma, Chronic Lymphocytic Leukemia, Chronic Myelogenous Leukemia, Colon Cancer, Cutaneous T-Cell Lymphoma, Endocrine Pancreas Islet Cell Carcinoma, Endometrial Cancer, Ependymoma, Epithelial Cancer, Esophageal Cancer, Ewing's Sarcoma and Related Tumors, Exocrine Pancreatic Cancer, Extracranial Germ Cell Tumor, Extragonadal Germ Cell Tumor, Extrahepatic Bile Duct Cancer, Eye Cancer, Female Breast Cancer, Gaucher's Disease, Gallbladder Cancer, Gastric Cancer, Gastrointestinal Carcinoid Tumor, Gastrointestinal Tumors, Germ Cell Tumors, Gestational TROPhoblastic Tumor, Hairy Cell Leukemia, Head and Neck Cancer, Hepatocellular Cancer, Hodgkin's Lymphoma, Hypergammaglobulinemia, Hypopharyngeal Cancer, Intestinal Cancers, Intraocular Melanoma, Islet Cell Carcinoma, Islet Cell Pancreatic Cancer, Kaposi's Sarcoma, Kidney Cancer, Laryngeal Cancer, Lip and Oral Cavity Cancer, Liver Cancer, Lung Cancer, Lymphoproliferative Disorders, Macroglobulinemia, Male Breast Cancer, Malignant Mesothelioma, Malignant Thymoma, Medulloblastoma, Melanoma, Mesothelioma, Metastatic Occult Primary Squamous Neck Cancer, Metastatic Primary Squamous Neck Cancer, Metastatic Squamous Neck Cancer, Multiple Myeloma, Multiple Myeloma/Plasma Cell Neoplasm, Myelodysplastic Syndrome, Myelogenous Leukemia, Myeloid Leukemia, Myeloproliferative Disorders, Nasal Cavity and Paranasal Sinus Cancer, Nasopharyngeal Cancer, Neuroblastoma, Non-Hodgkin's Lymphoma, Nonmelanoma Skin Cancer, Non-Small Cell Lung Cancer, Occult Primary Metastatic Squamous Neck Cancer, Oropharyngeal Cancer, Osteo-/Malignant Fibrous Sarcoma, Osteosarcoma/Malignant Fibrous Histiocytoma, Osteosarcoma/Malignant Fibrous Histiocytoma of Bone, Ovarian Epithelial Cancer, Ovarian Germ Cell Tumor, Ovarian Low Malignant Potential Tumor, Pancreatic Cancer, Paraproteinemias, Polycythemia vera, Parathyroid Cancer, Penile Cancer, Pheochromocytoma, Pituitary Tumor, Primary Central Nervous System Lymphoma, Primary Liver Cancer, Prostate Cancer, Rectal Cancer, Renal Cell Cancer, Renal Pelvis and Ureter Cancer, Retinoblastoma, Rhabdomyosarcoma, Salivary Gland Cancer, Sarcoidosis Sarcomas, Sezary Syndrome, Skin Cancer, Small Cell Lung Cancer, Small Intestine Cancer, Soft Tissue Sarcoma, Squamous Neck Cancer, Stomach Cancer, Supratentorial Primitive Neuroectodermal and Pineal Tumors, T-Cell Lymphoma, Testicular Cancer, Thymoma, Thyroid Cancer, Transitional Cell Cancer of the Renal Pelvis and Ureter, Transitional Renal Pelvis and Ureter Cancer, TROPhoblastic Tumors, Ureter and Renal Pelvis Cell Cancer, Urethral Cancer, Uterine Cancer, Uterine Sarcoma, Vaginal Cancer, Visual Pathway and Hypothalamic Glioma, Vulvar Cancer, Waldenstrom's Macroglobulinemia, Wilms' Tumor, and any other hyperproliferative disease, besides neoplasia, located in an organ system listed above.

The methods and compositions described and claimed herein may be used to treat malignant or premalignant conditions and to prevent progression to a neoplastic or malignant state, including but not limited to those disorders described above. Such uses are indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, BASIC PATHOLOGY, 2d Ed., W. B. Saunders Co., Philadelphia, pp. 68-79 (1976)).

Dysplasia is frequently a forerunner of cancer, and is found mainly in the epithelia. It is the most disorderly form of non-neoplastic cell growth, involving a loss in individual cell uniformity and in the architectural orientation of cells. Dysplasia characteristically occurs where there exists chronic irritation or inflammation. Dysplastic disorders which can be treated include, but are not limited to, anhidrotic ectodermal dysplasia, anterofacial dysplasia, asphyxiating thoracic dysplasia, atriodigital dysplasia, bronchopulmonary dysplasia, cerebral dysplasia, cervical dysplasia, chondroectodermal dysplasia, cleidocranial dysplasia, congenital ectodermal dysplasia, craniodiaphysial dysplasia, craniocarpotarsal dysplasia, craniometaphysial dysplasia, dentin dysplasia, diaphysial dysplasia, ectodermal dysplasia, enamel dysplasia, encephalo-ophthalmic dysplasia, dysplasia epiphysialis hemimelia, dysplasia epiphysialis multiplex, dysplasia epiphysialis punctata, epithelial dysplasia, faciodigitogenital dysplasia, familial fibrous dysplasia of jaws, familial white folded dysplasia, fibromuscular dysplasia, fibrous dysplasia of bone, florid osseous dysplasia, hereditary renal-retinal dysplasia, hidrotic ectodermal dysplasia, hypohidrotic ectodermal dysplasia, lymphopenic thymic dysplasia, mammary dysplasia, mandibulofacial dysplasia, metaphysial dysplasia, Mondini dysplasia, monostotic fibrous dysplasia, mucoepithelial dysplasia, multiple epiphysial dysplasia, oculoauriculovertebral dysplasia, oculodentodigital dysplasia, oculovertebral dysplasia, odontogenic dysplasia, opthalmomandibulomelic dysplasia, periapical cemental dysplasia, polyostotic fibrous dysplasia, pseudoachondroplastic spondyloepiphysial dysplasia, retinal dysplasia, septo-optic dysplasia, spondyloepiphysial dysplasia, and ventriculoradial dysplasia.

Additional pre-neoplastic disorders which can be treated include, but are not limited to, benign dysproliferative disorders (e.g., benign tumors, fibrocystic conditions, tissue hypertrophy, intestinal polyps or adenomas, and esophageal dysplasia), leukoplakia, keratoses, Bowen's disease, Farmer's Skin, solar cheilitis, and solar keratosis.

In preferred embodiments, the method of the invention is used to inhibit growth, progression, and/or metastasis of cancers, in particular those listed above.

Additional hyperproliferative diseases, disorders, and/or conditions include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, emangioblastoma, acoustic neuroma, oligodendroglioma, meningioma, melanoma, neuroblastoma, and retinoblastoma.

Expression Vectors

Still other embodiments may concern DNA sequences comprising a nucleic acid encoding an antibody, antibody fragment, cytokine or constituent fusion protein of a bsAb, such as a DNL™ construct. Fusion proteins may comprise an antibody or fragment or cytokine attached to, for example, an AD or DDD moiety.

Various embodiments relate to expression vectors comprising the coding DNA sequences. The vectors may contain sequences encoding the light and heavy chain constant regions and the hinge region of a human immunoglobulin to which may be attached chimeric, humanized or human variable region sequences. The vectors may additionally contain promoters that express the encoded protein(s) in a selected host cell, enhancers and signal or leader sequences. Vectors that are particularly useful are pdHL2 or GS. More preferably, the light and heavy chain constant regions and hinge region may be from a human EU myeloma immunoglobulin, where optionally at least one of the amino acid in the allotype positions is changed to that found in a different IgG1 allotype, and wherein optionally amino acid 253 of the heavy chain of EU based on the EU number system may be replaced with alanine See Edelman et al., *Proc. Natl. Acad. Sci. USA* 63: 78-85 (1969). In other embodiments, an IgG1 sequence may be converted to an IgG4 sequence.

The skilled artisan will realize that methods of genetically engineering expression constructs and insertion into host cells to express engineered proteins are well known in the art and a matter of routine experimentation. Host cells and methods of expression of cloned antibodies or fragments have been described, for example, in U.S. Pat. Nos. 7,531,327, 7,537,930, 7,785,880, 8,076,410, 8,153,433 and 8,372,603, the Examples section of each incorporated herein by reference.

Kits

Various embodiments may concern kits containing components suitable for treating or diagnosing diseased tissue in a patient. Exemplary kits may contain one or more bsAbs, ADCs, interferons, and/or checkpoint inhibitor antibodies as described herein. If the composition containing components for administration is not formulated for delivery via the alimentary canal, such as by oral delivery, a device capable of delivering the kit components through some other route may be included. One type of device, for applications such as parenteral delivery, is a syringe that is used to inject the composition into the body of a subject Inhalation devices may also be used. In certain embodiments, a therapeutic agent may be provided in the form of a prefilled syringe or autoinjection pen containing a sterile, liquid formulation or lyophilized preparation.

The kit components may be packaged together or separated into two or more containers. In some embodiments, the containers may be vials that contain sterile, lyophilized formulations of a composition that are suitable for reconstitution. A kit may also contain one or more buffers suitable for reconstitution and/or dilution of other reagents. Other containers that may be used include, but are not limited to, a pouch, tray, box, tube, or the like. Kit components may be packaged and maintained sterilely within the containers.

Another component that can be included is instructions to a person using a kit for its use.

EXAMPLES

The following examples are provided to illustrate, but not to limit, the claims of the present invention.

Example 1

T-Cell Redirecting Bispecific Antibody DOCK-AND-LOCK™ (DNL™) Complexes

Several species of exemplary leukocyte redirecting bispecific antibodies were made as DNL™ complexes, as described below. The complexes were effective to induce an immune response against appropriate target cells.

Materials and Methods

General techniques for making and using DOCK-AND-LOCK™ (DNL™) complexes are described in the Examples below. An exemplary leukocyte redirecting bispecific antibody with binding sites for CD3 and CD19 was made as a DNL™ complex, referred to as (19)-3s (FIG. 1). An anti-CD19 F(ab)$_2$ DNL module was constructed by recombinant fusion of a dimerization and docking domain (DDD2) at the carboxyl terminal end of the Fd chain. An anti-CD3-scFv module was designed from Okt3 mAb with addition of an anchor domain (AD2) and assembled in the format V$_H$-L1-V$_K$-L2-6H-L3-AD2 ("6H" disclosed as SEQ ID NO:105), where the V domains were fused via a flexible peptide linker and the AD2 peptide was preceded by a 6-His linker (SE ID NO:105). The sequences of the anti-CD3 variable regions, linkers and AD2 were as shown below.

encoding the Okt3scFv-AD2 polypeptide (SEQ ID NOs:96-101) was synthesized and cloned into the pdHL2 expression vector via 5' Xba 1 and 3' Eag I restriction sites. The construct comprised the V$_H$ domain fused to the V$_L$ in an scFv with the structure V$_H$-L1-V$_K$-L2-6H-L3-AD2 ("6H" disclosed as SEQ ID NO:105). The expressed protein had two amino acid substitutions from the original Okt3 mAb. A cysteine residue in the CDR-H3 was changed to serine (Kipryanov, 1997, *J Immunol Methods* 200:69-77). The penultimate residue of the V$_L$ was changed from aspartate to lysine.

The Okt3scFv-AD2 module was combined with various C$_H$1-DDD2-Fab modules to generate a panel of (X)-3s trivalent bsAbs (Table 6). The C$_H$1-DDD2-Fab-pdHL2 expression vectors were constructed as described previously for similar constructs (Rossi et al., 2008, *Cancer Res* 68:8384-92). Briefly, expression vectors encoding C$_H$1-DDD2-Fab were generated from the corresponding IgG-pdHL2 expression vectors by excising the coding sequence for the C$_H$1-Hinge-C$_H$2-C$_H$3 domains with Sac II and Eag I restriction enzymes and replacing it with a 507 bp sequence encoding C$_H$1-DDD2, which was excised from the C$_H$1-DDD2-Fab-hA20-pdHL2 expression vector (Rossi et al., 2008, *Cancer Res* 68:8384-92) with the same enzymes. C$_H$1-DDD2-Fab modules were derived from the humanized mAbs hA19 (anti-CD19), labetuzumab (hMN-14, anti-CEACAM5), clivatuzumab (hPAM4, anti-mucin), hMN-15 (anti-CEACAM6), hRS7 (anti-TROP-2), veltuzumab (hA20, anti-CD20), hL243 (anti-HLA-DR) and epratuzumab (hLL2, anti-CD22). The mAb designated hA19 was humanized from the mouse anti-CD19 mAb B43 (Uckun et al., 1988, *Blood* 71:13-29). Each expression vector was

```
V_H sequence of anti-CD3 scFv
                                                    (SEQ ID NO: 96)
QVQLQQSGAELARPGASVKMSCKASGYTFTRYTMHWVKQRPGQGLEWIGYINPSRGY

TNYNQKFKDKATLTTDKSSSTAYMQLSSLTSEDSAVYYCARYYDDHYSLDYWGQGTT

LTVSS

L1 Linker
                                                    (SEQ ID NO: 97)
GGGGSGGGGSGGGGS V_K sequence of anti-CD3 scFv
                                                    (SEQ ID NO: 98)
DIVLTQSPAIMSASPGEKVTMTCSASSSVSYMNWYQQKSGTSPKRWIYDTSKLASGVPA

HFRGSGSGTSYSLTISGMEAEDAATYYCQQWSSNPFTFGSGTKLEIKR

L2 Linker
                                                    (SEQ ID NO: 99)
GGGGS Poly-His-L3 Linker
                                                    (SEQ ID NO: 100)
HHHHHHGGGSG AD2
                                                    (SEQ ID NO: 101)
CGQIEYLAKQIVDNAIQQAGC
```

Expression Vectors and DNL™ Modules—

DNL™ complexes were constructed comprising antibody moieties against various disease-associated antigens, linked to an anti-CD3 antibody moiety, generally abbreviated as (X)-3s bsAbs. Independent production cell lines were developed in SpESFX-10 mouse myeloma cells (Rossi et al., 2011, *Biotechnol Prog* 27:766-75) for each of the DNL™ modules used to make the (X)-3s bsAbs. A cDNA sequence linearized by digestion with Sal I restriction enzyme and used to transfect SpESFX-10 cells by electroporation.

Clones were selected in media containing 0.2 μM methotrexate (MTX) and screened for protein expression by ELISA. Okt3scFv-AD2 was captured on Ni-NTA HisSorb plates (Qiagen) and detected with an anti-AD2 mAb. C$_H$1-DDD2-Fab modules were captured with goat-anti-human-kappa chain and detected with goat-anti-human-F(ab')$_2$-

HRP. Productivity of protein-expression was amplified by stepwise increases in MTX concentration up to 3 μM. Okt3scFv-AD2 and $C_H1$-DDD2-Fab modules were purified to homogeneity from the broth of roller bottle cultures by affinity chromatography using Ni-SEPHAROSE® and Kappa-Select resins, respectively. The DNL™ method was used to assemble (X)-3s bsAbs via the site-specific conjugation of mole equivalents of Okt3scFv-AD2 and $C_H1$-DDD2-Fab modules. For example, approximately 100 mg of (19)-3s were produced by combining 22 mg of Okt3scFv-AD2 with 80 mg of $C_H1$-DDD2-Fab-hA19. The mixture was reduced overnight at room temperature with 1 mM reduced glutathione prior to the addition of 2 mM oxidized glutathione. The (19)-3s was purified from the reaction mixture by sequential affinity chromatography with Kappa-Select and Ni-SEPHAROSE®. Additional (X)-3s constructs were assembled at various scales following a similar process.

TABLE 6

(X)-3s DNL ™ Constructs

| Code | Target | $C_H1$-DDD2-Fab | AD2-anti-CD3 |
| --- | --- | --- | --- |
| (19)-3s | CD19 | $C_H1$-DDD2-Fab-hA19 | scFv-AD2-Okt3 |
| (20)-3s | CD20 | $C_H1$-DDD2-Fab-hA20 | scFv-AD2-Okt3 |
| (22)-3s | CD22 | $C_H1$-DDD2-Fab-hLL2 | scFv-AD2-Okt3 |
| (C2)-3s | HLA-DR | $C_H1$-DDD2-Fab-hL243 | scFv-AD2-Okt3 |
| (M1)-3s | MUC5AC | $C_H1$-DDD2-Fab-hPAM4 | scFv-AD2-Okt3 |
| (14)-3s | CEACAM5 | $C_H1$-DDD2-Fab-hMN-14 | scFv-AD2-Okt3 |
| (15)-3s | CEACEAM6 | $C_H1$-DDD2-Fab-hMN-15 | scFv-AD2-Okt3 |
| (E1)-3s | TROP-2 | $C_H1$-DDD2-Fab-hRS7 | scFv-AD2-Okt3 |

Analytical Methods—

Size-exclusion high-performance liquid chromatography (SE-HPLC) was performed with an Alliance HPLC System with a BIOSUITE™ 250, 4-μm UHR SEC column (Waters Corp). Electrospray ionization time of flight (ESI-TOF) liquid chromatography/mass spectrometry (LC-MS) was performed with a 1200-series HPLC coupled with a 6210 TOF MS (Agilent Technologies, Santa Clara, Calif.). The (19)-3s was resolved by reversed phase HPLC (RP-HPLC) at 60° C., using a 14-min gradient of 30-80% acetonitrile in 0.1% aqueous formic acid with an Aeris widepore 3.6 μm C4 column (Phenomenex). For the TOF MS, the capillary and fragmentor voltages were set to 5500 and 300 V, respectively.

Cell Lines and Reagents—

Raji, Ramos, Daudi, LS174T and Capan-1 cell lines were purchased from the American Type Cell Culture Collection (ATCC, Manassas, Md.) and Nalm-6 cells were purchased from Deutsche Sammlung von Mikroorganismen and Zellinien (DSMZ, Braunchweig, Germany). All cell lines, except Capan-1, were maintained in RPMI-1640 containing 10% FBS, 1% L-glutamine, 1% penicillin-streptomycin and 1% MEM nonessential amino acids. Capan-1 cells were maintained with 20% FBS. All cell culture media and supplements were purchased from Life Technologies (Carlsbad, Calif.).

PBMCs and T Cell Isolation—

Human peripheral blood mononuclear cells (PBMC) were purified from whole donor blood (Blood Center of NJ, East Orange, N.J.) using UNI-SEP$_{MAXI}$ tubes (Novamed, Ltd, Jerusalem, Israel). CD3-positive T cells were isolated from PBMCs by negative selection using the Pan T Cell Isolation Kit (Miltenyi Biotec, Auburn, Calif.), according to the manufacturer's protocol. Efficiency of T cell isolation was assessed by FACS after staining the enriched T cells with anti-CD3-PE antibody. In some cases, further staining with CD-19 and CD-14 was performed as well to identify contaminating cells.

T Cell Activation—

Isolated T cells were plated in 6-well tissue culture plates at a final density of 2.25×10$^6$ cells/well. Daudi cells were added to some wells at a final density of 1.5×10$^6$ cells/well, other wells were left to contain only T cells. Alternatively, PBMCs were added to 6-well tissue culture plates at a final cell density of 6×10$^6$ cells/well. The volume of each well was brought up to 3 mL. To the appropriate wells, 3 ng/mL of (19)-3s, (M1)-3s or (19)-DDD2 was added. After incubation overnight at 37° C., 1 mL of each sample was removed. The cells were pelleted and labeled on ice with CD69-APC and CD3-PE for 20 minutes. Cells were washed 2 times with 1% BSA in PBS and analyzed using a FACSCALIBER™ flow cytometer (BD Biosciences, San Jose, Calif.).

T-Cell Proliferation—

PBMCs were seeded in T25 flasks at a concentration of 1×10$^6$ cells/mL containing the specified reagents. For B cell-depleted flasks, B cells were removed by negative selection using a B-cell isolation kit from Miltenyi according to manufacturer's protocol. On select days, 100 μL of media was removed from each flask, labeled with anti-CD7-APC for 20 minutes on ice, washed once and resuspended in 300 μL of 1% BSA/PBS containing 7-AAD. For each sample, the entire volume is analyzed using a FACSCALIBER™ flow cytometer. Each sample is counted in duplicate. Analysis is performed using FlowJo Software. For each sample, dead (7-AAD+) cells, and debris (based on forward vs. side scatter) was removed. Finally, live CD7+ cells were selected and plotted using Prism software.

Cell Binding Assays (Jurkat/Capan-1)—

Jurkat cells were stained with PKH26 Red Fluorescent Cell Linker Kit (Sigma) according to manufacturer's protocol. Capan-1 cells were stained with 5 μM CFSE (carboxyfluorescein diacetate succinimidyl ester, Life Technologies) according to manufacturer's protocol. Labeled Capan-1 cells were added to 8-well chamber slides (ThermoWaltham, Mass.) and allowed to attach overnight. The following day, media was removed and PKH26-labeled Jurkat cells were added in media containing 0.1 μg/mL of (E1)-3s, (M1)-3s or (19)-3s. Following a 1-hour incubation at 37° C., slides were washed with PBS to remove any unbound cells and observed by fluorescence microscopy.

Cell Binding Assays (Jurkat/Daudi)—

Jurkat and Daudi cells were labeled with anti-CD3-PE and anti-CD20-FITC, respectively. Labeled cells were then coincubated at a 2.5:1 ratio with 0.1 μg/mL (19)-3s for 30 minutes at room temperature. Aliquots of cells were then observed by fluorescence microscopy.

Cytotoxicity Assay (Hematologic Tumor Cell Lines)—

Target cells were labeled with PKH67 Green Fluorescent Cell Linker Kit (Sigma) according to the manufacturer's protocol. Briefly, 5×10$^6$ target cells were resuspended in 250 μL of diluent C. In a second tube 1 μL of PKH26 dye is added to 250 μL of diluent C. The cell suspension is then added to the dye solution, mixed thoroughly and incubated at RT for 2 minutes. The reaction was quenched by adding an equal volume of FBS. The labeled cells were then washed 3 times with complete RPMI. Unstimulated, isolated T cells were used as effector cells. Effector cells and PKH67-labeled target cells were combined at a 10:1 ratio and plated in 48-well plates containing serial dilutions of (19)-3s or (14)-3s. Each well contained 5×10$^4$ target cells and 5×10$^5$ effector cells. Jeko-1 assays were performed in 20% RPMI.

Plates were incubated for 18-24 hours in a 37° C. incubator containing 5% $CO_2$. Following incubation, all cells were removed from 48-well plates into flow cytometer tubes and resuspended in 1% BSA/PBS containing 1 ug/mL of 7AAD, to distinguish live from dead cells, and 30,000 COUNT-BRIGHT™ Absolute Counting Beads (Life Technologies). Cells were analyzed on a FACSCALIBER™ flow cytometer. For each sample, 8,000 COUNTBRIGHT™ beads were counted as a normalized reference. Data were analyzed using FlowJo software (Treestar, Inc., Ashland, Oreg.). For each sample, dead cells and debris were excluded and total live target cells were counted.

Cytotoxicity Assay (Solid Tumor Cell Lines)—

Target cells were labeled with PKH67 Green Fluorescent Cell Linker Kit (Sigma) following the same procedure as for staining with PKH23. Effector cells used were as follows: For Capan-1 assays, CD8+ enriched T cells were used, following purification from a CD8+ enrichment column (R&D Systems, Minneapolis, Minn.). For LS174T cells: Stimulated T cells were used after incubation of PBMC for 5 days in media containing 25 U/mL IL-2 and 50 ng/mL Okt3 Mab, followed by 2 days incubation in media containing 25 U/mL IL-2 alone. Effector cells and PKH67-labeled target cells were combined at a 3:1 ratio ($5 \times 10^4$ target cells and $1.5 \times 10^5$ effector cells/well) and plated over 48-well plates containing serial dilutions of (E1)-3s, (14)-3s or (19)-3s. Capan-1 assays were performed in 20% RPMI. Plates were incubated for 42-48 hours in a 37° C. incubator containing 5% $CO_2$. Following incubation, suspension cells were combined with trypsinized attached cells from all wells and transferred into flow cytometer tubes. Cells were washed one time and resuspended in 1% BSA/PBS containing 1 ug/mL of 7AAD, to distinguish live from dead cells, and 30,000 COUNTBRIGHT™ Absolute Counting Beads. Cells were analyzed on a FACSCALIBER™ flow cytometer. For each sample, 8,000 COUNTBRIGHT™ beads were counted as a normalized reference. Data were analyzed using FlowJo software (Treestar, Inc., Ashland, Oreg.). For each sample, dead cells and debris were excluded and total live target cells were counted.

In Vivo Efficacy—

Female NOD/SCID mice, 8 weeks old, were purchased from Charles River (Wilmington, Mass.). Mice were injected s.c. with a mixture of Raji ($1 \times 10^6$) and human PBMCs ($5 \times 10^6$ cells) mixed 1:1 with matrigel. Therapy began 1 hour later. Treatment regimens, dosages, and number of animals in each experiment are described in the Results. Animals were monitored daily for signs of tumor out-growth. Once tumors appeared, they were measured twice weekly. Tumor volume (TV) was determined by measurements in two dimensions using calipers, with volumes defined as: $L \times w^2/2$, where L is the longest dimension of the tumor and w the shortest. Efficacy was determined by a log-rank test using Prism GraphPad software (v5; LaJolla, Calif.) on Kaplan-Meier curves using survival surrogate endpoints as time for tumor progression (TTP) to 1.0 cm³. Significance was considered at $P<0.05$.

Results

Construction and Biochemical Analysis of Leukocyte Redirecting Bispecific Antibodies.

The DNL™ method was used to generate a panel of (X)-3s, leukocyte redirecting bsAbs for targeting of various tumor-associated antigens including CD19, CD20, HLA-DR, TROP-2, CEACAM5 and MUC5AC. The purity of these structures was demonstrated by SE-HPLC and SDS-PAGE analysis, where only bands representing the three constituent polypeptides (Okt3scFv-AD2, hA19-Fd-DDD2 and hA19 kappa) were evident (data not shown). LC-MS analysis identified a single RP-HPLC peak having a deconvoluted mass spectrum consistent (mass accuracy=11 ppm) with the calculated mass (137432.37 Da) of (19)-3s from its deduced amino acid sequence, including the predicted amino-terminal pyroglutamates on the Okt3scFv-AD2 and each of the two $C_H1$-DDD2-hA19 Fd chains (data not shown). No additional post-translational modifications, including glycosylation were indicated.

Immune Synapse Formation Between Daudi Burkitt Lymphoma and T Cells, Mediated by (19)-3s.

The effects of the leukocyte redirecting (19)-3s DNL™ complex on targeting effector T cells to $CD19^+$ lymphoma cells was examined (FIG. 2). Freshly isolated T cells were combined with Daudi cells at an E:T ratio of 2.5:1. Cells were treated with 0, 1 or 5 μg/mL of (19)-3s DNL™ complex for 30 min at room temperature prior to analysis by flow cytometry. Anti-CD20-FITC and anti-CD7-APC were used to identify Daudi and T cells, respectively. Co-binding was indicated as the % of $CD20^+/CD7^+$ events. After treatment with (19)-3s, 45.5% of flow events were CD20/CD7 dual-positive, indicating synapsed Daudi and T cells (FIG. 2A), compared to 2% measured for the mixed cells without antibody (FIG. 2B). Addition of (19)-3s resulted in association of >90% of the Daudi with T cells (FIG. 2C). These results show that the (19)-3s DNL™ complex was effective to direct T cells to the targeted antigen-expressing lymphoma cells.

Figure 3:
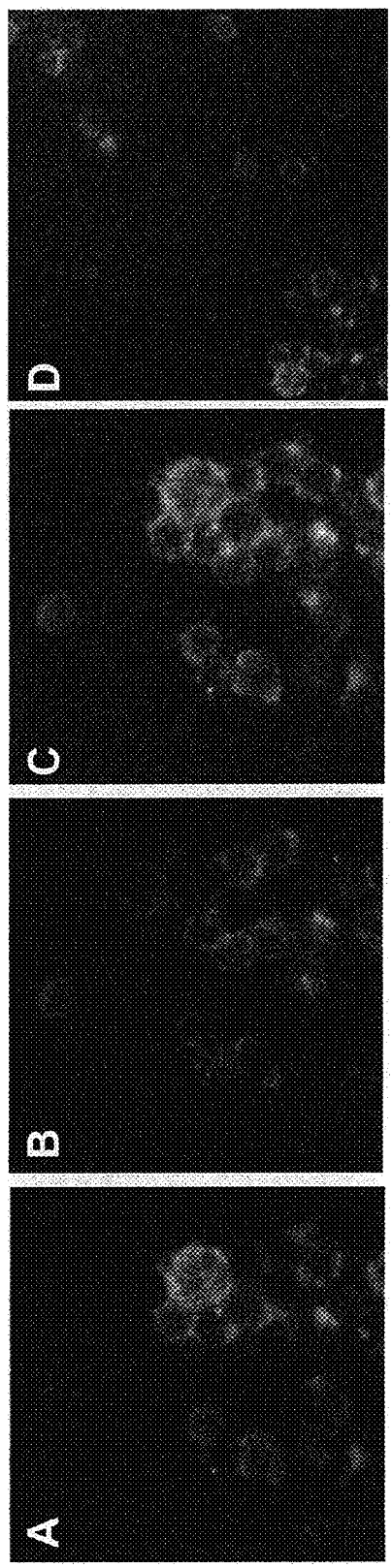
FIG. 3A. Jurkat (T cells) and Daudi (B cells) were combined at a 1:1 ratio, treated with 0.1 µg/mL (19)-3s for 30 minutes and stained with anti-CD20-FITC, prior to analysis by fluorescence microscopy.
FIG. 3B. Jurkat (T cells) and Daudi (B cells) were combined at a 1:1 ratio, treated with 0.1 µg/mL (19)-3s for 30 minutes and stained with anti-CD20-FITC and anti-CD3-PE, prior to analysis by fluorescence microscopy.
FIG. 3C. The merged image of FIGS. 3A and 3B reveals synapse formation between green-stained Daudi and red-stained Jurkat cells.
FIG. 3D. Synapse formation was not evident in the absence of (19)-3s.

Synapse formation between T cells and target lymphoma cells was demonstrated by fluorescence microscopy (FIG. 3) Jurkat (T cells) and Daudi (B cells) were combined at a 1:1 ratio, treated with 0.1 μg/mL of the (19)-3s DNL™ complex for 30 minutes and stained with anti-CD20-FITC (FIG. 3A) and anti-CD3-PE (FIG. 3B), prior to analysis by fluorescence microscopy. The merged image (FIG. 3C) reveals synapse formation between green-stained Daudi and red-stained Jurkat cells. Synapse formation was not evident in the absence of (19)-3s (FIG. 3D). FIG. 3C demonstrates that the target lymphoma cells are in direct contact with the targeted T cells.

Figure 4:
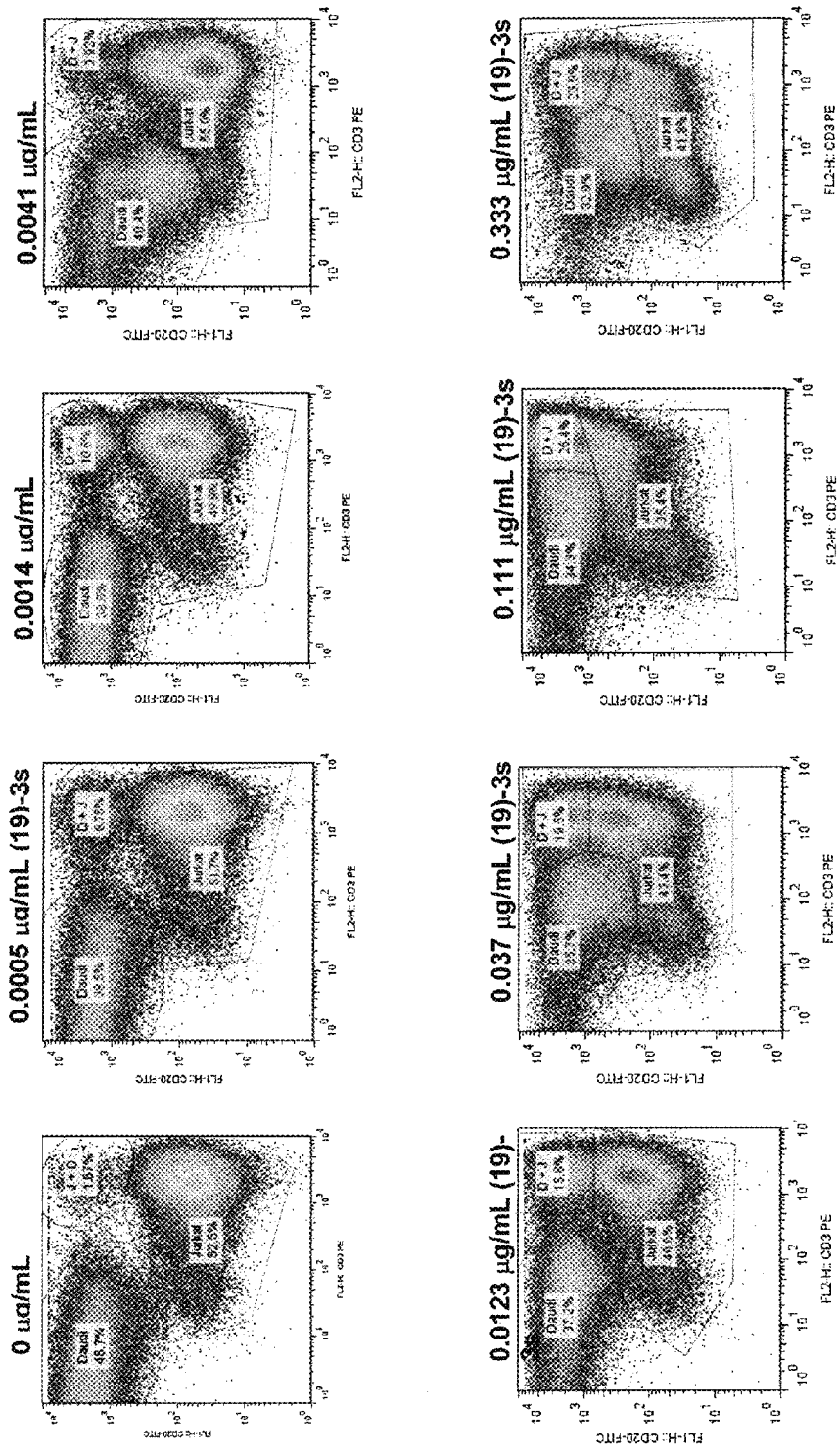
FIG. 4. Dose response analysis of (19)-3s mediated cell-to-cell association of Daudi and Jurkat cells as a function of increasing concentrations of (19)-3s.

A dose-response series was performed for (19)-3s mediated association of T cells to an exemplary B-cell lymphoma line (FIG. 4). As shown in FIG. 4, under the conditions of this experiment, saturation of (19)-3s-mediated cell-to-cell association of T cells to target cells was reached at a concentration between 0.037 and 0.111 μg/ml of the DNL™ complex.

Figure 5:
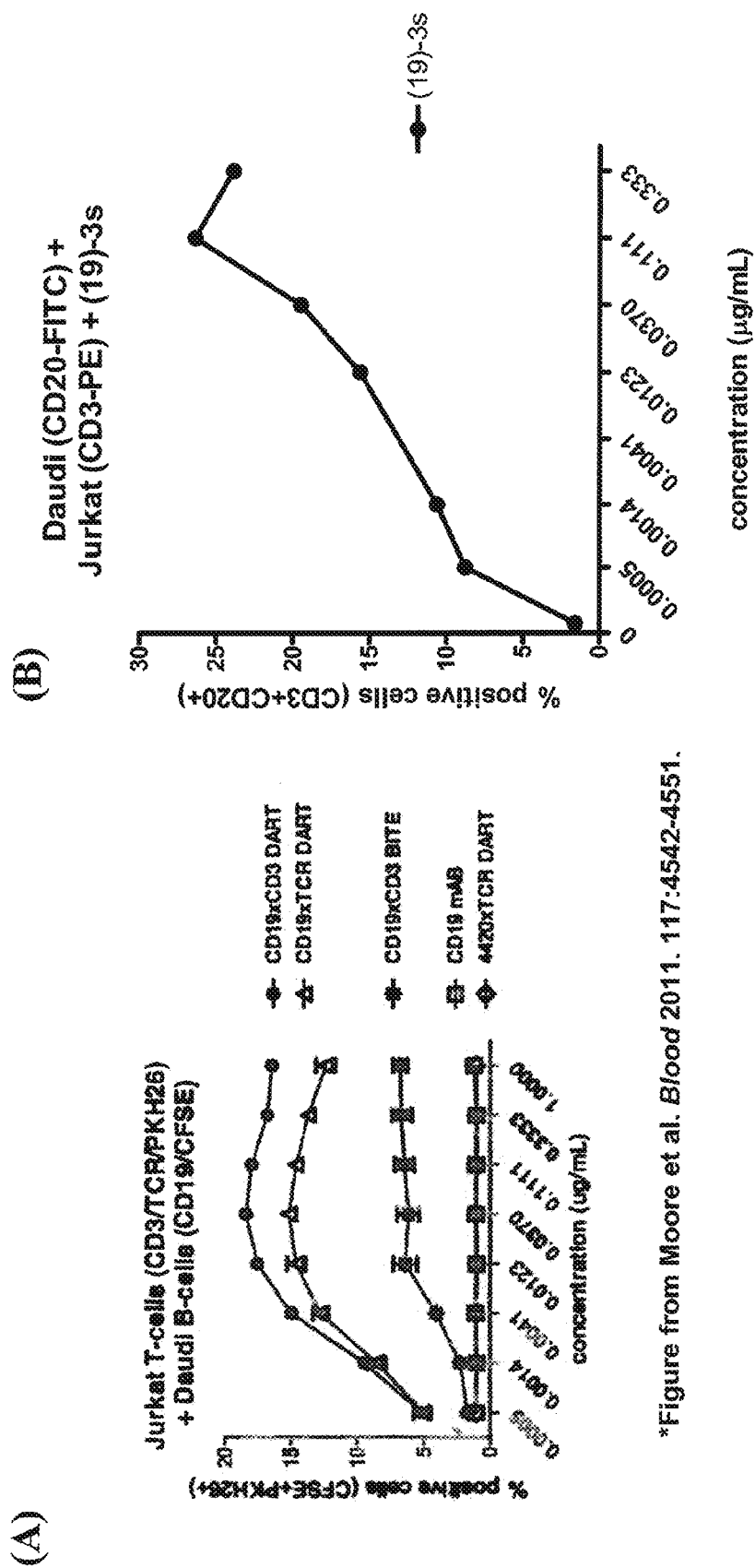
FIG. 5A. Comparison of cell-to-cell association mediated by BITE® and DART™. The data for BITE® and DART™ was taken from Moore et al. (2011, *Blood* 117:4542-4551.
FIG. 5B. Comparison of cell-to-cell association mediated by (19)-3s.

FIG. 5 shows a comparison of the relative efficacies of BITE® (FIG. 5A), DART™ (FIG. 5A) and DNL™ (FIG. 5B) anti-CD3×anti-CD19 complexes for redirecting T cells to targeted $CD19^+$ B cells. The data for BITE® and DART™ was obtained from Moore et al. (2011, *Blood* 117:4542-51). At the lowest concentration tested of 0.0005 μg/ml, the (19)-3s DNL™ complex was more effective than BITE® or DART™ at targeting T cells to B-cell lymphoma (FIG. 5). The (19)-3s DNL™ complex also induced a slightly higher maximum level of cell-to-cell association than the comparable BITE® and DART™ complexes (FIG. 5A). Although difficult to extrapolate from the single data points generated for the (19)-3s DNL™ complex, the $EC_{50}$ levels appeared to be similar for BITE®, DART™ and DNL™ (FIG. 5).

(19)-3s, (E1)-3s and (M1)-3s-Mediated Cell-Cell Association of T Cells to Target Tumor Cells.

To evaluate the ability of the T-cell redirecting BsAbs to facilitate the association of T cells to their target tumor cells, Jurkat T cells were coincubated with target tumor cells containing (X)-3s and evaluated by flow cytometry and fluorescence microscopy. Jurkat T cells are a CD4+ T cell leukemia line, chosen for their ability to demonstrate T cell binding without depletion of the FITC labeled Daudi cells in the presence of various concentrations of (19)-3s and analyzed by flow cytometry for the detection of double positive (CD3+CD20+) populations indicating T cell-B cell associated complexes. An apparent cell-cell association was seen following treatment with 0.5 ng/mL of (19)-3s and after treatment with 0.1 µg/mL over 25% of the cell population existed in a cell-cell association (FIG. 5). Fluorescent microscopy supports this data, as immune synapses are evident following treatment with 0.1 µg/mL (19)-3s (FIG. 4). No synapse formation was seen in the absence of (19)-3s (data not shown).

Figure 6:
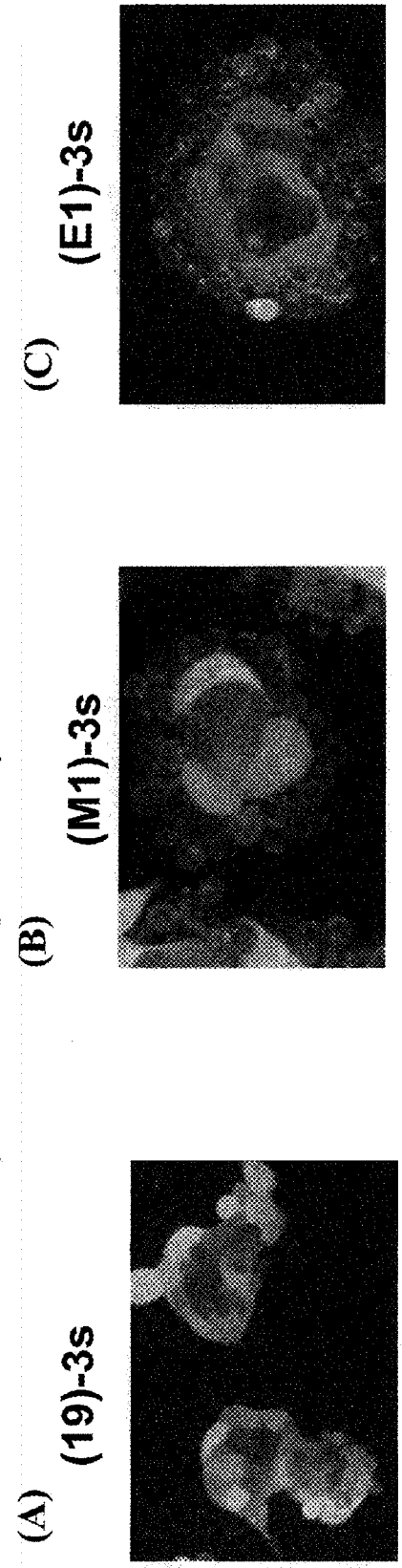
FIG. 6A. Synapse formation between T cells and Capan-1 pancreatic cancer cells mediated by (19)-3s control bsAb. CFSE-labeled Capan-1 cells were coincubated with PKH26-labeled Jurkat in the presence of the bsAb.
FIG. 6B. Synapse formation between T cells and Capan-1 pancreatic cancer cells mediated by (M1)-3s MUC5AC bsAb. CFSE-labeled Capan-1 cells were coincubated with PKH26-labeled Jurkat in the presence of the bsAb.
FIG. 6C. Synapse formation between T cells and Capan-1 pancreatic cancer cells mediated by (E1)-3s TROP-2 targeting bsAb. CFSE-labeled Capan-1 cells were coincubated with PKH26-labeled Jurkat in the presence of the bsAb.

This cell-cell association was observed in the pancreatic tumor line Capan-1 as well (FIG. 6). Capan-1 expresses high levels of TROP2 and moderate levels of MUC5AC. Therefore, both the TROP2-targeting bsAb, (E1)-3s (FIG. 6C), and MUC5AC-targeting bsAb, (M1)-3s (FIG. 6B) were compared to the non-targeting control bsAb, (19)-3s (FIG. 6A). CFSE-labeled Capan-1 cells were coincubated with PKH26-labeled Jurkat in the presence of these bsAbs. Fluorescent microscopy revealed, as expected, large T-cell/Capan complexes mediated by (E1)-3s, followed by smaller, yet substantial complexes mediated by (M1)-3s and relatively low complex formation following (19)-3s treatment (FIG. 6).

(19)-3s Specifically Induces T Cell Activation and Proliferation.

Figure 7:
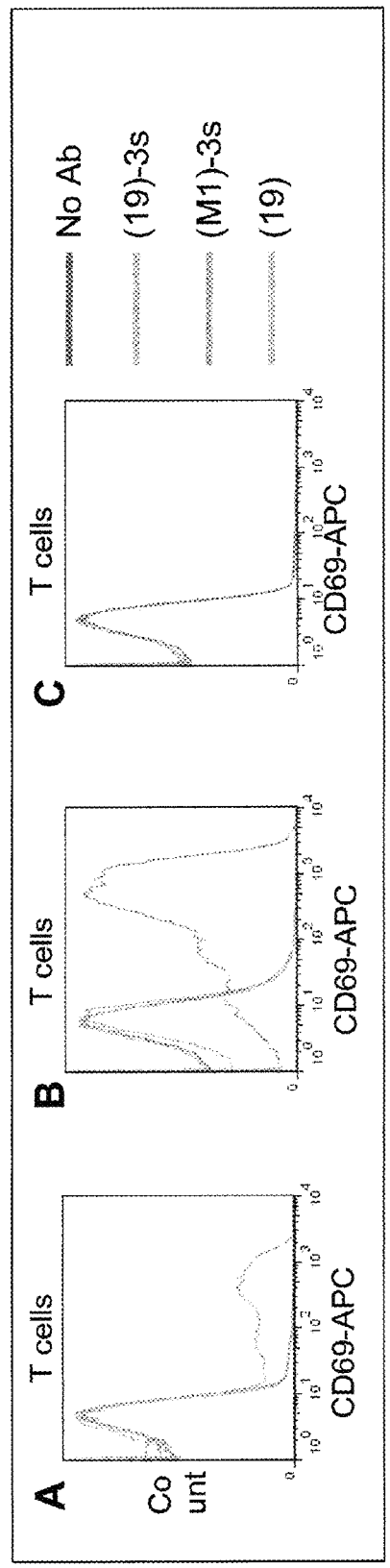
FIG. 7A. T-cell activation by (19)-3s. Upregulation of CD69 expression is an early event in T-cell activation. Daudi cells combined with PBMCs were treated overnight with the indicated antibodies, and stained with anti-CD3-PE and anti-CD69-APC, prior to analysis by flow cytometry. CD69 expression was evaluated following gating of T cells by forward vs. side scattering and anti-CD3 staining Combination of Daudi cells with an equal number of PBMCs resulted in 1.6% CD69+ T cells. Addition of 3 ng/mL (19)-3s induced 27% CD69+ T cells. Neither a control construct [(M1)-3s], which comprises the Okt3-scFv-AD2 module fused with a non-targeting F(ab)$_2$, nor the hA19-Fab-DDD2 module, induced T-cell activation.
FIG. 7B. T-cell activation by (19)-3s. Daudi cells combined with purified T cells were treated overnight with the indicated antibodies, and stained with anti-CD3-PE and anti-CD69-APC, prior to analysis by flow cytometry. CD69 expression was evaluated following gating of T cells by forward vs. side scattering and anti-CD3 staining Treatment of Daudi and purified T cells with (M1)-3s or hA19-Fab-DDD2 did not increase the number of CD69+ T cells (<4%), compared to the untreated cell mixture. Alternatively, (19)-3s induced robust T-cell activation, producing 80% CD69+ cells.
FIG. 7C. T-cell activation by (19)-3s. Purified T cells alone were treated overnight with the indicated antibodies, and stained with anti-CD3-PE and anti-CD69-APC, prior to analysis by flow cytometry. CD69 expression was evaluated following gating of T cells by forward vs. side scattering and anti-CD3 staining Without the addition of Daudi (target) cells, (19)-3s did not induce CD69 expression and T-cell activation. These results demonstrate that (19)-3s-mediated synapse formation between T cells and target cells is both required and sufficient for T-cell activation.

The ability of (19)-3s to activate T cells was evaluated either in PBMCs (FIG. 7A), or T cells coincubated with Daudi B cells (FIG. 7B), by measuring the expression levels of CD69, an early marker of T cell activation. Treatment with 3 ng/mL of (19)-3s induced T cell activation in T cells coincubated with Daudi B cells as indicated by a >50-fold increase in CD69 expression compared with non-targeting control antibodies, (19)-DDD2 and (M1)-3s, as well as T cells treated with (19)-3s without Daudi target cells (FIG. 7B). Similar results were observed when the antibodies were incubated with PBMCs, containing both T and B cells; (19)-3s stimulated CD69 expression levels >20-fold higher than non-targeting controls (FIG. 7A). In the absence of target cells, purified T cells treated with (19)-3s did not show activation (FIG. 7C).

Figure 8:
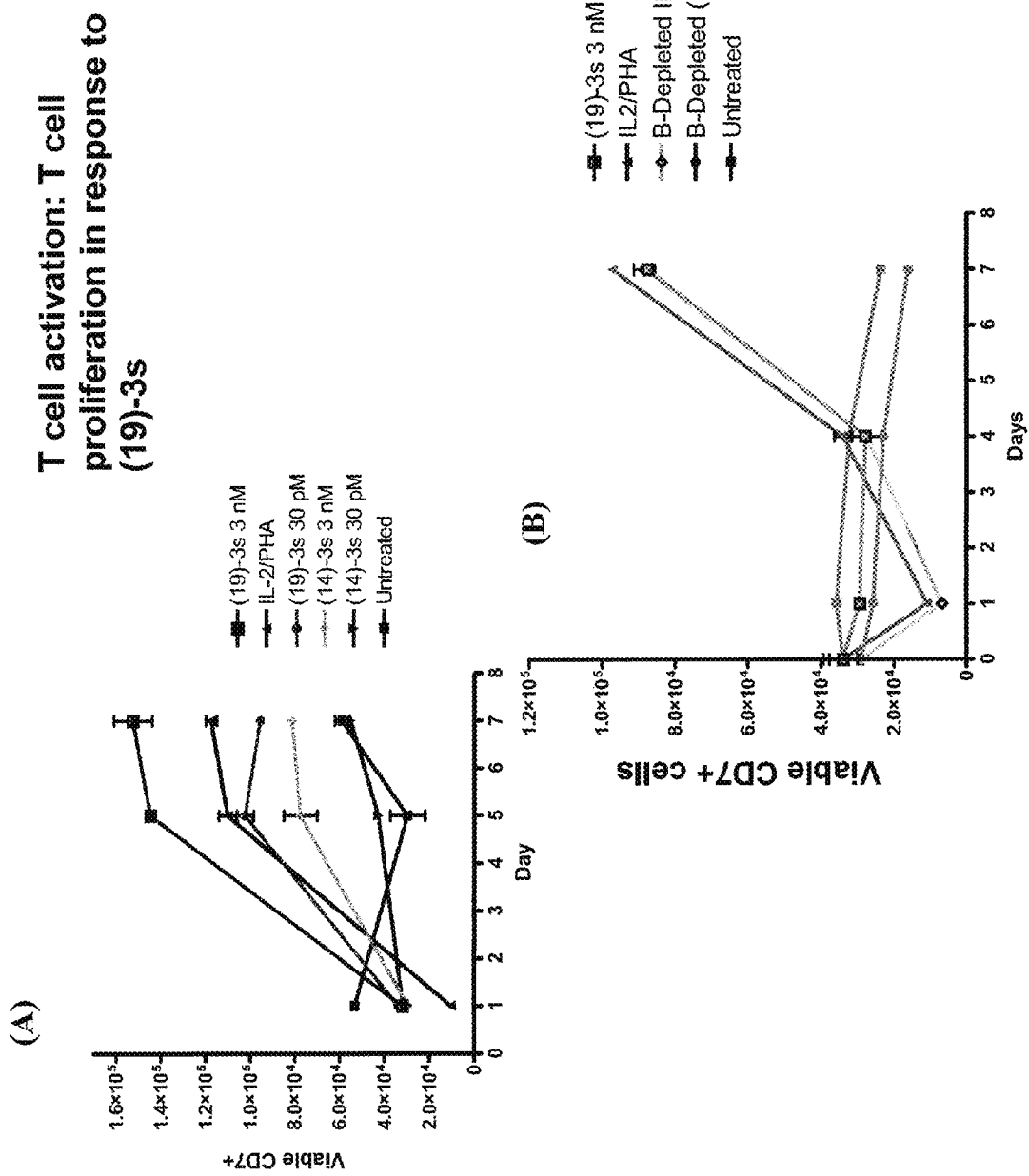
FIG. 8A. Induction of T-cell proliferation by (19)-3s. PBMCs were incubated with 3 nM or 30 pM of (19)-3s, compared to IL-2/PHA positive control and (14)-3s (non-target-binding control).
FIG. 8B. Induction of T-cell proliferation by (19)-3s. T cell proliferation was not observed in PBMCs depleted of B cells, indicating that target cells (B cells) are required for T-cell activation and proliferation.

T cell proliferation, as another indication of T cell activation, was evaluated after treatment of PBMCs with various CD3-targeting antibodies. (19)-3s at 3 nM or 30 µM induced T cell proliferation similar to that of the positive control IL-2/PHA (FIG. 8A). Non-targeting control antibody, (14)-3s, shows some non-specific T cell proliferation at the highest (3 nM) concentration (FIG. 8A). However, T cell proliferation was not observed in PBMCs depleted of B cells (FIG. 8B), suggesting that target cells are necessary for specific (19)-3s induced T cell proliferation.

(X)-3s Re-Directed T-Cell Mediated Killing of Malignant Cell Lines.

Figure 9:
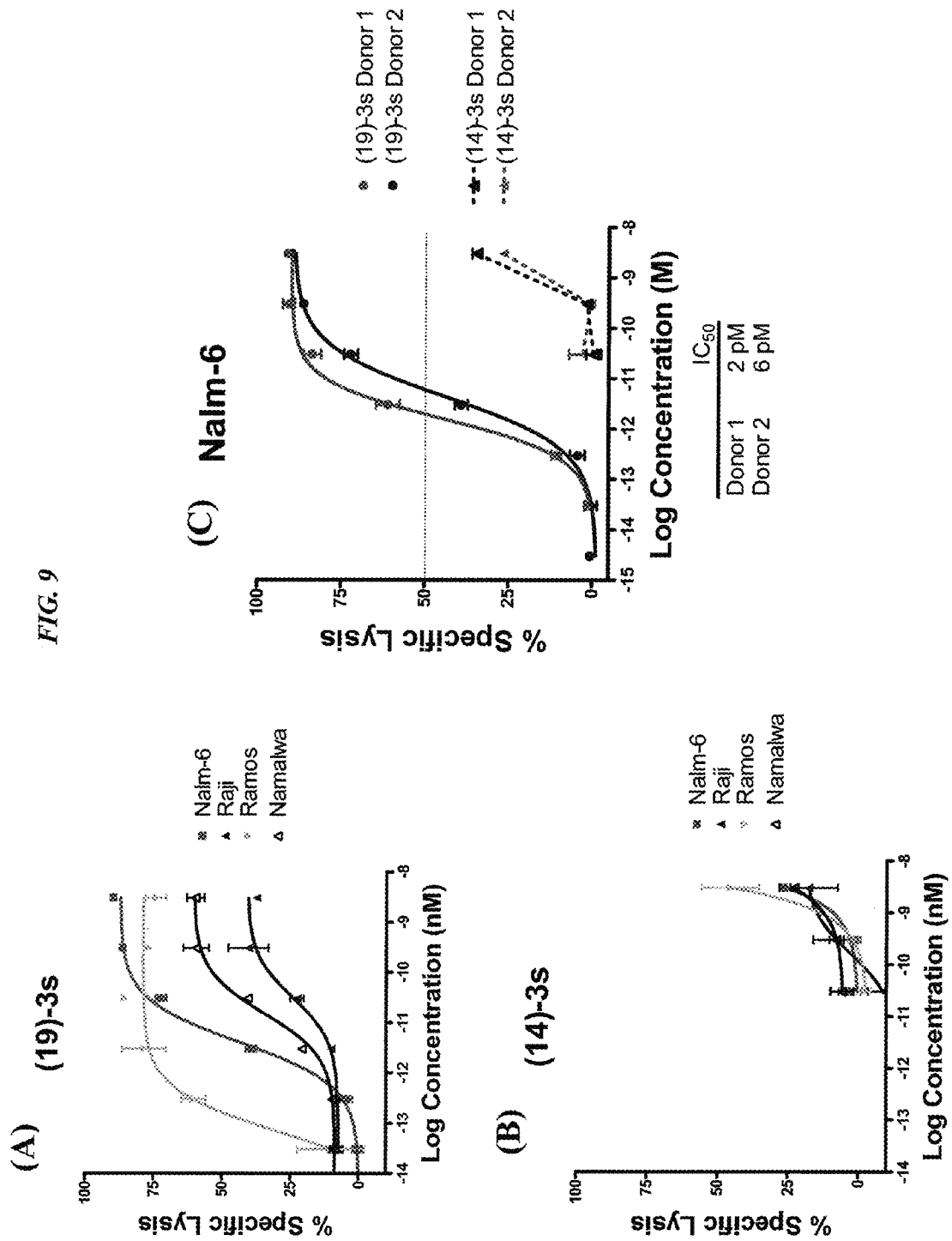
FIG. 9A. In vitro cytotoxicity of (19)-3s T-cell redirecting bsAbs. Dose-response curves for cytotoxicity to Nalm-6, Raji, Ramos and Namalwa cancer cells were determined for the (19)-3s DNL™ bsAb complex.
FIG. 9B. In vitro cytotoxicity of (19)-3s T-cell redirecting bsAbs. Dose-response curves for cytotoxicity to Nalm-6, Raji, Ramos and Namalwa cancer cells were determined for the (14)-3s (non-targeting) DNL™ bsAb complex.
FIG. 9C. Consistent results were observed using PBMCs, or T cells, obtained from two different donors and Nalm-6 cancer cells.

The cytotoxicity of each leukocyte targeting molecule was evaluated by its ability to mediate lysis of specific tumor target cells. For the hematologic tumor cell lines, a 10:1 E:T ratio using an unstimulated, enriched T cell population as the effector cells in an 18-24 hour assay demonstrated the optimal assay conditions. The CD19-targeting bsAb, (19)-3s induced the most potent specific killing of the relatively low CD19-expressing cell lines Ramos ($IC_{50}$=0.17 µM, $Lysis_{Max}$=79%) Daudi ($IC_{50}$=1 µM, $Lysis_{Max}$=60%), and Nalm6 ($IC_{50}$=6 µM, $Lysis_{Max}$=93%) (FIG. 9A). Interestingly, the high CD19-expressing cell lines, Namalwa ($IC_{50}$=63 µM, $Lysis_{Max}$=60%) and Raji ($IC_{50}$=3 nM, $Lysis_{Max}$=41%) were the least sensitive to (19)-3s (FIG. 9A). The non-targeting (14)-3s DNL™ construct had little cytotoxic effect in any of the cell lines tested (FIG. 9B). Consistent cytotoxic effects of the (19)-3s construct on the Nalm-6 ALL cell line were obtained with PBMCs obtained from two different donors (FIG. 9C).

Figure 10A:
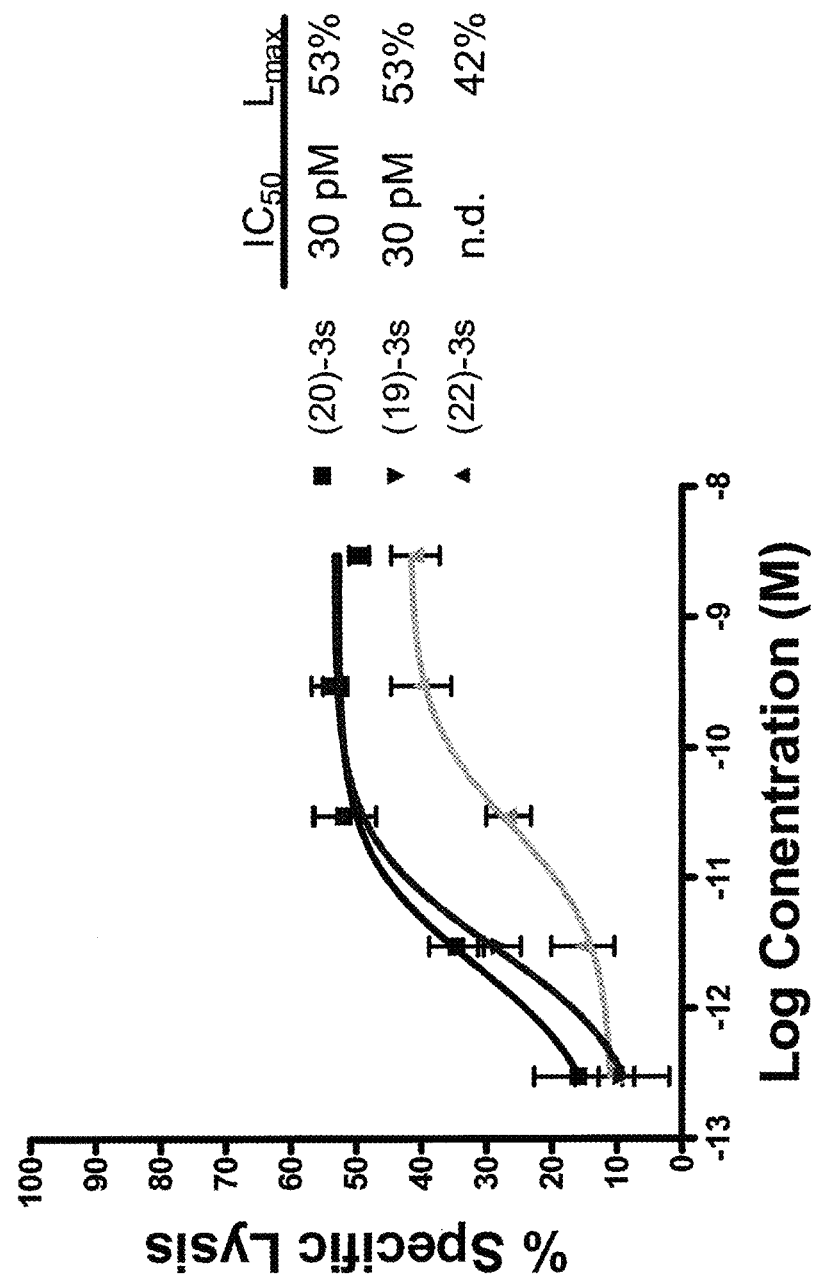
FIG. 10A. In vitro cytotoxicity of (20)-3s, (22)-3s and (C2)-3s T-cell redirecting bsAbs. Dose-response curves were determined for cytotoxicity to Namalwa cells induced by (20)-3s, (22)-3s and (C2)-3s T-cell redirecting bsAbs.
Figure 10B:
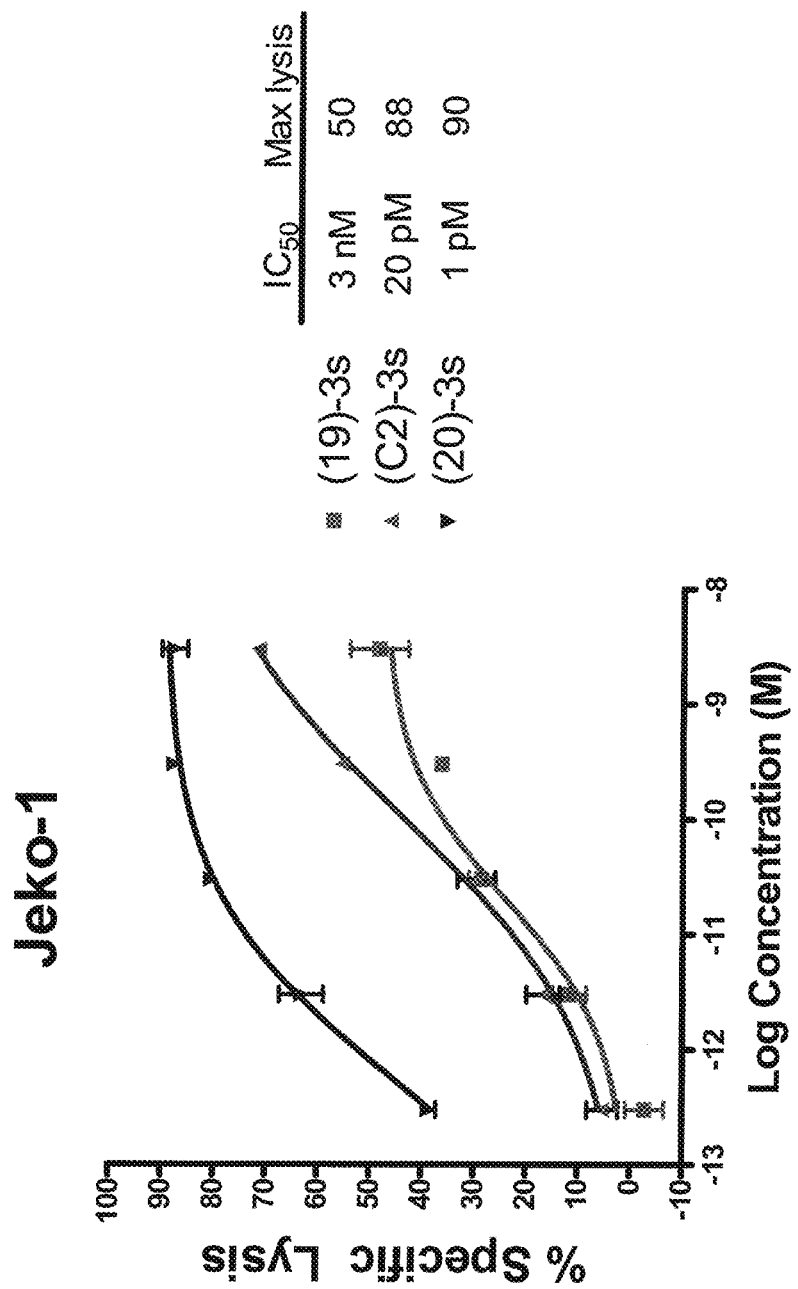
FIG. 10B. In vitro cytotoxicity of (20)-3s, (22)-3s and (C2)-3s T-cell redirecting bsAbs. Dose-response curves were determined for cytotoxicity to Jeko cells induced by (20)-3s, (22)-3s and (C2)-3s T-cell redirecting bsAbs.
Figure 10C:
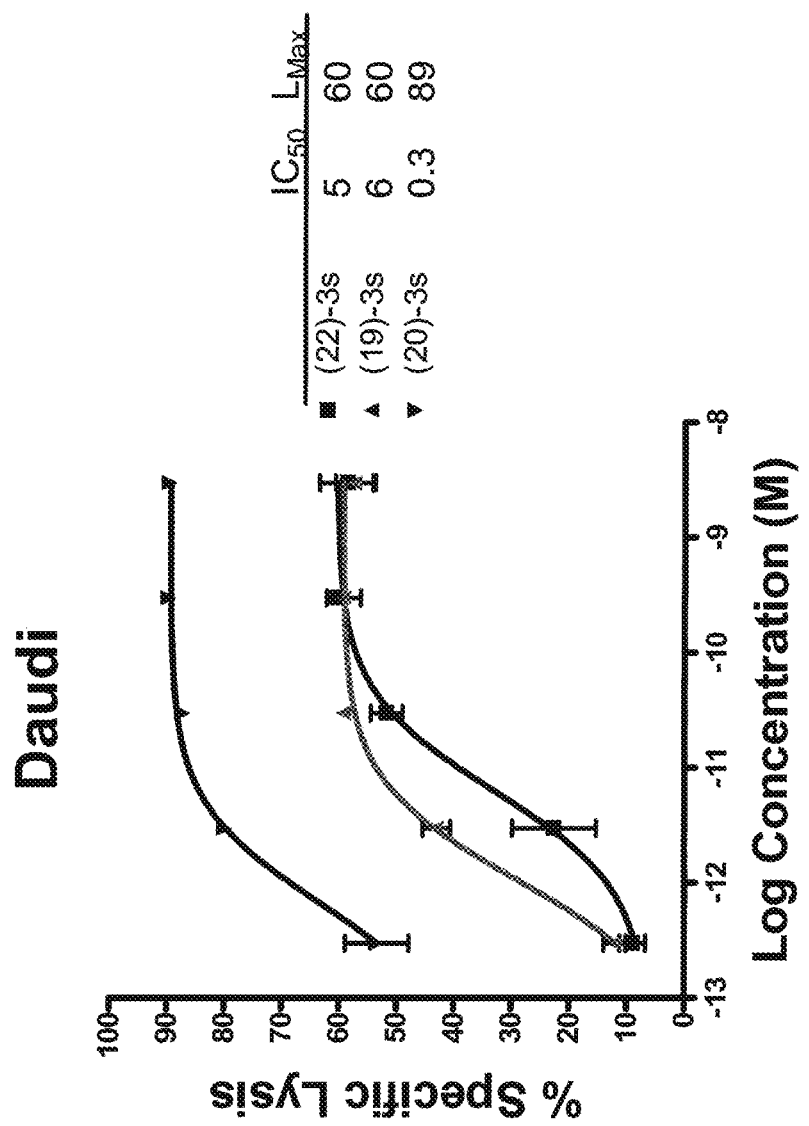
FIG. 10C. In vitro cytotoxicity of (20)-3s, (22)-3s and (C2)-3s T-cell redirecting bsAbs. Dose-response curves were determined for cytotoxicity to Daudi cells induced by (20)-3s, (22)-3s and (C2)-3s T-cell redirecting bsAbs.

The in vitro cytotoxic effects of (20)-3s, (22)-3s and (C2)-3s T-cell redirecting bsAbs were determined in several cell lines (FIG. 10). The CD22-targeting bsAb, (22)-3s, demonstrated potent ($IC_{50}$=5 µM, $Lysis_{Max}$=60%) specific T-cell mediated lysis in the CD22-positive Daudi cell line (FIG. 10C), but not in the CD22-negative Namalwa cells (FIG. 10A).

The CD20-targeting bsAb, (20)-3s demonstrated the highest potency in the higher-expressing CD20 cell lines, Daudi ($IC_{50}$=<0.3 µM, $Lysis_{Max}$=90%) (FIG. 10C) and Jeko ($IC_{50}$=1 µM, $Lysis_{Max}$=90%) (FIG. 10B), compared to the lower CD20-expressing Namalwa cell line ($IC_{50}$=30 µM, $Lysis_{Max}$=53%) (FIG. 10A).

The HLA-DR-targeting bsAb, (C2)-3s was tested in the HLA-DR expressing Jeko-1 cell line ($IC_{50}$=20 µM, $Lysis_{Max}$=88%) (FIG. 10B).

At an E:T ratio of 10:1, using isolated T cells as effector cells, the bsAbs induced potent T cell-mediated cytotoxicity in various B cell malignancies, including Burkitt lymphoma (Daudi, Ramos, Namalwa) mantle cell lymphoma (Jeko-1) and acute lymphoblastic leukemia (Nalm-6) (Table 7). A non-tumor binding control, (14)-3s, induced only moderate T-cell killing at >10 nM. The nature of the antigen/epitope, particularly its size and proximity to the cell surface, appears to be more important than antigen density for T-cell retargeting potency (Table 7). It is likely that (20)-3s is consistently more potent than (19)-3s and (C2)-3s, even when the expression of CD19 or HLA-DR is considerably higher than CD20, as seen with Namalwa and Jeko-1, respectively (Table 7). This is likely because the CD20 epitope comprises a small extracellular loop having close proximity to the cell surface. When compared directly using Daudi, (22)-3s was the least potent. Compared to CD19 and CD20, CD22 is expressed at the lowest density, is a rapidly internalizing antigen, and its epitope is further away from the cell surface. Each of these factors may contribute to its reduced potency. Finally, sensitivity to T-cell retargeted killing is cell-line-dependent, as observed using (19)-3s, where Raji ($IC_{50}$>3 nM) is largely unresponsive yet Ramos ($IC_{50}$=2 µM) is highly sensitive, even though the former expresses higher CD19 antigen density (Table 7).

In conclusion, (19)-3s, (20)-3s, (22)-3s and (C2)-3s bind to T cells and target B cells simultaneously and induce T-cell-mediated killing in vitro. The modular nature of the DNL method allowed the rapid production of several related conjugates for redirected leukocyte killing of various B cell malignancies, without the need for additional recombinant engineering and protein production. The close proximity of the CD20 extracellular epitope to the cell surface resulted in the highest potency for (20)-3s.

TABLE 7

| | | Antigen Expression[2] | | | | IC$_{50}$[4] (pM) | | | |
|---|---|---|---|---|---|---|---|---|---|
| Cell Line | Type[1] | CD19 | CD20 | CD22 | HLA- | (19)-3s | (20)- | (22)-3s | (C2)- |
| Daudi | BL | 1.00 | 1.00 | 1.00 | 1.00 | 1 | 0.3 | 6 | N.D. |
| Ramos | BL | 0.76 | 0.65 | 0.26 | 0.36 | 2 | 0.4 | N.D. | 2 |
| Nalm-6 | ALL | 1.63 | 0.05 | 0.19 | 0.17 | 6 | N.D. | N.D. | N.D. |
| Namalwa | BL | 0.76 | 0.11 | 0.05 | 0.40 | 63 | 30 | >3000 | N.D. |
| Raji | BL | 1.41 | 0.69 | 0.59 | 0.84 | >3000 | N.D. | N.D. | N.D. |
| Jeko-1 | MCL | 0.89 | 1.02 | 0.05 | 1.06 | 3000 | 1 | N.D. | 20 |

[1]BL, Burkitt lymphoma; ALL, acute lymphoblastic leukemia; MCL, mantle cell lymphoma.
[2]Expression level determined by flow cytometry and normalized to that of Daudi.
[3]IC$_{50}$, the picomolar concentration that achieved 50% target cell killing.

Figure 11:
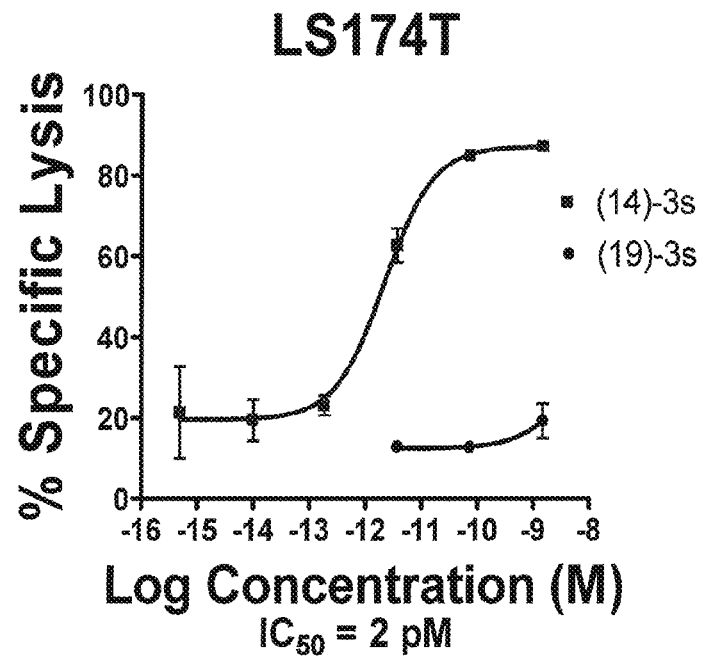
FIG. 11A. In vitro cytotoxicity of T-cell redirecting bsAbs in solid tumor cell lines. Dose-response curves were determined for cytotoxicity to the LS174T colon adenocarcinoma cell line for the (14)-3s bsAb, compared to non-targeting (19)-3s bsAb.
FIG. 11B. In vitro cytotoxicity of T-cell redirecting bsAbs in solid tumor cell lines. Dose-response curves were determined for cytotoxicity to the Capan-1 pancreatic adenocarcinoma cell line for the (E1)-3s bsAb, compared to non-targeting (19)-3s bsAb.
FIG. 11C. In vitro cytotoxicity of T-cell redirecting bsAbs in solid tumor cell lines. Dose-response curves were determined for cytotoxicity to the NCI-N87 gastric carcinoma cell line for the (E1)-3s and (15)-3s bsAbs, compared to non-targeting (19)-3s bsAb.
Figure 11:
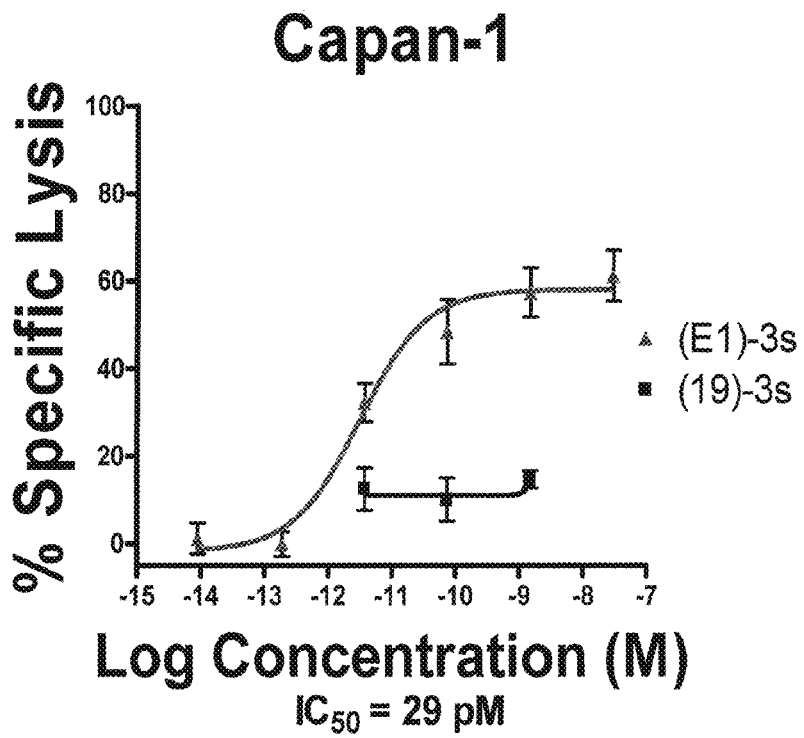
Figure 11C:
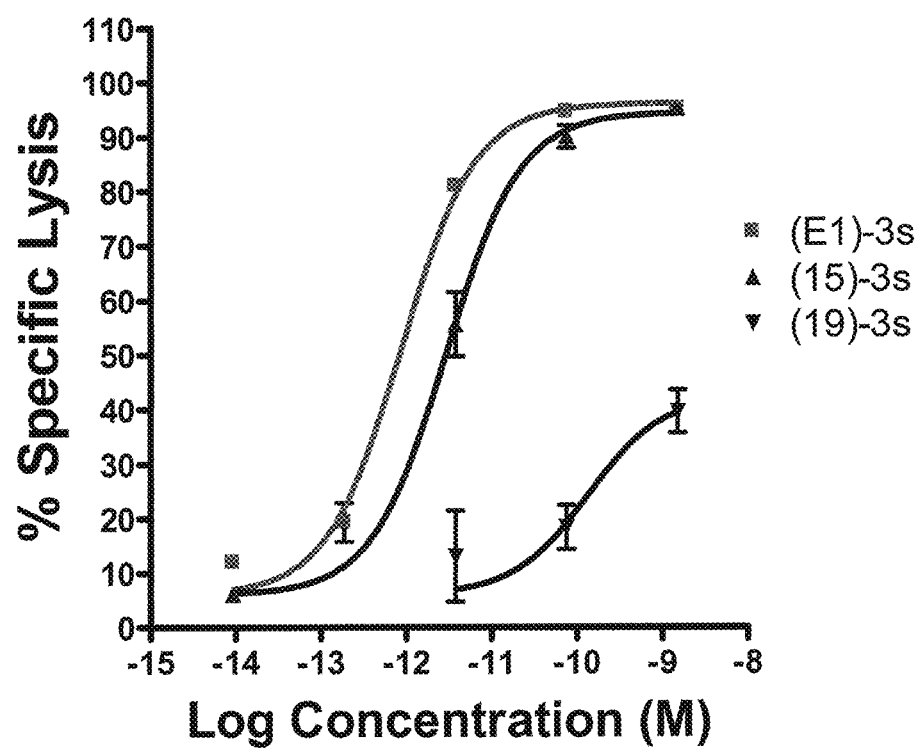

The in vitro cytotoxic effects of leukocyte redirecting bsAbs were also determined in solid tumor cells (FIG. 11). For the solid tumor cell lines, optimal assay conditions were determined to be a 3:1 E:T ratio using stimulated T cells in a 42-48 hour assay. Each bsAb induced specific T-cell mediated lysis of the tumor target cells. The CEACAM5-expressing human colon adenocarcinoma cell line, LS-174T, demonstrated potent specific lysis (IC$_{50}$=2 pM) following treatment with (14)-3s (FIG. 11A). (E1)-3s mediated potent specific lysis of the TROP2 expressing Capan-1 human pancreatic adenocarcinoma cell line (IC$_{50}$=29 μM) (FIG. 11B). The gastric carcinoma cell line NCI-N87, which expresses high levels of both CEACAM6 and TROP2 demonstrated very potent specific lysis to both T-cell targeting molecules, (15)-3s and (E1)-3s (IC$_{50}$=3 μM and 0.85 μM respectively) (FIG. 11C). The non-targeting control antibody, (19)-3s, induced low (<20%) non-specific lysis at concentrations >1 nM for Capan-1 and LS174T, and moderate (~40%) non-specific lysis in NCI-N87 cells (FIG. 11A-C). A summary of the in vitro cytotoxicity data for various leukocyte redirecting bsAbs in a variety of tumor cell lines is shown in FIG. 12. The various constructs showed a maximal cell lysis of up to 90% or more of the targeted tumor cells, with IC$_{50}$ values for cell lines expressing the targeted antiben that were generally in the low picomolar range (FIG. 12).

Example 2

In Vivo Studies of Leukocyte Redirecting DNL™ Complex

One potential limitation of small (<60 kDa) scFv-based constructs, such as BITE® and DART™, is the requirement for administration by long-term continuous infusion, due to their toxicity and rapid clearance from circulation. Because the molecular size of DNL™ bsAbs is above the threshold typically associated with renal clearance, it should exhibit slower clearance from circulation. We measured the pharmacokinetic parameters in mice following a single bolus i.v. injection of 5 mg/kg of the (19)-3s bsAb (data not shown). A biphasic clearance was observed with a t½α and t½β of 1.1 and 5.1 h, respectively, resulting in an area under the curve of 1880 pmol*h/mL (data not shown), which was nearly 6-fold greater than that reported for MT103 (anti-CD19×anti-CD3 BITE®) administered at the same molar concentration (US Patent US2010/0303827A1). The major difference is apparently a longer t½α for (19)-3s (data not shown). Because of the potentially advantageous properties of (19)-3s, we evaluated the possibility of using less frequent dosing schedules rather than daily dosing, which is typically used for BITE® in animal studies.

Figure 13:
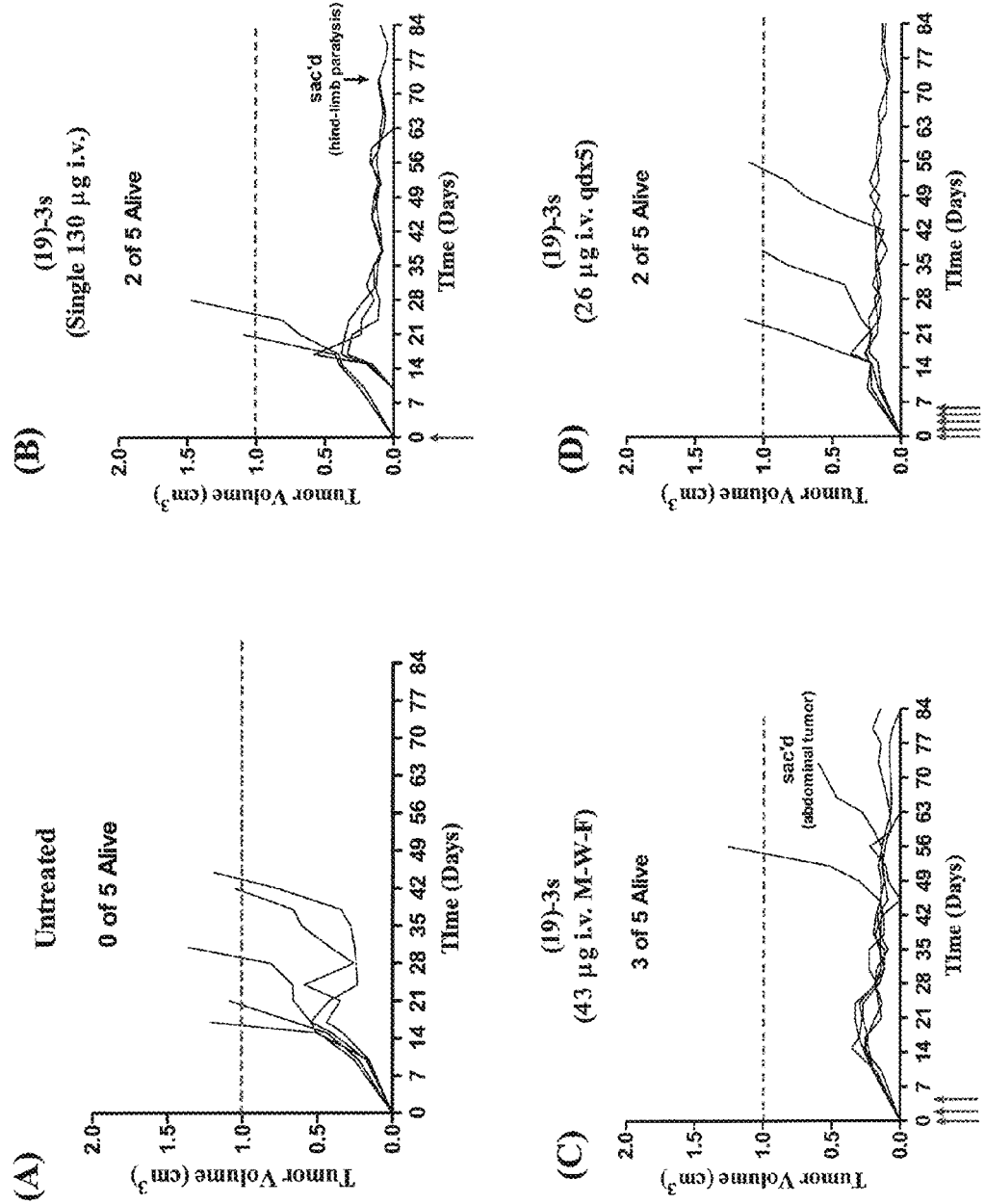
FIG. 13A. In vivo retargeting of Raji lymphoma xenografts using (19)-3s bsAb. NOD/SCID mice bearing Raji Burkitt lymphoma ($1 \times 10^6$ cells) xenografts, reconstituted with human PBMCs ($5 \times 10^6$ cells) and treated with (19)-3s for only 1 week, administered as indicated by the arrows. Control with untreated cells.
FIG. 13B. In vivo retargeting of Raji lymphoma xenografts using (19)-3s bsAb. NOD/SCID mice bearing Raji Burkitt lymphoma ($1 \times 10^6$ cells) xenografts, reconstituted with human PBMCs ($5 \times 10^6$ cells) and treated with (19)-3s for only 1 week, administered as indicated by the arrows. Cells were treated with a single dose of 130 µg.
FIG. 13C. In vivo retargeting of Raji lymphoma xenografts using (19)-3s bsAb. NOD/SCID mice bearing Raji Burkitt lymphoma ($1 \times 10^6$ cells) xenografts, reconstituted with human PBMCs ($5 \times 10^6$ cells) and treated with (19)-3s for only 1 week, administered as indicated by the arrows. Cells were treated 3× with 43 µg per dose.
FIG. 13D. In vivo retargeting of Raji lymphoma xenografts using (19)-3s bsAb. NOD/SCID mice bearing Raji Burkitt lymphoma ($1 \times 10^6$ cells) xenografts, reconstituted with human PBMCs ($5 \times 10^6$ cells) and treated with (19)-3s for only 1 week, administered as indicated by the arrows. Cells were treated 5× with 26 µg per dose.
Figure 14:
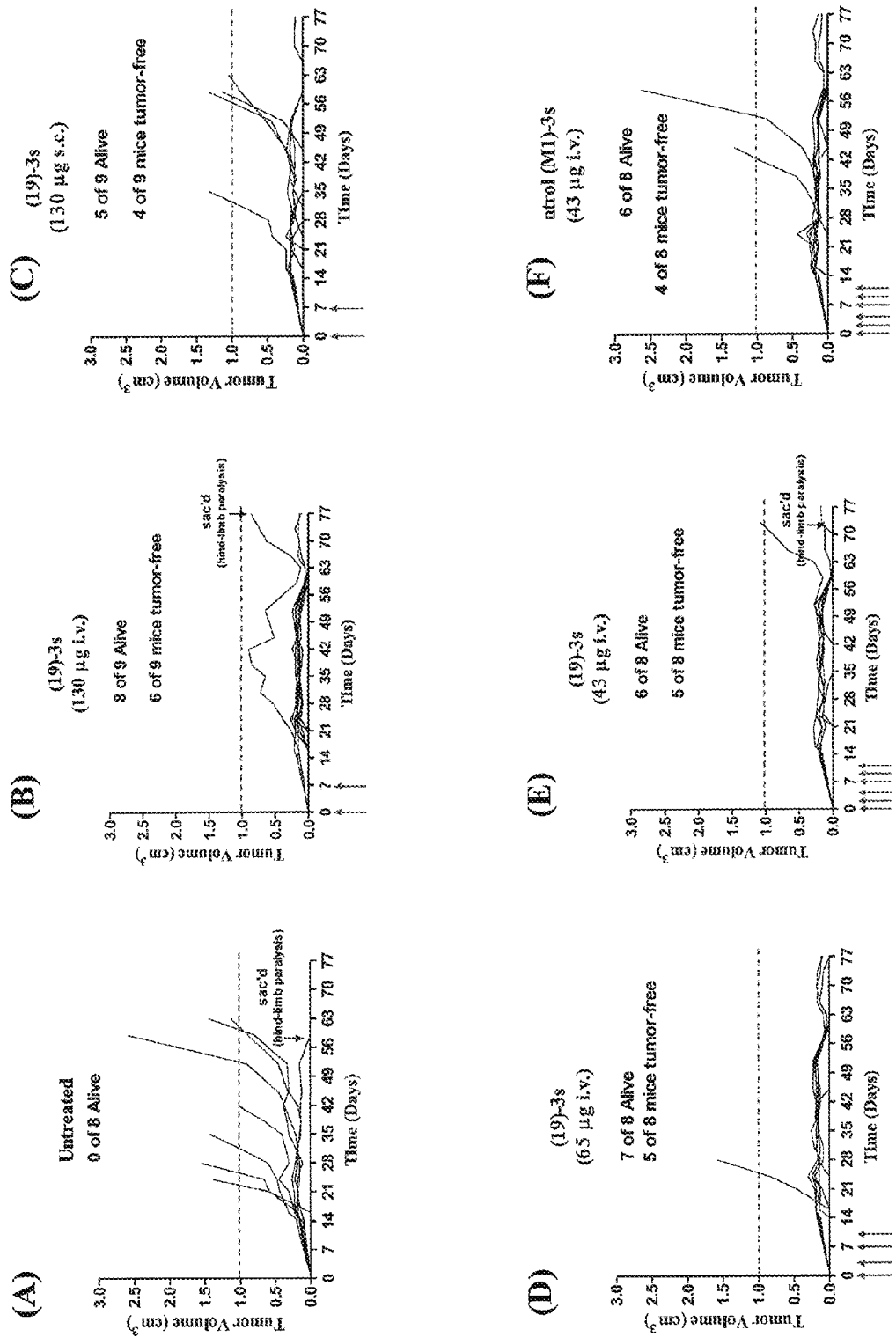
FIG. 14A. Effect of repeated dosing on in vivo retargeting of Raji lymphoma using (19)-3s bsAb. NOD/SCID mouse xenografts were prepared as indicated in the legend to FIG. 13. The (19)-3s was administered as indicated by the arrows.
FIG. 14B. Effect of repeated dosing on in vivo retargeting of Raji lymphoma xenografts using (19)-3s bsAb. The (19)-3s was administered as indicated by the arrows. Cells were treated 2× with 130 µg per dose of (19)-3s administered i.v.
FIG. 14C. Effect of repeated dosing on in vivo retargeting of Raji lymphoma xenografts using (19)-3s bsAb. The (19)-3s was administered as indicated by the arrows. Cells were treated treated 2× with 130 µg per dose of (19)-3s administered s.c.
FIG. 14D. Effect of repeated dosing on in vivo retargeting of Raji lymphoma xenografts using (19)-3s bsAb. The (19)-3s was administered as indicated by the arrows. Cells were treated treated 4× with 65 µg per dose of (19)-3s administered i.v.
FIG. 14E. Effect of repeated dosing on in vivo retargeting of Raji lymphoma xenografts using (19)-3s bsAb. The (19)-3s was administered as indicated by the arrows. Cells were treated treated 6× with 43 µg per dose of (19)-3s administered i.v.
FIG. 14F. Effect of repeated dosing on in vivo retargeting of Raji lymphoma xenografts using (19)-3s bsAb. The (19)-3s was administered as indicated by the arrows. Cells were treated treated 6× with 43 µg per dose of control (M1)-3s administered i.v.

A pilot study was performed using Raji human Burkitt lymphoma xenografts in NOD/SCID mice reconstituted with human PBMCs (FIG. 13, FIG. 14). Raji cells (1×10$^6$ cells/mouse) were combined with freshly isolated PBMCs (5×10$^6$ cells/mouse) from a single healthy donor, mixed 1:1 with matrigel, and injected SC into all of the animals in the study on Day 0. Groups of 5 mice received i.v. injections of (19)-3s totaling 130 μg as a single dose on Day 0 (FIG. 13B), three doses of 43 μg (Days 0, 2 and 4) (FIG. 13C) or five daily doses of 26 μg (Days 0-5) (FIG. 13D). The untreated group (FIG. 13A), which was inoculated with the same cell mixture but did not receive (19)-3s, had a median survival time (MST) of 31 days. Each therapy regimen improved survival (P≤0.05), with the three dose (every other day) schedule providing the greatest survival benefit (MST=91 days; P=0.0018 by log-rank analysis).

A follow-up study was begun to determine the efficacy of less frequent dosing (FIG. 14). Groups of 9 NOD/SCID mice were inoculated with Raji and PBMCs in a similar fashion as above. In this study, therapy was extended to two weeks, compared to one week in the first study. Groups received i.v. injections of (19)-3s totaling 360 μg as 2×130-μg (FIG. 14B), 4×65-μg (FIG. 14D) or 6×43-μg doses over two weeks (FIG. 14E). An additional group was administered 2×130-μg doses SC, instead of i.v. (FIG. 14C). For comparison, control groups of untreated mice (FIG. 14A) or mice treated with non-targeting (M1)-3s antibody (FIG. 14F) were prepared. As of Day 28, each of the (19)-3s treatment groups had significantly smaller AUC than the untreated control (P<0.05). Surprisingly, two weekly doses via the SC route was apparently as effective as greater frequency i.v. dosing.

Figure 15:
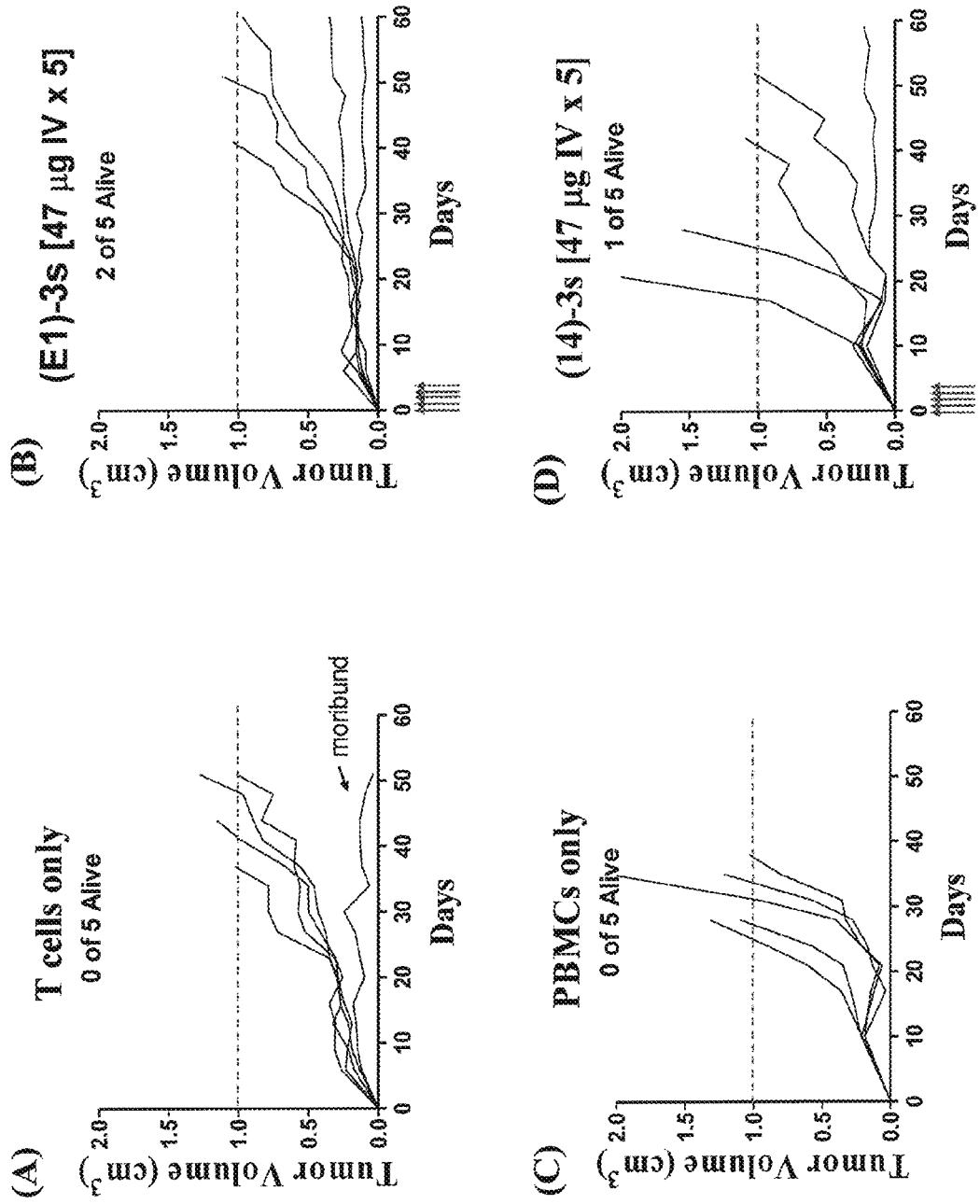
FIG. 15A. In vivo efficacy of T-cell retargeting bsAbs in solid tumor xenografts. NOD/SCID mouse xenografts were prepared with LS174T colon adenocarcinoma. Mice were administered T cells only without bsAb.
FIG. 15B. In vivo efficacy of T-cell retargeting bsAbs in solid tumor xenografts. NOD/SCID mouse xenografts were prepared with LS174T colon adenocarcinoma. Mice were treated with (E1)-3s bsAb as indicated.
FIG. 15C. In vivo efficacy of T-cell retargeting bsAbs in solid tumor xenografts. NOD/SCID mouse xenografts were prepared with Capan-1 pancreatic carcinoma. Mice were administered PBMCs only without bsAb.
FIG. 15D. In vivo efficacy of T-cell retargeting bsAbs in solid tumor xenografts. NOD/SCID mouse xenografts were prepared with Capan-1 pancreatic carcinoma. Mice were treated with (14)-3s bsAb as indicated.

In vivo studies were also performed using solid tumors (FIG. 15). NOD/SCID mouse xenografts were prepared as described above, for the LS174T colon adenocarcinoma (FIG. 15A, FIG. 15B) or Capan-1 pancreatic carcinoma (FIG. 15C, FIG. 15D). In each case, mice administered the targeting (E1)-3s (FIG. 15B) or (14)-3s (FIG. 15D) bsAb DNL™ constructs showed improved survival compared to controls.

In conclusion, the leukocyte-retargeting bsAbs, including (19)-3s, (E1)-3s and (M1)-3s DNL™ constructs, mediated synapse formation between T cells and B cells, colon adenocarcinoma or pancreatic carcinoma cells, respectively, via monovalent and bivalent binding to CD3 and CD19, respectively. T-cell activation, proliferation and target cell killing were induced by the DNL™ bsAbs at pM concentrations in an ex vivo setting. Advantageous properties of the DNL™ bsAbs, including bivalent tumor binding and slower clearance, would allow for less frequent dosing and possibly SC administration, compared to BITE® or DART™ constructs, which are administered i.v. daily in animal models and as a continuous infusion in the clinic. The modular nature of the DNL™ method allows the rapid production of a large number of related conjugates for redirected leukocyte killing of various malignancies, without the need for additional recombinant engineering and protein production.

The person of ordinary skill in the art will realize that other antibodies that bind to CD3 or other leukocyte antigens, as well as other antibodies that bind to CD19 or other disease-associated antigens are known in the art and any such antibody can be used to make F(ab)$_2$, scFv or other antibody fragments using techniques well known in the art. Such alternative antibodies or fragments thereof may be utilized in the instant methods and compositions. As discussed below, methods of making DOCK-AND-LOCK™ (DNL™) complexes may be applied to incorporate any known antibodies or antibody fragments into a stable, physiologically active complex.

Example 3

Interferon-α Enhances the Cytotoxic Effect of Leukocyte Redirecting Bispecific Antibodies The therapeutic efficacy of an anti-human Trop-2×anti-human CD3 bispecific antibody ((E1)-3s), made from hRS7 and OKT3 as a DNL™ complex, was tested for its ability to delay tumor outgrowth of Capan-1 human pancreatic adenocarcinoma tumor cells when mixed with human T-cells and injected into mice. The effect of interferon-α (either in the form of E1*-2b or PEGASYS®) when combined with this therapy was also evaluated.

Methods

Five week-old female NOD/SCID mice were injected s.c. with a mixture of Capan-1 (5×10$^6$) and human T-cells (2.5×10$^6$ cells) mixed 1:1 with matrigel (E:T ratio of 1:2). There were six different treatment groups of 8 mice each. Treatment consisted of one group receiving 47 μg (E1)-3s i.v. every day for five days starting 1 hour after the administration of the Capan-1/T-cell mixture. Two groups were treated with equimolar amounts of IFN, one received the DNL molecule made from IFN-α2b-DDD2-CK-hRS7 IgG1 (E1*-2b; 2.5 μg s.c. weekly×4 wks) while another received PEGASYS® (Roche; 0.6 μg s.c. weekly×4 wks). Two other groups received a combination of (E1)-3s plus E1*2b or (E1)-3s plus PEGASYS®. The final group control group remained untreated. Table 8 summarizes the various treatment groups.

TABLE 8

Treatment Groups for (E1)-3s Therapy
(E1)-3s Therapy of a Human Pancreatic Carcinoma
Xenograft (Capan-1) in NOD/SCID Mice

| Group | (N) | Amount Injected | Schedule |
|---|---|---|---|
| 1 | 8 | Untreated | N.A. |
| 2 | 8 | (E1)-3s (47 μg i.v.) | qdx5 |
| 3 | 8 | E1*-2b (2.5 μg s.c.) | qwkx4 |
| 4 | 8 | PEGASYS ® (0.6 μg s.c.) | qwkx4 |
| 5 | 8 | (E1)-3s + E1*-2b | qdx5 + qwkx4 |
| 6 | 8 | (E1)-3s + PEGASYS | qdx5 + qwkx4 |

Mice were monitored daily for signs of tumor out-growth. All animals had their tumors measured twice weekly once tumors began to come up. Mice were euthanized for disease progression if their tumor volumes exceeded 1.0 cm$^3$ in size.

Results

Figure 16:
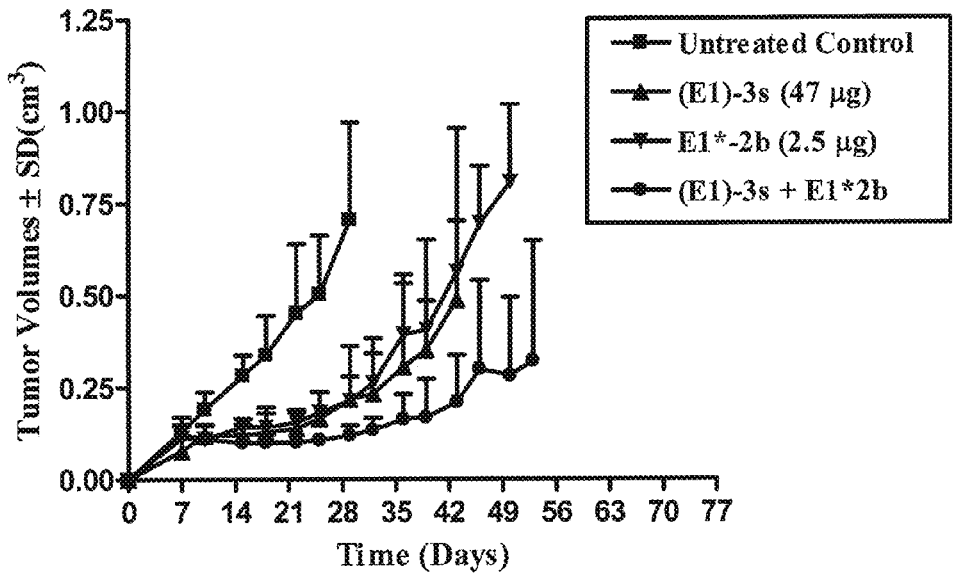
FIG. 16A. In vivo inhibition of tumor growth by (E1)-3s DNL™ complex in the presence or absence of interferon-α. Capan-1 pancreatic carcinoma xenografts in NOD/SCID mice were treated with anti-TROP-2×anti-CD3 bsAb with or without added interferon-α. The interferon-α was added in the form of a TROP-2 targeting DNL™ complex.
FIG. 16B. In vivo inhibition of tumor growth by (E1)-3s DNL™ complex in the presence or absence of interferon-α. Capan-1 pancreatic carcinoma xenografts in NOD/SCID mice were treated with anti-TROP-2×anti-CD3 bsAb with or without added interferon-α. The interferon-α was added as the commercially available PEGASYS® (peginterferon alfa-2a).
Figure 16:
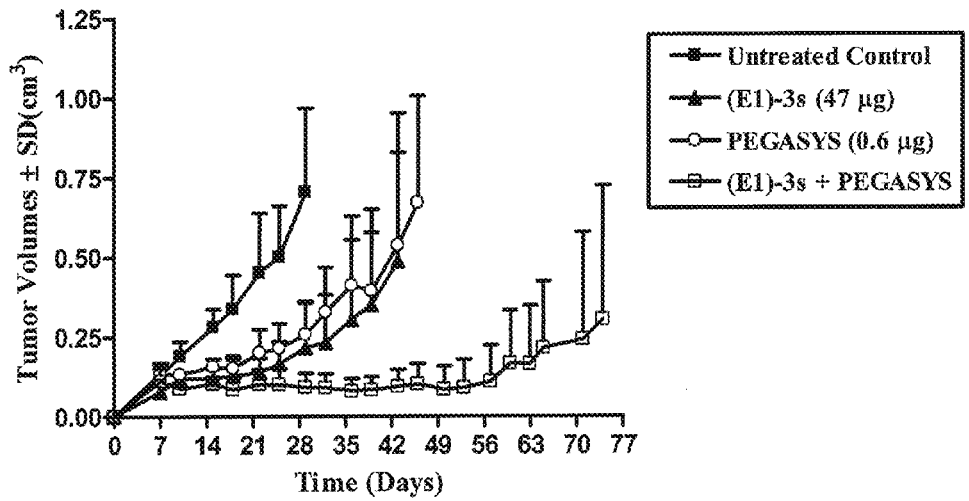

Mean tumor volumes for the various groups are shown in FIG. 16. The data containing PEGASYS® groups (FIG. 16B) are shown on a separate graph from the E1*2b groups (FIG. 16A) for clarity. All treatments were significantly better at controlling tumor growth in terms of area-under-the-curve (AUC) when compared to the untreated mice out to day 29, which was when the first mouse in the untreated group was euthanized for disease progression (P<0.0009; AUC$_{29\ days}$). Combining (E1)-3s with PEGASYS® resulted in the best anti-tumor response overall in terms of tumor out-growth (FIG. 16B). This treatment was significantly better than any of the individual treatments (P<0.042; AUC) as well as superior to the combination of (E1)-3s plus E1*-2b (P=0.0312; AUC$_{53\ days}$) (FIG. 16A). The combination of (E1)-3s plus E1*2b could significantly control tumor growth when compared to E1*2b or PEGASYS® alone (P<0.0073; AUC$_{46\ days}$) but not (E1)-3s alone (FIG. 16A-B). There were no significant differences between mice treated with (E1)-3s, PEGASYS®, or E1*-2b (FIG. 16A-B).

Figure 17:
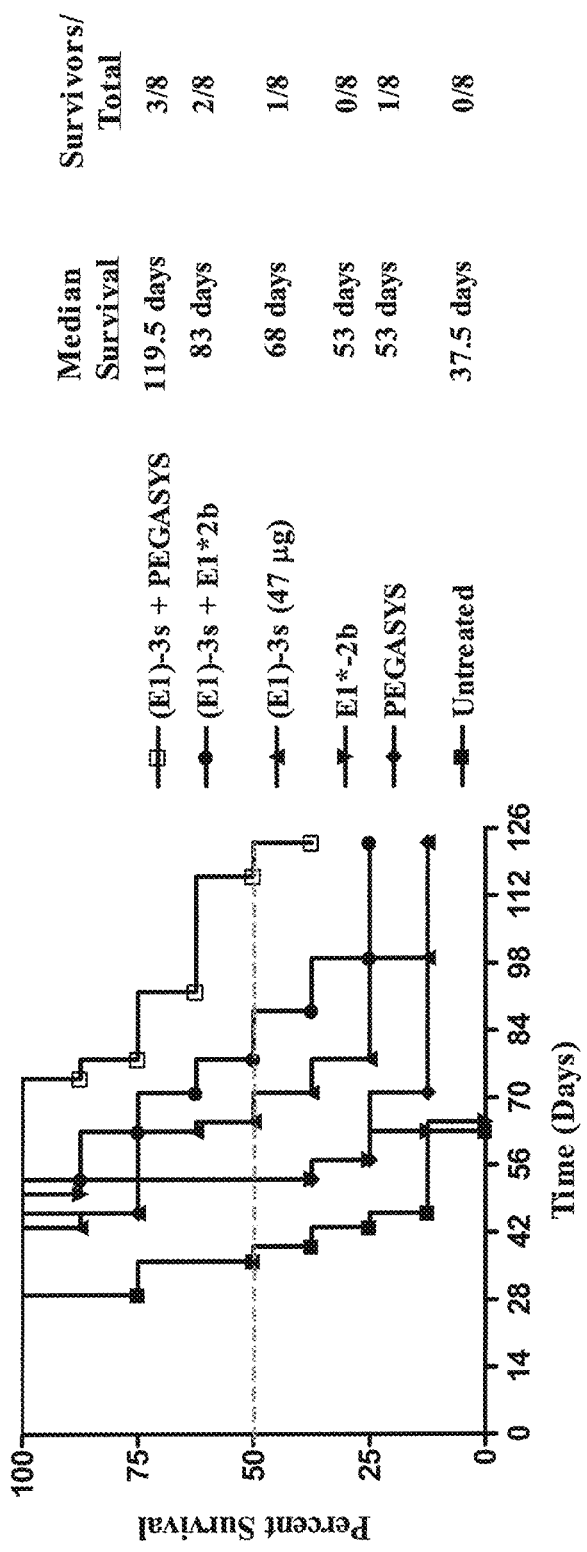
FIG. 17. Survival curves for NOD/SCID mice treated with (E1)-3s with or without interferon-α. Controls were untreated or treated with interferon-α alone.

In terms of survival, all treatments provide a significant survival benefit when compared to the untreated mice (P<0.0112; log-rank) (FIG. 17). As of day 81, there was no significant difference in median survival times (MST) between mice treated with the combination of (E1)-3s plus E1*-2b and those treated (E1)-3s plus PEGASYS® (MST=79.5 and >81 days, respectively) (FIG. 17). The mice treated with (E1)-3s plus PEGASYS® had a significantly improved survival outcome than any of the individual treatments (P<0.0237) (FIG. 17). Mice treated with (E1)-3s plus E1*2b had a survival benefit when compared to mice treated with E1*-2b alone (MST=53 days; P<0.0311) but not when compared to mice treated with just (E1)-3s or PEGASYS® alone (MST=68 and 53 days, respectively) (FIG. 17). Treatment with (E1)-3s provided a significant improvement in survival when compared to mice treated with E1*-2b (P=0.0406) but not when compared to mice treated with PEGASYS® alone (FIG. 17). There was no significant differences between mice treated with only E1*2b and those treated with PEGASYS® alone (FIG. 17).

The results demonstrate that addition of interferon-α provides a substantial increase in survival and decrease in tumor growth when combined with a leukocyte redirecting bsAb. The person of ordinary skill will realize that the improved efficacy observed with addition of type I or type III interferons (interferon-α, interferon-β, or interferon-λ) is not limited to the specific (E1)-3s bsAb, but will be observed with other leukocyte redirecting bsAbs, made either as DNL™ complexes or in other forms, such as BITE® or DART™.

Example 4

Further Studies on Interferon-α Combination Therapy with Leukocyte-Redirecting Bispecific Antibodies In the Example above, the combination of (E1)-3s plus PEGASYS® proved to be a very effective treatment in the control of tumor growth. In order to confirm these results and extend them, a study was performed in which two new groups were added. First, a control group for (E1)-3s was included in which an equimolar amount of TF12 was administered to animals. TF12 consists of two hRS7-Fab molecules linked to one non-targeting 679 Fab (anti-HSG). Additionally, since Capan-1 is sensitive to IFN, another group was added in which the effect of PEGASYS® on Capan-1 tumor growth was assessed without the benefit of T cells.

After the mice (40) were injected with the Capan-1/T-cell mixture, they were randomized into five treatment groups. One hour later, one group of 11 mice received 47 µg (E1)-3s i.v. every day starting 1 h post-tumor cell injection and continued for four more consecutive days (qdx5). One group of 7 animals received interferon in the form of PEGASYS® s.c. on a weekly basis for four weeks. Another group received a combination of (E1)-3s i.v. plus PEGASYS® s.c. Untreated control animals receive Capan-1/T cells but no treatment. A further control group received TF12 at amounts equivalent to the (E1)-3s in terms of moles (57 µg qdx5). Group 6 mice (8 animals) received a separate injection of only Capan-1 cells (i.e., no T cells) and was treated with PEGASYS®. All therapy injections were in a volume of 100 µL. Table 9 summarizes the various groups.

TABLE 9

Treatment Groups for (E1)-3s and TF12 Therapy (E1)-3s Therapy of a Human Pancreatic Carcinoma Xenograft (Capan-1) in NOD/SCID Mice

| Group | (N) | Amount Injected | Schedule |
|---|---|---|---|
| 1 | 7 | Untreated (Capan-1 + T cells only) | N.A. |
| 2 | 11 | (E1)-3s (47 µg i.v.) | qdx5 |
| 3 | 7 | TF12 (57 µg i.v.) | qdx5 |
| 4 | 7 | PEGASYS ® (0.6 µg s.c.) | qwkx4 |
| 5 | 8 | (E1)-3s + PEGASYS ® | qdx5 + qwkx4 |
| 6 | 8 | PEGASYS ® (0.6 µg s.c.) (Capan-1 cells only) | qwkx4 |

Mice were monitored daily for signs of tumor out-growth. All animals had their tumors measured twice weekly once tumors began to come up. Mice were euthanized for disease progression if their tumor volumes exceeded 1.0 cm³ in size.

Results

Mean tumor growth (FIG. 18) and survival curves (FIG. 19) are shown. While not different from each other, mice treated with (E1)-3s, PEGASYS®, or PEGASYS® (without T cells), demonstrated significant anti-tumor effects when compared to TF12 and untreated control groups (P<0.0102; AUC). On the day this experiment ended (day 59), the mean tumor volume for the mice treated with the combination of (E1)-3s plus PEGASYS® was 0.083±0.048 cm³. Overall, this treatment group demonstrated a significant anti-tumor effect when compared to all the other treatment groups (P<0.0072; AUC).

Figure 18:
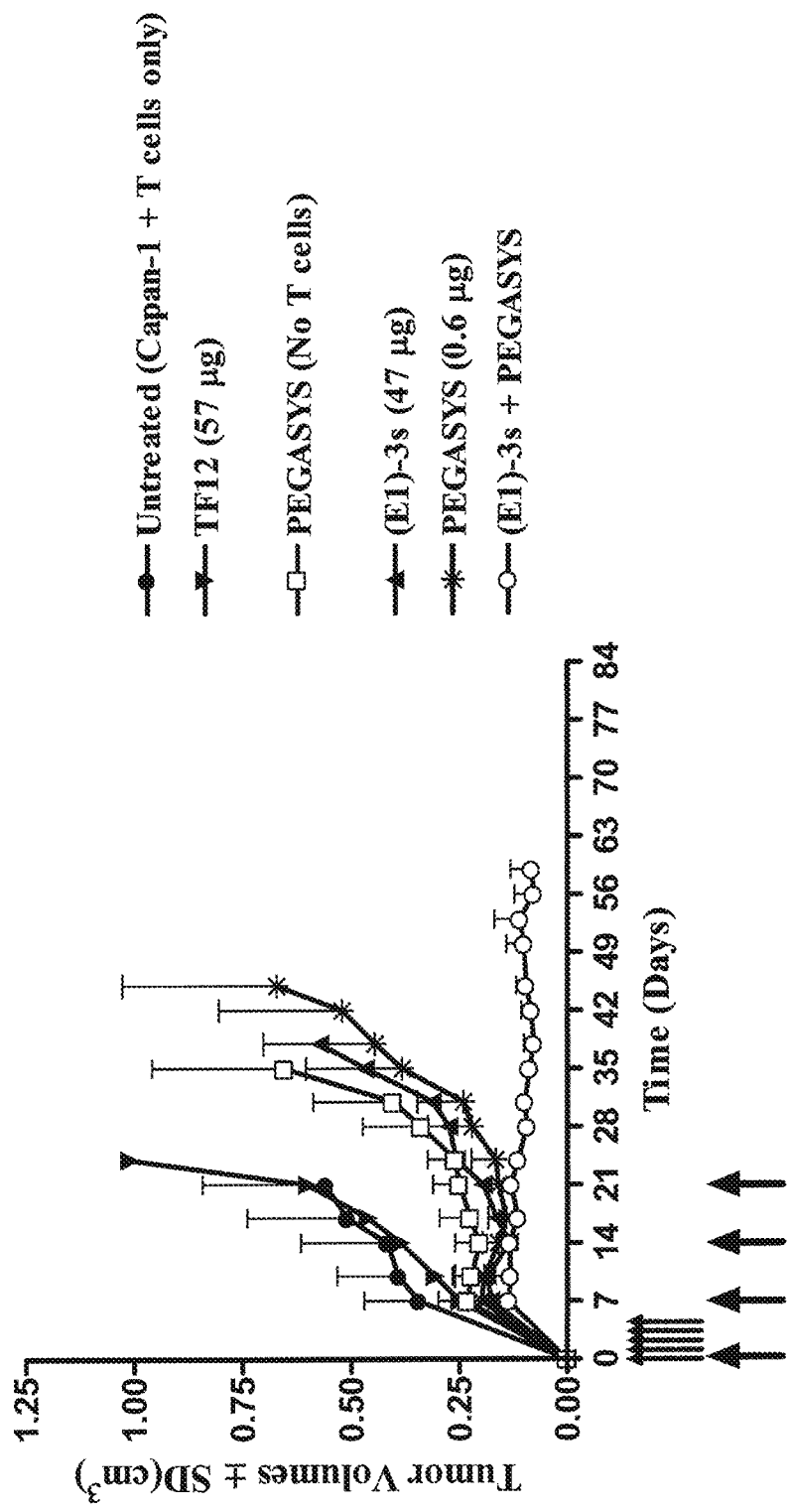
FIG. 18. In vivo inhibition of tumor growth by (E1)-3s DNL™ complex in the presence or absence of interferon-α, compared to TF12 control. Capan-1 pancreatic carcinoma xenografts in NOD/SCID mice were treated with anti-TROP-2×anti-CD3 bsAb with or without added interferon-α, added as PEGASYS®, compared to untreated control, TF12 control or PEGASYS® alone.
Figure 19:
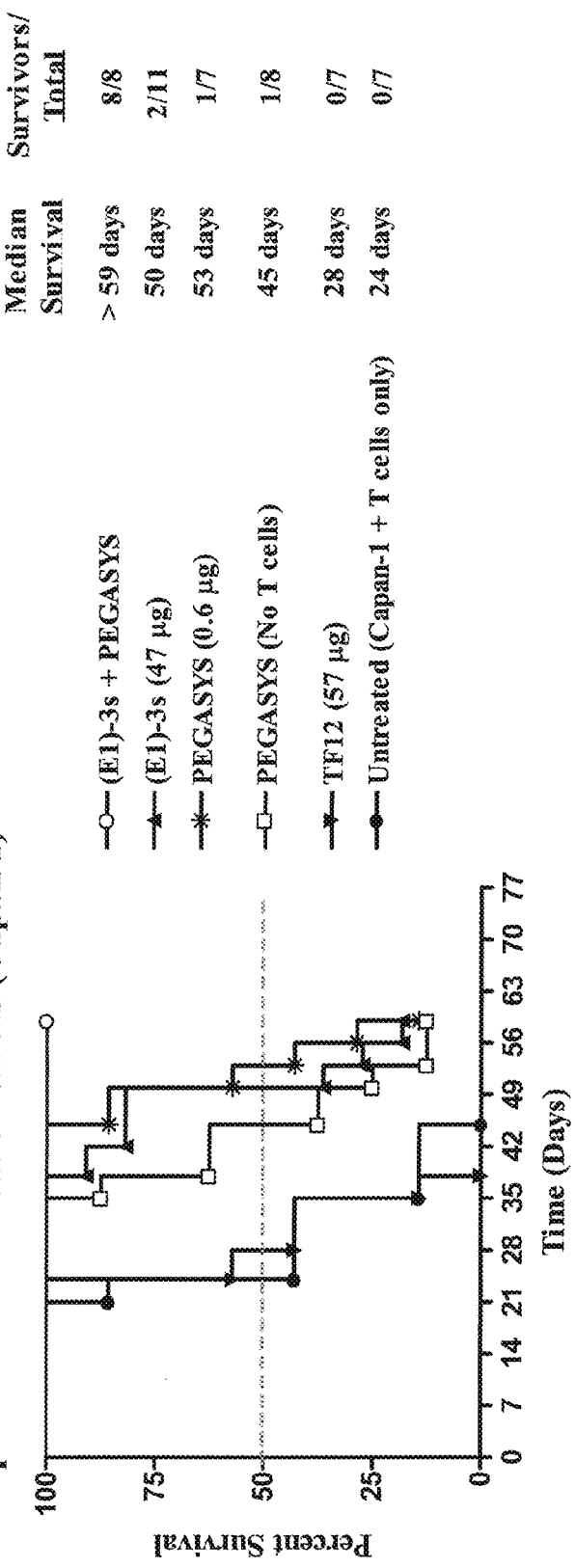
FIG. 19. Survival curves for NOD/SCID mice treated with (E1)-3s with or without interferon-α (PEGASYS®). Controls were untreated or treated with PEGASYS® alone or TF12 alone.

Each individual treatment (PEGASYS®, PEGASYS® without T cells, and (E1)-3s) significantly improved survival in comparison to both the TF12 and untreated control groups (P<0.0059; log-rank) (FIG. 18, FIG. 19). All the groups except the combination of (E1)-3s plus PEGASYS® reached their respective MSTs. No animals were euthanized for disease progression (TV>1.0 cm³) in this combination group. Importantly, the combination of (E1)-3s plus PEGASYS® provided a significant survival benefit when compared to all other treatments (P<0.0007; log-rank) (FIG. 18, FIG. 19).

Example 5

Effect of Interferon-α Combination Therapy with T-Cell-Redirecting Bispecific Antibodies in Human Gastric Cancer The methods and compositions disclosed in the preceding two Examples were used to study the effects of leukocyte redirecting bsAbs alone or in combination with interferon-α (PEGASYS®) in the IFN-refractory NCI-N87 human gastric tumor line. Mice were injected s.c. with 5×10⁶ NCI-N87 cells+2.5×10⁶ T Cells (1:2 E:T ratio) mixed with matrigel and therapy started 1 h later. The treatment groups are shown in Table 10.

TABLE 10

Treatment Groups for (E1)-3s and TF12 Therapy (E1)-3s Therapy of a Human Gastric Carcinoma Xenograft (NCI-N87) in NOD/SCID Mice

| Group | (N) | Amount Injected | Schedule |
|---|---|---|---|
| 1 | 8 | Untreated (NCI-N87 + T-cells only) | N.A. |
| 2 | 8 | (E1)-3s (47 µg i.v.) | qdx5 |
| 3 | 8 | TF12 (57 µg i.v.) | qdx5 |
| 4 | 8 | PEGASYS (0.6 µg s.c.) | qwkx4 |
| 5 | 8 | TF12 + PEGASYS | qdx5 + qwkx4 |
| 6 | 8 | (E1)-3s + PEGASYS | qdx5 + qwkx4 |

Figure 20:
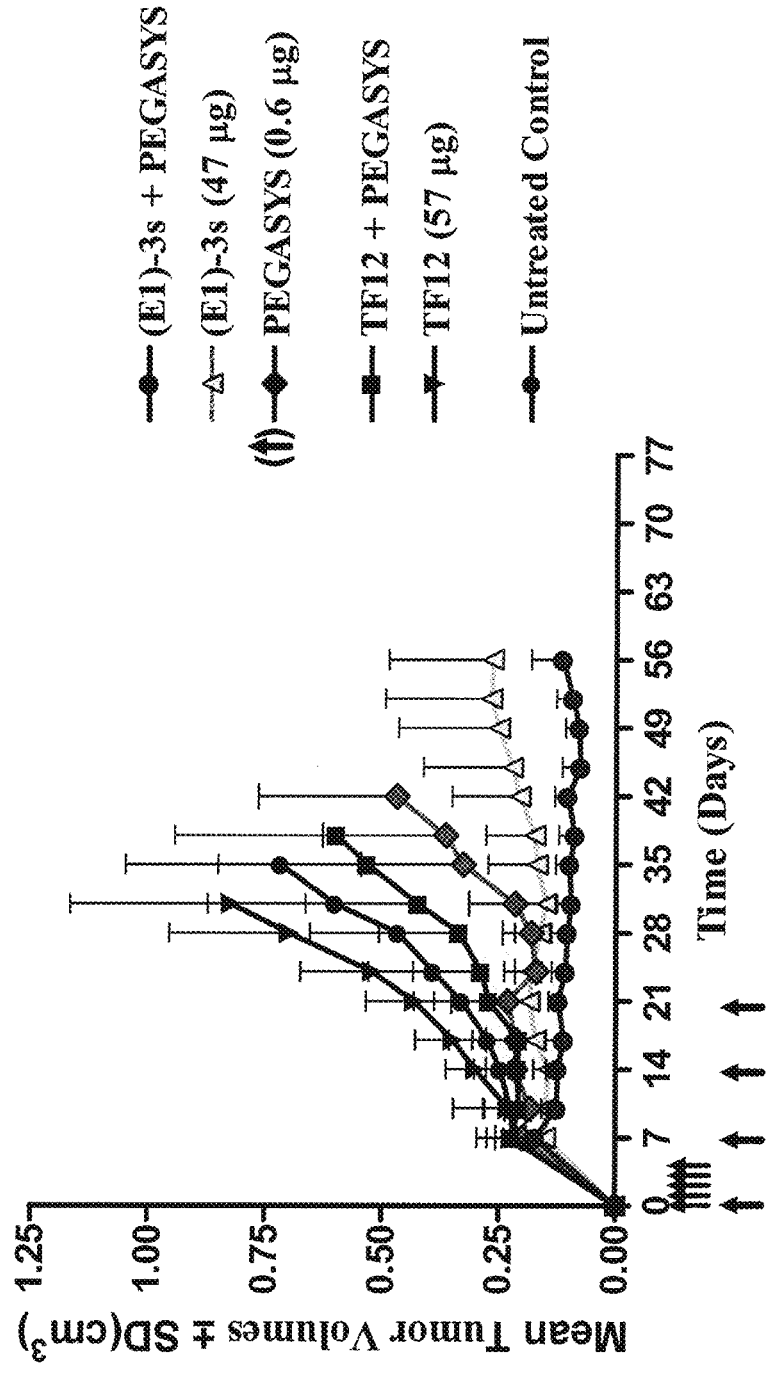
FIG. 20. In vivo inhibition of tumor growth by (E1)-3s DNL™ complex in the presence or absence of interferon-α, compared to TF12 control. NCI-N87 human gastric cancer xenografts in NOD/SCID mice were treated with anti-TROP-2×anti-CD3 bsAb with or without added interferon-α, added as PEGASYS®, compared to untreated control, TF12 control or PEGASYS® alone.

The effects of leukocyte redirecting bsAb (E1)-3s alone or in combination with interferon are shown in FIG. 20 and FIG. 21. The (E1)-3s bsAb was effective to reduce tumor growth and increase survival in gastric cancer. Significantly, the combination with interferon-α enhanced the effect of leukocyte redirecting bsAb, even in an interferon resistant tumor. The combination therapy was more effective than either agent added alone. Controls with mice treated with TF12 bsAb alone or in combination with interferon-α showed little effect on tumor growth or mortality, compared to untreated animals.

Example 6

In Vivo Therapeutic Use of Antibody-Drug Conjugates (ADCs) in Preclinical Models of Human Pancreatic or Colon Carcinoma CL2A-SN-38-antibody conjugates were prepared as previously described (see, e.g., U.S. Pat. Nos. 7,999,083 and 8,080,250). Immune-compromised athymic nude mice (female), bearing subcutaneous human pancreatic or colon tumor xenografts were treated with either specific CL2A-SN-38 conjugate or control conjugate or were left untreated. The therapeutic efficacies of the specific conjugates were observed. In a Capan 1 pancreatic tumor model, specific CL2A-SN-38 conjugates of hRS7 (anti-TROP2), hPAM4 (anti-MUC5ac), and hMN-14 (anti-CEACAM5) antibodies showed better efficacies than control hA20-CL2A-SN-38 conjugate (anti-CD20) and untreated control (not shown). Similarly in a BXPC3 model of human pancreatic cancer, the specific hRS7-CL2A-SN-38 showed better therapeutic efficacy than control treatments (not shown). Likewise, in an aggressive LS174T model of human colon carcinoma, treatment with specific hMN-14-CL2A-SN-38 was more efficacious than non-treatment (not shown).

Example 7

In Vivo Therapy of Lung Metastases of GW-39 Human Colonic Tumors in Nude Mice Using ADC hMN-14-[CL2-SN-38], IMMU-130

A lung metastatic model of colonic carcinoma was established in nude mice by i.v. injection of GW-39 human colonic tumor suspension, and therapy was initiated 14 days later. Specific anti-CEACAM5 antibody conjugate, hMN14-CL2-SN-38, as well as nontargeting anti-CD22 MAb control conjugate, hLL2-CL2-SN-38 and equidose mixtures of hMN14 and SN-38 were injected at a dose schedule of q4d×8, using different doses. Selective therapeutic effects were observed with the hMN-14 ADC (not shown). At a dosage of 250 µg, the mice treated with hMN14-CL2-SN-38 showed a median survival of greater than 107 days. Mice treated with the control conjugated antibody hLL2-CL2-SN-38, which does not specifically target lung cancer cells, showed median survival of 77 days, while mice treated with unconjugated hMN14 IgG and free SN-38 showed a median survival of 45 days, comparable to the untreated saline control of 43.5 days. A significant and surprising increase in effectiveness of the conjugated, cancer cell targeted antibody-SN-38 conjugate, which was substantially more effective than unconjugated antibody and free chemotherapeutic agent alone, was clearly seen (not shown). The dose-responsiveness of therapeutic effect of conjugated antibody was also observed (not shown). These results demonstrate the clear superiority of the SN-38-antibody conjugate compared to the combined effect of both unconjugated antibody and free SN-38 in the same in vivo human lung cancer system.

Example 8

Use of ADC (IMMU-132 or hRS7-SN-38) to Treat Therapy-Refractive Metastatic Colonic Cancer (mCRC)

The patient was a 62-year-old woman with mCRC who originally presented with metastatic disease in January 2012. She had laparoscopic ileal transverse colectomy as the first therapy a couple of weeks after diagnosis, and then received 4 cycles of FOLFOX (leucovorin, 5-fluorouracil, oxaliplatin) chemotherapy in a neoadjuvant setting prior to right hepatectomy in March 2012 for removal of metastatic lesions in the right lobe of the liver. This was followed by an adjuvant FOLFOX regimen that resumed in June, 2012, for a total of 12 cycles of FOLFOX. In August, oxaliplatin was dropped from the regimen due to worsening neurotoxicity. Her last cycle of 5-FU was on Sep. 25, 2012.

CT done in January 2013 showed metastases to liver. She was then assessed as a good candidate for enrollment to IMMU-132 (hRS7-SN-38) investigational study. Comorbidities in her medical history include asthma, diabetes mellitus, hypertension, hypercholesteremia, heart murmur, hiatal hernia, hypothyroidism, carpel tunnel syndrome, glaucoma, depression, restless leg syndrome, and neuropathy. Her surgical history includes tubo-ligation (1975), thyroidectomy (1983), cholescystectomy (2001), carpel tunnel release (2008), and glaucoma surgery.

At the time of entry into this therapy, her target lesion was a 3.1-cm tumor in the left lobe of the liver. Non-target lesions included several hypo-attenuated masses in the liver. Her baseline CEA was 781 ng/mL.

IMMU-132 was given on a once-weekly schedule by infusion for 2 consecutive weeks, then a rest of one week, this constituting a treatment cycle. These cycles were repeated as tolerated. The first infusion of IMMU-132 (8 mg/kg) was started on Feb. 15, 2013, and completed without notable events. She experienced nausea (Grade 2) and fatigue (Grade 2) during the course of the first cycle and has been continuing the treatment since then without major adverse events. She reported alopecia and constipation in March 2013. The first response assessment done (after 6 doses) on Apr. 8, 2013 showed a shrinkage of target lesion by 29% by computed tomography (CT). Her CEA level decreased to 230 ng/mL on Mar. 25, 2013. In the second response assessment (after 10 doses) on May 23, 2013, the target lesion shrank by 39%, thus constituting a partial response by RECIST criteria. She has been continuing treatment, receiving 6 cycles constituting 12 doses of hRS7-SN-38 (IMMU-132) at 8 mg/kg. Her overall health and clinical symptoms improved considerably since starting this investigational treatment.

Example 9

ADC Therapy with IMMU-132 for Metastatic Solid Cancers

IMMU-132 is an ADC comprising the active metabolite of CPT-11, SN-38, conjugated by a pH-sensitive linker (average drug-antibody ratio=7.6) to the hRS7 anti-Trop-2 humanized monoclonal antibody, which exhibits rapid internalization when bound to Trop-2. IMMU-132 targets Trop-2, a type 1 transmembrane protein expressed in high prevalence and specificity by many carcinomas. This Example reports a Phase I clinical trial of 25 patients with different metastatic cancers (pancreatic, 7; triple-negative breast [TNBC], 4; colorectal [CRC], 3; gastric, 3; esophageal, prostatic, ovarian, non-small-cell lung, small-cell lung [SCLC], renal, tonsillar, urinary bladder, 1 each) after failing a median of 3 prior treatments (some including topoisomerase-I and -II inhibiting drugs).

IMMU-132 was administered in repeated 21-day cycles, with each treatment given on days 1 and 8. Dosing started at 8 mg/kg/dose (i.e., 16 mg/kg/cycle), and escalated to 18 mg/kg before encountering dose-limiting neutropenia, in a 3+3 trial design. Fatigue, alopecia, and occasional mild to moderate diarrhea were some of the more common non-hematological toxicities, with 2 patients also reporting a rash. Over 80% of 24 assessable patients had stable disease or tumor shrinkage (SD and PR) among the various metastatic cancers as best response by CT. Three patients (CRC, TNBC, SCLC) have PRs by RECIST; median TTP for all patients, excluding those with pancreatic cancer, is >18 weeks. Neutropenia has been controlled by dose reduction to 8-10 mg/kg/dose (16-20 mg/kg/cycle).

Immunohistochemistry showed strong expression of Trop-2 in most archived patient tumors, but it is not detected in serum. Corresponding reductions in blood tumor marker titers (e.g., CEA, CA19-9) reflected tumor responses. No anti-antibody or anti-SN-38 antibodies have been detected despite repeated dosing. Peak and trough assessments of IMMU-132 concentrations in the serum show that the conjugate clears completely within 7 days, an expected finding based on in vitro studies showing 50% of the SN-38 is released in the serum every day. These results indicate that this novel ADC, given in doses ranging from 16-24 mg/kg per cycle, shows a high therapeutic index in diverse metastatic solid cancers.

Example 10

IMMU-130, an SN-38 ADC that Targets CEACAM5, is Therapeutically Active in Metastatic Colorectal Cancer (mCRC)

IMMU-130, an ADC of SN-38 conjugated by a pH-sensitive linker (7.6 average drug-antibody ratio) to the humanized anti-CEACAM5 antibody (labetuzumab), is completing two Phase I trials. In both, eligible patients with advanced mCRC were required to have failed/relapsed standard treatments, one being the topoisomerase-I inhibiting drug, CPT-11 (irinotecan), and an elevated plasma CEA (>5 ng/mL).

IMMU-130 was administered every 14 days (EOW) at doses starting from 2.0 mg/kg in the first protocol (IMMU-130-01). Febrile neutropenia occurred in 2 of 3 patients at 24 mg/kg; otherwise at ≤16 mg/kg, neutropenia (≥Grade 2) was observed in 7 patients, with one also experiencing thrombocytopenia. One patient [of 8 who received ≥4 doses (2 cycles)] showed a 40.6% decrease in liver (starting at 7 cm) and lung target lesions (PR by RECIST) for 4.7 months, with no major toxicity, tolerating a total of 18 doses at 16 mg/kg. The study is continuing at 12 mg/kg EOW.

Since SN-38 is most effective in S-phase cells, a more protracted exposure could improve efficacy. Thus, in a second Phase I trial (IMMU-130-02), dosing was intensified to twice-weekly, starting at 6 mg/kg/dose for 2 weeks (4 doses) with 1 week off, as a treatment cycle, in a 3+3 trial design. Neutropenia and manageable diarrhea were the major side effects, until dose reduction to 4.0 mg/kg twice-weekly, with early results indicating multiple cycles are well-tolerated. Currently, tumor shrinkage occurred in 3 patients, with 1 in continuing PR (−46%) by RECIST, among 6 patients who completed ≥4 doses (1 cycle). In both trials, CEA blood titers correlated with tumor response, and high levels did not interfere with therapy. There have been no anti-antibody or anti-SN-38 antibody reactions, based on ELISA tests. In each study, the ADC was cleared by 50% within the first 24 h, which is much longer exposure than with typical doses of the parental molecule, CPT-11. These results indicate that this novel ADC, given in different regimens averaging ~16-24 mg/kg/cycle, shows a high therapeutic index in advanced mCRC patients. Since CEACAM5 has elevated expression in breast and lung cancers, as well as other epithelial tumors, it may be a useful target in other cancers as well.

Example 11

Antitumor Activity of Checkpoint Inhibitor Antibody Alone or Combined with T-Cell Redirecting bsAb, IFN-α or ADC To determine if the antitumor activity of the exemplary checkpoint inhibitor antibody, ipilimumab (anti-CTLA4) is synergistic with or inhibited by the addition of other therapeutic agents, CTLA4 mAb is evaluated alone or in combination with the exemplary T-cell redirecting bsAb (E1)-3s, with interferon-α (PEGINTERFERON®), or with the exemplary ADC hRS7-SN-38 (IMMU-132) in murine tumor models. M109 lung carcinoma, SA1N fibrosarcoma, and CT26 colon carcinoma models are chosen based on different sensitivity to the various agents and CTLA4 blockade. Human T cells are co-administered with the antibodies.

All compounds are tested at their optimal dose and schedule. When used in combination, CTLA4 mAb is initiated one day after the first dose of IMMU-132, (E1)-3s or interferon-α. Percent tumor growth inhibition and number of days to reach target tumor size are used to evaluate efficacy. Antitumor activity is scored as: complete regression (CR; non-palpable tumor) or partial regression (PR; 50% reduction in tumor volume). Synergy is defined as antitumor activity significantly superior (p<0.05) to the activity of monotherapy with each agent.

In the SA1N fibrosarcoma tumor model, which is sensitive to CTLA4 blockade and modestly sensitive to (E1)-3s, interferon-α, and IMMU-132, borderline synergy is evident with the combination of CTLA4 mAb and (E1)-3s, whereas no effect is observed with interferon-α. IMMU-132 monotherapy does not produce significant SA1N antitumor activity. However, combining IMMU-132 with CTLA4 mAb results in synergy. In the M109 lung metastasis model and CT26 colon carcinoma model, synergy is detected for CTLA4 mAb combined with each of IMMU-132, (E1)-3s and interferon-α.

In summary, addition of CTLA4 mAb to interferon-α, IMMU-132, or (E1)-3s results in model-dependent synergistic activities. Synergy is observed regardless of the immunogenicity of the tumor and only when at least one of the therapies is active. All combination regimens are well-tolerated and the combination therapies do not appear to inhibit CTLA4 mAb activity. Synergy is observed in tumors unresponsive to CTLA4 mAb alone, suggesting that the other therapeutic agents might induce immunogenic cell death.

Example 12

Combination Therapy with ADC (IMMU-132) and Interferon-α (PEGINTERFERON®) to Treat Refractory, Metastatic, Non-Small Cell Lung Cancer The patient is a 60-year-old man diagnosed with non-small cell lung cancer. The patient is given chemotherapy regimens of carboplatin, bevacizumab for 6 months and shows a response, and then after progressing, receives further courses of chemotherapy with carboplatin, etoposide, TAXOTERE®, gemcitabine over the next 2 years, with occasional responses lasting no more than 2 months. The patient then presents with a left mediastinal mass measuring 6.5×4 cm and pleural effusion.

After signing informed consent, the patient is given IMMU-132 at a dose of 18 mg/kg every other week. After the first week of treatment, the patient is given combination therapy with IMMU-132 and PEGINTERFERON®. During the first two injections, brief periods of neutropenia and diarrhea are experienced, with 4 bowel movements within 4 hours, but these resolve or respond to symptomatic medications within 2 days. After a total of 6 infusions of IMMU-132 and 5 infusions of PEGINTERFERON®, CT evaluation of the index lesion shows a 22% reduction, just below a partial response but definite tumor shrinkage. The patient continues with this therapy for another two months, when a partial response of 45% tumor shrinkage of the sum of the diameters of the index lesion is noted by CT, thus constituting a partial response by RECIST criteria. The combination therapy appears to provide a synergistic response, compared to the two agents administered separately.

Example 13

Combination Therapy with ADC (IMMU-130) and T-Cell Redirecting bsAb (MT100) to Treat Advanced Colonic Cancer The patient is a 75-year-old woman initially diagnosed with metastatic colonic cancer (Stage 1V). She has a right partial hemicolectomy and resection of her small intestine and then receives FOLFOX, FOLFOX+bevacizumab, FOLFIR1+ramucirumab, and FOLFIR1+cetuximab therapies for a year and a half, when she shows progression of disease, with spread of disease to the posterior cul-de-sac, omentum, with ascites in her pelvis and a pleural effusion on the right side of her chest cavity. Her baseline CEA titer just before this therapy is 15 ng/mL. She is given 6 mg/kg IMMU-130 (anti-CEACAM5-SN-38) twice weekly for 2 consecutive weeks, and then one week rest (3-week cycle). After the first cycle, the patient is given combination therapy with IMMU-132 and the leukocyte redirecting bsAb MT110, which is administered by continuous infusion on the same 3-week cycle. After 5 cycles, which are tolerated very well, without any major hematological or non-hematological toxicities, her plasma CEA titer shrinks modestly to 1.3 ng/mL, but at the 8-week evaluation she shows a 21% shrinkage of the index tumor lesions, which increases to a 27% shrinkage at 13 weeks. Surprisingly, the patient's ascites and pleural effusion both decrease (with the latter disappearing) at this time, thus improving the patient's overall status remarkably. The combination therapy appears to provide a synergistic response, compared to the two agents administered separately.

Example 14

Combination Therapy with ADC (IMMU-130), T-Cell Redirecting bsAb ((E1)-3s) and Interferon-α to Treat Gastric Cancer Patient with Stage 1V Metastatic Disease The patient is a 52-year-old male who sought medical attention because of gastric discomfort and pain related to eating for about 6 years, and with weight loss during the past 12 months. Palpation of the stomach area reveals a firm lump which is then gastroscoped, revealing an ulcerous mass at the lower part of his stomach. This is biopsied and diagnosed as a gastric adenocarcinoma. Laboratory testing reveals no specific abnormal changes, except that liver function tests, LDH, and CEA are elevated, the latter being 10.2 ng/mL. The patent then undergoes a total-body PET scan, which discloses, in addition to the gastric tumor, metastatic disease in the left axilla and in the right lobe of the liver (2 small metastases). The patient has his gastric tumor resected, and then has baseline CT measurements of his metastatic tumors. Four weeks after surgery, he receives 3 courses of combination chemotherapy consisting of a regimen of cisplatin and 5-fluorouracil (CF), but does not tolerate this well, so is switched to treatment with docetaxel. It appears that the disease is stabilized for about 4 months, based on CT scans, but then the patient's complaints of further weight loss, abdominal pain, loss of appetite, and extreme fatigue cause repeated CT studies, which show increase in size of the metastases by a sum of 20% and a suspicious lesion at the site of the original gastric resection.

The patient is then given experimental therapy with IMMU-130 (anti-CEACAM5-SN-38) on a weekly schedule of 8 mg/kg. After the first week, combination therapy with IMMU-130, (E1)-3s and interferon-α is initiated. The patient exhibits no evidence of diarrhea or neutropenia over the following 4 weeks. The patient then undergoes a CT study to measure his metastatic tumor sizes and to view the original area of gastric resection. The radiologist measures, according to RECIST criteria, a decrease of the sum of the metastatic lesions, compared to baseline prior to therapy, of 23%. There does not seem to be any clear lesion in the area of the original gastric resection. The patient's CEA titer at this time is 7.2 ng/mL, which is much reduced from the baseline value of 14.5 ng/mL. The patient continues on weekly combination therapy, and after a total of 13 infusions, his CT studies show that one liver metastasis has disappeared and the sum of all metastatic lesions is decreased by 41%, constituting a partial response by RECIST. The patient's general condition improves and he resumes his usual activities while continuing to receive maintenance therapy every third week. At the last measurement of blood CEA, the value is 4.8 ng/mL, which is within the normal range for a smoker, which is the case for this patient.

Example 15

General Techniques for DOCK-AND-LOCK™

The general techniques discussed below may be used to generate DNL™ complexes with AD or DDD moieties attached to any antibodies or antigen-binding antibody fragments, using the disclosed methods and compositions.

Expression Vectors

The plasmid vector pdHL2 has been used to produce a number of antibodies and antibody-based constructs. See Gillies et al., *J Immunol Methods* (1989), 125:191-202; Losman et al., Cancer (Phila) (1997), 80:2660-6. The dicistronic mammalian expression vector directs the synthesis of the heavy and light chains of IgG. The vector sequences are mostly identical for many different IgG-pdHL2 constructs, with the only differences existing in the variable domain ($V_H$ and $V_L$) sequences. Using molecular biology tools known to those skilled in the art, these IgG expression vectors can be converted into Fab-DDD or Fab-AD expression vectors.

To generate Fab-DDD expression vectors, the coding sequences for the hinge, CH2 and CH3 domains of the heavy chain were replaced with a sequence encoding the first 4 residues of the hinge, a 14 residue linker and a DDD moiety, such as the first 44 residues of human RIIα (referred to as DDD1, SEQ ID NO:1). To generate Fab-AD expression vectors, the sequences for the hinge, CH2 and CH3 domains of IgG were replaced with a sequence encoding the first 4 residues of the hinge, a 15 residue linker and an AD moiety, such as a 17 residue synthetic AD called AKAP-IS (referred to as AD1, SEQ ID NO:3), which was generated using bioinformatics and peptide array technology and shown to bind RIIα dimers with a very high affinity (0.4 nM). See Alto, et al. *Proc. Natl. Acad. Sci., U.S.A* (2003), 100:4445-50. Two shuttle vectors were designed to facilitate the conversion of IgG-pdHL2 vectors to either Fab-DDD1 or Fab-AD1 expression vectors, as described below.

Preparation of CH1

The CH1 domain was amplified by PCR using the pdHL2 plasmid vector as a template. The left PCR primer consisted of the upstream (5') end of the CH1 domain and a SacII restriction endonuclease site, which is 5' of the CH1 coding sequence. The right primer consisted of the sequence coding for the first 4 residues of the hinge (PKSC, SEQ ID NO:102) followed by four glycines and a serine, with the final two codons (GS) comprising a Bam HI restriction site. The 410 bp PCR amplimer was cloned into the PGEMT® PCR cloning vector (PROMEGA®, Inc.) and clones were screened for inserts in the T7 (5') orientation.

A duplex oligonucleotide was synthesized to code for the amino acid sequence of DDD1 preceded by 11 residues of the linker peptide, with the first two codons comprising a BamHI restriction site. A stop codon and an EagI restriction site are appended to the 3' end. The encoded polypeptide sequence is shown below.

(SEQ ID NO: 103)
GSGGGGSGGGGSHIQIPPGLTELLQGYTVEVLRQQPPDLVEFAVEYFTR

LREARA

Two oligonucleotides, designated RIIA1-44 top and RIIA1-44 bottom, which overlap by 30 base pairs on their 3' ends, were synthesized and combined to comprise the central 154 base pairs of the 174 bp DDD1 sequence. The oligonucleotides were annealed and subjected to a primer extension reaction with Taq polymerase. Following primer extension, the duplex was amplified by PCR. The amplimer was cloned into PGEMT® and screened for inserts in the T7 (5') orientation.

A duplex oligonucleotide was synthesized to code for the amino acid sequence of AD1 preceded by 11 residues of the linker peptide with the first two codons comprising a BamHI restriction site. A stop codon and an EagI restriction site are appended to the 3' end. The encoded polypeptide sequence is shown below.

(SEQ ID NO: 104)
GSGGGGSGGGGSQIEYLAKQIVDNAIQQA

Two complimentary overlapping oligonucleotides encoding the above peptide sequence, designated AKAP-IS Top and AKAP-IS Bottom, were synthesized and annealed. The duplex was amplified by PCR. The amplimer was cloned into the PGEMT® vector and screened for inserts in the T7 (5') orientation.

Ligating DDD1 with CH1

A 190 bp fragment encoding the DDD1 sequence was excised from PGEMT® with BamHI and NotI restriction enzymes and then ligated into the same sites in CH1-PGEMT® to generate the shuttle vector CH1-DDD1-PGEMT®.

Ligating AD1 with CH1

A 110 bp fragment containing the AD1 sequence was excised from PGEMT® with BamHI and NotI and then ligated into the same sites in CH1-PGEMT® to generate the shuttle vector CH1-AD1-PGEMT®.

With this modular design either CH1-DDD1 or CH1-AD1 can be incorporated into any IgG construct in the pdHL2 vector. The entire heavy chain constant domain is replaced with one of the above constructs by removing the SacII/EagI restriction fragment (CH1-CH3) from pdHL2 and replacing it with the SacII/EagI fragment of CH1-DDD1 or CH1-AD1, which is excised from the respective PGEMT® shuttle vector.

C-DDD2-Fd-hMN-14-pdHL2

C-DDD2-Fd-hMN-14-pdHL2 is an expression vector for production of C-DDD2-Fab-hMN-14, which possesses a dimerization and docking domain sequence of DDD2 (SEQ ID NO:2) appended to the carboxyl terminus of the Fd of hMN-14 via a 14 amino acid residue Gly/Ser peptide linker. The fusion protein secreted is composed of two identical copies of hMN-14 Fab held together by non-covalent interaction of the DDD2 domains.

The expression vector was engineered as follows. Two overlapping, complimentary oligonucleotides, which comprise the coding sequence for part of the linker peptide and residues 1-13 of DDD2, were made synthetically. The oligonucleotides were annealed and phosphorylated with T4 PNK, resulting in overhangs on the 5' and 3' ends that are compatible for ligation with DNA digested with the restriction endonucleases BamHI and PstI, respectively.

The duplex DNA was ligated with the shuttle vector CH1-DDD1-PGEMT®, which was prepared by digestion with BamHI and PstI, to generate the shuttle vector CH1-DDD2-PGEMT®. A 507 bp fragment was excised from CH1-DDD2-PGEMT® with SacII and EagI and ligated with the IgG expression vector hMN-14(I)-pdHL2, which was prepared by digestion with SacII and EagI. The final expression construct was designated C-DDD2-Fd-hMN-14-pdHL2. Similar techniques have been utilized to generated DDD2-fusion proteins of the Fab fragments of a number of different humanized antibodies.

h679-Fd-AD2-pdHL2 h679-Fab-AD2, was designed to pair to C-DDD2-Fab-hMN-14. h679-Fd-AD2-pdHL2 is an expression vector for the production of h679-Fab-AD2, which possesses an anchoring domain sequence of AD2 (SEQ ID NO:4) appended to the carboxyl terminal end of the CH1 domain via a 14 amino acid residue Gly/Ser peptide linker. AD2 has one cysteine residue preceding and another one following the anchor domain sequence of AD1.

The expression vector was engineered as follows. Two overlapping, complimentary oligonucleotides (AD2 Top and AD2 Bottom), which comprise the coding sequence for AD2 and part of the linker sequence, were made synthetically. The oligonucleotides were annealed and phosphorylated with T4 PNK, resulting in overhangs on the 5' and 3' ends that are compatible for ligation with DNA digested with the restriction endonucleases BamHI and SpeI, respectively.

The duplex DNA was ligated into the shuttle vector CH1-AD1-PGEMT®, which was prepared by digestion with BamHI and SpeI, to generate the shuttle vector CH1-AD2-PGEMT®. A 429 base pair fragment containing CH1 and AD2 coding sequences was excised from the shuttle vector with SacII and EagI restriction enzymes and ligated into h679-pdHL2 vector that prepared by digestion with those same enzymes. The final expression vector is h679-Fd-AD2-pdHL2.

Generation of TF2 DNL™ Construct

A trimeric DNL™ construct designated TF2 was obtained by reacting C-DDD2-Fab-hMN-14 with h679-Fab-AD2. A pilot batch of TF2 was generated with >90% yield as follows. Protein L-purified C-DDD2-Fab-hMN-14 (200 mg) was mixed with h679-Fab-AD2 (60 mg) at a 1.4:1 molar ratio. The total protein concentration was 1.5 mg/ml in PBS containing 1 mM EDTA. Subsequent steps involved TCEP reduction, HIC chromatography, DMSO oxidation, and IMP 291 affinity chromatography. Before the addition of TCEP, SE-HPLC did not show any evidence of $a_2b$ formation. Addition of 5 mM TCEP rapidly resulted in the formation of $a_2b$ complex consistent with a 157 kDa protein expected for the binary structure. TF2 was purified to near homogeneity by IMP 291 affinity chromatography (not shown). IMP 291 is a synthetic peptide containing the HSG hapten to which the 679 Fab binds (Rossi et al., 2005, Clin Cancer Res 11:7122s-29s). SE-HPLC analysis of the IMP 291 unbound fraction demonstrated the removal of $a_4$, $a_2$ and free kappa chains from the product (not shown).

The functionality of TF2 was determined by BIACORE® assay. TF2, C-DDD1-hMN-14+h679-AD1 (used as a control sample of noncovalent $a_2b$ complex), or C-DDD2-hMN-14+h679-AD2 (used as a control sample of unreduced $a_2$ and b components) were diluted to 1 µg/ml (total protein) and passed over a sensorchip immobilized with HSG. The response for TF2 was approximately two-fold that of the two control samples, indicating that only the h679-Fab-AD component in the control samples would bind to and remain on the sensorchip. Subsequent injections of WI2 IgG, an anti-idiotype antibody for hMN-14, demonstrated that only TF2 had a DDD-Fab-hMN-14 component that was tightly associated with h679-Fab-AD as indicated by an additional signal response. The additional increase of response units resulting from the binding of WI2 to TF2 immobilized on the sensorchip corresponded to two fully functional binding sites, each contributed by one subunit of C-DDD2-Fab-hMN-14. This was confirmed by the ability of TF2 to bind two Fab fragments of WI2 (not shown).

Production of TF10 DNL™ Construct

A similar protocol was used to generate a trimeric TF10 DNL™ construct, comprising two copies of a C-DDD2-Fab-hPAM4 and one copy of C-AD2-Fab-679. The TF10 bispecific ([hPAM4]$_2$×h679) antibody was produced using the method disclosed for production of the (anti CEA)$_2$×anti HSG bsAb TF2, as described above. The TF10 construct bears two humanized PAM4 Fabs and one humanized 679 Fab.

The two fusion proteins (hPAM4-DDD2 and h679-AD2) were expressed independently in stably transfected myeloma cells. The tissue culture supernatant fluids were combined, resulting in a two-fold molar excess of hPAM4-DDD2. The reaction mixture was incubated at room temperature for 24 hours under mild reducing conditions using 1 mM reduced glutathione. Following reduction, the reaction was completed by mild oxidation using 2 mM oxidized glutathione. TF10 was isolated by affinity chromatography using IMP291-affigel resin, which binds with high specificity to the h679 Fab.

Example 16

Production of AD- and DDD-Linked Fab and IgG Fusion Proteins from Multiple Antibodies Using the techniques described in the preceding Example, the IgG and Fab fusion proteins shown in Table 11 were constructed and incorporated into DNL™ constructs. The fusion proteins retained the antigen-binding characteristics of the parent antibodies and the DNL™ constructs exhibited the antigen-binding activities of the incorporated antibodies or antibody fragments.

TABLE 11

| Fusion proteins comprising IgG or Fab | |
|---|---|
| Fusion Protein | Binding Specificity |
| C-AD1-Fab-h679 | HSG |
| C-AD2-Fab-h679 | HSG |
| C-(AD)$_2$-Fab-h679 | HSG |
| C-AD2-Fab-h734 | Indium-DTPA |
| C-AD2-Fab-hA20 | CD20 |
| C-AD2-Fab-hA20L | CD20 |
| C-AD2-Fab-hL243 | HLA-DR |
| C-AD2-Fab-hLL2 | CD22 |
| N-AD2-Fab-hLL2 | CD22 |
| C-AD2-IgG-hMN-14 | CEACAM5 |
| C-AD2-IgG-hR1 | IGF-1R |
| C-AD2-IgG-hRS7 | EGP-1 |
| C-AD2-IgG-hPAM4 | MUC |
| C-AD2-IgG-hLL1 | CD74 |
| C-DDD1-Fab-hMN-14 | CEACAM5 |
| C-DDD2-Fab-hMN-14 | CEACAM5 |
| C-DDD2-Fab-h679 | HSG |
| C-DDD2-Fab-hA19 | CD19 |
| C-DDD2-Fab-hA20 | CD20 |
| C-DDD2-Fab-hAFP | AFP |
| C-DDD2-Fab-hL243 | HLA-DR |
| C-DDD2-Fab-hLL1 | CD74 |
| C-DDD2-Fab-hLL2 | CD22 |
| C-DDD2-Fab-hMN-3 | CEACAM6 |
| C-DDD2-Fab-hMN-15 | CEACAM6 |
| C-DDD2-Fab-hPAM4 | MUC |
| C-DDD2-Fab-hR1 | IGF-1R |
| C-DDD2-Fab-hRS7 | EGP-1 |
| N-DDD2-Fab-hMN-14 | CEACAM5 |

Example 17

Production and Use of a DNL™ Construct Comprising Two Different Antibody Moieties and a Cytokine In certain embodiments, trimeric DNL™ constructs may comprise three different effector moieties, for example two different antibody moieties and a cytokine moiety. We report here the generation and characterization of a bispecific MAb-IFNα, designated 20-C2-2b, which comprises two copies of IFN-α2b and a stabilized F(ab)$_2$ of hL243 (humanized anti-HLA-DR; IMMU-114) site-specifically linked to veltuzumab (humanized anti-CD20). In vitro, 20-C2-2b inhibited each of four lymphoma and eight myeloma cell lines, and was more effective than monospecific CD20-targeted MAb-IFNα or a mixture comprising the parental antibodies and IFNα in all but one (HLA-DR$^-$/CD20$^-$) myeloma line (not shown), suggesting that 20-C2-2b is useful for the treatment of various hematopoietic disorders. The 20-C2-2b displayed greater cytotoxicity against KMS 12-BM (CD20$^+$/HLA-DR$^+$ myeloma) than monospecific MAb-IFNα that targets only HLA-DR or CD20 (not shown), indicating that all three components in 20-C2-2b can contribute to toxicity.

Antibodies

The abbreviations used in the following discussion are: 20 ($C_H3$-AD2-IgG-v-mab, anti-CD20 IgG DNL™ module); C2 ($C_H1$-DDD2-Fab-hL243, anti-HLA-DR Fab$_2$ DNL™ module); 2b (dimeric IFNα2B-DDD2 DNL™ module); 734 (anti-in-DTPA IgG DNL™ module used as non-targeting control). The following MAbs were provided by Immunomedics, Inc.: veltuzumab or v-mab (anti-CD20IgG$_1$), hL243γ4p (Immu-114, anti-HLA-DR IgG$_4$), a murine anti-IFNα MAb, and rat anti-idiotype MAbs to v-mab (WR2) and hL243 (WT).

DNL™ Constructs

Monospecific MAb-IFNα (20-2b-2b, 734-2b-2b and C$_{2-2}$b-2b) and the bispecific HexAb (20-C2-C2) were generated by combination of an IgG-AD2-module with DDD2-modules using the DNL™ method, as described in the preceding Examples. The 734-2b-2b, which comprises tetrameric IFNα2b and MAb h734 [anti-Indium-DTPA IgG$_1$], was used as a non-targeting control MAb-IFNα.

The construction of the mammalian expression vector as well as the subsequent generation of the production clones and the purification of $C_H3$-AD2-IgG-v-mab are disclosed in the preceding Examples. The expressed recombinant fusion protein has the AD2 peptide linked to the carboxyl terminus of the $C_H3$ domain of v-mab via a 15 amino acid long flexible linker peptide. Co-expression of the heavy chain-AD2 and light chain polypeptides results in the formation of an IgG structure equipped with two AD2 peptides. The expression vector was transfected into Sp/ESF cells (an engineered cell line of Sp2/0) by electroporation. The pdHL2 vector contains the gene for dihydrofolate reductase, thus allowing clonal selection, as well as gene amplification with methotrexate (MTX). Stable clones were isolated from 96-well plates selected with media containing 0.2 µM MTX. Clones were screened for $C_H3$-AD2-IgG-vmab productivity via a sandwich ELISA. The module was produced in roller bottle culture with serum-free media.

The DDD-module, IFNα2b-DDD2, was generated as discussed above by recombinant fusion of the DDD2 peptide to the carboxyl terminus of human IFNα2b via an 18 amino acid long flexible linker peptide. As is the case for all DDD-modules, the expressed fusion protein spontaneously forms a stable homodimer.

The $C_H1$-DDD2-Fab-hL243 expression vector was generated from hL243-IgG-pdHL2 vector by excising the sequence for the $C_H1$-Hinge-$C_H2$-$C_H3$ domains with SacII and EagI restriction enzymes and replacing it with a 507 bp sequence encoding $C_H1$-DDD2, which was excised from the C-DDD2-hMN-14-pdHL2 expression vector with the same enzymes. Following transfection of $C_H1$-DDD2-Fab-hL243-pdHL2 into Sp/ESF cells by electroporation, stable, MTX-resistant clones were screened for productivity via a sandwich ELISA using 96-well microtiter plates coated with mouse anti-human kappa chain to capture the fusion protein, which was detected with horseradish peroxidase-conjugated goat anti-human Fab. The module was produced in roller bottle culture.

Roller bottle cultures in serum-free H-SFM media and fed-batch bioreactor production resulted in yields comparable to other IgG-AD2 modules and cytokine-DDD2 modules generated to date. $C_H3$-AD2-IgG-v-mab and IFNα2b-DDD2 were purified from the culture broths by affinity chromatography using MABSELECT™ (GE Healthcare) and HIS-SELECT® HF Nickel Affinity Gel (Sigma), respectively, as described previously (Rossi et al., Blood 2009, 114:3864-71). The culture broth containing the $C_H1$-DDD2-Fab-hL243 module was applied directly to KAPPASELECT® affinity gel (GE-Healthcare), which was washed to baseline with PBS and eluted with 0.1 M Glycine, pH 2.5.

Generation of 20-C2-2b by DNL™

Three DNL™ modules ($C_H3$-AD2-IgG-v-mab, $C_H1$-DDD2-Fab-hL243, and IFN-α2b-DDD2) were combined in equimolar quantities to generate the bsMAb-IFNα, 20-C2-2b. Following an overnight docking step under mild reducing conditions (1 mM reduced glutathione) at room temperature, oxidized glutathione was added (2 mM) to facilitate disulfide bond formation (locking). The 20-C2-2b was purified to near homogeneity using three sequential affinity chromatography steps. Initially, the DNL™ mixture was purified with Protein A (MABSELECT™), which binds the $C_H3$-AD2-IgG-v-MAb group and eliminates un-reacted IFNα2b-DDD2 or $C_H1$-DDD2-Fab-hL243. The Protein A-bound material was further purified by IMAC using HIS-SELECT® HF Nickel Affinity Gel, which binds specifically to the IFNα2b-DDD2 moiety and eliminates any constructs lacking this group. The final process step, using an hL243-anti-idiotype affinity gel removed any molecules lacking $C_H1$-DDD2-Fab-hL243.

The skilled artisan will realize that affinity chromatography may be used to purify DNL™ complexes comprising any combination of effector moieties, so long as ligands for each of the three effector moieties can be obtained and attached to the column material. The selected DNL™ construct is the one that binds to each of three columns containing the ligand for each of the three effector moieties and can be eluted after washing to remove unbound complexes.

The following Example is representative of several similar preparations of 20-C2-2b. Equimolar amounts of $C_H3$-AD2-IgG-v-mab (15 mg), $C_H1$-DDD2-Fab-hL243 (12 mg), and IFN-α2b-DDD2 (5 mg) were combined in 30-mL reaction volume and 1 mM reduced glutathione was added to the solution. Following 16 h at room temperature, 2 mM oxidized glutathione was added to the mixture, which was held at room temperature for an additional 6 h. The reaction mixture was applied to a 5-mL Protein A affinity column, which was washed to baseline with PBS and eluted with 0.1 M Glycine, pH 2.5. The eluate, which contained ~20 mg protein, was neutralized with 3 M Tris-HCl, pH 8.6 and dialyzed into HIS-SELECT® binding buffer (10 mM imidazole, 300 mM NaCl, 50 mM NaH$_2$PO$_4$, pH 8.0) prior to application to a 5-mL HIS-SELECT® IMAC column. The column was washed to baseline with binding buffer and eluted with 250 mM imidazole, 150 mM NaCl, 50 mM NaH$_2$PO$_4$, pH 8.0.

The IMAC eluate, which contained ~11.5 mg of protein, was applied directly to a WP (anti-hL243) affinity column, which was washed to baseline with PBS and eluted with 0.1 M glycine, pH 2.5. The process resulted in 7 mg of highly purified 20-C2-2b. This was approximately 44% of the theoretical yield of 20-C2-2b, which is 50% of the total starting material (16 mg in this example) with 25% each of 20-2b-2b and 20-C2-C2 produced as side products.

Generation and Characterization of 20-C2-2b

The bispecific MAb-IFNα was generated by combining the IgG-AD2 module, $C_H3$-AD2-IgG-v-mab, with two different dimeric DDD-modules, $C_H1$-DDD2-Fab-hL243 and IFNα2b-DDD2. Due to the random association of either DDD-module with the two AD2 groups, two side-products, 20-C2-C2 and 20-2b-2b are expected to form, in addition to 20-C2-2b.

Non-reducing SDS-PAGE (not shown) resolved 20-C2-2b (~305 kDa) as a cluster of bands positioned between those of 20-C2-C2 (~365 kDa) and 20-2b-2b (255 kDa). Reducing SDS-PAGE resolved the five polypeptides (v-mab HC-AD2, hL243 Fd-DDD2, IFNα2b-DDD2 and co-migrating v-mab and hL243 kappa light chains) comprising 20-C2-2b (not shown). IFNα2b-DDD2 and hL243 Fd-DDD2 are absent in 20-C2-C2 and 20-2b-2b. MABSELECT™ binds to all three of the major species produced in the DNL™ reaction, but removes any excess IFNα2b-DDD2 and $C_H1$-DDD2-Fab-hL243. The HIS-SELECT® unbound fraction contained mostly 20-C2-C2 (not shown). The unbound fraction from WT affinity chromatography comprised 20-2b-2b (not shown). Each of the samples was subjected to SE-HPLC and immunoreactivity analyses, which corroborated the results and conclusions of the SDS-PAGE analysis.

Following reduction of 20-C2-2b, its five component polypeptides were resolved by RP-HPLC and individual ESI-TOF deconvoluted mass spectra were generated for each peak (not shown). Native, but not bacterially-expressed recombinant IFNα2, is O-glycosylated at Thr-106 (Adolf et al., Biochem J 1991; 276 (Pt 2):511-8). We determined that ~15% of the polypeptides comprising the IFNα2b-DDD2 module are O-glycosylated and can be resolved from the non-glycosylated polypeptides by RP-HPLC and SDS-PAGE (not shown). LC/MS analysis of 20-C2-2b identified both the O-glycosylated and non-glycosylated species of IFNα2b-DDD2 with mass accuracies of 15 ppm and 2 ppm, respectively (not shown). The observed mass of the O-glycosylated form indicates an O-linked glycan having the structure NeuGc-NeuGc-Gal-GalNAc, which was also predicted (<1 ppm) for 20-2b-2b (not shown). LC/MS identified both v-mab and hL243 kappa chains as well as hL243-Fd-DDD2 (not shown) as single, unmodified species, with observed masses matching the calculated ones (<35 ppm). Two major glycoforms of v-mab HC-AD2 were identified as having masses of 53,714.73 (70%) and 53,877.33 (30%), indicating G0F and G1F N-glycans, respectively, which are typically associated with IgG (not shown). The analysis also confirmed that the amino terminus of the HC-AD2 is modified to pyroglutamate, as predicted for polypeptides having an amino terminal glutamine.

SE-HPLC analysis of 20-C2-2b resolved a predominant protein peak with a retention time (6.7 min) consistent with its calculated mass and between those of the larger 20-C2-C2 (6.6 min) and smaller 20-2b-2b (6.85 min), as well as some higher molecular weight peaks that likely represent non-covalent dimers formed via self-association of IFNα2b (not shown).

Immunoreactivity assays demonstrated the homogeneity of 20-C2-2b with each molecule containing the three functional groups (not shown). Incubation of 20-C2-2b with an excess of antibodies to any of the three constituent modules resulted in quantitative formation of high molecular weight immune complexes and the disappearance of the 20-C2-2b peak (not shown). The HIS-SELECT® and WT affinity unbound fractions were not immunoreactive with WT and anti-IFNα, respectively (not shown). The MAb-IFNα showed similar binding avidity to their parental MAbs (not shown).

IFNα Biological Activity

The specific activities for various MAb-IFNα were measured using a cell-based reporter gene assay and compared to peginterferon alfa-2b (not shown). Expectedly, the specific activity of 20-C2-2b (2454 IU/pmol), which has two IFNα2b groups, was significantly lower than those of 20-2b-2b (4447 IU/pmol) or 734-2b-2b (3764 IU/pmol), yet greater than peginterferon alfa-2b (P<0.001) (not shown). The difference between 20-2b-2b and 734-2b-2b was not significant. The specific activity among all agents varies minimally when normalized to IU/pmol of total IFNα. Based on these data, the specific activity of each IFNα2b group of the MAb-IFNα is approximately 30% of recombinant IFNα2b (4000 IU/pmol).

In the ex-vivo setting, the 20-C2-2b DNL™ construct depleted lymphoma cells more effectively than normal B cells and had no effect on T cells (not shown). However, it did efficiently eliminate monocytes (not shown). Where v-mab had no effect on monocytes, depletion was observed following treatment with hL243a4p and MAb-IFNα, with 20-2b-2b and 734-2b-2b exhibiting similar toxicity (not shown). Therefore, the predictably higher potency of 20-C2-2b is attributed to the combined actions of anti-HLA-DR and IFNα, which may be augmented by HLA-DR targeting. These data suggest that monocyte depletion may be a pharmacodynamic effect associated anti-HLA-DR as well as IFNα therapy; however, this side effect would likely be transient because the monocyte population should be repopulated from hematopoietic stem cells.

The skilled artisan will realize that the approach described here to produce and use bispecific immunocytokine, or other DNL™ constructs comprising three different effector moieties, may be utilized with any combinations of antibodies, antibody fragments, cytokines or other effectors that may be incorporated into a DNL™ construct, for example the combination of anti-CD3 and anti-CD19 or other anti-TAA with IFNα2b.

Example 18

Use of NK-Targeted Leukocyte-Redirecting bsAbs

The use of bsAbs to retarget leukocytes is not limited to antibodies against T cells. In alternative embodiments, bsAbs that bind to monocytes, NK cells or neutrophils may also be used for retargeting purposes.

CD16 is an activating low-affinity Fc-γ receptor for IgG, which is highly expressed by the $CD56^{dim}$ subset of NK cells (Gleason et al., 2012, Mol Cancer Ther 11:2674-84). In addition to their use in NK cell retargeting, bsAbs comprising an anti-CD16 antibody component have the ability to activate NK-mediated cytotoxicity through direct signaling of CD16, inducing directed secretion of lytic granules and target cell death (Gleason et al., 2012).

A CD16/CD19 bispecific killer cell engager (BiKE) and a CD16/CD19/CD22 trispecific killer cell engager (TriKe) are prepared according to (Gleason et al., 2012, Mol Cancer Ther 11:2674-84), using DNA shuffling and ligation techniques as previously reported (Vallera et al., 2005, Clin Cancer Res 11:3879-88). The expressed BiKE and TriKE are purified by sequential ion exchange and size-exclusion column chromatography. Resting PBMCs are exposed to primary ALL and CLL tumor cells in the presence of CD16/CD19 BiKE or CD16/CD19/CD22 TriKE (10 μg/mL). A significant increase in cytotoxicity to tumor cells is observed in the presence of the BiKE or TriKE, compared to cells without retargeting antibody. No effect is observed on tumor cells exposed to BiKE or TriKE in the absence of PBMCs. The TriKE has a greater effect on tumor cell toxicity relative to the BiKE, indicating that binding to an additional tumor cell antigen may enhance the retargeting effect. Similar results are obtained using purified NK cells instead of PBMCs.

A CD16/CD33 BiKE is prepared as disclosed in Wiernik et al. (2013, Clin Cancer Res 19:3844-55. The BiKE is administered to nude mice injected with human HL60 promyelocytic leukemia xenograft cells, co-administered with human PBMCs. The BiKE treated mice show a decreased mortality and tumor growth rate compared to mice treated with control bsAbs. Addition of an anti-CD33-SN-38 ADC further enhances the cytotoxic effect of the BiKE.

Example 19

Inhibition of HIV Infection In Vitro and In Vivo Using Conjugated Anti-HIV Antibodies Summary To demonstrate the efficacy of an immunoconjugate against HIV-1, murine monoclonal antibody (Mab) against the envelope antigen of HIV (P4/D10) was conjugated with the conventional anti-cancer drug, doxorubicin, and tested against infectious virus and infected cells, both in vitro and in vivo. P4/D10 antibody was incubated with free virus (neutralization) or HIV-infected cells (inhibition) and the resulting infection was measured by a p24 capture enzyme-linked immunosorbent assay. In an HIV-1/MuLV mouse challenge model the ability of the conjugate to inhibit infection in vivo was measured.

Doxorubicin-conjugated P4/D10 neutralized HIV-1$_{IIIB}$ and eliminated intercellular spread and HIV replication in infected Jurkat cells in vitro. It also protected mice from challenge with HIV-1$_{IIIB}$/MuLV at an eight-fold lower concentration than needed for free antibody, whereas no effects were observed for free drug or irrelevant conjugate controls.

These results demonstrate that doxorubicin was concentrated to HIV-infected cells by the P4/D10 antibody, significantly (P=0.0001) contributing to HIV elimination. The same compositions and methods are of use to eradicate remaining antigen-expressing T-cells in patients treated with ART (anti-retroviral therapy).

In this study, we conjugated doxorubicin, an anticancer anthracycline with known pharmacology, toxicology, and antitumor activity in patients, to a neutralizing and ADCC-mediating monoclonal antibody (Mab) developed against the HIV-1 outer envelope gp120 (third variable loop region).

The P4/D10 antibody conjugated to doxorubicin was tested in vitro for its efficacy in eliminating HIV-1-infected cells among non-infected cells and in a mouse model by removing HIV-1/MuLV (murine leukemia virus) infected syngeneic cells from the intraperitoneal cavity. The anti-gp120 antibody, P4/D10, neutralizes HIV-1 virus and mediates ADCC (Broliden et al., 1990). It has also been used in its unconjugated form in a phase-I clinical trial for late-stage HIV-1 infected individuals, where it decreased HIV antigens for an extended period of time (Hinkula et al., 1994). The present study was the first to examine the combination of P4/D10 in a drug-conjugated form in a preclinical HIV model, in comparison to free Mab, free drug, and the irrelevant antibodies hRS7 (Stein et al., *Int J Cancer* 1993, 55:938-946) and hLL1 Griffiths et al., *Clin Cancer Res* 2003, 9:6567-6571; Sapra et al., *Clin Cancer Res* 2005, 11:5257-5264), that were conjugated similarly with doxorubicin.

Materials and Methods

Antibodies and Drug Conjugation.

Conjugation of doxorubicin with the IgG1κ anti-gp120 antibody P4/D10 (Broliden et al., 1990) and the control antibodies, as well as the preparation of the bifunctional doxorubicin hydrazone derivative with a maleimide group, were performed according to Griffiths et al. (2003). Briefly, antibodies P4/D10, hLL1 (humanized anti-CD74), and hRS7 (humanized anti-EGP-1) in a final concentration of approximately 9 mg/ml, were mildly reduced with DTT (dithiothreitol) in PBS (pH 7.5) containing 5 mM EDTA, using about 2.2 mM final DTT concentration, corresponding to a 38-fold molar excess of the reductant with respect to the antibodies. The solutions were incubated at 37° C. for 40 min. The reduced Mabs were purified on spin-columns of Sephadex G50/80 in 50 mM sodium acetate buffer containing 150 mM NaCl and 2 mM EDTA (pH 5.3). The number of thiol groups generated on the antibodies was determined by Ellman's assay. For conjugation, mildly reduced antibodies at 6.5 mg/ml were mixed with the bifunctional doxorubicin. The incubates were kept on ice for 15 min, and purified on spin columns of G50/80 in 0.1 M sodium acetate (pH 6.5), followed by passage through a short column of Bio-Beads SM2 (Bio-Rad, Hercules, Calif.) equilibrated in the same buffer. The products were analyzed for doxorubicin/Mab substitution ratios by measuring absorbance. Size-exclusion HPLC analyses were performed on an analytical BioSil 250 column.

A GMP-produced lot of IgG from HIV infected patients (HIVIgG) (Guay et al. *AIDS* 2002, 16:1391-1400) was used as positive control and sera from HIV-negative individuals as negative controls. Free doxorubicin, as well as the anti-cancer humanized Mabs LL1 and RS7, similarly conjugated with doxorubicin, were included as controls for the conjugated P4/D10 antibody.

HIV-1 Neutralization Assay.

Doxorubicin P4/D10, unlabelled P4/D10, HIV immunoglobulin (HIVIgG), and HIV-negative serum were mixed with the HIV-1 isolate HIV-1$_{IIIB}$ (LAI) and incubated for 1 h at 37° C. before 50,000 Jurkat T-cells/well were added. After 1 h of incubation, the cells were washed with medium and new complete medium added (200 µl/well). After 7 days of culture, the amount of p24 produced was measured by a p24 capture ELISA (enzyme-linked immunosorbent assay) and the percent inhibition of HIV-1 p24 production was calculated.

HIV-1 Inhibition In Vitro.

Jurkat T-cells were infected with HIV-1$_{IIIB}$ by mixing 5–10×10$^6$ cells with 100× TCID$_{50}$ HIV-1$_{IIIB}$ and incubating for 1 h at 37° C. The cells were washed in medium and incubated at 37° C. Every third day, medium was changed and supernatant checked for p24 production. When close to 100% of the cells were infected, different proportions of HIV-1$_{IIIB}$-infected cells were mixed with uninfected cells. The cells were treated with serial dilutions of antibodies, serum, or free doxorubicin from 100 to 0.00001 µg/ml. After seven days of culture at 37° C., HIV-1 p24 inhibition was measured and supernatants from cells previously treated with 0.1-10 µg/ml of doxorubicin-P4/D10, unconjugated P4/D10, and 0.05-0.5 mg/ml HIV-negative serum were collected and transferred to fresh Jurkat T-cells to test if infectious HIV was identified by the p24 ELISA at days 3, 7, 10, 12, and 15 after initiation of the culture.

HIV-1/MuLV Challenge Model.

A human T-cell line, CEM-1B, with a genetically integrated MuLV genome was infected with HIV-1$_{IIIB}$, which led to the production of pseudoviruses with the HIV-1 genome and the MuLV envelope (Adang et al., PNAS USA 1999, 96:12749-753; Hinkula et al., *Cells Tissues Organs* 2004, 177:169-184). These virus supernatants were used to infect splenocytes from C57Bl/6×DBA F1 K$^{b/d}$ mice transgenic for HLA-A201. Isogenic mice were challenged with HIV-1$_{IIIB}$/MuLV infected splenocytes i.p. and were immediately given conjugated antibodies, free antibodies or free doxorubicin i.p. Ten days after challenge, mice were sacrificed and peritoneal cells collected. Peritoneal cells were pelleted and added to 1×10$^6$ HIV susceptible Jurkat T-cells or human PBMC grown in 24-well plates. From these secondary cultures, supernatant was removed and fresh medium added every 3-4 days. The amount of infectious HIV recovered in the supernatant was measured for 3 weeks by p24 ELISA.

Statistical Analysis.

To compare the in vitro HIV-1 neutralizing capacities of the anti-gp120 Mabs and control antibodies, Student's t-test and the non-parametric Kruskal-Wallis test were used. Statistical comparisons between the groups of mice treated with different antibodies were performed using the nonparametric Mann-Whitney U and Kruskal-Wallis tests. A difference was considered significant when a p-value of <0.05 was obtained. A non-parametric one-way ANOVA test was performed using GraphPad Prism version 4.0a (GraphPad Software, San Diego, Calif.) and was used for comparisons of HIV-1 isolation and p24 antigen positivity between the study groups.

Results

The number of thiol groups generated on the respective antibodies by mild reduction, as well as the doxorubicin/Mab substitution ratios in the final purified conjugates, ranged between 8.8 (P4/D10, hRS7) and 9.4 (hLL1), giving a ratio of approximately 9 drug molecules per IgG. High-pressure liquid chromatographic analyses showed that the conjugates and the native Mabs possessed similar retention times, with zero to minimal aggregation (data not shown).

No significant difference in HIV-1 neutralizing capacity of free HIV-1 virus (not shown) could be shown between the doxorubicin-conjugated P4/D10 Mab and either unconjugated P4/D10 Mab or the HIVIgG antibodies. However, all anti HIV-1 specific antibodies were significantly better then the negative control serum (p=0.001) at neutralizing HIV-1$_{IIIB}$.

When 3% HIV-1$_{IIIB}$ infected Jurkat cells were mixed with 97% uninfected cells, doxorubicin-P4/D10 mediated a significantly (p=0.002) stronger inhibition of intercellular spread of HIV-1 infection than free P4/D10, doxorubicin-conjugated control antibody, hLL1, or free doxorubicin at a concentration of 0.5 or 0.05 µg/ml (not shown). Similar results were seen at all other concentrations of infected and uninfected cells. It was of particular interest that the intercellular spread of infection appeared to be inhibited even more potently than the effect obtained with doxorubicin-P4/D10 as a neutralizing agent. Also, no infectious virus could be found in the cultures treated with high doses of doxorubicin-P4/D10, since no p24 production was detected after transfer of supernatants from these cell cultures to uninfected Jurkat cells (data not shown). The significant difference in effect between doxorubicin-P4/D10 and unconjugated P4/D10 could not have been predicted from the results on neutralization of free HIV-1 virus (not shown).

To test the efficacy of doxorubicin-P4/D10 antibody in vivo, mice were given isogeneic HIV/MuLV-infected cells together with conjugates intraperitoneally. Peritoneal cells were harvested 10 days later and infectious HIV was demonstrated in all controls, similar to previous studies (Hinkula et al., 2004). The doxorubicin-P4/D10 antibody protected mice completely against challenge with HIV-1 infected primary lymphoid cells (p=0.0001) (not shown). No infectious HIV was recovered from peritoneal cells after challenge and treatment with 100 µg of doxorubicin-P4/D10 antibody. When mice were treated with 100 µg of unconjugated P4/D10 antibody, all were positive for p24 production. Complete protection by antibody alone was seen only when the dose was increased eight-fold, to 800 µg unconjugated P4/D10 per mouse. None of the doxorubicin-conjugated control antibodies (hLL1 or hRS7) provided any protection at doses of 100-200 µg, nor did doses of 100-400 µg of free doxorubicin.

Discussion

The results above show that the total virus-inhibiting properties of an antibody directed against the envelope of HIV-1 could be amplified significantly by coupling to doxorubicin. Doxorubicin-P4/D10 was capable of eliminating HIV-1 infected cells in vitro, as well as in an experimental in vivo challenge model. The ability of the unconjugated P4/D10 Mab to mediate ADCC against HIV-1 infected target cells as well as neutralizing HIV-1 (Broliden et al., 1990; Hinkula et al., 1994) may enhance its efficacy as a drug immunoconjugate in a non-toxic manner.

An anticancer anti-CD74 Mab, LL1, conjugated similarly to doxorubicin, has at very low doses shown remarkable activity in vitro and in human xenograft models of non-Hodgkin's lymphoma or multiple myeloma (Griffiths et al., 2003; Sapra et al., 2005). These studies, as well as toxicology in monkeys, indicated that only very high doses of the immunoconjugate would result in evidence of bone marrow suppression, but no cardiac toxicity related to doxorubicin was observed (Sapra et al., 2005). To avoid virus escape, antibodies directed against both conserved and variable sites of accessible epitopes of HIV should be tested together (Trkola et al., 2005; Ferrantelli et al., *J Infect Dis* 2004, 189:2167-2173).

In previous in vitro studies, HIV-1 specific immunoglobulins conjugated to *Pseudomonas* exotoxin A (PE40) removed HIV-1 infected cells (Pincus et al., 2003; Ashorn et al., *Proc Natl Acad Sci USA* 1990, 87:8889-8893). However, in clinical trials, PE40 coupled to CD4 cells proved to be immunogenic and hepatotoxic (Davey et al., 1994; Ramachandran et al., 1994). Thus, the present results, showing efficacy of a doxorubicin-Mab conjugate with little or no side effects, are surprising and unexpected. The toxicity of PE40-CD4 might be explained by formation of toxic complexes with free gp120, which is present in high concentrations in non-ART treated patients with high viral load (Berger et al., 1998). In order to avoid potential toxicity problems associated with high viral loads, molecules targeting HIV-envelope-specific epitopes should preferably be used in the setting when viral burden is low, such as during ART, early in HIV infection or even shortly after a known or potential exposure to infection with HIV. For example, health care workers exposed to accidental needle stick with HIV-contaminated or potentially contaminated blood or other fluids may be treated with a conjugated antibody according to the disclosed methods. As a result of the anticellular activity of the doxorubicin-P4/D10 conjugate, the addition of a drug conjugate to patients treated with ART may eliminate antigen-carrying cells as well as free virions, and thus reduce the viral load even further. The skilled artisan will realize that the claimed compositions and methods are not limited to a doxorubicin conjugate of P4/D10, but rather may utilize other known cytotoxic agents conjugated to P4/D10 or to other known anti-HIV antibodies.

In other embodiments, in order to avoid non-specific toxicity, bispecific antibodies and other pretargeting strategies may be used, in which antibody targeting and delivery of the toxic agent are separated (Wu et al., 2005). This strategy has shown promising results both in preclinical and in clinical cancer trials (Forero et al., *Blood* 2004, 104:227-236; Rossi et al., *Clin Cancer Res* 2005, 11:7122s-7129s). For in vivo use in human subjects, human or humanized forms of antibody for repeated clinical use are preferred.

Example 20

Treatment of an HIV-Infected Patient with ADC and T-Cell Redirecting bsAb

A 47-year old male patient is determined to be seropositive for HIV. The patient has a CD4 count of less than 200/mm$^3$. The patient is treated with a standard regimen of the non-nucleoside reverse transcriptase inhibitor nevirapine. CD4 cell count improves to 300/mm$^3$, but the patient is still seropositive for HIV. The patient is treated with humanized doxorubicin-P4/D10 antibody followed by a leukocyte redirecting (P4/D10)-3s bsAb. The patient's CD4 count improves to over 350/mm$^3$ and the patient is no longer seropositive for HIV. One year later, the patient remains asymptomatic and there is no detectable presence of HIV infection.

Example 21

Trivalent Antibodies for Therapeutic Use

A trivalent, trispecific cell targeting construct is made as described in patent EP1309795B1 comprising: (i) chimerizing or humanizing a mouse anti-CD16 mab as described in U.S. Pat. No. 618,728 from which the Fab of claim 1 of EP1309795 is derived; (ii) constructing a single chain antibody comprised of the Fv of the humanized anti-HLA-DR antibody described in U.S. Pat. No. 7,512,189, and joining the scFv by a linker to the carboxyl terminal of the light chain of the anti-CD16 Fab of (i); and (iii) constructing a single chain of the Fv of the humanized anti-CD19 described in U.S. Pat. No. 8,486,395 and joining the scFv by a linker to the carboxyl terminal of the CH1 of the anti-CD16 Fab of (ii).

The trivalent construct is administered to a subject with non-Hodgkin's lymphoma, in combination with hLL2-SN38. A partial response is observed and the tumor shows a regression in size that lasts for 12 months.

All of the COMPOSITIONS and METHODS disclosed and claimed herein can be made and used without undue experimentation in light of the present disclosure. While the compositions and methods have been described in terms of preferred embodiments, it is apparent to those of skill in the art that variations may be applied to the COMPOSITIONS and METHODS and in the steps or in the sequence of steps of the METHODS described herein without departing from the concept, spirit and scope of the invention. More specifically, certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method of inducing a T-cell mediated immune response against a human cancer cell that expresses MUC5ac, or CEACAM5, comprising administering to a subject with a human cancer that expresses MUC5ac or CEACAM5 a leukocyte redirecting bispecific antibody comprising a first antibody or antigen-binding fragment thereof that binds to human CD3 and a second antibody or antigen-binding fragment thereof that binds to a human target antigen selected from the group consisting of MUC5ac, and CEACAM5;

wherein administration of the bispecific antibody induces a leukocyte-mediated immune response against the cancer and wherein the bispecific antibody comprises: (i) a first antibody moiety conjugated to an AD (anchoring domain) moiety from an AKAP protein; and (ii) a second antibody moiety conjugated to a DDD (dimerization and docking domain) moiety, wherein the amino acid sequence of said DDD moiety is residues 1-44 of human protein kinase A (PKA) RIIα, and wherein two copies of the DDD moiety form a dimer that binds to one copy of the AD moiety to form the bispecific antibody.

2. The method of claim 1, further comprising administering interferon-a to the subject.

3. The method of claim 1, wherein the second antibody is selected from the group consisting of hPAM4 (anti-MUC5ac) and hMN-14 (anti-CEACAM5).

4. The method of claim 2, wherein the interferon is administered as free interferon, PEGylated interferon, an interferon fusion protein or interferon conjugated to an antibody.

5. The method of claim 1, wherein the cancer is selected from the group consisting of oral cavity cancer, gastrointestinal tract cancer, colon cancer, stomach cancer, lung cancer, breast cancer, ovarian cancer, prostate cancer, uterine cancer, urinary bladder cancer, pancreatic cancer, and kidney cancer.

6. The method of claim 1, further comprising administering a therapeutic agent to the subject.

7. The method of claim 6, wherein the therapeutic agent is selected from the group consisting of a drug, a toxin, an enzyme, a cytotoxic agent, an anti-angiogenic agent, a pro-apoptotic agent, a hormone, an immunomodulator, a cytokine, a chemokine, a boron compound and a radioisotope.

8. The method of claim 7, wherein the drug is selected from the group consisting of 5-fluorouracil, afatinib, aplidin, azaribine, anastrozole, anthracyclines, axitinib, bendamustine, bleomycin, bortezomib bosutinib, bryostatin-1, busulfan, calicheamycin, camptothecin, carboplatin, 10-hydroxycamptothecin, carmustine, celecoxib, chlorambucil, cisplatinum, Cox-2 inhibitors, irinotecan (CPT-11), SN-38, cladribine, camptothecans, crizotinib, cyclophosphamide, cytarabine, dacarbazine, dasatinib, dinaciclib, docetaxel, dactinomycin, daunorubicin, doxorubicin, 2-pyrrolinodoxorubicine (2P-DOX), cyano-morpholino doxorubicin, doxorubicin glucuronide, epirubicin glucuronide, erlotinib, estramustine, epidophyllotoxin, erlotinib, entinostat, etoposide (VP16), etoposide glucuronide, etoposide phosphate, exemestane, fingolimod, floxuridine (FUdR), 3',5'-O-dioleoyl-FudR (FUdR-dO), fludarabine, flutamide, flavopiridol, fostamatinib, ganetespib, gefitinib, gemcitabine, hydroxyurea, ibrutinib, idarubicin, idelalisib, ifosfamide, imatinib, L-asparaginase, lapatinib, lenolidamide, leucovorin, lomustine, mechlorethamine, melphalan, mercaptopurine, 6-mercaptopurine, methotrexate, mitoxantrone, mithramycin, mitomycin, mitotane, navelbine, neratinib, nilotinib, nitrosurea, olaparib, plicomycin, procarbazine, paclitaxel, pentostatin, Pro-2-P-Dox, raloxifene, semustine, sorafenib, streptozocin, sunitinib, tamoxifen, temazolomide, transplatinum, thalidomide, thioguanine, thiotepa, teniposide, topotecan, uracil mustard, vatalanib, vinorelbine, vinblastine, vincristine, and vinca alkaloids.

9. The method of claim 7, wherein the chemokine is selected from the group consisting of RANTES, MCAF, MIP1-alpha, MIP1-Beta and IP-10.

10. The method of claim 7, wherein the immunomodulator is selected from the group consisting of a cytokine, a stem cell growth factor, a lymphotoxin, a hematopoietic factor, a colony stimulating factor (CSF), an interferon (IFN), erythropoietin and thrombopoietin.

11. The method of claim 7, wherein the cytokine is selected from the group consisting of human growth hormone, N-methionyl human growth hormone, bovine growth hormone, parathyroid hormone, thyroxin, insulin, proinsulin, relaxin, prorelaxin, follicle stimulating hormone (FSH), thyroid stimulating hormone (TSH), luteinizing hormone (LH), hepatic growth factor, prostaglandin, fibroblast growth factor, prolactin, placental lactogen, OB protein, tumor necrosis factor-α, tumor necrosis factor-β, mullerian-inhibiting substance, mouse gonadotropin-associated peptide, inhibin, activin, vascular endothelial growth factor, integrin, thrombopoietin (TPO), a nerve growth factor (NGF), NGF-β, platelet-growth factor, a transforming growth factors (TGF), TGF-α, TGF-β, insulin-like growth factor-I, insulin-like growth factor-II, erythropoietin (EPO), an osteoinductive factor, an interferon, interferon-α, interferon-β, interferon-λ, a colony stimulating factors (CSF), macrophage-CSF (M-CSF), granulocyte-macrophage-CSF (GM-CSF), granulocyte-CSF (G-CSF), interleukin-1 (IL-1), IL-1α, IL-2, IL-3, IL-4, IL-5, IL-6, IL-7, IL-8, IL-9, IL-10, IL-11, IL-12, IL-13, IL-14, IL-15, IL-16, IL-17, IL-18, IL-21, LIF, kit-ligand, FLT-3, angiostatin, thrombospondin, endostatin, tumor necrosis factor and LT (lymphotoxin).

12. A method of inducing an immune response to cancer comprising administering to a human subject with a cancer that expresses MUC5ac a leukocyte redirecting bispecific antibody comprising a first antibody or antigen-binding fragment thereof that binds to human CD3 and a second antibody or antigen-binding fragment thereof that binds to human MUC5ac, wherein administration of the bispecific antibody induces a leukocyte-mediated immune response against the MUC5ac-expressing cancer and wherein the bispecific antibody comprises: (i) a first antibody moiety conjugated to an AD (anchoring domain) moiety from an AKAP protein; and (ii) a second antibody moiety conjugated to a DDD (dimerization and docking domain) moiety, wherein the amino acid sequence of said DDD moiety is residues 1-44 of human protein kinase A (PKA) RIIα, and wherein two copies of the DDD moiety form a dimer that binds to one copy of the AD moiety to form the complex.

13. A method of inducing an immune response to cancer comprising administering to a human subject with a cancer that expresses CEACAM5 a leukocyte redirecting bispecific antibody comprising a first antibody or antigen-binding fragment thereof that binds to human CD3 and a second antibody or antigen-binding fragment thereof that binds to human CEACAM5, wherein administration of the bispecific antibody induces a leukocyte-mediated immune response against the CEACAM5-expressing cancer and wherein the bispecific antibody comprises: (i) a first antibody moiety conjugated to an AD (anchoring domain) moiety from an AKAP protein; and (ii) a second antibody moiety conjugated to a DDD (dimerization and docking domain) moiety, wherein the amino acid sequence of said DDD moiety is residues 1-44 of human protein kinase A (PKA) RIIα, and wherein two copies of the DDD moiety form a dimer that binds to one copy of the AD moiety to form the complex.

* * * * *